US012758543B2

(12) United States Patent
Bishop et al.

(10) Patent No.: US 12,758,543 B2
(45) Date of Patent: *Oct. 13, 2026

(54) COMBINATION SEROTONIN SPECIFIC REUPTAKE INHIBITOR AND SEROTONIN 1A RECEPTOR PARTIAL AGONIST FOR REDUCING L-DOPA-INDUCED DYSKINESIA

(71) Applicants: The Research Foundation for The State University of new York, Binghamton, NY (US); Rosalind Franklin University of Medicine and Science, North Chicago, IL (US); Board of Trustees of Michigan State University, East Lansing, MI (US)

(72) Inventors: Christopher Roy Bishop, Vestal, NY (US); Anthony West, North Chicago, IL (US); Fredric Manfresson, Grand Rapids, MI (US)

(73) Assignee: The Research Foundation for The State University of New York, Binghamton, NY (US)

(*) Notice: Subject to any disclaimer, the term of this patent is extended or adjusted under 35 U.S.C. 154(b) by 1124 days.

This patent is subject to a terminal disclaimer.

(21) Appl. No.: 17/288,822

(22) PCT Filed: Oct. 25, 2019

(86) PCT No.: PCT/US2019/058199

§ 371 (c)(1), (2) Date: Apr. 26, 2021

(87) PCT Pub. No.: WO2020/087031

PCT Pub. Date: Apr. 30, 2020

(65) Prior Publication Data

US 2021/0393621 A1 Dec. 23, 2021

Related U.S. Application Data

(60) Provisional application No. 62/751,247, filed on Oct. 26, 2018.

(51) Int. Cl.

| | |
|---|---|
| ***A61K 31/496*** | (2006.01) |
| ***A61K 9/00*** | (2006.01) |
| ***A61K 31/00*** | (2006.01) |
| ***A61K 31/13*** | (2006.01) |
| ***A61K 31/198*** | (2006.01) |
| ***A61K 31/4545*** | (2006.01) |
| ***A61K 31/495*** | (2006.01) |
| ***A61K 31/55*** | (2006.01) |
| ***A61K 45/06*** | (2006.01) |
| ***A61P 25/16*** | (2006.01) |

(52) U.S. Cl.

CPC .......... *A61K 31/496* (2013.01); *A61K 9/0053* (2013.01); *A61K 31/13* (2013.01); *A61K 31/198* (2013.01); *A61K 31/4545* (2013.01); *A61K 31/495* (2013.01); *A61K 31/55* (2013.01); *A61K 31/658* (2023.05); *A61K 45/06* (2013.01); *A61P 25/16* (2018.01)

(58) Field of Classification Search

CPC ................................ A61P 25/16; A61P 25/14

See application file for complete search history.

(56) References Cited

U.S. PATENT DOCUMENTS 12,285,426 B2 * 4/2025 Bishop .................. A61K 45/06

FOREIGN PATENT DOCUMENTS

EP 3360542 8/2018

OTHER PUBLICATIONS

Dawson et al., “Vilazodone: a 5-HT1a receptor agonist/serotonin transporter inhibitor for the treatment of affective disorders”, 2009, CNS Neuroscience & Therapeutics, 15, pp. 107-117 (Year: 2009).*
Carta et al., “Serotonin system implication in L-DOPA-induced dyskinesia: from animal models to clinical investigations”, 2014, Frontiers in Neurology, 5, pp. 1-4 (Year: 2014).*
Viibryd, “Viibryd (vilazodone hydrochloride)”, 2014, Forest Laboratories, pp. 1-17 (Year: 2014).*
Dos-Santos-Pereira et al., “Co-administration of cannabidiol and capsazepine reduce L-DOPA-induced dyskinesia in mice: Possible mechanism of action”, 2016, Neurobiology of Disease, 94, pp. 179-195 (Year: 2016).*
Mahableshwarkar et al., “A randomized, double-blind trial of 2.5 mg and 5 mg vortioxetine (Lu AA21004) versus placebo for 8 weeks in adults with major depressive disorder”, 2013, Current Medical Research & Opinion, 29, pp. 217-226 (Year: 2013).*
Miguelez et al., “The acute and long-term L-DOPA effects are independent from changes in the activity of dorsal raphe serotonergic neurons in 6-OHDA lesioned rats”, 2016, British Journal of Pharmacology, 173, pp. 2135-2146 (Year: 2016).*

(Continued)

*Primary Examiner* — Brenda L Coleman
*Assistant Examiner* — Madeline E Braun
(74) *Attorney, Agent, or Firm* — Hoffberg & Associates; Steven M. Hoffberg

(57) ABSTRACT

A method of treating and attenuating L-DOPA-induced dyskinesia, comprising administering an effective dose of at least one pharmacological agent, e.g., vilazodone, having serotonin-specific reuptake inhibition (SSRI) and serotonin receptor 1A (5-HT1AR) partial agonism activity, in conjunction with L-DOPA. Other agents, such as an L-DOPA decarboxylase inhibitor, e.g., carbidopa, or other adjunct treatments may also be provided.

20 Claims, 18 Drawing Sheets

Specification includes a Sequence Listing.

(56) References Cited

OTHER PUBLICATIONS

Sinemet, "Sinemet (carbidopa levodopa)", 2014, Merck & Co., pp. 1-10 (Year: 2014).*
Zhang et al., "Neurochemical and behavioral effects of hypidone hydrochloride (YL-0919): a novel combined selective 5-HT reuptake inhibitor and partial 5-HT1a agonist", 2017, British Journal of Pharmacology, 174, pp. 769-780 (Year: 2017).*
Terrie, "Monitoring Combination Drug Therapy", 2010, Pharmacy Times, 76, pp. 1-14 (Year: 2010).*
Sanchez et al., "Vortioxetine, a novel antidepressant with multimodal activity: Review of preclinical and clinical data", 2015, Pharmacology & Therapeutics, 145, pp. 43-57 (Year: 2015).*
Cowen, "Psychopharmacology of 5-HT1A Receptors", 2000, Nuclear Medicine & Biology, 27, pp. 437-439 (Year: 2000).*
Adamec, Robert, Gerd D. Bartoszyk, and Paul Burton. "Effects of systemic injections of vilazodone, a selective serotonin reuptake inhibitor and serotonin 1A receptor agonist, on anxiety induced by predator stress in rats." European Journal of Pharmacology 504, No. 1-2 (2004): 65-77.
Ahlskog, J. Eric, and Manfred D. Muenter. "Frequency of levodopa-related dyskinesias and motor fluctuations as estimated from the cumulative literature." Movement disorders: official journal of the Movement Disorder Society 16, No. 3 (2001): 448-458.
Altwal, Feras, Connor Moon, Anthony R. West, and Heinz Steiner. "The multimodal serotonergic agent vilazodone inhibits L-DOPA-induced gene regulation in striatal projection neurons and associated dyskinesia in an animal model of Parkinson's disease." Cells 9, No. 10 (2020): 2265.
Artigas, Francesc. "Future directions for serotonin and antidepressants." ACS chemical neuroscience 4, No. 1 (2013): 5-8.
Ashby Jr, Charles R., John H. Kehne, Gerd D. Bartoszyk, Matthew J. Renda, Maria Athanasiou, Kerri A. Pierz, and Christoph A. Seyfried. "Electrophysiological evidence for rapid 5-HT1A autoreceptor inhibition by vilazodone, a 5-HT1A receptor partial agonist and 5-HT reuptake inhibitor." European journal of pharmacology 714, No. 1-3 (2013): 359-365.
Bartoszyk, Gerd D., Rainer Hegenbart, and Herbert Ziegler. "EMD 68843, a serotonin reuptake inhibitor with selective presynaptic 5-HT1 A receptor agonistic properties." European journal of pharmacology 322, No. 2-3 (1997): 147-153.
Bishop, Christopher, Jessica A. George, William Buchta, Adam A. Goldenberg, Mohamed Mohamed, Sando O. Dickinson, Satie Eissa, and Karen L. Eskow Jaunarajs. "Serotonin transporter inhibition attenuates 1-DOPA-induced dyskinesia without compromising 1-DOPA efficacy in hemi-parkinsonian rats." European Journal of Neuroscience 36, No. 6 (2012): 2839-2848.
Chen, Hong-xia, Zeng-liang Jin, Li-ming Zhang, Rui Xue, Xiao-dan Xu, Nan Zhao, Zhi-kun Qiu et al. "Antidepressant-like activity of YL-0919: a novel combined selective serotonin reuptake inhibitor and 5-HT1A receptor agonist." PLoS One 8, No. 12 (2013): e83271.
Chung, Kathryn A., Nichole E. Carlson, and John G. Nutt. "Short-term paroxetine treatment does not alter the motor response to levodopa in PD." Neurology 64, No. 10 (2005): 1797-1798.
Conti, Melissa M., Corinne Y. Ostock, David Lindenbach, Adam A. Goldenberg, Elias Kampton, Rich Dell'isola, Aaron C. Katzman, and Christopher Bishop. "Effects of prolonged selective serotonin reuptake inhibition on the development and expression of L-DOPA-induced dyskinesia in hemi-parkinsonian rats." Neuropharmacology 77 (2014): 1-8.
Dawson, Lee A., and Jeannette M. Watson. "Vilazodone: A 5-HT1A receptor agonist/serotonin transporter inhibitor for the treatment of affective disorders." CNS neuroscience & therapeutics 15, No. 2 (2009): 107-117.
Dekundy, Andrzej, Martin Lundblad, Wojciech Danysz, and M. Angela Cenci. "Modulation of L-DOPA-induced abnormal involuntary movements by clinically tested compounds: further validation of the rat dyskinesia model." Behavioural brain research 179, No. 1 (2007): 76-89.
Del-Bel, Elaine, Fernando Eduardo Padovan-Neto, Rita Raisman-Vozari, and Marcio Lazzarini. "Role of nitric oxide in motor control: implications for Parkinson's disease pathophysiology and treatment." Current pharmaceutical design 17, No. 5 (2011): 471-488.
Dos-Santos-Pereira, Mauricio, Celia Aparecida da-Silva, Francisco Silveira Guimaraes, and Elaine Del-Bel. "Co-administration of cannabidiol and capsazepine reduces L-DOPA-induced dyskinesia in mice: possible mechanism of action." Neurobiology of disease 94 (2016): 179-195.
Durif, F., M. Vidailhet, A. M. Bonnet, J. Blin, and Y. Agid. "Levodopa-induced dyskinesias are improved by fluoxetine." Neurology 45, No. 10 (1995): 1855-1858.
Fidalgo, Camino, W. K. D. Ko, Elisabetta, Tronci, Q. Li, Roberto. Stancampiano, Q. Chuan, E. Bezard, and Manolo Carta. "Effect of serotonin transporter blockade on L-DOPA-induced dyskinesia in animal models of Parkinson's disease." Neuroscience 298 (2015): 389-396.
Forest Pharmaceuticals, Viibryd (Vilazodone HCI) Highlights of Prescribing Information (2012).
Goetz, Christopher G., Philippe Damier, Christine Hicking, Eugene Laska, Thomas Müller, C. Warren Olanow, Olivier Rascol, and Hermann Russ. "Sarizotan as a treatment for dyskinesias in Parkinson's disease: a double-blind placebo-controlled trial." Movement disorders: official journal of the Movement Disorder Society 22, No. 2 (2007): 179-186.
Hammerstad, John P., Julie Carter, John G. Nutt, George C. Casten, R. C. Shrotriya, Donald R. Alms, and Davis Temple. "Buspirone in Parkinson's disease." Clinical neuropharmacology 9, No. 6 (1986): 556-560.
Heinrich, Timo, Henning Böttcher, Rolf Gericke, Gerd D. Bartoszyk, Soheila Anzali, Christoph A. Seyfried, Hartmut E. Greiner, and Christoph Van Amsterdam. "Synthesis and structure-activity relationship in a class of indolebutylpiperazines as dual 5-HT1A receptor agonists and serotonin reuptake inhibitors." Journal of medicinal chemistry 47, No. 19 (2004): 4684-4692.
Hopkins, Corey R. "Acs chemical neuroscience molecule spotlight on Viibryd (vilazodone)." ACS chemical neuroscience 2, No. 10 (2011): 554-554.
Hughes, Zoë A., Kathryn R. Starr, Christopher J. Langmead, Matthew Hill, Gerd D. Bartoszyk, James J. Hagan, Derek N. Middlemiss, and Lee A. Dawson. "Neurochemical evaluation of the novel 5-HT1A receptor partial agonist/serotonin reuptake inhibitor, vilazodone." European journal of pharmacology 510, No. 1-2 (2005): 49-57.
Inden, Masatoshi, Mari Abe, Hideaki Minamino, Kazuyuki Takata, Kanji Yoshimoto, Ikuo Tooyama, and Yoshihisa Kitamura. "Effect of selective serotonin reuptake inhibitors via 5-HT1A receptors on L-DOPA-induced rotational behavior in a hemiparkinsonian rat model." Journal of pharmacological sciences 119, No. 1 (2012): 10-19.
Isaacson, Stuart H., Stanley Fahn, Rajesh Pahwa, Caroline M. Tanner, Alberto J. Espay, Claudia Trenkwalder, Charles H. Adler, Rajiv Patni, and Reed Johnson. "Parkinson's patients with dyskinesia switched from immediate release amantadine to open-label ADS-5102." Movement disorders clinical practice 5, No. 2 (2018): 183-190.
Jenner, Peter. "The treatment of levodopa-induced dyskinesias: Surfing the serotoninergic wave." Movement Disorders 33, No. 11 (2018): 1670-1672.
Khan, Arif. "Vilazodone, a novel dual-acting serotonergic antidepressant for managing major depression." Expert opinion on investigational drugs 18, No. 11 (2009): 1753-1764.
Kuan, Wei-Li, Jing-Wei Zhao, and Roger A. Barker. "The role of anxiety in the development of levodopa-induced dyskinesias in an animal model of Parkinson's disease, and the effect of chronic treatment with the selective serotonin reuptake inhibitor citalopram." Psychopharmacology 197, No. 2 (2008): 279-293.
Lanza, Kathryn, and Christopher Bishop. "Serotonergic targets for the treatment of L-DOPA-induced dyskinesia." Journal of Neural Transmission 125, No. 8 (2018): 1203-1216.
Linazasoro, G. "Worsening of Parkinson's disease by citalopram." Parkinsonism & related disorders 6, No. 2 (2000): 111-113.

(56) References Cited

OTHER PUBLICATIONS

Lindenbach, D., N. Palumbo, C. Y. Ostock, N. Vilceus, M. M. Conti, and C. Bishop. "Side effect profile of 5-HT treatments for Parkinson's disease and L-DOPA-induced dyskinesia in rats." British journal of pharmacology 172, No. 1 (2015): 119-130.
Mahableshwarkar, Atul R., Paula L. Jacobsen, and Yinzhong Chen. "A randomized, double-blind trial of 2.5 mg and 5 mg vortioxetine (Lu AA21004) versus placebo for 8 weeks in adults with major depressive disorder." Current medical research and opinion 29, No. 3 (2013): 217-226.
Meadows, Samantha M., Melissa M. Conti, Libby Gross, Nicole E. Chambers, Yarden Avnor, Corinne Y. Ostock, Kathryn Lanza, and Christopher Bishop. "Diverse serotonin actions of vilazodone reduce 1-3, 4-dihidroxyphenylalanine-induced dyskinesia in hemi-parkinsonian rats." Movement Disorders 33, No. 11 (2018): 1740-1749.
Miguelez, C., S. Navailles, P. De Deurwaerdere, and L. Ugedo. "The acute and long-term L-DOPA effects are independent from changes in the activity of dorsal raphe serotonergic neurons in 6-OHDA lesioned rats." British Journal of Pharmacology 173, No. 13 (2016): 2135-2146.
Morelli, Emanuela, Holly Moore, Tahilia J. Rebello, Neil Gray, Kelly Steele, Ennio Esposito, Jay A. Gingrich, and Mark S. Ansorge. "Chronic 5-HT transporter blockade reduces DA signaling to elicit basal ganglia dysfunction." Journal of Neuroscience 31, No. 44 (2011): 15742-15750.
Oosting, Ronald S., Johnny SW Chan, Berend Olivier, and Pradeep Banerjee. "Vilazodone does not inhibit sexual behavior in male rats in contrast to paroxetine: a role for 5-HT1A receptors?. " Neuropharmacology 107 (2016): 271-277.
Page, Michelle E., John F. Cryan, Arthur Sullivan, Ashutosh Dalvi, Berangere Saucy, David R. Manning, and Irwin Lucki. "Behavioral and neurochemical effects of 5-{4-[4-(5-cyano-3-indolyl)-butyl)-butyl]-1-piperazinyl}-benzofuran-2-carboxamide (EMD 68843): a combined selective inhibitor of serotonin reuptake and 5-hydroxytryptamine1A receptor partial agonist." The Journal of pharmacology and experimental therapeutics 302, No. 3 (2002): 1220-1227.
Pahwa, Rajesh, Caroline M. Tanner, Robert A. Hauser, Kapil Sethi, Stuart Isaacson, Daniel Truong, Lynn Struck et al. "Amantadine extended release for levodopa-induced dyskinesia in Parkinson's disease (EASED Study)." Movement Disorders 30, No. 6 (2015): 788-795.
PCT/US19/58199 Written Opinion and Search Report Jan. 21, 2020.
Rampello, Liborio, Santina Chiechio, Rocco Raffaele, Ignazio Vecchio, and Francesco Nicoletti. "The SSRI, citalopram, improves bradykinesia in patients with Parkinson's disease treated with L-dopa." Clinical neuropharmacology 25, No. 1 (2002): 21-24.
Richard, Irene Hegeman, Angeline Maughn, and Roger Kurlan. "Do serotonin reuptake inhibitor antidepressants worsen Parkinson's disease? A retrospective case series." Movement disorders: official journal of the Movement Disorder Society 14, No. 1 (1999): 155-157.
Roberts, Claire, Jim J. Hagan, Gerd D. Bartoszyk, and James NC Kew. "Effect of vilazodone on 5-HT efflux and re-uptake in the guinea-pig dorsal raphe nucleus." European journal of pharmacology 517, No. 1-2 (2005): 59-63.
Sahli, Zeyad T., Pradeep Banerjee, and Frank I. Tarazi. "The preclinical and clinical effects of vilazodone for the treatment of major depressive disorder." Expert opinion on drug discovery 11, No. 5 (2016): 515-523.
Sellnow, Rhyomi C., Jordan H. Newman, Nicole Chambers, Anthony R. West, Kathy Steece-Collier, Ivette M. Sandoval, Matthew J. Benskey, Christopher Bishop, and Fredric P. Manfredsson. "Regulation of dopamine neurotransmission from serotonergic neurons by ectopic expression of the dopamine D2 autoreceptor blocks levodopa-induced dyskinesia." Acta neuropathologica communications 7, No. 1 (2019): 8.
Sinemet® (carbodopa levodopa) tablets, Merck & Co. 2014.
Taylor, A., Meadows, S., Chambers, N., Avnor, Y., Vilceus, N., Gross. L., & Bishop. C., Poster: "Prophylactic Effects of Atypical Anti-Depressant Vilazodone on L-DOPA-Induced Dyskinesia and Striatal Gene Expression", 2016.
Treit, Dallas, Aldemar Degroot, and Gerd D. Bartoszyk. "Systemic EMD 68843 injections reduce anxiety in the shock-probe, but not the plus-maze test." European journal of pharmacology 414, No. 2-3 (2001): 245-248.
Van de Vijver, D. A. M. C., R. A. C. Roos, P. A. F. Jansen, A. J. Porsius, and A. De Boer. "Start of a selective serotonin reuptake inhibitor (SSRI) and increase of antiparkinsonian drug treatment in patients on levodopa." British journal of clinical pharmacology 54, No. 2 (2002): 168-170.
Wang, Panpan, Fengyuan Yang, Hong Yang, Xiaofei Xu, Duo Liu, Weiwei Xue, and Feng Zhu. "Identification of dual active agents targeting 5-HT1A and SERT by combinatorial virtual screening methods." Bio-medical materials and engineering 26, No. 1_suppl (2015): S2233-S2239.
Zhang, Li-Ming, Xiao-Yun Wang, Nan Zhao, Yu-Lu Wang, Xiao-Xu Hu, Yu-Hua Ran, Yan-Qin Liu, You-Zhi Zhang, Ri-Fang Yang, and Yun-Feng Li. "Neurochemical and behavioural effects of hypidone hydrochloride (YL-0919): a novel combined selective 5-HT reuptake inhibitor and partial 5-HT1A agonist." British journal of pharmacology 174, No. 9 (2017): 769-780.

* cited by examiner

*P < 0.05 vs all;
+P < 0.05 vs VZD (0) + LD (0);
^P < 0.05 vs VZD (0) + LD (6);
§P < 0.05 vs Baseline Scaffold N1
(5HT1A:-11.1, SERT:-11.1)

Scaffold N2
(5HT1A:-11.5, SERT:-10.7)

Scaffold N3
(5HT1A:-11.3, SERT:-11.3)

Scaffold N4
(5HT1A:-10.7, SERT:-10.4)

Scaffold N5
(5HT1A:-12.1; SERT:-11.3)

Scaffold N6
(5HT1A:-10.7; SERT:-10.4)

Scaffold N7
(5HT1A:-11.5, SERT:-10.8)

Scaffold N8
(5HT1A:-10.3, SERT:-10.5)

Scaffold N9
(5HT1A:-10.5, SERT:-10.7)

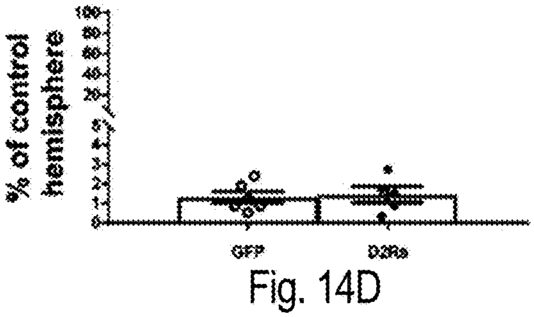
Fig. 14D
Fig. 14E Fig. 14H
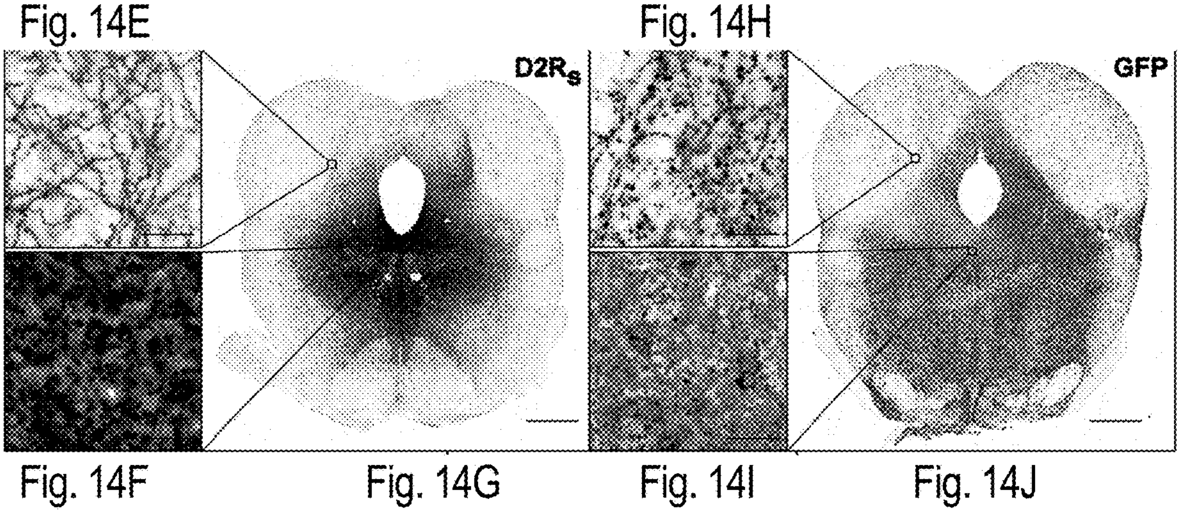
Fig. 14F Fig. 14G Fig. 14I Fig. 14J
Fig. 14K Fig. 14L Fig. 14M
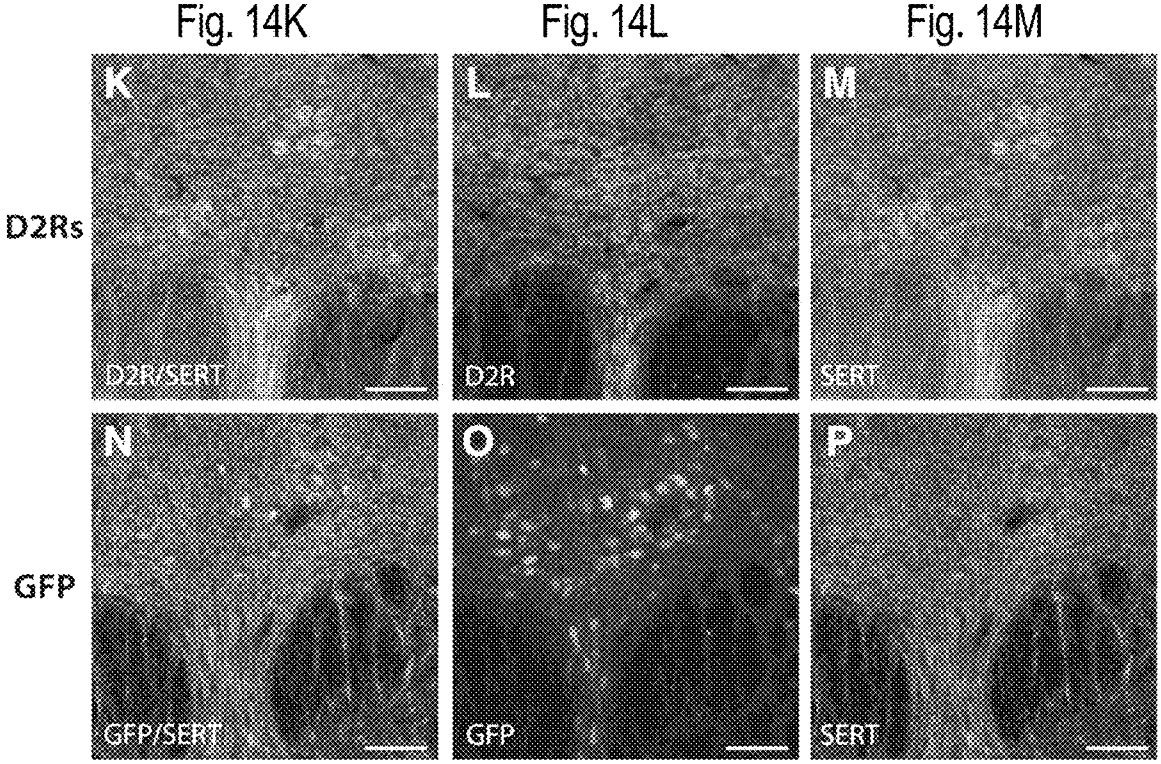
Fig. 14N Fig. 14O Fig. 14P

SKF-81297 0.8mg/kg

COMBINATION SEROTONIN SPECIFIC REUPTAKE INHIBITOR AND SEROTONIN 1A RECEPTOR PARTIAL AGONIST FOR REDUCING L-DOPA-INDUCED DYSKINESIA

CROSS REFERENCE TO RELATED APPLICATIONS

The present application is a 35 U.S.C. § 371 National Stage Application of PCT/US2019/58199, filed Oct. 25, 2019, which claims benefit of priority from U.S. Provisional Patent Application No. 62/751,247, filed Oct. 26, 2018, each of which is expressly incorporated herein by reference in its entirety.

FIELD OF THE INVENTION

The present invention relates to combination therapies for neurological diseases, and more particularly to use of vilazodone, a selective serotonin reuptake inhibitor and 5-HT1A partial agonist, to counteract dyskinesias which result from L-DOPA administration, e.g., in Parkinson's disease.

BACKGROUND OF THE INVENTION

Parkinson's disease affects an estimated 10 million individuals worldwide. Nearly all patients will receive the drug L-DOPA for treatment at some point. Of these, 90% will eventually suffer from debilitating choreic and dystonic side-effects of L-DOPA, called dyskinesia. Preclinical work, using a validated animal model of Parkinson's disease, has shown that the FDA-approved anti-depressant Vilazodone significantly reduces dyskinesia and maintains the efficacy of L-DOPA.

Although treatment with the dopamine precursor L-DOPA remains the gold-standard treatment for Parkinson's Disease (PD), long-term L-DOPA induces abnormal involuntary movements, called L-DOPA-induced dyskinesia (LID) in nearly 90% of patients within 10 years of commencing treatment.

Parkinson's disease (PD) is a long-term degenerative disorder of the central nervous system that mainly affects the motor system. [NINDS 2016] The motor symptoms of the disease result from the death of cells in the substantia nigra, a region of the midbrain. [NINDS 2016] This results in not enough dopamine in these areas. [NINDS 2016] The reason for this cell death is poorly understood, but involves the build-up of proteins into Lewy bodies in the neurons. [Kalia 2016] en.wikipedia.org/wiki/Parkinson % 27s_disease There is no cure for Parkinson's disease, with treatment directed at improving symptoms. [NINDS 2016][Samii 2004] Initial treatment is typically with the antiparkinson medication levodopa (L-DOPA), with dopamine agonists being used once levodopa becomes less effective. [Sveinbjornsdottir 2016] As the disease progresses and neurons continue to be lost, these medications become less effective while at the same time they produce a complication marked by involuntary writhing movements. [Sveinbjornsdottir 2016]Diet and some forms of rehabilitation have shown some effectiveness at improving symptoms. [Barichella 2009] [Ahlskog 2011] Surgery to place microelectrodes for deep brain stimulation has been used to reduce motor symptoms in severe cases where drugs are ineffective. [NINDS 2016] Evidence for treatments for the non-movement-related symptoms of PD, such as sleep disturbances and emotional problems, is less strong. [Kalia 2016] In 2015, PD affected 6.2 million people and resulted in about 117,400 deaths globally. [GBD 2015 Disease Injury Incidence Prevalence Collaborators] [GBD 2015 Mortality Causes of Death Collaborators] Parkinson's disease typically occurs in people over the age of 60, of which about one percent are affected. [NINDS 2016] [Carroll 2016] Males are more often affected than females at a ratio of around 3:2. [Kalia 2016] When it is seen in people before the age of 50, it is called young-onset PD. [Mosley 2010] The movement difficulties found in PD are called parkinsonism and a number of different disorders feature parkinsonism. "Parkinsonism" is defined as bradykinesia (slowness in initiating voluntary movements, with progressive reduction in speed and range of repetitive actions such as voluntary finger-tapping [Ling 2012]) in combination with one of three other physical signs: muscular (lead-pipe or cogwheel) rigidity, tremor at rest, and postural instability. [Parkinson's Disease vs. Parkinsonism] [Queen Square Brain Bank diagnostic criteria for Parkinson's disease]

Parkinson's disease is the most common form of parkinsonism and is sometimes called "idiopathic parkinsonism", meaning parkinsonism with no identifiable cause. [Samii 2004] [Schrag 2007] Identifiable causes of parkinsonism include toxins, infections, side effects of drugs, metabolic derangement, and brain lesions such as strokes. Several neurodegenerative disorders also may present with parkinsonism and are sometimes referred to as "atypical parkinsonism" or "Parkinson plus" syndromes (illnesses with parkinsonism plus some other features distinguishing them from PD). They include multiple system atrophy, progressive supranuclear palsy, corticobasal degeneration, and dementia with Lewy bodies (DLB). [Samii 2004] [Nuytemans 2010]

Parkinson's disease is a synucleinopathy (due to an abnormal accumulation of alpha-synuclein protein in the brain), distinguishing it from other neurodegenerative diseases, such as Alzheimer's disease where the brain accumulates tau protein. [Galpern 2006] Dementia with Lewy bodies is another synucleinopathy and it has close pathological similarities with PD, especially with the subset of PD cases with dementia known as Parkinson's disease dementia. The relationship between PD and DLB is complex and incompletely understood. [Aarsland 2009] They may represent parts of a continuum with variable distinguishing clinical and pathological features or they may prove to be separate diseases. [Aarsland 2009]

The most recognizable symptoms in Parkinson's disease are movement ("motor") related. [Jankovic 2008] Non-motor symptoms, which include autonomic dysfunction, neuropsychiatric problems (mood, cognition, behavior or thought alterations), and sensory (especially altered sense of smell) and sleep difficulties, are also common. Some of these non-motor symptoms may be present at the time of diagnosis. [Jankovic 2008] Four motor symptoms are considered cardinal in PD: tremor, slowness of movement (bradykinesia), rigidity, and postural instability. [Jankovic 2008] Parkinson's disease can cause neuropsychiatric disturbances, which can range from mild to severe. This includes disorders of cognition, mood, behavior, and thought. [Jankovic 2008] Cognitive disturbances can occur in the early stages of the disease and sometimes prior to diagnosis, and increase in prevalence with duration of the disease. [Jankovic 2008] [Caballol 2007] The most common cognitive deficit in PD is executive dysfunction, which can include problems with planning, cognitive flexibility, abstract thinking, rule acquisition, inhibiting inappropriate actions, initiating appropriate actions, working memory, and control of attention. [Caballol

[Parker 2013] Other cognitive difficulties include slowed cognitive processing speed, impaired recall and impaired perception and estimation of time. [Caballol 2007] [Parker 2013] Nevertheless, improvement appears when recall is aided by cues. [Caballol 2007] Visuospatial difficulties are also part of the disease, seen for example when the individual is asked to perform tests of facial recognition and perception of the orientation of drawn lines. [Caballol 2007] [Parker 2013] Impulse control disorders including pathological gambling, compulsive sexual behavior, binge eating, compulsive shopping and reckless generosity can be caused by medication, particularly orally active dopamine agonists. The dopamine dysregulation syndrome-with wanting of medication leading to overusage-is a rare complication of levodopa use (Giovannoni, et al. 2000). Punding in which complicated repetitive aimless stereotyped behaviors occur for many hours is another disturbance caused by anti-Parkinson medication. In addition to neuropsychiatric and motor symptoms, PD can impair other functions. Sleep problems are a feature of the disease and can be worsened by medications. [Jankovic 2008] Symptoms can manifest as daytime drowsiness (including sudden sleep attacks resembling narcolepsy), disturbances in REM sleep, or insomnia. [Jankovic 2008] REM behavior disorder (RBD), in which patients act out dreams, sometimes injuring themselves or their bed partner, may begin many years before the development of motor or cognitive features of PD or DLB. [Kim 2014]

Alterations in the autonomic nervous system can lead to orthostatic hypotension (low blood pressure upon standing), oily skin and excessive sweating, urinary incontinence, and altered sexual function. [Jankovic 2008] Constipation and impaired stomach emptying (gastric dysmotility) can be severe enough to cause discomfort and even endanger health. [Barichella 2009] Changes in perception may include an impaired sense of smell, disturbed vision, pain, and paresthesia (tingling and numbness). [Jankovic 2008] All of these symptoms can occur years before diagnosis of the disease. [Jankovic 2008]

Genes implicated in the development of PD include SNCA, LRRK2, GBA, PRKN, PINK1, PARK7, VPS35, EIF4G1, DNAJC13 and CHCHD2. [Kalia 2015] SNCA gene mutations are important in PD because the protein that gene encodes, alpha-synuclein, is the main component of the Lewy bodies that accumulate in the brains of people with PD. [Lesage 2009] Mutations in some genes, including SNCA, LRRK2 and GBA, have been found to be risk factors for "sporadic" (non-familial) PD. [Lesage 2009] Mutations in the gene LRRK2 are the most common known cause of familial and sporadic PD, accounting for approximately 5% of individuals with a family history of the disease and 3% of sporadic cases. [Davie 2008] [Lesage 2009] A mutation in GBA presents the greatest genetic risk of developing Parkinsons disease. [Kalia 2015] Several Parkinson-related genes are involved in the function of lysosomes, organelles that digest cellular waste products. It has been suggested that some cases of PD may be caused by lysosome dysfunctions that reduce the ability of cells to break down alpha-synuclein. [Gan—Or 2015]

The main pathological characteristics of PD are cell death in the brain's basal ganglia (affecting up to 70% of the dopamine secreting neurons in the substantia nigra pars *compacta* by the end of life) [Davie and the presence of Lewy bodies (accumulations of the protein alpha-synuclein) in many of the remaining neurons. This loss of neurons is accompanied by the death of astrocytes (star-shaped glial cells) and a significant increase in the number of microglia (another type of glial cell) in the substantia nigra. [Dickson 2007] There are five major pathways in the brain connecting other brain areas with the basal ganglia. These are known as the motor, oculo-motor, associative, limbic and orbitofrontal circuits, with names indicating the main projection area of each circuit. [Obeso 2008] All of them are affected in PD, and their disruption explains many of the symptoms of the disease, since these circuits are involved in a wide variety of functions, including movement, attention and learning. [Obeso 2008] The basal ganglia are believed to normally exert a constant inhibitory influence on a wide range of motor systems, preventing them from becoming active at inappropriate times. When a decision is made to perform a particular action, inhibition is reduced for the required motor system, thereby releasing it for activation. Dopamine acts to facilitate this release of inhibition, so high levels of dopamine function tend to promote motor activity, while low levels of dopamine function, such as occur in PD, demand greater exertions of effort for any given movement. Thus, the net effect of dopamine depletion is to produce hypokinesia, an overall reduction in motor output. [Obeso 2008] Drugs that are used to treat PD, conversely, may produce excessive dopamine activity, allowing motor systems to be activated at inappropriate times and thereby producing dyskinesias. [Obeso 2008]

There is no cure for Parkinson's disease, but medications, surgery, and physical treatment can provide relief and are much more effective than treatments available for other neurological disorders like Alzheimer's disease, motor neuron disease, and Parkinson plus syndromes. The main families of drugs useful for treating motor symptoms are levodopa (always combined with a DOPA decarboxylase inhibitor and sometimes also with a catechol O-methyl transferase (COMT) inhibitor), dopamine agonists and monoamine oxidase (MAO)-B inhibitors.

Three stages may be distinguished: an initial stage in which the individual with PD has already developed some disability requiring pharmacological treatment, a second stage associated with the development of complications related to levodopa usage, and a third stage when symptoms unrelated to dopamine deficiency or levodopa treatment may predominate. [The non-motor and non-dopaminergic features of PD]

Treatment in the first stage aims for an optimal trade-off between symptom control and treatment side-effects. The start of levodopa treatment may be postponed by initially using other medications such as MAO-B inhibitors and dopamine agonists instead, in the hope of delaying the onset of complications due to levodopa use. [Symptomatic pharmacological therapy in Parkinson's disease] However, levodopa is still the most effective treatment for the motor symptoms of PD and should not be delayed in patients whose quality of life is impaired by those symptoms. Levodopa-related dyskinesias correlate more strongly with duration and severity of the disease than duration of levodopa treatment, so delaying this therapy may not really provide much longer dyskinesia-free time than early use. [Zhang 2016]

In the second stage the aim is to reduce PD symptoms while controlling fluctuations in the effect of the medication. Sudden withdrawals from medication or overuse have to be managed. [Symptomatic pharmacological therapy in Parkinson's disease] When oral medications are not enough to control symptoms, surgery, deep brain stimulation, subcutaneous waking day apomorphine infusion and enteral dopa pumps can be of use. [Pedrosa 2013] The third stage presents many challenging problems requiring a variety of treatments for psychiatric symptoms, orthostatic hypotension, bladder dysfunction, etc. [Pedrosa 2013] In the final stages of the disease, palliative care is provided to improve quality of life. [Palliative care in Parkinson's disease]

The motor symptoms of PD are the result of reduced dopamine production in the brain's basal ganglia. Dopamine does not cross the blood-brain barrier, so it cannot be taken as a medicine to boost the brain's depleted levels of dopamine. However, a prodrug of dopamine, levodopa, can pass through to the brain where it is readily converted to dopamine, and administration of levodopa temporarily diminishes the motor symptoms of PD. Levodopa has been the most widely used PD treatment for over 40 years. [Symptomatic pharmacological therapy in Parkinson's disease]

Only 5-10% of levodopa crosses the blood-brain barrier. Much of the remainder is metabolized to dopamine elsewhere in the body, causing a variety of side effects including nausea, vomiting and orthostatic hypotension. [Maria 2017] Carbidopa and benserazide are dopa decarboxylase inhibitors which do not cross the blood-brain barrier and inhibit the conversion of levodopa to dopamine outside the brain, reducing side effects and improving the availability of levodopa for passage into the brain. One of these drugs is usually taken along with levodopa, often combined with levodopa in the same pill. [Oertel 2017]

Levodopa use leads in the long term to the development of complications: involuntary movements called dyskinesias, and fluctuations in the effectiveness of the medication. [Symptomatic pharmacological therapy in Parkinson's disease] When fluctuations occur, a person can cycle through phases with good response to medication and reduced PD symptoms ("on" state), and phases with poor response to medication and significant PD symptoms ("off" state). [Symptomatic pharmacological therapy in Parkinson's disease] Using lower doses of levodopa may reduce the risk and severity of these levodopa-induced complications. [Aquino 2015] A former strategy to reduce levodopa-related dyskinesia and fluctuations was to withdraw levodopa medication for some time. This is now discouraged since it can bring on dangerous side effects such as neuroleptic malignant syndrome. [Symptomatic pharmacological therapy in Parkinson's disease] Most people with PD will eventually need levodopa and will later develop levodopa-induced fluctuations and dyskinesias. [Symptomatic pharmacological therapy in Parkinson's disease] There are controlled-release versions of levodopa. Older controlled-release levodopa preparations have poor and unreliable absorption and bioavailability and have not demonstrated improved control of PD motor symptoms or a reduction in levodopa-related complications when compared to immediate release preparations. A newer extended-release levodopa preparation does seem to be more effective in reducing fluctuations but in many patients, problems persist. Intestinal infusions of levodopa (Duodopa) can result in striking improvements in fluctuations compared to oral levodopa when the fluctuations are due to insufficient uptake caused by gastroparesis. Other oral, longer acting formulations are under study and other modes of delivery (inhaled, transdermal) are being developed. [Oertel 2017]

Tolcapone inhibits the activity of COMT, an enzyme which degrades dopamine. [Symptomatic pharmacological therapy in Parkinson's disease] It has been used to complement levodopa; however, its usefulness is limited by possible complications such as liver damage. [Symptomatic pharmacological therapy in Parkinson's disease] A similarly effective drug, entacapone, has not been shown to cause significant alterations of liver function. [Symptomatic pharmacological therapy in Parkinson's disease] Licensed preparations of entacapone contain entacapone alone or in combination with carbidopa and levodopa. [Symptomatic pharmacological therapy in Parkinson's disease]

Several dopamine agonists that bind to dopamine receptors in the brain have similar effects to levodopa. [Symptomatic pharmacological therapy in Parkinson's disease] These were initially used as a complementary therapy to levodopa for individuals experiencing levodopa complications (on-off fluctuations and dyskinesias); they are now mainly used on their own as first therapy for the motor symptoms of PD with the aim of delaying the initiation of levodopa therapy and so delaying the onset of levodopa's complications. [Symptomatic pharmacological therapy in Parkinson's disease] [Goldenberg 2008] Dopamine agonists include bromocriptine, pergolide, pramipexole, ropinirole, piribedil, cabergoline, apomorphine and lisuride. Though dopamine agonists are less effective than levodopa at controlling PD motor symptoms, they are usually effective enough to manage these symptoms in the first years of treatment. [Samii 2004] Dyskinesias due to dopamine agonists are rare in younger people who have PD but, along with other complications, become more common with older age at onset. [Samii 2004] Thus dopamine agonists are the preferred initial treatment for younger onset PD, and levodopa is preferred for older onset PD. [Samii 2004] Dopamine agonists produce significant, although usually mild, side effects including drowsiness, hallucinations, insomnia, nausea, and constipation. [Symptomatic pharmacological therapy in Parkinson's disease] Sometimes side effects appear even at a minimal clinically effective dose, leading the physician to search for a different drug. [Symptomatic pharmacological therapy in Parkinson's disease] Agonists have been related to impulse control disorders (such as compulsive sexual activity, eating, gambling and shopping) even more strongly than levodopa. [Ceravolo 2009] They tend to be more expensive than levodopa. [Samii 2004]

Apomorphine, a non-orally administered dopamine agonist, may be used to reduce off periods and dyskinesia in late PD. [Symptomatic pharmacological therapy in Parkinson's disease] It is administered by intermittent injections or continuous subcutaneous infusions. [Symptomatic pharmacological therapy in Parkinson's disease] Since secondary effects such as confusion and hallucinations are common, individuals receiving apomorphine treatment are closely monitored. [Symptomatic pharmacological therapy in Parkinson's disease] Two dopamine agonists that are administered through skin patches (lisuride and rotigotine) and are useful for people in the initial stages and possibly to control off states in those in the advanced state. [Tolosa 2007]

MAO-B inhibitors (safinamide, selegiline and rasagiline) increase the amount of dopamine in the basal ganglia by inhibiting the activity of monoamine oxidase B (MAO-B), an enzyme which breaks down dopamine. [Symptomatic pharmacological therapy in Parkinson's disease] Like dopamine agonists, their use may delay the commencement of levodopa therapy in early disease, but MAO-B inhibitors produce more adverse effects and are less effective than levodopa at controlling PD motor symptoms. There are few studies of their effectiveness in the advanced stage, although results suggest that they are useful to reduce fluctuations between on and off periods. [Symptomatic pharmacological therapy in Parkinson's disease] An initial study indicated that selegiline in combination with levodopa increased the risk of death, but this was later disproven. [Symptomatic pharmacological therapy in Parkinson's disease]

Other drugs such as amantadine and anticholinergics may be useful as treatment of motor symptoms. However, the evidence supporting them lacks quality, so they are not first choice treatments. [Symptomatic pharmacological therapy in Parkinson's disease] In addition to motor symptoms, PD is accompanied by a diverse range of symptoms. A number of drugs have been used to treat some of these problems. [Non-motor features of Parkinson's disease] Examples are the use of quetiapine for psychosis, cholinesterase inhibitors for dementia, and modafinil for daytime sleepiness. [Non-motor features of Parkinson's disease] [Hasnain 2009] In 2016 pimavanserin was approved for the management of Parkinson's disease psychosis. [FDA approves first drug to treat hallucinations and delusions associated with Parkinson's disease] Doxepin and rasagline may reduce physical fatigue in PD. [Elbers 2015]

Surgery for PD can be divided in two main groups: lesional and deep brain stimulation (DBS). Target areas for DBS or lesions include the thalamus, the globus pallidus or the subthalamic nucleus. [Surgery for Parkinson's disease] Deep brain stimulation is the most commonly used surgical treatment, involves the implantation of a medical device called a neurostimulator, which sends electrical impulses to specific parts of the brain. DBS is recommended for people who have PD with motor fluctuations and tremor inadequately controlled by medication, or to those who are intolerant to medication, as long as they do not have severe neuropsychiatric problems. [Bronstein 2011] Other, less common, surgical therapies involve intentional formation of lesions to suppress overactivity of specific subcortical areas. For example, pallidotomy involves surgical destruction of the globus pallidus to control dyskinesia. [Surgery for Parkinson's disease] Repetitive transcranial magnetic stimulation temporarily improves levodopa-induced dyskinesias. [Koch 2010]

Motor symptoms, if not treated, advance aggressively in the early stages of the disease and more slowly later. Untreated, individuals are expected to lose independent ambulation after an average of eight years and be bedridden after ten years. [Poewe 2006] Medication has improved the prognosis of motor symptoms, while at the same time it is a new source of disability, because of the undesired effects of levodopa after years of use. [Poewe 2006] In people taking levodopa, the progression time of symptoms to a stage of high dependency from caregivers may be over 15 years. [Poewe 2006] However, it is hard to predict what course the disease will take for a given individual. [Poewe 2006] Age is the best predictor of disease progression. [Obeso 2010] The rate of motor decline is greater in those with less impairment at the time of diagnosis, while cognitive impairment is more frequent in those who are over 70 years of age at symptom onset. [Obeso 2010]

Since current therapies improve motor symptoms, disability at present is mainly related to non-motor features of the disease. [Obeso 2010] Nevertheless, the relationship between disease progression and disability is not linear. Disability is initially related to motor symptoms. [Poewe 2006] As the disease advances, disability is more related to motor symptoms that do not respond adequately to medication, such as swallowing/speech difficulties, and gait/balance problems; and also to levodopa-induced complications, which appear in up to 50% of individuals after 5 years of levodopa usage. [Poewe 2006] Finally, after ten years most people with the disease have autonomic disturbances, sleep problems, mood alterations and cognitive decline. [Poewe 2006] All of these symptoms, especially cognitive decline, greatly increase disability. [Obeso 2010] [Poewe 2006]

Investigations on neuroprotection are at the forefront of PD research. Several molecules have been proposed as potential treatments. [Obeso 2010] However, none of them have been conclusively demonstrated to reduce degeneration. [Obeso 2010] Agents currently under investigation include anti-apoptotics (omigapil, CEP-1347), antiglutamatergics, monoamine oxidase inhibitors (selegiline, rasagiline), promitochondrials (coenzyme Q10, creatine), calcium channel blockers (isradipine) and growth factors (GDNF). [Obeso 2010] Preclinical research also targets alpha-synuclein. [Dimond 2010] A vaccine that primes the human immune system to destroy alpha-synuclein, PD01A (developed by Austrian company, Affiris), has entered clinical trials in humans.

An antiparkinson medication is a type of drug which is intended to treat and relieve the symptoms of Parkinson's disease. Most of these agents act by either increasing dopamine activity or reducing acetylcholine activity in the central nervous system. en.wikipedia.org/wiki/Antiparkinson_medication. The goal of the most common Antiparkinson drugs is to either replace the dopamine levels in the brain, or mimic the actions of dopamine. The main categories of Antiparkinson drugs are anticholinergic drugs and dopaminergic drugs. Anticholinergic drugs block the action of acetylcholine, compensating for the low levels of dopamine. As stated before, dopaminergic drugs aim to replace dopamine or inhibit the degradation of dopamine in the brain. [Parkinson's UK. "Anticholinergics"] Once a preliminary diagnosis is made, carbidopa-levodopa can be given as an antiparkinson medication. If this medication shows improvement, doctors will likely confirm their diagnosis. This standard treatment for Parkinson's disease is referred to as L-DOPA, the precursor of dopamine. L-DOPA causes the person's remaining dopaminergic neurons to produce and secrete more dopamine, counteracting the effects of Parkinson's disease. However, eventually the nigrostriatal dopaminergic neurons in the brain drop to a low enough count where the symptoms of Parkinson's disease become worse. This is due to the short half-life of L-DOPA in the body; typically 1.5-2 hours. [NIH DailyMed. "Sinemet"] L-DOPA also activates DA neurons in the mesolimbic/mesocortical system and produces side effects such as hallucinations and delusions. [Psychology of Behavior (11 ed.)]

A medicine that can be given with L-DOPA, or separately, is deprenyl. Deprenyl inhibits the activity of the enzyme MAO-B, which then will slow the progression of Parkinson's disease. Deprenyl, however, does not completely stop the degeneration of dopaminergic neurons. [Psychology of Behavior (11 ed.)] Deprenyl delays the time before other antiparkinson drugs, like L-DOPA, need to be used. [Tetrud 1989]

Tyrosine hydroxylase catalyzes the formation of L-DOPA, the rate-limiting step in the biosynthesis of dopamine. [Haavik 1998] In other words, it is a precursor to neurotransmitters and increases plasma neurotransmitter levels of dopamine and norepinephrine. [Rasmussen 1983] This medication should not be used when taking L-DOPA, as L-DOPA interferes with the absorption of Tyrosine. [University of Maryland Medical Center. "Tyrosine"]

Apomorphine has also been used to treat Parkinson's disease. It is referred to as a dopamine receptor agonist. However, it does cause severe side effects when used on its own. [Parkinson's Disease Treatment]

Anticholinergic drugs include benzhexol and orphenadrine. These drugs reduce the effect of acetylcholine in the brain by antagonizing cholinergic receptors. This helps restore the acetylcholine/dopamine balance within the brain. Again with these treatments, about 70% of patients taking anticholinergics develop serious side effects, including hallucinations, dyskinetic movements, vision effects, difficulty swallowing, dry mouth and urine retention. [Parkinson's Disease Treatment]

N-phenyl-7-(hydroxylimino) cyclopropa [b] chromen-1a-carboxamide (PHCCC) is now being studied as a selective allosteric potentiator of mGluR4. Metabotropic glutamate receptor 4 (mGluR4) is a potential drug target for Parkinson's disease. PHCCC selectively potentiated agonist-induced mGluR4 activity in cells expressing this receptor and did not itself act as an agonist. PHCCC also potentiated the effect of L-(+)-2-amino-4-phosphonobutyric acid in inhibiting transmission at the striatopallidal synapse. This is significant due to the striatopallidal synapse being proposed as a target for Parkinson's disease treatment. This might restore balance in the basal ganglia motor circuit. [Marino 2003]

COMT inhibitors block one of two ways levodopa can be inactivated before it reaches the central nervous system (CNS) and is activated to dopamine; peripheral inhibitors of DOPA decarboxylase (AADC) block the second way. (Dopamine in the periphery only causes side effects, no antiparkinson effect.) MAO-B inhibitors slow down degradation of dopamine in the CNS. [Mutschler 2001]

Pharmacological treatment of Parkinson's disease includes dopaminergic precursors. (Preferred over other medications to prevent undesirable sympathomimetic side effects: Tyrosine; L-DOPA (levodopa)); COMT inhibitors (Prevent the peripheral metabolism of levodopa by COMT and hence increase its brain levels: Entacapone; Opicapone; Tolcapone (also acts in the central nervous system [Dinnendahl 1998])); Peripheral aromatic L-amino acid decarboxylase inhibitors ((DOPA decarboxylase inhibitors). Prevent the peripheral metabolism of levodopa by decarboxylases and hence increase its brain levels: Benserazide; Carbidopa); Selective monoamine oxidase B inhibitors (Prevent the metabolism of dopamine by MAOB and hence increase its brain levels: Selegiline; Rasagiline); and Dopamine receptor agonists (Directly increase the activity of the dopamine system: Apomorphine; Bromocriptine; Pramipexole; Ropinirole; Rotigotine; Anticholinergics; Antimuscarinics; Benzatropine; Diphenhydramine; Dimenhydrinate; Scopolamine).

Segawa Syndrome (SS) also known as Dopamine-responsive dystonia (DRD), Segawa's disease, Segawa's dystonia and hereditary progressive dystonia with diurnal fluctuation, is a rare genetic movement disorder which usually manifests itself during early childhood at around ages 5-8 years (variable start age). en.wikipedia.org/wiki/Segawa_Syndrome. Characteristic symptoms are increased muscle tone (dystonia, such as clubfoot) and Parkinsonian features, typically absent in the morning or after rest but worsening during the day and with exertion. Children with SS are often misdiagnosed as having cerebral palsy. The disorder responds well to treatment with levodopa. SS is typically characterized by signs of parkinsonism that may be relatively subtle. Such signs may include slowness of movement (bradykinesia), tremors, stiffness and resistance to movement (rigidity), balance difficulties, and postural instability. Approximately 25 percent also have abnormally exaggerated reflex responses (hyperreflexia), particularly in the legs. These symptoms can result in a presentation that is similar in appearance to that of Parkinson's Disease. Many patients experience improvement with sleep, are relatively free of symptoms in the morning, and develop increasingly severe symptoms as the day progresses (i.e., diurnal fluctuation). Accordingly, this disorder has sometimes been referred to as "progressive hereditary dystonia with diurnal fluctuations." Yet some SS patients do not experience such diurnal fluctuations, causing many researchers to prefer other disease terms. In those with SS, symptoms typically dramatically improve with low-dose administration of levodopa (L-DOPA). L-DOPA exists as a biochemically significant metabolite of the amino acid phenylalanine, as well as a biological precursor of the catecholamine dopamine, a neurotransmitter. (Neurotransmitters are naturally produced molecules that may be sequestered following the propagation of an action potential down a nerve towards the axon terminal, which in turn may cross the synaptic junction between neurons, enabling neurons to communicate in a variety of ways.) Low-dose L-DOPA usually results in near-complete or total reversal of all associated symptoms for these patients. In addition, the effectiveness of such therapy is typically long term, without the complications that often occur for those with Parkinson's disease who undergo L-DOPA treatment. Thus, most experts indicate that this disorder is most appropriately known as dopa-responsive dystonia (SS). Autosomal dominant and autosomal recessive forms of the disease have been reported. Mutations in several genes have been shown to cause dopamine-responsive dystonia. The precursor of the neurotransmitter dopamine, L-DOPA, is synthesized from tyrosine by the enzyme tyrosine hydroxylase and utilizes tetrahydrobiopterin (BH4) as a cofactor. A mutation in the gene GCH1, which encodes the enzyme GTP cyclohydrolase I, disrupts the production of BH4, decreasing dopamine levels (hypodopaminergia). This results in autosomal-dominant SS. Mutations in the genes for tyrosine hydroxylase and sepiapterin reductase result in autosomal-recessive forms of the disease. When the latter enzyme is affected, the condition tends to be more severe. The activity of dopaminergic neurons in the nigrostriatal pathway normally peaks during the morning and also decreases with age until after age 20, which explains why the symptoms worsen during the course of the day and with increasing age until the third decade of life.

Encephalitis lethargica is an atypical form of encephalitis. Also known as "sleeping sickness" or "sleepy sickness" (distinct from tsetse fly-transmitted sleeping sickness). The disease attacks the brain, leaving some victims in a statue-like condition, speechless and motionless. No recurrence of the epidemic has since been reported, though isolated cases continue to occur. ["Lodosyn", Drugs 2012] [Bandolier Patients may experience abnormal eye movements ("oculogyric crises"), [Broadley 2010] parkinsonism, upper body weakness, muscular pains, tremors, neck rigidity, and behavioral changes including psychosis. Klazomania (a vocal tic) is sometimes present. The causes of encephalitis lethargica (EL) are uncertain. Some studies have explored its origins in an autoimmune response, and, separately or in relation to an immune response, links to pathologies of infectious disease-viral and bacterial. An enterovirus was discovered in EL cases from the epidemic. Diplococcus has also been implicated as a cause of EL. Modern treatment approaches to encephalitis lethargica include immunomodulating therapies, and treatments to remediate specific symptoms. The disease becomes progressive, with evidence of brain damage similar to Parkinson's disease. Treatment is then symptomatic Levodopa (L-DOPA) and other anti-parkinson drugs often produce dramatic responses; however, most people given L-DOPA experience ameliorations of the disease that are short lived. [Kohnstamm 1934] [Foster 2004].

L-DOPA also known as levodopa or L-3,4-dihydroxyphenylalanine is an amino acid that is made and used as part of the normal biology of humans, as well as some animals and plants. en.wikipedia.org/wiki/L-DOPA. Humans, as well as a portion of the other animals that utilize L-DOPA in their biology, make it via biosynthesis from the amino acid L-tyrosine by action of tyrosine hydroxylase. L-DOPA is the precursor to the neurotransmitters dopamine, norepinephrine, and epinephrine, which are collectively known as catecholamines. Furthermore, L-DOPA itself mediates neurotrophic factor release by the brain and CNS. [Lopez 2008] [Hiroshima 2014] L-DOPA can be manufactured and in its pure form is sold as a psychoactive drug with the INN levodopa; trade names include Sinemet, Pharmacopa, Atamet, Stalevo, Madopar, and Prolopa. As a drug, it is used in the clinical treatment of Parkinson's disease and dopamine-responsive dystonia. L-DOPA crosses the blood-brain barrier, whereas dopamine itself cannot. Dopamine is formed by the decarboxylation of L-DOPA by aromatic L-amino acid decarboxylase (AADC). L-DOPA can be directly metabolized by catechol-O-methyl transferase to 3-O-methyldopa, and then further to vanillactic acid. This metabolic pathway is nonexistent in the healthy body, but becomes important after peripheral L-DOPA administration in patients with Parkinson's disease or in the rare cases of patients with AADC enzyme deficiency. [Hyland 1992] Thus, L-DOPA is used to increase dopamine concentrations in the treatment of Parkinson's disease and dopamine-responsive dystonia. Once L-DOPA has entered the central nervous system, it is converted into dopamine by the enzyme aromatic L-amino acid decarboxylase, also known as DOPA decarboxylase. Pyridoxal phosphate (vitamin B6) is a required cofactor in this reaction, and may occasionally be administered along with L-DOPA, usually in the form of pyridoxine.

Besides the central nervous system, L-DOPA is also converted into dopamine from within the peripheral nervous system. Excessive peripheral dopamine signaling causes many of the adverse side effects seen with sole L-DOPA administration. To bypass these effects, it is standard clinical practice to coadminister (with L-DOPA) a peripheral DOPA decarboxylase inhibitor (DDCI) such as carbidopa (medicines containing carbidopa, either alone or in combination with L-DOPA, are branded as Lodosyn, Sinemet (Merck Sharp & Dohme Limited), Pharmacopa (Jazz Pharmaceuticals), Atamet (UCB), and Stalevo (Orion Corporation) or with a benserazide (combination medicines are branded Madopar or Prolopa), to prevent the peripheral synthesis of dopamine from L-DOPA. Coadministration of pyridoxine without a DDCI accelerates the peripheral decarboxylation of L-DOPA to such an extent that it negates the effects of L-DOPA administration, a phenomenon that historically caused great confusion. In addition, L-DOPA, co-administered with a peripheral DDCI, has been investigated as a potential treatment for restless leg syndrome. However, studies have demonstrated "no clear picture of reduced symptoms". ["L-dopa for RLS". Bandolier]

The two types of response seen with administration of L-DOPA a short-duration response related to the half-life of the drug, and a longer-duration response that depends on the accumulation of effects over at least two weeks, during which AFosB accumulates in nigrostriatal neurons. In the treatment of Parkinson's disease, this response is evident only in early therapy, as the inability of the brain to store dopamine is not yet a concern.

L-Phenylalanine, L-tyrosine, and L-DOPA are all precursors to the biological pigment melanin. The enzyme tyrosinase catalyzes the oxidation of L-DOPA to the reactive intermediate dopaquinone, which reacts further, eventually leading to melanin oligomers. In addition, tyrosinase can convert tyrosine directly to L-DOPA in the presence of a reducing agent such as ascorbic acid. (Oxidation of tyrosine residues in proteins by tyrosinase. Formation of protein-bonded 3,4-dihydroxyphenylalanine and 5-S-cysteinyl-3,4-dihydroxyphenylalanine).

Serious effects of chronic L-DOPA administration in the treatment of Parkinson's disease, which include: End-of-dose deterioration of function; On/off oscillations; Freezing during movement; Dose failure (drug resistance); Dyskinesia at peak dose (levodopa-induced dyskinesia); and Possible dopamine dysregulation: The long-term use of L-DOPA in Parkinson's disease has been linked to the so-called dopamine dysregulation syndrome. [Merims 2008] Clinicians try to avoid these side effects by limiting L-DOPA doses as much as possible until absolutely necessary.

A retrospective analysis comparing the incidence of age-related macular degeneration (AMD) between patients taking versus not taking L-DOPA found that the drug delayed onset of AMD by around 8 years, for both dry and wet AMD. [Brilliant 2015]

Vilazodone (United States trade name Viibryd) is a (EMD 68843; 5-{4-[4-(5-cyano-3-indolyl)-butyl]-1-piperazinyl}-benzofuran-2-carboxamide hydrochloride) is a combined serotonin-specific reuptake inhibitor (SSRI) and 5-HT1A receptor partial agonist, and serotonergic antidepressant developed by Merck KGaA [Clinical Data's Vilazodone Patient Enrollment Over One Third Complete] and licensed by Clinical Data, a biotech company purchased by Forest Laboratories in 2011. [Xconomy: Blend Therapeutics Taps Former Clinical Data Chief Fromkin As New CEO] en.wikipedia.org/wiki/Vilazodone.

Vilazodone was approved in 2011 by the FDA for use in the United States to treat major depressive disorder. [FDA approves Clinical Data Inc's antidepressant] [FDA approves Clinical Data Inc's antidepressant] [Clinical Data, Inc.-Clinical Data, Inc. Submits New Drug Application for Vilazodone for the Treatment of Major Depressive Disorder] Its mechanism of action is believed to be a combination of SSRI-like activity (SERT inhibition) and 5HT1AR partial agonism, like the structurally related anxiolytic buspirone. As such it can be compared to vortioxetine, and these two drugs are sometimes used as the prototypical members of the class of serotonin modulator/stimulator antidepressants. Vilazodone acts as a serotonin reuptake inhibitor (IC50=2.1 nM; Ki=0.1 nM) and 5-HT1A receptor partial agonist (IC50=0.2 nM; IA=~ 60-70%). [Wang 2013] [Hughes 2005] It has negligible affinity for other serotonin receptors such as 5-HT1D, 5-HT2A, and 5-HT2C. [Hughes 2005] [Page 2002] It also exhibits clinically unimportant inhibitory activity at the norepinephrine and dopamine transporters (Ki=56 nM for NET and 37 nM for DAT). [VIIBRYD (vilazodone hydrochloride) tablet VIIBRYD (vilazodone hydrochloride) kit (Forest Laboratories, Inc.)] Vilazodone is best absorbed with food and has a bioavailability of 72% under fed conditions. The Cmax increased between 147%-160% and the AUC increased between 64%-85% of vilazodone when it was administered with either a fatty or light meal. [Cruz 2012]

Vilazodone is an indolalkylamine that acts as both a potent SSRI (IC50=0.2 nM, Ki=0.1 nM) and a 5-HT1A receptor partial agonist (IC50=0.5 nM). While vilazodone exhibits high affinity toward the 5-HT1A reuptake site, it does not bind to the norepinephrine (Ki=56 nM) or dopamine (Ki=37 nM) reuptake sites as avidly. [Glazer WM. A new antidepressant. Behav Healthc 2011; 31 (6): 38-40] The 5-HT1A partial agonist activity of vilazodone may eliminate the efficacy lag phase observed with SSRIs, thereby effectively reducing patient response time. [Glazer 2011]

Vilazodone is 60 times more selective for the 5-HT1A receptor than buspirone, the only 5-HT1A receptor partial agonist that is approved for clinical use as an antidepressant. [Page 1999] Vilazodone is a combined serotonin reuptake inhibitor (SRI) and 5-HT1A receptor partial agonist (SPARI). SRI mechanisms yield an increase in synaptic 5-HT through serotonin transporter reuptake inhibition. This produces a desensitization and/or downregulation of presynaptic 5-HT1A autoreceptors. As these autoreceptors are now over stimulated, the 5-HT neuron interprets this initially as toxic activity. As these autoreceptors become less effective due to over stimulation and desensitization, they offer less autoreceptor inhibition to the 5-HT neuron and excess 5-HT is next released at the neuron terminals as a result. By directly agonizing the 5-HT1A receptors in the central nervous system, vilazodone likely allows a faster or greater volume of 5-HT1A receptor desensitization/downregulation up front. This essentially lowers the 5-HT neurons' ability to regulate 5-HT output, thus increasing 5-HT neuronal firing and activity. This 5-HT facilitation approach may then directly stimulate postsynaptic 5-HT1A heteroreceptors downstream which may actually promote even more neuronal firing and activity of 5-HT or other monoamine neurons. [Singh M, Schwartz TL. Clinical utility of vilazodone for the treatment of adults with major depressive disorder and theoretical implications for future clinical use. Neuropsychiatr Dis Treat. 2012; 8:123] Accordingly, vilazodone has been shown to reduce the sensitivity of 5-HT1A autoreceptors in the dorsal raphe nuclei more rapidly than the SSRIs fluoxetine and paroxetine. [Ashby 2013] Unlike vilazodone, administration of 5-HT1A receptor agonists or partial agonists such as buspirone, 8-hydroxy-2-(dipropylamino)tetralin hydrobromide (8—OH-DPAT), and MKC-242 caused an increase in extracellular dopamine and norepinephrine in the rat brain. [Done 1994] [Suzuki 1995] [Chen 1995] [Gobert 1998] Molecular experiments using ligand-facilitated binding of [35S] GTPγS to Gi proteins together with the 5-HT1A receptor expressed in SF9 cells showed that compared to vehicle, vilazodone (partial agonist) increased binding by fourfold, whereas the full agonist 8—OH-DPAT increased binding by eightfold. [Hughes et al. 2005]

Vilazodone has high affinity for SERT and achieved 100% occupancy at 10 mg/kg and 50% occupancy at 1-3 mg/kg in rat cortex and hippocampus ex vivo. [Hughes et al. 2005] This differs from in vivo occupancy, which is difficult to assume, because intrinsic activity depends on the receptor reserve available and concentration of endogenous agonist (i.e., 5-HT); notably, vilazodone (1 and 10 mg/kg) caused no change in extracellular levels of norepinephrine or dopamine. [Hughes et al. 2005] Moreover, the SSRI activity of vilazodone is 30 times more potent than fluoxetine, which likely contributes to a faster proposed onset of action. [Kehne JH, Bartoszyk GD, Greiner HE, editors. In vitro characterization of vilazodone as a dual-acting serotonin reuptake receptor and 5-HT1A receptor partial agonist. Poster presented at: 65th Annual Meeting of the Society of Biological Psychiatry Meeting; 2010] [Page et al. (2002)] compared brain 5-HT levels in response to systemic injection with fluoxetine or vilazodone in rats. In that study, 5-HT levels measured 3 h after injection revealed that acute administration of vilazodone produced larger maximal increases of extracellular 5-HT than the SSRI fluoxetine in both the ventral hippocampus (558 vs. 274%) and the frontal cortex (527 vs. 165%). [Page 2002] Despite these encouraging results, there is currently no clinical data that compares the onset of action of vilazodone to other antidepressants. See, [Zeyad 2016].

Vortioxetine, sold under the trade names Trintellix and Brintellix, is an antidepressant medication that is used to treat depression. en.wikipedia.org/wiki/Vortioxetine. It increases serotonin concentrations in the brain by inhibiting its reuptake in the synapse, and by modulating (activating certain receptors while blocking, or antagonizing, others) certain serotonin receptors. This puts it in the class of atypical antidepressants known as serotonin modulators and stimulators. Vortioxetine is used as a treatment for major depressive disorder. [Connolly 2016] [Köhler 2016] [Kelliny 2015] Vortioxetine is both a serotonin transport inhibitor (Ki=1.6 nM, IC50=5.4 nM) and a 5-HT1A agonist Ki=15 nM, IC50=200 nM, IA=96%).

Vortioxetine, is a 5-$HT_3$, 5-$HT_7$ and 5-$HT_{1D}$ receptor antagonist, 5-HT 1B receptor partial agonist, 5-$HT_{1A}$ receptor agonist and serotonin (5-HT) transporter (SERT) inhibitor. Vortioxetine increases serotonergic, noradrenergic, dopaminergic, cholinergic, histaminergic and glutamatergic neurotransmission in brain structures associated with MDD. These multiple effects likely derive from its interaction with 5-HT-receptor-mediated negative feedback mechanisms controlling neuronal activity. In particular, 5-$HT_3$ receptors may play a prominent role, since their blockade i) increases pyramidal neuron activity by removing 5-$HT_3$ receptor-mediated excitation of GABA interneurons, and ii) augments SSRI effects on extracellular 5-HT. However, modulation of the other 5-HT receptor subtypes also likely contributes to vortioxetine's pharmacological effects. Preclinical animal models reveal differences from SSRIs and SNRIs, including antidepressant-like activity, increased synaptic plasticity and improved cognitive function. The clinically effective dose range (5-20 mg/day) for antidepressive activity spans ~50 to 80% SERT occupancy. SERT and 5-$HT_3$ receptors are primarily occupied at 5 mg, while at 20 mg, all targets are likely occupied at functionally relevant levels. The side-effect profile is similar to that of SSRIs. [Sanchez 2015]

Hypidone hydrochloride, YL-0919, is an investigational combined selective serotonin reuptake inhibitor and 5-HT1A receptor agonist. YL-0919 displays partial 5-HT1A receptor agonist properties, producing a greater impact on extracellular 5-HT levels than a conventional SSRI (fluoxetine), as well as significant antidepressant and anxiolytic effects. YL-0919 treatment rapidly influenced the synaptic plasticity (enhancing LTP) of rats, at doses close to those producing antidepressant-like effects, YL-0919 did not result in a marked inhibition of sexual function.

[Wang 2015] describe combinatorial virtual screening methods to assess drug candidates for SERT (serotonin reuptake blockage) and 5-HT1A receptor partial agonism (SPARI). They report that while vilazodone is unique as a clinically-approved drug, other candidates show promise with corresponding activities. 168 candidates were identified, of which 130 out of 168 were previously unknown dual active compounds. 91 out of 130 ranked higher than vilazodone by Vina (its predicted affinities are −10.5 and −10.3 kcal/mol for 5-HT1A and SEAR respectively). These 91 molecules covered 15 scaffolds, 24 of which are structurally dissimilar to known inhibitors. FIG. 5 illustrates 9 scaffolds, 6 of which have already shown antidepressant therapeutic effects. LY367265 of Scaffold N1 (indole derivatives) was a potential antidepressant drug targeted 5HT2A and SERT, and the affinity Ki is 490 nM in rat cerebral cortex [Bishop Scaffold N2 (2-(benzo[d]isoxazol-3-yl)-7-(phenoxymethyl) octahydropyrido[1,2-a]pyrazine) was used for psychosis therapy as agonists or antagonists of serotonin 1A or 1D receptors, and was pointed out that they may be potentially useful for treating a wide variety of conditions co-administered with 5-HT reuptake inhibitors [Michael 1999]. Scaffold N3 (tetrahydrobenzazepine derivatives) was an antipsychotic dopamine (D3) Antagonist [Hadley 2000]. Scaffold N4 (substituted heteroaromatic octahydroindolizinyl indoles) was reported to have valuable pharmacological properties, especially to treat migraine and associated disorders as 5-HT1F Agonist [Filla 1999]. Scaffold N5 (pyrimidin-4-one derivatives) was reported to treat disorders such as depression, impulsive behavior, anxiety, schizophrenia, Parkinson's disease, cognition disorder, libido disorder, sexual dysfunction, appetite disorder and sleep disorder as 2/5-HT2C double antagonists [La Vielle 2002]. Scaffold N6 (fused indole derivatives) are MCH receptor modulators used in obesity, anxiety and mood disorders therapy [Chen 2002]. In addition, docking results reveal that the 9 identified novel compounds bind to each targets have similar mode with vilazodone.

Cannabidiol (CBD) is a naturally occurring cannabinoid constituent of *cannabis*. It is one of at least 113 cannabinoids identified in hemp plants, accounting for up to 40% of the plant's extract. The United States, Food and Drug Administration approval of cannabidiol as a prescription drug called Epidiolex for medical uses has been limited to two rare forms of childhood epilepsy. CBD has been found to interact with a variety of different biological targets, including cannabinoid receptors and other neurotransmitter receptors. The mechanism of action of CBD in terms of its psychoactive and therapeutic effects is not fully clear.

Tetrahydrocannabinol (THC) and cannabidiol (CBD) are two types of cannabinoids found naturally in the resin of the marijuana plant, both of which interact with the cannabinoid receptors that are found throughout the body. Although THC and CBD have been the most studied cannabinoids, there are many others identified to date including cannabinol (CBN), cannabigerol (CBG), Cannabidivarin (CBDV), and Tetrahydrocannabivarin (THCV) that can be found within the medical *cannabis*. While both CBD and THC are used for medicinal purposes, they have different receptor activity, function, and physiological effects. If not provided in their activated form (such as through synthetic forms of THC like Dronabinol or Nabilone), THC and CBD are obtained through conversion from their precursors, tetrahydrocannabinolic acid-A (THCA-A) and cannabidiolic acid (CBDA), through decarboxylation reactions. This can be achieved through heating, smoking, vaporization, or baking of dried unfertilized female *cannabis* flowers.

The primary psychoactive component of *Cannabis*, delta 9-tetrahydrocannabinol (A9-THC), demonstrates its effects through weak partial agonist activity at Cannabinoid-1 (CB1R) and Cannabinoid-2 (CB2R) receptors. This activity results in the well-known effects of smoking *cannabis* such as increased appetite, reduced pain, and changes in emotional and cognitive processes. In contrast to THC's weak agonist activity, CBD has been shown to act as a negative allosteric modulator of the cannabinoid CB1 receptor, the most abundant G-Protein Coupled Receptor (GPCR) in the body. Allosteric regulation is achieved through the modulation of receptor activity on a functionally distinct site from the agonist or antagonist binding site which is clinically significant as direct agonists (such as THC) are limited by their psychomimetic effects such as changes to mood, memory, and anxiety.

Cannabidiol has very low affinity for the cannabinoid CB1 and CB2 receptors but is said to act as an indirect antagonist of these receptors. Cannabidiol has been found to act as an antagonist of GPR55, a G protein-coupled receptor and putative cannabinoid receptor that is expressed in the caudate nucleus and putamen in the brain. It has also been found to act as an inverse agonist of GPR3, GPR6, and GPR12. Although currently classified as orphan receptors, these receptors are most closely related phylogenetically to the cannabinoid receptors. In addition to orphan receptors, CBD has been shown to act as a serotonin 5-HT1A receptor partial agonist, and this action may be involved in its antidepressant, anxiolytic, and neuroprotective effects. It is an allosteric modulator of the p-and o-opioid receptors as well. The pharmacological effects of CBD have additionally been attributed to PPARy agonism and intracellular calcium release. CBD may exert some of its pharmacological action through its inhibition of fatty acid amide hydrolase (FAAH), which may in turn increase the levels of endocannabinoids, such as anandamide, produced by the body. It has also been speculated that some of the metabolites of CBD have pharmacological effects that contribute to the biological activity of CBD. CBD does not appear to have any psychotropic ("high") effects such as those caused by A9-THC in marijuana, but may have anti-anxiety and anti-psychotic effects.

In addition to the well-known activity on CB1 and CB2 receptors, there is further evidence that CBD also activates 5-HT1A/2A/3A serotonergic and TRPV1-2 vanilloid receptors, antagonizes alpha-1 adrenergic and u-opioid receptors, inhibits synaptosomal uptake of noradrenaline, dopamine, serotonin and gamma-aminobutyric acid (GABA), and cellular uptake of anandamide, acts on mitochondria Ca2+ stores, blocks low-voltage-activated (T-type) Ca2+channels, stimulates activity of the inhibitory glycine-receptor, and inhibits activity of fatty amide hydrolase (FAAH).

Nabiximols (brand name Sativex) is an aerosolized mist for oral administration containing a near 1:1 ratio of CBD and THC. The drug was approved by Canadian authorities in 2005 to alleviate pain associated with multiple sclerosis. Medical reviews published in 2017 and 2018 incorporating numerous clinical trials concluded that cannabidiol is an effective treatment for certain types of childhood epilepsy. An orally administered cannabidiol solution (brand name Epidiolex) was approved by the US Food and Drug Administration in June 2018 as a treatment for two rare forms of childhood epilepsy, Lennox-Gastaut syndrome and Dravet syndrome.

SUMMARY OF THE INVENTION

Levodopa-induced dyskinesias (LID) are a prevalent side effect of chronic treatment with levodopa (L-DOPA) for the motor symptoms of Parkinson's disease (PD). It has long been hypothesized that serotonergic neurons of the dorsal raphe nucleus (DRN) are capable of L-DOPA uptake and dysregulated release of dopamine (DA), and that this "false neurotransmission" phenomenon is a main contributor to LID development. Indeed, many preclinical studies have demonstrated LID management with serotonin receptor agonist treatment, but unfortunately, promising preclinical data has not been translated in large-scale clinical trials. Importantly, while there is an abundance of convincing clinical and preclinical evidence supporting a role of maladaptive serotonergic neurotransmission in LID expression, there is no direct evidence that dysregulated DA release from serotonergic neurons impacts LID formation. The DA autoreceptor D2Rs (or GFP) was ectopically expressed in the DRN of 6-hydroxydopamine (6—OHDA) lesioned rats. No negative impact on the therapeutic efficacy of L-DOPA was seen with rAAV-D2Rs therapy. However, D2Rs treated animals, when subjected to a LID-inducing dose regimen of L-DOPA, remained completely resistant to LID, even at high doses. Moreover, the same subjects remained resistant to LID formation when treated with direct DA receptor agonists, suggesting D2Rs activity in the DRN blocked dyskinesogenic L-DOPA priming of striatal neurons. In vivo microdialysis confirmed that DA efflux in the striatum was reduced with rAAV-D2Rs treatment, providing explicit evidence that abnormal DA release from DRN neurons can affect LID. This is the first direct evidence of dopaminergic neurotransmission in DRN neurons and its modulation with rAAV-D2Rs gene therapy confirms the serotonin hypothesis in LID, demonstrating that regulation of serotonergic neurons achieved with a gene therapy approach offers a novel and potent antidyskinetic therapy.

The present invention provides a therapy to attenuate or treat L-DOPA-induced dyskinesia. In general, a serotonin-specific transporter (SERT) inhibitory agent and 5-HT 1A receptor agonist or partial agonist, preferably the same composition, are administered to a patient undergoing L-DOPA therapy, and optionally the L-DOPA, the SERT-active and 5-HT 1A active agent, and optionally other agents useful in treating dyskinesias or their underlying causes, or remedying the side effects of various agents administered to these patients, or treating comorbidities of these patients, may also be coadministered or provided within the same dosage form. The dosage form is preferably, but need not necessarily be, an oral dosage form. Various agents which can be combined or coadministered are described herein or incorporated herein by reference.

Vilazodone, a multi-target anti-depressant which acts at both the 5-HT1A receptor and the serotonin transporter, potently suppressed L-DOPA induced dyskinesia (LID) and maintained these effects for several weeks without altering L-DOPA's positive anti-Parkinsonian effects. On that basis, it is believed that not only Vilazodone, but the class of drugs with corresponding effects, will also provide benefit for LID, of any etiology. For example, Vilazodone might also be applied to tardive dyskinesia for schizophrenic patients taking typical anti-psychotics. Further Vilazodone, and other drugs with corresponding modes of action, also find potential for use in non-motor neural deficits associated with L-DOPA administration.

There is currently only one medication available for L-DOPA-induced dyskinesia, Amantadine (Endo Pharmaceuticals). It does not work through the same mechanism as Vilazodone and its effectiveness is modest and transient in many patients. Amantadine side effects also increase non-compliance. Amantadine, if tolerated, can be used in conjunction with Vilazodone to ameliorate the dyskinesia attributed to chronic L-DOPA administration.

In preclinical in vivo investigations, Vilazodone is shown to be more effective than Amantadine in a validated rodent model at reducing the development and expression of L-DOPA-induced dyskinesia. Vilazodone maintained its effectiveness over 3 weeks indicating a potent and stable response. Further, side effect profiles of Vilazodone are less than what is reported in humans taking these drugs such as Amantadine.

Rodent Parkinson model experiments testing Vilazodone-based prevention and intervention approaches for LID. [Taylor 2016] disclosed an experimental design and results for the prevention, but not intervention, of LID. The poster did not disclose that, with chronic administration, Vilazodone treatment significantly enhanced the pro-motor effects of L-DOPA.

Serotonin-specific reuptake inhibitors (SSRIs) and 5-hydroxy tryptamine receptor 1A (5-HT1AR) partial agonists have been used separately for LID, with only limited results and specific issues associated with the individual use of either approach. Vilazodone mechanisms of action combines both effects and, the combination of the two mechanisms of action for LID (by using two separate substances or using dual-action substance other than Vilazodone) has not been previously tested. The limited benefits provided by drugs with either mode action would not have lead to an expectation that the SSRI and 5-HT1AR partial agonists to be successfully combined into a therapy. Parkinson's disease (PD) is characterized by the progressive loss of dopamine (DA) neurons in the substantia nigra [Jankovic 2008]. Prolonged use of the DA replacement therapy L-DOPA, though efficacious, frequently results in debilitating abnormal involuntary movements (AIMs), known as L-DOPA induced dyskinesia (LID) [Conti 2014]. C-fos, a marker for neural activation, is a precursor to the transcription factor, Fos, which can modify expression of striatal opioid genes like preprodynorphin (PPD) and preproenkephaline (PPE) [Cenci 1998]. C-fos, PPD and preprotachykinin (PPT) are markers of direct pathway activity, resulting in the initiation of movement [Young

[Cenci 1998] [Herrera 1996], while PPE is indicative of movement inhibition via the indirect pathway [Young 1991] [Herrera 1996].

Although the cause of LID is multifaceted, repeated exposure to L-DOPA and DA agonists is associated with altered striatal expression of dyskinesia-related genes such as PPD, PPT, PPE and c-fos [Berke 1998] [Young 1991] [Bishop 2009]. A large body of literature suggests that raphe-striatal serotonin (5-HT) projections contribute to LID by converting and releasing exogenous L-DOPA [Conti 2014] [Carta

[Bishop 2012]. Due to the absence of feedback mechanisms, like D2 autoreceptors, 5-HT neuron-release of DA is uncontrolled [Bishop 2012], ostensibly resulting in upregulation of dyskinetogenic gene expression. Vilazodone (VZD) is a selective 5-HT reuptake inhibitor (SSRI) and 5-HT1A receptor (5-HT1AR) partial agonist [Hughes 2005] [Schwartz 2011]. Administration of either SSRIs or 5-HT1A agonists have shown pre-clinical anti-LID efficacy, however clinical translation has been limited by worsening parkinsonism or limited anti-dyskinetic efficacy [Goetz 2007]. Vilazodone is uniquely situated (as the sole FDA approved drug with both SSRI and 5-HT1A agonist activity) to act at both SERT and 5-HT1AR to optimize LID reductions, while maintaining L-DOPA efficacy [Conti 2014]. While L-DOPA did not increase striatal PPT (FIG. 6B), Vilazodone significantly reduced it, implicating a direct pathway action independent of DA stimulation. The 2016 poster hypothesized that Vilazodone would prevent LID development without affecting L-DOPA efficacy, and that administering Vilazodone would block L-DOPA-induced upregulation of striatal PPT (FIG. 6B), PPE (FIG. 6C), PPD (FIG. 6D), and c-fos (FIG. 6E) gene expression.

Recent studies in dyskinetic parkinsonian models have implicated serotonergic raphe-striatal terminals in the uptake and conversion of L-DOPA to dopamine (DA), as well as the non-physiological release of DA and serotonin (5-HT) which may underlie the pathophysiological mechanisms of LIDs. Indeed, the utility of co-treatments with either selective 5-HT reuptake inhibitors (SSRIs) which block the 5-HT transporter (SERT), or selective 5-HT1A/B receptor (5-HT1A/Br) ligands which stimulate 5-HT autoreceptors to potentially suppress DA release from 5-HT terminals, has been assessed in pre-clinical models and clinical trials. Many of the drugs tested were found to reduce LIDs, but unfortunately also reduced the prokinetic effects of L-DOPA. A goal was to identify a multimodal 5-HT drug which can act to attenuate the expression and severity of LIDs, without interfering with the antiparkinsonian efficacy of L-DOPA.

Vilazodone is of interest in this regard as it is known to exhibit a potent SSRI-like action, along with 5-HT1Ar partial agonism property. Unilateral 6-hydroxy dopamine (6—OHDA)-lesioned rats modeling PD were treated with either vehicle and L-DOPA (5.0 mg/kg), vilazodone (10.0 mg/kg) and L-DOPA, or escitalopram (12.5 mg/kg) and L-DOPA. Rats were treated for 5 consecutive days/week, for 2 weeks. On the second day of each week, stepping tests were performed prior to drug administration, and 60 minutes post L-DOPA treatment. Behavioral assessment of LIDs was performed (30-180 min) at the end of each week. Vilazodone pretreatment (30 min) significantly reduced LIDs in 6—OHDA lesioned rats, but had no effects on forelimb akinesia or L-DOPA-induced prokinetic effects. Escitalopram pretreatment also induced a significant reduction in total LIDs score but interfered with the therapeutic efficacy of L-DOPA. Electrophysiological studies were conducted to assess the impact of these treatments on corticostriatal transmission and striatal neuronal activity. The current results indicate that together with L-DOPA, multimodal 5-HT drugs such as vilazodone may be safe and efficacious co-therapies for reducing side-effects such as hyperkinesia and dystonia in PD patients, potentially allowing for more flexibility in L-DOPA dose ranges and protracted chronic treatment.

Pair housed adult male Sprague-Dawley rats (~300g), received unilateral sham (n=8) or 6-hydroxydopamine (6—OHDA; n=30) infusions into the medial forebrain bundle (MFB) to deplete striatal DA. Abnormal Involuntary Movements (AIMs) were assessed using scale tests of LID severity [Lundblad 2002], analyzing three behaviors: 1. Axial-twisting of the trunk to the side contralateral to lesion; 2. Limb-up and down, side-to-side or uncontrollable movement of the right forelimb; and 3. Orolingual-asymmetric jaw tremors and tongue protrusions. AIMs were observed for 60 sec every 10 min for 180 min after L-DOPA. Behaviors were rated on a scale of 0 (absent)-4 (severe). L-DOPA efficacy was measured by dragging each rat 90 cm in 10 sec and counting the number of steps taken with the lesioned and non-lesioned paw, in a Forepaw Adjusting Steps (FAS) [Chang 1999] test. Percent intact scores were calculated by dividing the number of lesioned forepaw steps by the number of intact forepaw steps and then multiplying the result by 100.

For gene expression real time Reverse Transcript-Polymerase Chain Reaction (RT-PCR) was performed on striatal tissue taken from animals on treatment 1 h post injection on day 23. PPT (FIG. 6B), PPE (FIG. 6C), PPD (FIG. 6D), c-fos (FIG. 6E) and 5-HT1A (FIG. 6F) mRNA were quantified. GAPDH was used as a control, as shown on FIG. 6A. Data is presented as percent change in expression compared to non-lesioned striatum treated with VZD (0)+LD (0).

Vilazodone, a mixed SSRI and 5-HT1A partial agonist, prevents LID development, without chronic reductions in L-DOPA's therapeutic efficacy. This mirrors previous work with either SSRIs or 5-HT1A partial agonists [Dupre 2007]. While Vilazodone reduced striatal PPT (FIG. 6B), it did not appear to be affected by L-DOPA treatment and is therefore not a likely mechanism for the behavioral effects seen. PPE was significantly upregulated in all L-DOPA-treated, lesioned *striata* (FIG. 6C) [Tel 2002] [Herrero 1995], however, higher doses of Vilazodone partially reduced this increase. Notably, L-DOPA treatment significantly increased PPD and c-fos in the lesioned striatum (FIGS. 6D and 6E) [Bishop 2009]. This was significantly attenuated by both doses of Vilazodone, demonstrating a strong association between a normalization of direct pathway activity and the anti-LID effects of Vilazodone.

Vilazodone thus appeared to prevent LID development, while maintaining the motor benefits of L-DOPA. These behavioral changes were concurrent with reduced expression of striatal transcripts characteristically elevated in the dyskinetic state, suggesting key points of therapeutic articulation for PD patients.

It is therefore an object of the invention to provide a pharmaceutical dosage form, comprising L-DOPA and at least one agent having activity as an SSRI and a 5-HT1AR agonist.

It is another object to provide a method of treating L-DOPA-induced dyskinesia (LID) in a patient receiving L-DOPA and having LID, comprising administering at least one agent having activity as an SSRI and a 5-HT1AR agonist, to a patient receiving L-DOPA, in a sufficient amount, and for a sufficient duration, to treat the LID. It is a further object to provide a method of attenuating L-DOPA-induced dyskinesia (LID) in a patient receiving L-DOPA, and at risk of LID, comprising administering at least one agent having activity as an SSRI and a 5-HT1AR agonist, to a patient receiving L-DOPA, in a sufficient amount, and for a sufficient duration, to attenuate the LID. It is also an object to provide a method, comprising administering L-DOPA to a patient, and further administering at least one agent having activity as an SSRI and a 5-HT1AR agonist, to reduce L-DOPA-induced dyskinesia.

A still further object provides a method, comprising administering a pharmaceutically acceptable dosage form to a patient, comprising an effective amount of L-DOPA to treat a movement disorder, and an effective amount of at least one agent having activity as an SSRI and a 5-HT1AR agonist, to reduce L-DOPA-induced dyskinesia.

Another object provides a method of treating or reducing risk of a dyskinesia in a patient, comprising administering at least one agent having activity as an SSRI and a 5-HT1AR agonist, in a sufficient amount, and for a sufficient duration, to treat the dyskinesia, and a pharmaceutically acceptable dosage form or kit containing one or more such dosage forms, for effecting the treatment or reducing the risk. It is a further object to provide a pharmaceutical dosage form, comprising L-DOPA and at least one agent having activity as an SSRI and a 5-HT1AR agonist. The at least one agent may comprise an SSRI and a 5-HT1AR partial agonist, substantially without 5-HT2BR activity. The at least one agent may comprise a serotonin partial agonist and reuptake inhibitor or (SPARI). The patient has, for example, an L-DOPA induced dyskinesia (LID) or is at risk of future LID. The method may further comprise administering L-DOPA to the patient, and the at least one agent is administered according to a protocol effective to reduce LID. The L-DOPA and the at least one agent may be administered to the patient within a common pharmaceutically acceptable dosage form comprising an effective amount of the L-DOPA to treat a movement disorder in the patient, and an effective amount of the at least one agent to reduce LID. The at least one agent may comprise vilazodone, vortioxetine, and/or hypidone. The method may further comprise administering a peripherally-acting DOPA decarboxylase inhibitor, e.g., carbidopa, benserazide, methyldopa, a-difluoromethyl-DOPA, and/or 3',4',5,7-Tetrahydroxy-8-methoxyisoflavone. The method may further comprise administering a Catechol-O-methyl transferase inhibitor, e.g., entacapone, opicapone, and/or tolcapone. The method may further comprise administering a monoamine oxidase type B inhibitor, e.g., selegiline, rasagiline, isocarboxazid, phenelzine, tranylcypromine, linezolid, and/or methylene blue. The method may further comprise administering a dopamine receptor agonist, e.g., apomorphine, bromocriptine, pramipexole, ropinirole, and/or rotigotine. The method may further comprise administering an anticholinergic agent, an antimuscarinic agent, benzatropine, diphenhydramine, dimenhydrinate, scopolamine, cannabidiol (CBD), cannabidiolic acid (CBDA), and/or other cannabinoids. The at least one agent may comprise an SSRI and a 5-HT1AR partial agonist, substantially without 5-HT2BR activity. The at least one agent having activity as an SSRI and a 5-HT1AR agonist may consist essentially of a single compound, or be provided as a combination of different compounds. The at least one agent may comprise a serotonin partial agonist and reuptake inhibitor (SPARI). The at least one agent may desensitize serotonin 1A autoreceptors. The L-DOPA and the at least one agent having activity as an SSRI and a 5-HT1AR agonist may be coadministered within a single oral dosage form.

The patient may have Parkinson's Disease, a pathological reduction in the dopamine secreting neurons in the substantia nigra, multiple system atrophy, progressive supranuclear palsy, corticobasal degeneration, dementia with Lewy bodies, Encephalitis lethargica, or Dopamine-responsive dystonia (DRD), for example. The pharmaceutically acceptable dosage form may be orally administrable. The pharmaceutical dosage form may comprise, for example, 100-250 mg L-DOPA, at least 10-25 mg of a peripherally-acting DOPA decarboxylase inhibitor, and between 2.5-40 mg vilazodone. The L-DOPA may be provided with an extended release pharmacokinetic profile. The L-DOPA may be provided within a controlled release coating for oral administration or provided within a controlled release coating.

A further object provides a method of treating a human receiving L-DOPA for treatment of Parkinson's disease, and suffering from or at risk of L-DOPA-induced dyskinesia (LID), comprising administering a sufficient amount of a pharmaceutically acceptable dosage form of a single compound which is both an SSRI and a 5-HT1AR partial agonist, selected from the group consisting of vilazodone, vortioxetine, and hypidone, to treat or reduce risk of LID.

The at least one agent may be administered to a patient with, or included in a common formulation with, an anticholinergic agent. The at least one agent may be administered to a patient with, or included in a common formulation with, an antimuscarinic agent. The at least one agent may be administered to a patient with, or included in a common formulation with, at least one of benzatropine, diphenhydramine, dimenhydrinate, and/or scopolamine. The at least one agent may be administered to a patient with, or included in a common formulation with, a cannabinoid, e.g., at least one of cannabidiol (CBD) and cannabidiolic acid (CBDA), tetrahydrocannabinol (THC), or the like. Various GABAergic agents may also be coadministered. The at least one agent may comprise an SSRI and a 5-HT1AR partial agonist, substantially without 5-HT2BR activity. The at least one agent may comprise a serotonin partial agonist and reuptake inhibitor (SPARI). The at least one agent may desensitize serotonin 1A autoreceptors. The L-DOPA and the at least one agent having activity as an SSRI and a 5-HT1AR agonist may be coadministered, e.g., within a single oral dosage form, and therefore be orally administrable. The L-DOPA may be provided with in a formulation which displays an extended release pharmacokinetic profile. The at least one agent having activity as an SSRI and a 5-HT1AR agonist may consist essentially of a single compound. The patient may have, or be at risk of developing, LID. The patient may receive L-DOPA for treatment of Parkinson's Disease, a pathological reduction in the dopamine secreting neurons in the substantia nigra; multiple system atrophy; progressive supranuclear palsy; corticobasal degeneration; dementia with Lewy bodies; Encephalitis lethargica; or Dopamine-responsive dystonia (DRD). The pharmaceutical dosage form may comprise, for example 100-250 mg L-DOPA, at least 10-25 mg of a peripherally-acting DOPA decarboxylase inhibitor, and between 2.5-10 mg vilazodone.

Further objects will become apparent.

BRIEF DESCRIPTION OF THE DRAWINGS

(FIG. 2A) AIMs and (FIG. 2B) FAS were evaluated on days 1, 8, 15, and 22. AIMs values expressed are the median sum of axial, limb, and orolingual (ALO) behaviors. ALO AIMs were evaluated every 10 min for 3 h post-LD administration. Values are expressed as medians [+median absolute difference (M.A.D.)]. FAS were evaluated 60 min post LD and are expressed as the mean overall steps ipsilateral to lesion divided by the mean overall steps contralateral to lesion multiplied by 100. Values are expressed as means+standard error of the mean (S.E.M.). * p<0.05 vs all; +p<0.05 vs VZD (0)+LD (0); § p<0.05 vs Baseline; ^p<0.05 vs VZD (0)+LD (6).

FIG. 17A-17*l* show that D2Rs-injected animals do not develop severe AIMs with DA agonist treatment.

DETAILED DESCRIPTION OF THE PREFERRED EMBODIMENTS

Example 1

Figure 1A:
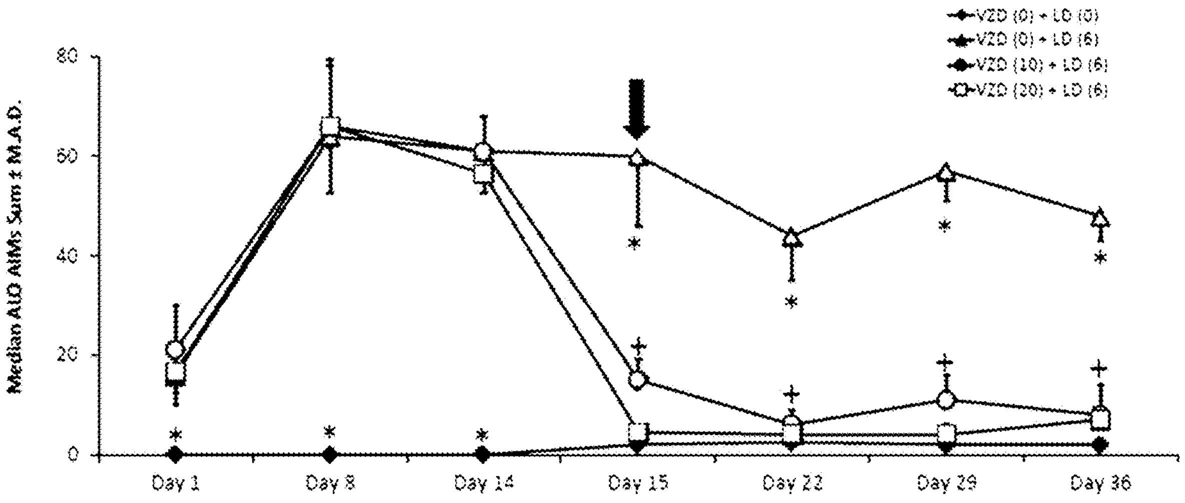
FIGS. 1A-1B show effects of prolonged Vilazodone (VZD) treatment on established L-DOPA (LD)-induced dyskinesia (LID). Forepaw adjusting steps (FAS) baseline data was collected 3-weeks post-lesion. Subjects were then primed for 14 days with LD (0 or 6 mg/kg; s.c.) and abnormal involuntary movements (AIMs) were evaluated on days 1, 8 and 14. On day 15, animals began receiving daily injections of VZD (0, 10, or 20 mg/kg; s.c.) 5 min prior to vehicle or LD. AIMs (FIG. 1A) and FAS (FIG. 1B) were monitored on days 15, 22, 29, and 36 of the experiment. Axial, limb, and orolingual (ALO) AIMs were evaluated every 10 min for 3 h after L-DOPA administration and the values are expressed as the median sum of ALO behaviors [+median absolute difference (M.A.D.)]. FAS were evaluated 60 min post-LD with values expressed as the mean overall steps ipsilateral to lesion divided by the mean overall steps contralateral to lesion multiplied by 100 [+standard error of the mean (S.E.M.)]. * $p<0.05$ vs all; +$p<0.05$ vs VZD (0)+LD (0); § $p<0.05$ vs Baseline; ^$p<0.05$ vs VZD (0)+LD (6).

The serotonergic system is a well-established modulator of L-DOPA-induced dyskinesia (LID). To date, targeting serotonin (5-HT) transporters (SERT) or 5-HT1A receptors (5-HT1AR) has shown promise in reducing LID, however these strategies have yet to translate clinically. Ideally, a compound acting at both known anti-dyskinetic sites could optimize such 5-HT-mediated approaches. Vilazodone (VZD) is an FDA-approved antidepressant that acts as a selective serotonin reuptake inhibitor and a partial 5-HT1AR agonist, situating Vilazodone in a unique position to reduce LID, without compromising L-DOPA-mediated motor improvements.

In Experiments 1 and 2, L-DOPA-naïve and L-DOPA-primed animals were co-administered Vilazodone and L-DOPA daily for 3 weeks to model sub-chronic use. In these experiments, Vilazodone significantly suppressed developing and established LID, without compromising the pro-motor effects of L-DOPA therapy. Post-mortem neurochemical analysis revealed that in the dopamine (DA)-depleted striatum, Vilazodone-L-DOPA co-treatment increased DA content, suggesting a normalization of DA kinetics in dyskinetic brain. Analysis of striatal gene expression revealed that Vilazodone treatment reduced L-DOPA-induced c-Fos and preprodynorphin mRNA overexpression, indicative of attenuated DA D1 receptor-mediated direct pathway over-activity.

In Experiment 3, when tested against 5-HT1AR and 5-HT1B receptor (5-HT1BR) antagonists, WAY100635 and NAS-181, respectively, WAY100635 alone partially attenuated Vilazodone's anti-dyskinetic efficacy, suggesting both SERT-dependent effects and 5-HT1AR in Vilazodone actions. Such findings implicate mechanisms of action for Vilazodone and its potential for repositioning against LID development and expression in PD.

L-3,4-dihidroxyphenylalanine (L-DOPA) remains the standard treatment for late-stage Parkinson's disease (PD) symptom management (Mercuri and Bernardi, 2005). Unfortunately, its chronic administration often results in abnormal involuntary movements (AIMs) termed L-DOPA-induced dyskinesia (LID; García-Ruiz et al., 2011). LID pathogenesis is multifaceted, but unregulated dopamine (DA) release from raphe-striatal serotonin (5-HT) neurons is associated with LID in both PD patients and experimental models (de la Fuente-Fernández et al., 2004; Navailles et al., 2010). This 5-HT gain-of-function is supported by evidence of increased striatal 5-HT innervation (Zeng et al., 2010), 5-HT transporter (SERT) expression (Rylander et al., 2010; Politis et al., 2014), and SERT: DA transporter (DAT) ratios (Conti et al., 2016; Roussakis et al., 2016), all which positively correlate with LID.

To treat LID, current serotonergic strategies have focused primarily on 5-HT1A receptors (5-HT1AR) or more recently SERT. 5-HT1AR agonists and selective 5-HT reuptake inhibitors (SSRIs) reduce LID in animal models (Bishop et al., 2012; Conti et al., 2014; Fidalgo et al., 2015; Huot et al., 2015). Despite their pre-clinical efficacy, 5-HT1AR agonists produce mild anti-dyskinetic efficacy and/or worsening motor symptoms in large clinical cohorts (Kannari et al., 2002; Goetz et al., 2007). Eltoprazine, a selective 5-HT1A/1B partial agonist, displays anti-dyskinetic efficacy in rodents, non-human primates, and patients though it too may attenuate L-DOPA's benefits (Bezard et al., 2013; Svenningsson et al., 2015). Clinical assessment of chronic SSRIs is limited to retrospective analyses reporting delays in LID onset, LID severity and reduced peak-dose LID (Mazzucchi et al., 2015).

Serotonergic compounds reduce LID through a diverse set of actions. For example, in the dorsal raphe nucleus (DRN), 5-HT1AR agonists temper raphe-striatal DA release via by stimulation of local 5-HT1AR auto-receptors (Eskow et al., 2009; Navailles et al., 2010), whereas in the striatum, they mitigate striatal over activity through local hetero-receptors (Bishop et al., 2009; Meadows et al., 2017; Muñoz et al., 2008). In comparison, SSRIs appear to increase endogenous 5-HT at DRN 5-HT1AR autoreceptors to reduce LID while coincidentally blocking striatal DA uptake through SERT to maintain L-DOPA's anti-parkinsonian effects (Kannari et al., 2006; Navailles et al., 2010; Larsen et al., 2011; Conti et al., 2014). Therefore, combining the activity of SSRIs and 5-HT1AR agonists may enhance the anti-dyskinetic potential of both targets.

Vilazodone (VZD), an FDA-approved SSRI and 5-HT1AR partial agonist (Cruz, 2012; Owen, 2011) was during chronic treatment to suppress both LID development and expression hemi-parkinsonian rats, while maintaining L-DOPA efficacy. Neurochemical and cellular analyses revealed target specific modulation of monoamine neurotransmission and dyskinesia-related gene expression, suggesting engagement of unique mechanisms to optimize L-DOPA therapy.

Materials and methods: Studies used adult male Sprague-Dawley rats (N=85, 250g upon arrival; Harlan Farms, NY, USA), housed in plastic cages (22×45×23 cm) with ad libitum access to standard laboratory chow (Rodent Diet 5001; Lab Diet, Brentwood, MO) and water. The colony room was set on a 12 h light/dark cycle (lights on at 07:00 h) at 22-23° C. and animals were maintained in accordance with the Institutional Animal Care and Use Committee of Binghamton University and the 'Guide for the Care and Use of Laboratory Animals' (Institute of Laboratory Animal Resources, National Academic Press, 2011).

6-Hydroxydopamine-lesion surgeries: One week after arrival, rats received unilateral vehicle or 6-hydroxydopamine (6—OHDA) injections to the left medial forebrain bundle (MFB) to destroy DA neurons.

Rats were administered Desipramine HCl (25 mg/kg, i.p.; Sigma, St. Louis, MO) and buprenorphine HCl (0.03 mg/kg, i.p.; Reckitt Benckiser Pharmaceuticals Inc., Richmond, VA) 30 and 5 min prior to surgery to protect norepinephrine neurons and provide analgesia respectively. Rats were anesthetized with inhalant isoflurane (2-3%; Sigma) in oxygen (2.5 L/min), and placed in a stereotaxic apparatus (Kopf Instruments, Tujunga, CA). MFB injection coordinates were AP: −1.8 mm, ML: +2.0 mm, DV: −8.6 mm relative to bregma, with the incisor bar 5.0 mm below the interaural line (Paxinos and Watson, 1998). For infusions, a 26-gauge needle delivered 4 μL 6—OHDA (0 or 3 ug/uL; Sigma) dissolved in 0.9% NaCl+0.1% ascorbic acid at 2 μL/min. The needle was withdrawn 5 min post-infusion. Rats were provided with soft chow and saline to facilitate recovery and allowed 3 weeks before experimentation.

Figure 1B:
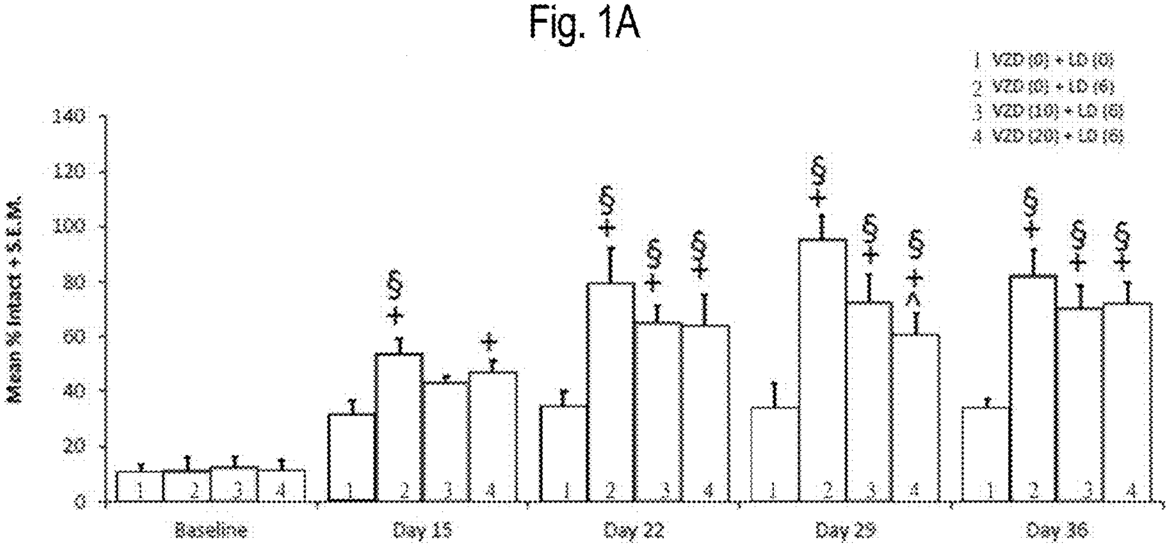

Experiment 1: Chronic intervention with Vilazodone in L-DOPA-primed, hemi-parkinsonian rats Rats (n=30) were rendered hemi-parkinsonian with unilateral 6—OHDA lesions of the left MFB. Three-weeks post-lesion, animals were divided into 2 equally disabled groups, measured by forepaw adjusting steps (FAS, see below). One group (n=8) began receiving 14 days of daily vehicle (0.9% NaCl+0.1% ascorbic acid) and the other (n=22) received L-DOPA methyl ester (6 mg/kg, s.c.; Sigma)+DL-serine 2-(2,3,4-trihydroxybenzyl) hydrazine hydrochloride (benserazide; 15 mg/kg, s.c.; Sigma), hereafter L-DOPA, dissolved in vehicle at a volume of 1 mL/kg. Treatment persisted for 14 days to produce stable AIMs expression (Putterman et al., 2007; Conti et al., 2014). Thereafter, L-DOPA-treated animals with Axial, Limb, and Orolingual (ALO) AIMs (see description below, FIG. 1A)<30 were excluded from the study and the remaining L-DOPA-treated animals were divided into 3 equally dyskinetic groups. The 4 groups were: 6—OHDA Lesion+VZD, (0)+LD (0), 6—OHDA Lesion+VZD (0)+LD (6), 6—OHDA Lesion+VZD (10)+LD (6), and 6—OHDA Lesion+VZD (20)+LD (6). Vilazodone was administered 5 min prior to L-DOPA (0 or 6 mg/kg; s.c.) in a between-subjects design. Daily injections continued over 23 days, with behavior assayed on Days 15, 22, 29, and 36. On Day 37, animals were killed 60 min post-treatment. Left and right dorsal striata and DRN were dissected and flash frozen for HPLC analyses. Results of a forepaw adjusting steps test (FAS) are shown in FIG. 1B.

Experiment 2: Chronic prevention with Vilazodone in L-DOPA-naïve, hemi-parkinsonian rats Another cohort (n=38) received unilateral vehicle or 6—OHDA lesions. After recovery, FAS established baseline motor disability. 6—OHDA-lesioned animals were divided into 3 equally disabled groups. Rats then received daily injections of Vilazodone (0, 10, or 20 mg/kg, s.c.) 5 min prior to L-DOPA (0 or 6 mg/kg; s.c.) for 23 days in a between-subjects design. The 4 groups were: Sham+VZD (0)+LD (0), 6—OHDA Lesion+VZD (0)+LD (6), 6—OHDA Lesion+VZD (10)+LD (6), and 6—OHDA Lesion+VZD (20) +LD (6). AIMs (FIG. 1A) and FAS (FIG. 2B) were measured on Days 1, 8, 15, and 22 of treatment. On Day 23, animals were decapitated 60 min post-L-DOPA and left and right posterodorsal striata dissected for real time reverse transcription polymerase chain reaction (RT-PCR).

Experiment 3: Characterizing the role of the 5-HT1AR and 5-HT1BR in Vilazodone's effects All 6—OHDA-lesioned rats (n=17) were tested on the FAS prior to treatment regimens to establish baseline motor performance. Three-weeks post-surgery, all rats were primed with L-DOPA (6 mg/kg, s.c.) for 14 days. On days 1, 8, and 14 of L-DOPA treatment ALO AIMs were observed and rats with ALO AIMs scores <30 by day 14 were excluded in the study. Experiments began 3 days after cessation of priming and testing occurred every 3-4 days until completion.

One group of rats (n=9) received vehicle or the selective 5-HT1AR antagonist N-[2-[4 (2-Methoxyphenyl)-1-piperazinyl]ethyl]-N-2-pyridinylcyclohexanecarboxamide maleate salt (WAY100635; 0.5 mg/kg, s.c.; Sigma) 5 min prior to vehicle or Vilazodone (10 mg/kg; s.c.) in a counterbalanced within-subjects design. All rats received injections of L-DOPA (6 mg/kg; s.c.) administered 5 min after their second injection after which AIMs rating commenced.

A second group of animals (n=8) received dH2O vehicle or the selective 5-HT1BR antagonist (R)-(+)-2-(3-morpholinomethyl-2H-chromen-8-yl)oxymethyl-morpholine methane-sulfonate (NAS-181; 3.0 mg/kg, s.c.; Fisher Scientific Hampton, NH) 5 min prior to vehicle or Vilazodone (10 mg/kg; s.c.) in a counterbalanced within-subjects design. All rats received injections of L-DOPA (6 mg/kg; s.c.) administered 5 min after their second injection after which AIMs were rated.

Behavioral Analyses

Abnormal involuntary movements (AIMs): The AIMs procedure measures rodent dyskinesia severity (Bishop et al., 2012). Beginning 10 min post-treatment, a trained and blinded observer assigned a severity score (0-4) to each of the ALO AIMs based on 1 min ratings every 10 min for 3 h: 0, not present; 1, present from 1-29 s; 2, present 30-59 s; 3, present all 60 s, but interruptible by a cylinder tap; 4, present 60 s and not interruptible by a cylinder tap.

Forepaw adjusting steps (FAS): The FAS test is a measure of forelimb akinesia performed according to previous protocols (Bishop et al., 2012; Chang et al., 1999). Data are presented as mean percent intact stepping where the sum of the total steps with the lesioned forepaw was divided by the total steps with the unlesioned forepaw multiplied by 100. Lower percent intact scores indicate greater forelimb akinesia. Prior to baseline, rats received 2 acclimation periods. On-treatment FAS was performed 60 min post-L-DOPA.

High-performance liquid chromatography (HPLC): HPLC, a method for semi-automated catecholamine analysis with coulometric detection, was performed according to prior protocols (Bishop et al., 2009) to determine the tissue levels of monoamines, their metabolites, and monoamine turnover in the striatum and DRN. The limit of detection for DOPAC, DA, 5-hydroxyindoleacetic acid (5-HIAA) and 5-HT was 10-10 M. Final oxidation current values were plotted on a standard curve from 10-6 M to 10-9 M and expressed as pg of monoamine or metabolite per mg of tissue unless otherwise specified.

Real-time RT-PCR: Striatal gene expression was measured by post-mortem analysis of c-Fos, preprodynorphin (PPD), preproenkephalin (PPE),) and 5-HT1AR mRNA expression normalized to the housekeeper gene glyceraldehyde-3-phosphate dehydrogenase (GAPDH). Tissue was processed with RNeasy mini protocol (Qiagen, Hilden Germany), as detailed in prior work (Barnum et al., 2008). The following primer sequences were used:

| | | |
|---|---|---|
| GAPDH | SEQ ID NO. 001 | 5'-GTGCCAGCCTCGTCTCATAG-3'/ |
| | SEQ ID NO. 002 | 5'-AGAGAAGGCAGCCCTGGTAA-3' |
| c-Fos | SEQ ID NO. 003 | 5'-CCAAGCGGAGACAGATCAAC-3'/ |
| | SEQ ID NO. 004 | 5'-AAGTCCAGGGAGGTCACAGA-3' |
| PPD | SEQ ID NO. 005 | 5'-GGGTTCGCTGGATTCAAATA-3'/ |
| | SEQ ID NO. 006 | 5'-TGTGTGGAGAGGGACACTCA-3' |
| PPE | SEQ ID NO. 007 | 5'-AAAATCTGGGAGACCTGCAA-3'/ |
| | SEQ ID NO. 008 | 5'-CATGAAACCGCCATACCTCT-3' |
| 5-HT1AR | SEQ ID NO. 009 | 5'-GATCTCGCTCACTTGGCTCA-3'/ |
| | SEQ ID NO. 010 | 5'-AAAGCGCCGAAAGTGGAGTA-3'. |

Statistical analyses: Parametric data are expressed as mean±standard error of the mean (SEM). FAS data were analyzed by 5×4 (Day×Treatment) mixed model ANOVAs. HPLC data were analyzed by 2×4 (Side×Treatment) and one-factor ANOVAs. RT-PCR data are reported as percent change from striata of vehicle-treated sham animals. Scores >2 S.D.s from the group mean were discarded and replaced with the new group mean (except for GAPDH). The data were analyzed using a 2×4 (Lesion×Treatment) mixed-model ANOVA. One subject was dropped from RT-PCR analysis because GAPDH was an outlier. Fisher's LSD post-hocs or planned comparisons between key conditions were employed as outlined below. Non-parametric AIMs data were expressed as medians±median absolute deviation (MAD). For within-subject designs, ALO AIMs were analyzed by Friedman ANOVAs and Wilcoxon post-hoc tests. ALO AIMs of between-subject designs were evaluated with Kruskal-Wallis ANOVAs and Mann-Whitney post-hocs. All statistical analyses were performed using SPSS 19.0 (IBM, Chicago, IL) with alpha set at 0.05.

Results

Experiment 1-Chronic Vilazodone reduces established LID: AIMs were monitored to determine Vilazodone-mediated changes to LID. During 14 days of priming, L-DOPA-treated groups did not significantly differ from each other, but each group produced significantly greater LID than animals administered L-DOPA vehicle (all x2, (3)>17.481, p<0.02; FIG. 1A). On the first day of Vilazodone treatment, both doses dramatically reduced AIMs compared to animals receiving Vilazodone (0 mg/kg)+L-DOPA (6 mg/kg) and this effect persisted throughout treatment (Z≤-3.13, all p<0.002). The high dose (20 mg/kg) initially had greater anti-LID efficacy than the lower dose (10 mg/kg; Z=−1.99, p=. 047), but this effect dissipated after the first week.

FAS was employed to measure treatment effects on motor performance. A 5×4 mixed ANOVA revealed a main effect of treatment (F3,26=12.00, p=0.00) and day (F4, 104=23.79, p=0.00), with a significant interaction (F12,104=2.28, p=0.013). As shown in FIG. 1B, Vilazodone (0 mg/kg)+L-DOPA (6 mg/kg)-treated rats displayed significant improvements on motor performance over baseline (all p<0.02), while improvements in rats treated with Vilazodone emerged 7 days later (all p<0.001). L-DOPA-treated groups displayed significantly better stepping then Vilazodone (0 mg/kg)+L-DOPA (0 mg/kg)-treated animals by Day 22 (all p<0.05). Although the high dose of Vilazodone depressed stepping compared to Vilazodone (0 mg/kg)+L-DOPA (6 mg/kg)-treated animals on Day 29 (20 mg/kg; p=0.026), this effect was transient.

Vilazodone modifies DA and 5-HT content in L-DOPA-primed and treated rats: Rats in Experiment 1 were killed 60 min post-L-DOPA and tissue was processed for HPLC analysis to determine the effects of treatment on striatal and raphe tissue neurochemistry. In striatum, a 2×4 (Lesion× Treatment) ANOVA revealed main effects of lesion on DA (F1,52=922.23, p=0.00), DOPAC (F1,52=696.86, p=0.00), DA turnover (F1,52=24.78, p=0.00), 5-HT (F1,52=6.54, p=0.014), 5-HIAA (F1,52=31.34, p=0.00), and 5-HT turnover (F1,52=51.92, p=0.00), a main effect of treatment on DA turnover (F3,52=2.82, p=0.048), 5-HIAA (F3,52=9.83, p=0.00), and 5-HT turnover (F3,52=6.15, p=0.001), and an interaction of lesion by treatment on DA turnover (F3, 52=4.25, p=0.009; Table 1). Planned comparisons revealed that both doses of Vilazodone significantly increased DA in the lesioned striatum compared to groups receiving Vilazodone vehicle (0 mg/kg; all p<0.05), without altering significant L-DOPA-induced decreases in DA turnover (all p<0.05). Vilazodone (20 mg/kg) attenuated 5-HIAA compared to all other treatments (all p<0.05) and reduced 5-HT Turnover compared to Vilazodone (0 mg/kg)+L-DOPA (0 mg/kg) (p=0.026).

Figure 2A:
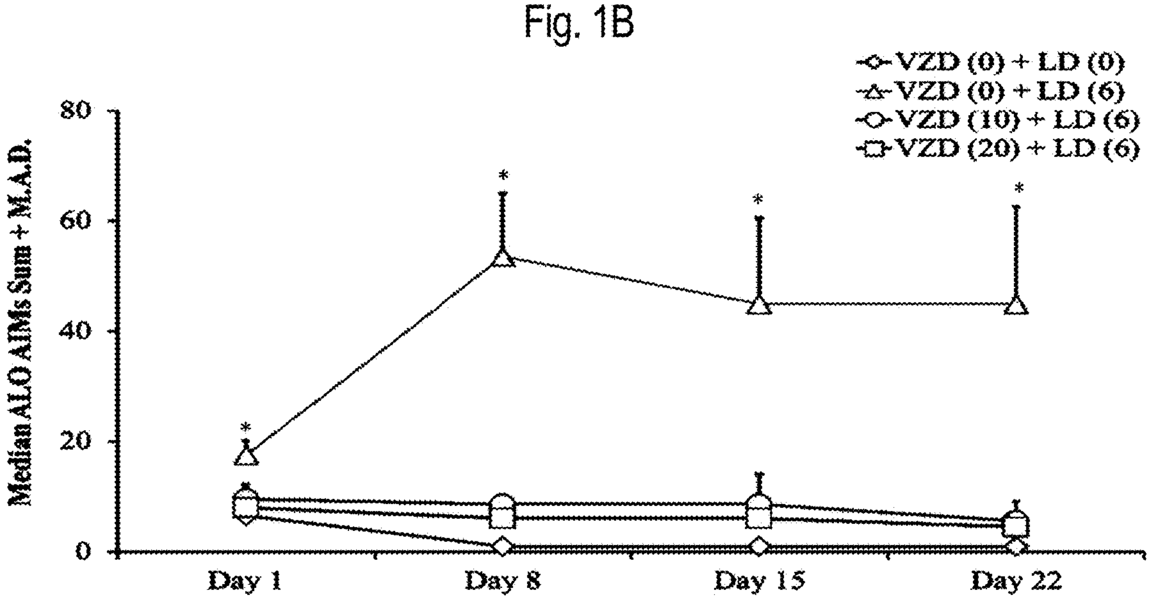
FIGS. 2A-2B show effects of prolonged Vilazodone (VZD) treatment on L-DOPA (LD)-induced dyskinesia (LID) development in treatment naïve rats. Baseline forepaw adjusting step (FAS) data was collected 3 weeks after sham or-dopamine lesion surgery, but prior to LD exposure. Sham animals received daily VZD (0 mg/kg)+L-DOPA (0 mg/kg) and 6—OHDA-lesioned animals received daily VZD (0, 10 or 20 mg/kg; s.c.)+LD (6 mg/kg; s.c.). All VZD injections were administered 5 min prior to LD.

LID development was assessed. As shown in FIG. 2A, co-administration of Vilazodone with L-DOPA in treatment naïve subjects significantly attenuated the development of LID across 3 weeks of treatment (all Days, x2, (3)>14.90, p<0.002). For the duration of the experiment, both doses (10 or 20 mg/kg) of Vilazodone provided such protection compared to Vilazodone (0 mg/kg)+L-DOPA (6 mg/kg) treated animals (all Z≤-2.77, all p<0.007).

Figure 2B:
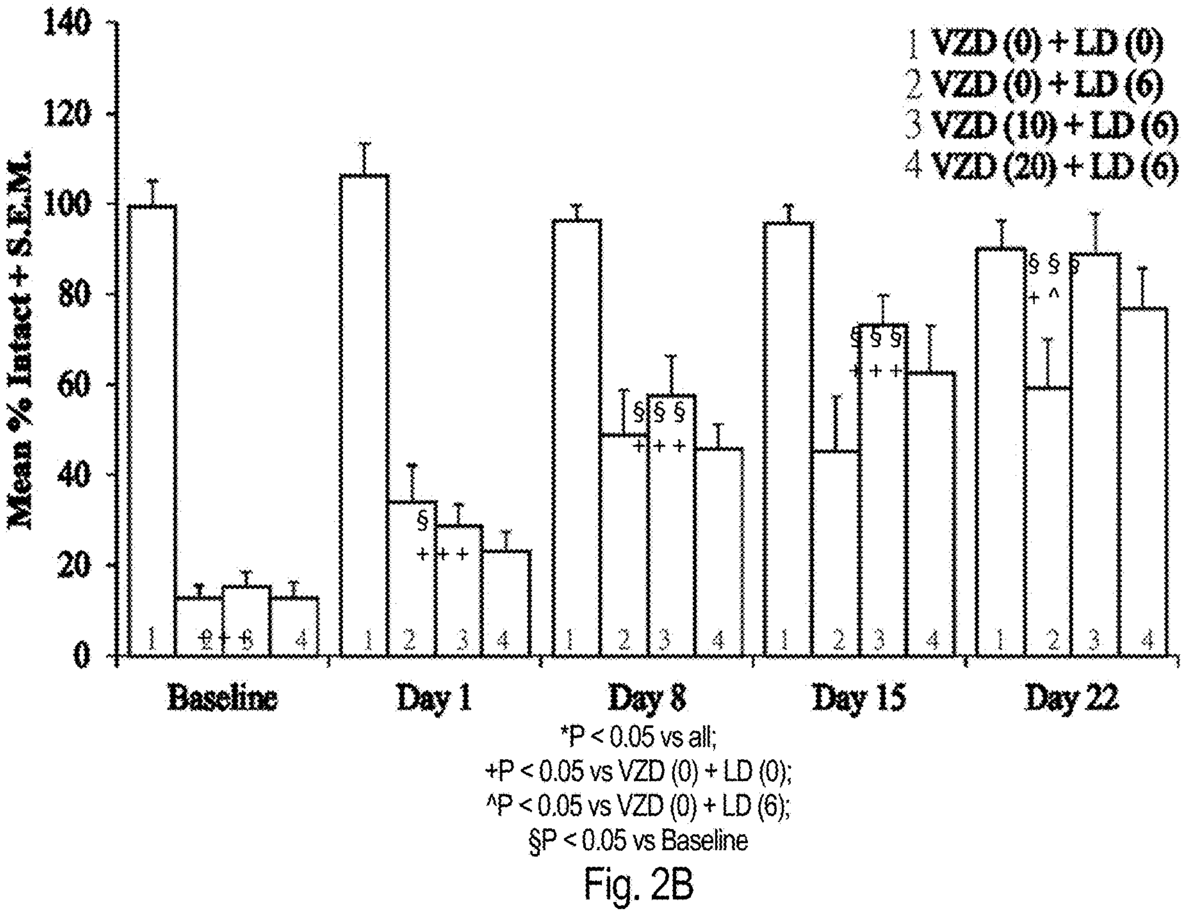
Figure 3A:
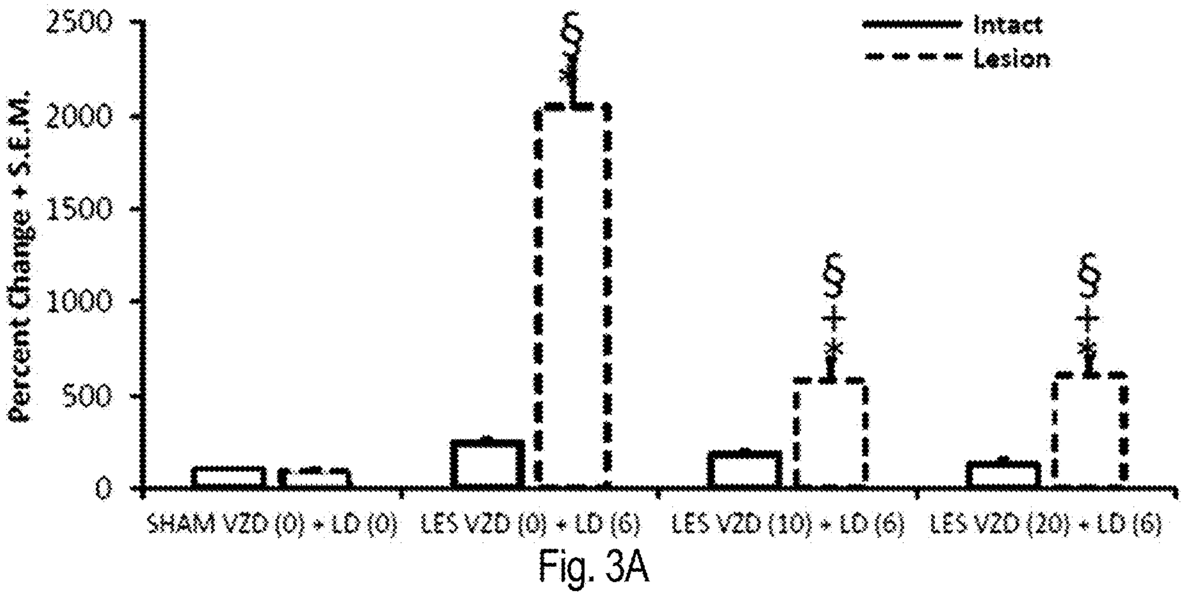
FIGS. 3A-3D show effects of dopamine lesion, L-DOPA (LD), and Vilazodone (VZD) on gene expression of striatal (FIG. 3A) c-Fos (FIG. 3B), preprodynorphin (PPD), (FIG. 3C) preproenkephalin (PPE) and (FIG. 3D) 5-HT1A Receptor (5-HT1AR) mRNA. Rats from experiment 2 given VZD (0, 10 or 20 mg/kg, s.c.) 5 min prior to LD (0 or 6 mg/kg, s.c.) daily for 22 days in a between-subjects design were decapitated on-treatment 60 min post-injection on day 23, and the right (intact; INT) and left (lesion; LES) posterior striata were dissected for subsequent Real-Time Reverse Transcription-Polymerase Chain Reaction (RT-PCR) analysis. Bars denote percent change in expression compared with control [sham lesioned treated with VZD (0)+LD (0)] for (A) PPE, (B) PPD, (C) c-Fos, and (D) 5-HT1AR mRNA expression. * p<0.05 vs Sham VZD (0)+LD (0); § p<0.05 vs all INT within subjects; +p<0.05 vs LES VZD (0)+LD (6).
Figure 3B:
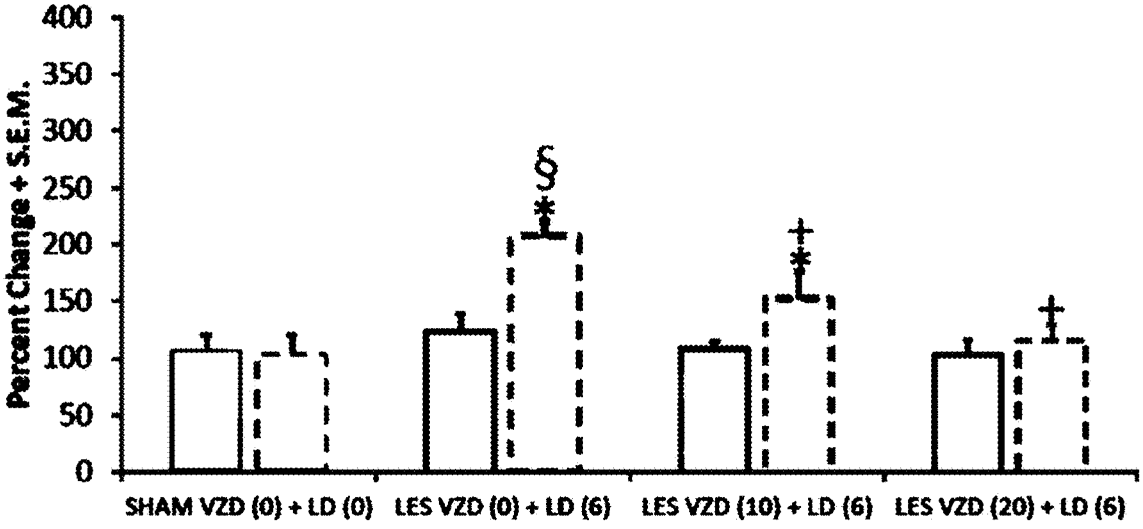
Figure 3C:
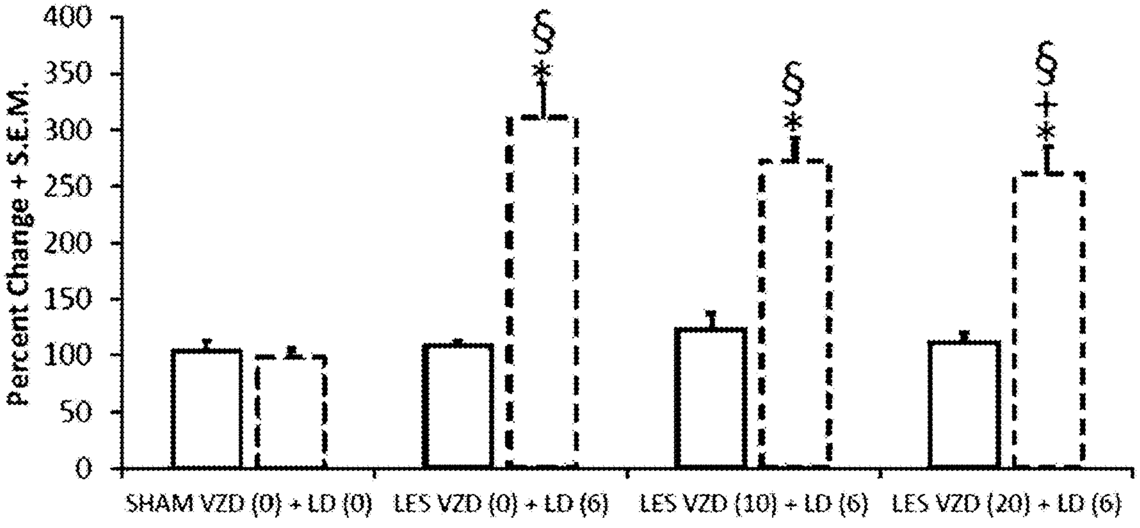
Figure 3D:
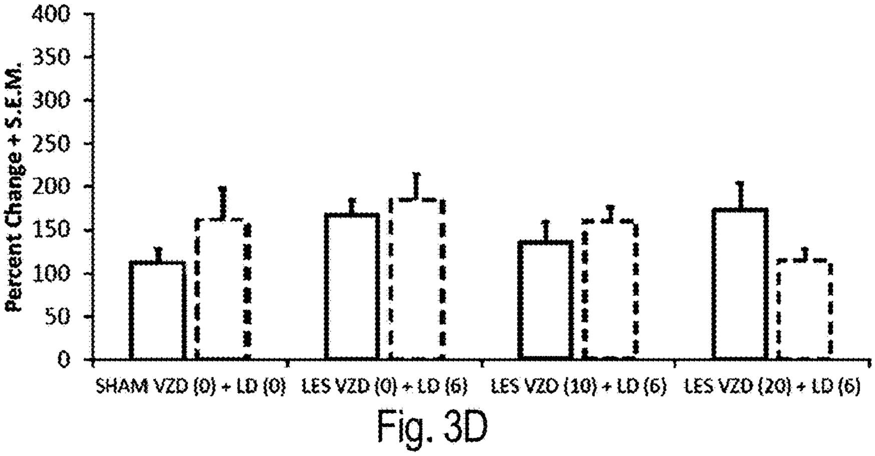

Analyses of FAS revealed main effects of day (F4, 136=32.89, p=0.00), treatment (F3,34=23.01, p=0.00) a significant interaction of day and treatment (F12,136=6.66, p=0.00; FIG. 2B). Vilazodone (0 mg/kg)+L-DOPA (6 mg/kg) treated animals showed significant increases in motor ability on each test day (all p<0.01). Vilazodone-treated groups showed significant increases in stepping, relative to baseline, from Day 8 thereafter (all p=0.00). Interestingly, by Day 15, Vilazodone treatment significantly enhanced the pro-motor effects of L-DOPA, as Vilazodone (10 mg/kg)+L-DOPA (6 mg/kg) treated rats stepped better than Vilazodone (0)+L-DOPA (6 mg/kg; both p<0.01) and equivalent to sham-lesioned rats.

TABLE 1

| Structure | Treatment (mg/kg) | DA* | DOPAC* | DA Turnover* | 5-HT* | 5-HIAA* | 5-HT Turnover* |
|---|---|---|---|---|---|---|---|
| Striatum | | | | | | | |
| Intact | VZD(0) + LD(0) | 4584 ± 354 | 3310 ± 207 | 0.73 ± 0.03+ | 366 ± 47.8 | 706 ± 62.8 | 2.02 ± 0.12+ |
| | VZD(0) + LD(6) | 4561 ± 210 | 4051 ± 224 | 0.89 ± 0.04 | 241 ± 29.6^ | 650 ± 68.9 | 2.77 ± 0.15+ |
| | VZD(10) + LD(6) | 4827 ± 222 | 4138 ± 332^ | 0.85 ± 0.05 | 326 ± 24.3 | 470 ± 35.5^# | 1.45 ± 0.04 |
| | VZD(20) + LD(6) | 4560 ± 337 | 3839 ± 306 | 0.84 ± 0.03 | 305 ± 33.5 | 422 ± 38.6^# | 1.41 ± 0.07 |
| Lesion | VZD(0) + LD(0) | 40.2 ± 7.26 | 93.7 ± 8.35 | 3.50 ± 1.43+ | 245 ± 32.3 | 1047 ± 54.9 | 5.12 ± 0.99 |
| | VZD(0) + LD(6) | 83.3 ± 7.99 | 127 ± 30.7 | 1.42 ± 0.23 | 264 ± 39.6 | 907 ± 82.5 | 3.93 ± 0.63 |
| | VZD(10) + LD(6) | 128 ± 14.2^# | 193 ± 20.5^ | 1.56 ± 0.18 | 261 ± 30.7 | 842 ± 78.8 | 3.38 ± 0.31 |
| | VZD(20) + LD(6) | 128 ± 26.2^# | 190 ± 44.6 | 1.50 ± 0.15 | 223 ± 23.8 | 596 ± 55.1+ | 2.84 ± 0.33^ |
| DorsalRaphe | VZD(0) + LD(0) | 48.6 ± 2.87+ | 248 ± 29.8+ | 5.06 ± 0.57 | 4448 ± 494 | 2643 ± 387 | 0.58 ± 0.04 |
| Nucleus | VZD(0) + LD(6) | 112 ± 10.7 | 1114 ± 211 | 10.3 ± 1.76^ | 5457 ± 786 | 2778 ± 261 | 0.57 ± 0.09 |
| | VZD(10) + LD(6) | 153 ± 22.9 | 1175 ± 234 | 7.60 ± 0.78 | 7013 ± 462^ | 2541 ± 187 | 0.37 ± 0.02^# |
| | VZD(20) + LD(6) | 128 ± 15.2 | 909 ± 186 | 7.19 ± 1.12 | 5946 ± 776 | 1985 ± 345 | 0.32 ± 0.03^# |

L-DOPA (LD)-primed rats were treated with Vilazodone (VZD; 0, 10, or 20 mg/kg, s.c.) 5 min prior to LD (0 or 6 mg/kg, s.c.) for 22 days. On the final treatment day, animals were sacrificed 60 min post-LD treatment and left and right *striata* and dorsal raphe nucleus (DRN) were collected for high performance liquid chromatography (HPLC) analysis. Values (means±standard mean error) are expressed as picograms of monoamine or metabolite per milligram wet tissue weight. Turnover estimates were determined by dividing a subject's metabolite value by its corresponding monoamine. Differences were assessed by a 2×4 (lesion×treatment) ANOVA, followed by Fisher's LSD post-hocs when appropriate. * p<0.01 vs lesion vs intact; +p<. 05 vs all; ^p<0.05 vs VZD (0)+LD (0); #p<0.05 vs VZD (0)+LD (6)

Analyses of the DRN revealed a main effect of treatment on DA (F3,26=9.88, p=0.00), DOPAC (F3,26=5.86, p=0.003), DA Turnover (F3,26=3.66, p=0.025) and 5-HT Turnover (F3,26=6.94, p=0.001). Post-hoc analysis revealed that L-DOPA treatment significantly increased DRN levels of DA, DOPAC and DA Turnover (all p<0.05), while only DA Turnover was attenuated in animals treated with Vilazodone (10 or 20 mg/kg). Interestingly, planned comparisons revealed Vilazodone (10 mg/kg) significantly increased DRN 5-HT while both doses of Vilazodone attenuated 5-HT Turnover (all p<0.05).

Figure 6A:
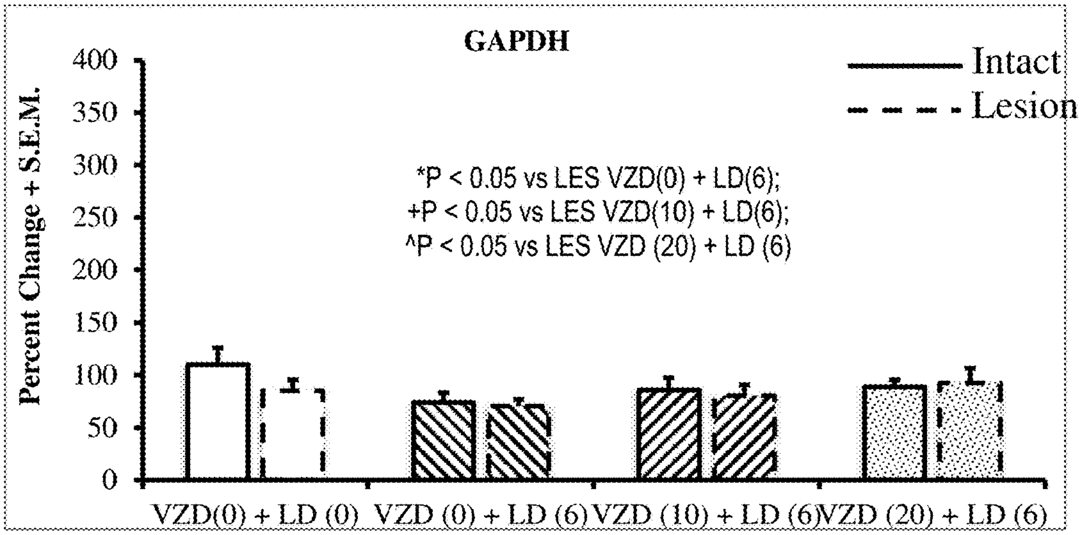
FIGS. 6A-6F show gene expression based on real time Reverse Transcript-Polymerase Chain Reaction (RT-PCR) on striatal tissue mRNA taken from animals on treatment 1 h post injection on day 23, for GAPDH (Control FIG. 6A, PPT (FIG. 6B), PPE (FIG. 6C), PPD (FIG. 6D), c-fos (FIG. 6E) and 5-HT1A (FIG. 6F). Data is presented as percent change in expression compared to non-lesioned striatum treated with VZD (0)+LD (0).
Figure 6B:
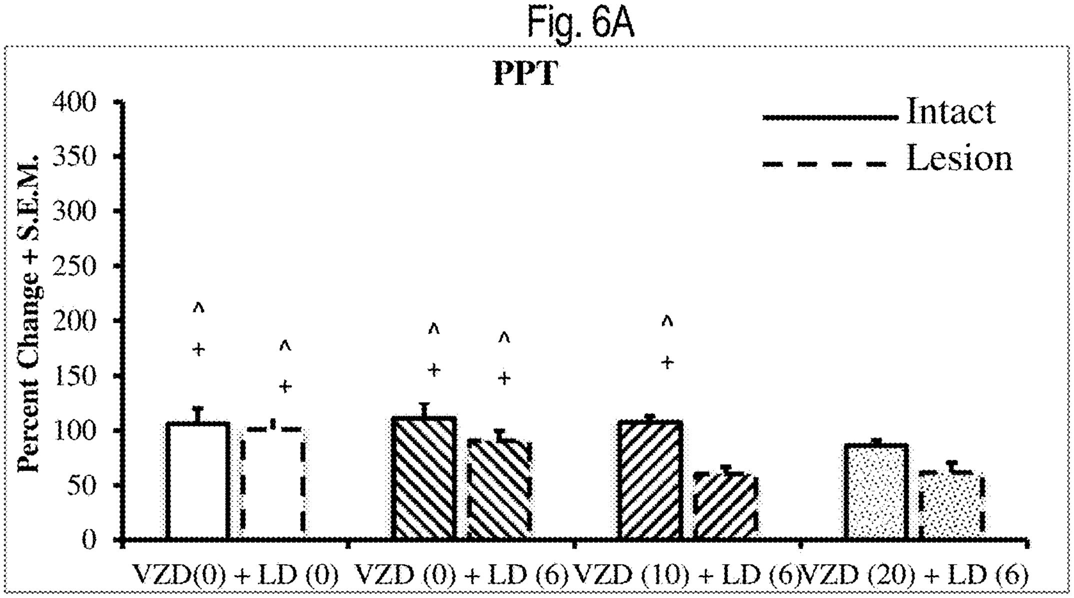
Figure 6C:
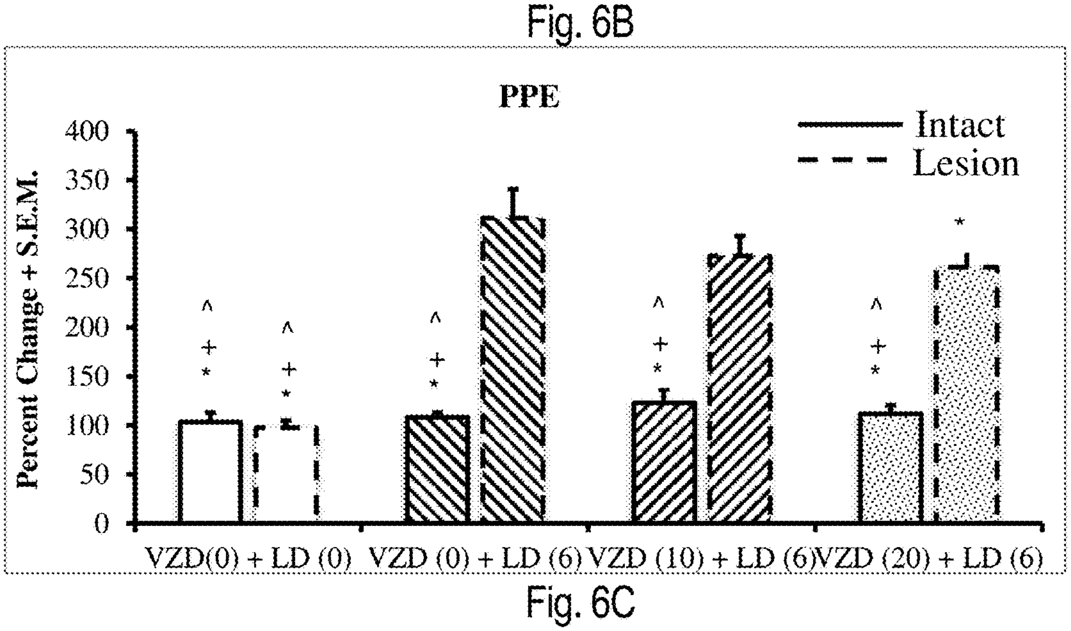
Figure 6D:
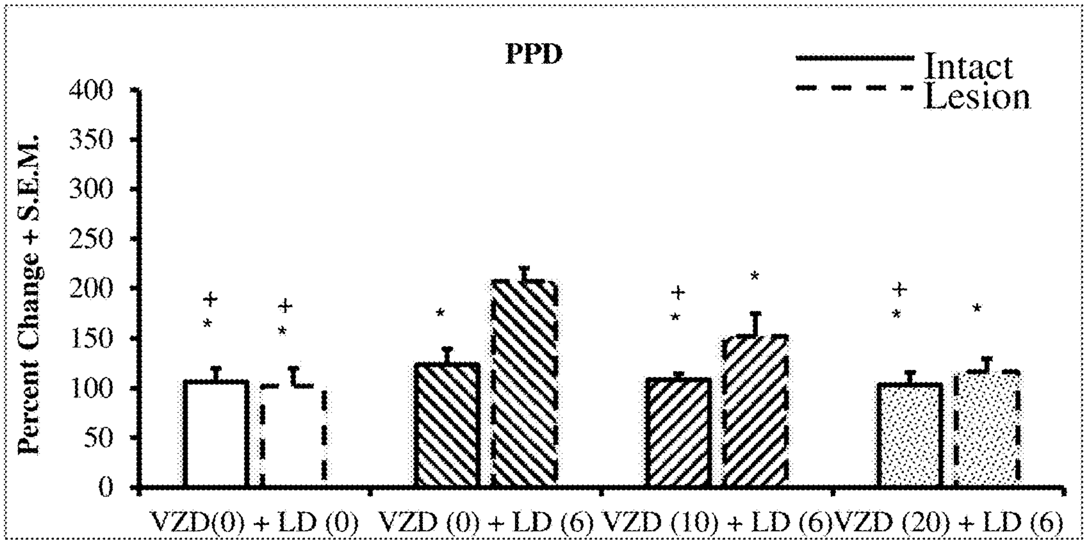
Figure 6E:
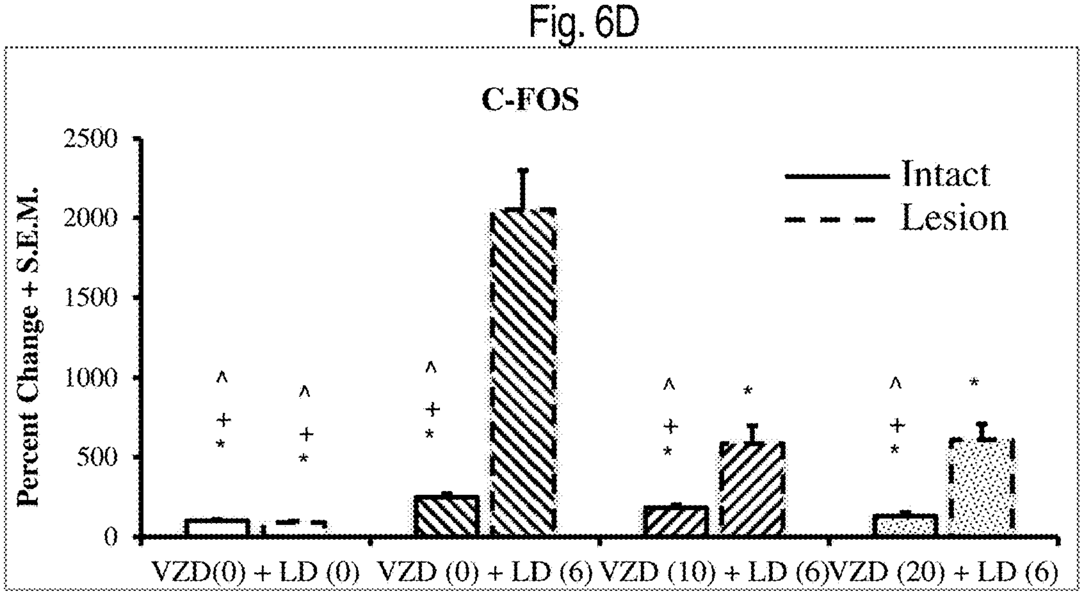
Figure 6F:
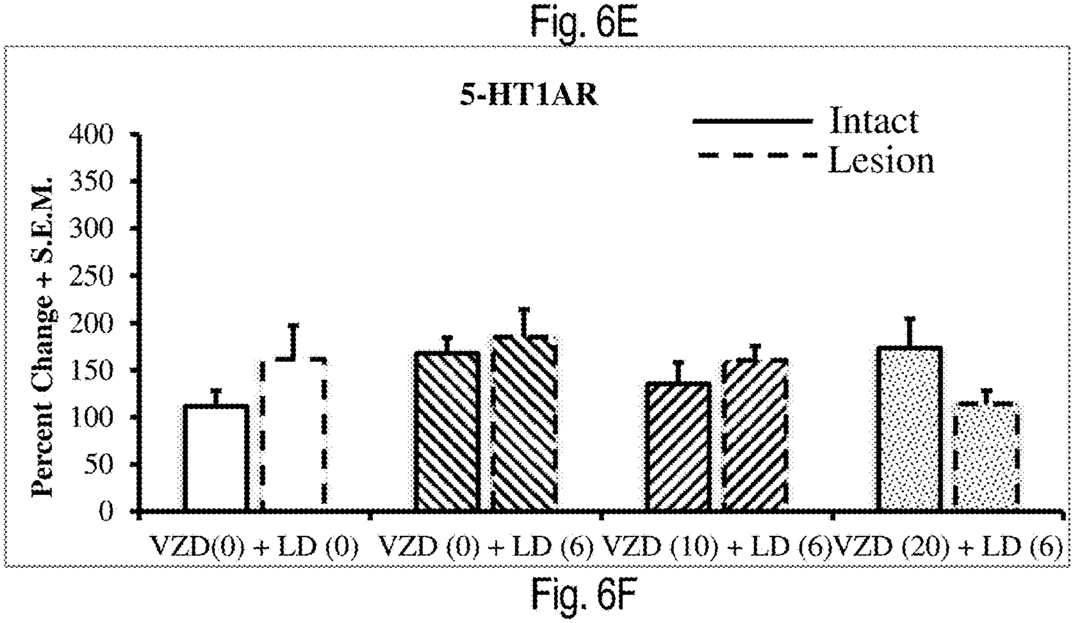

Experiment 2-Chronic Vilazodone blocks LID development: In Experiment 2, the ability of Vilazodone to prevent L-DOPA-induced striatal c-Fos, PPD and PPE, up-regulation is attenuated by Vilazodone: All animals in Experiment 2 were killed on treatment and striatal tissue was analyzed with Real Time RT-PCR to determine if Vilazodone alters dyskinesia-associated striatal gene expression. A 2×4 (Side ×Treatment) ANOVA revealed similar effect patterns in striatal PPD and c-Fos (Fig.FIGS. 6D and 6E) were similar; with main effects of side (PPD, F1,36=9.87, p=0.002; c-Fos, F1,36=75.44, p=0.00) and treatment (PPD, F3,36=6.56, p=0.0006; c-Fos, F3,36=34.80, p=0.00), as well as significant side×treatment interactions (PPD, F3,36=3.08, p=0.033; c-Fos, F3,36=26.33, p=0.00). Post hoc comparisons revealed that chronic L-DOPA significantly increased PPD in the lesioned *striata* and this was dose-dependently attenuated by Vilazodone (all p<0.05). Likewise, L-DOPA potentiated c-Fos in lesioned striata, which was diminished by either dose of Vilazodone (10 or 20 mg/kg) (all p<0.05). Analysis of striatal PPE revealed significant main effects of treatment (F3,36=13.63, p=0.00) and lesion (F1,36=94.41, p=0.00), with a significant side x treatment interaction (F3,36=11.31, p=0.00; FIG. 6C). L-DOPA treatment significantly increased PPE in the lesioned striata and was modestly, though significantly reduced by 20 mg/kg Vilazodone (all p<0.05). There were no significant effects on GAPDH (FIG. 6A) or 5-HT1AR mRNA (FIG. 6F).

Figure 4A:
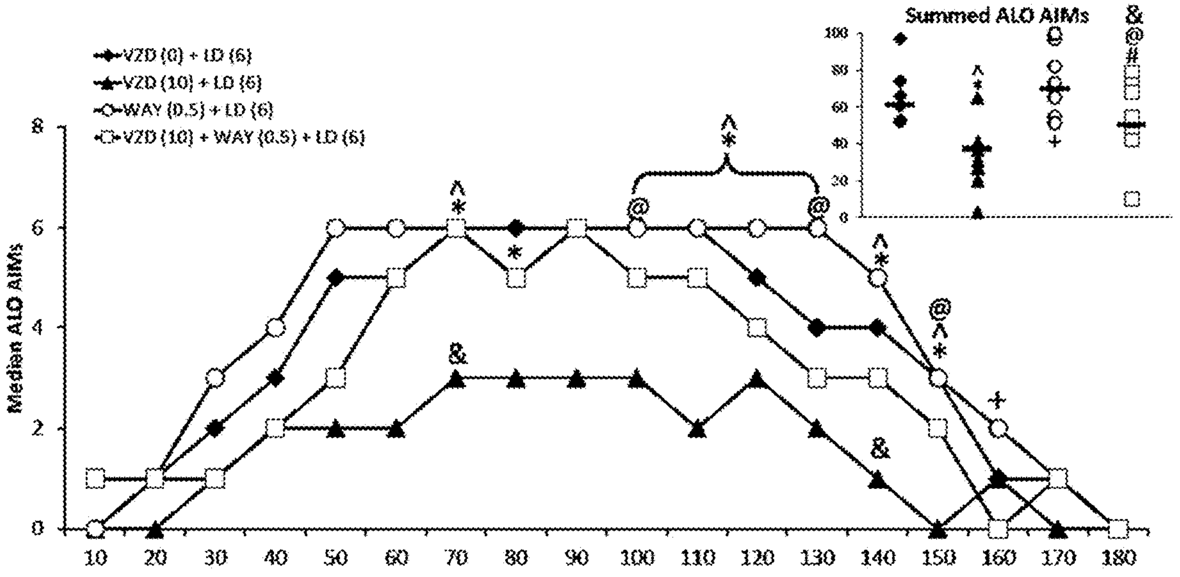
FIGS. 4A and 4B show contribution of 5-HT1A and 5-HT1B receptors (5-HT1AR and 5-HT1BR) in Vilazodone's (VZD) effects against L-DOPA (LD)-induced abnormal involuntary movements (AIMs). In each study, the LD-primed rats received (FIG. 4A) the 5-HT1AR antagonist WAY100635 [WAY; 0 or 0.5 mg/kg, s.c.] or (FIG. 4B) the 5-HT1BR antagonist NAS [NAS; 0 or 0.3 mg/kg, s.c.]) 5 min prior to VZD (0 or 10 mg/kg, s.c.) injected 5 min prior to LD (6 mg/kg, s.c.) in a within-subjects counterbalanced design. ALO AIMs were evaluated and are shown for every 10 min for 3 h after LD administration. Values are expressed as medians and summed total ALO AIMs for individual rats are shown in the inset. * p<0.05 VZD (0)+LD (6) vs. VZD (10)+LD (6); +p<0.05 VZD (0)+LD (6) vs antagonist (WAY or NAS)+LD (6); ^p<0.05 VZD (10)+LD (6) vs. antagonist (WAY or NAS)+LD (6); @p<0.05 antagonist+LD (6) vs. VZD (10)+antagonist+LD (6); &p<0.05 VZD (10)+LD (6) vs. VZD (10)+antagonist+LD (6); #p<0.05 VZD (0)+LD (6) vs. VZD (10)+antagonist+LD (6).

Experiment 3-Vilazodone works via 5-HT1AR but not 5-HT1BR: Pharmacologic antagonism of 5-HT1Rs was used to understand Vilazodone anti-LID efficacy. Testing 5-HT1AR contributions, analyses of summed ALO scores revealed a main effect of treatment on LID (x2, (3)>17.76, p=0.0005; FIG. 4A). Vilazodone (10) significantly reduced ALO AIMs, compared to Vilazodone vehicle (Z=2.6655, p=0.008). Importantly, WAY100635 (WAY 0.5) partially reversed the anti-dyskinetic efficacy of Vilazodone (10) when co-administered (Z=1.95, p=0.05). Time course analysis revealed that Vilazodone reduced peak dyskinesia, but seems have little effect on LID duration (all x2, (3)>16.03, all p<0.05; FIG. 4A).

Figure 4B:
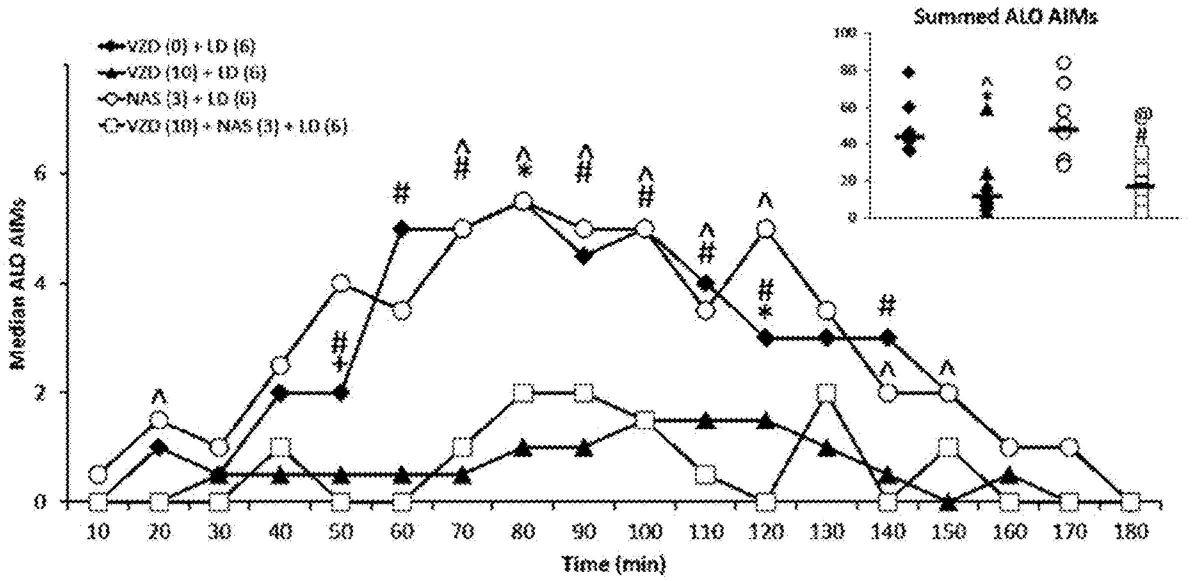
Figure 5:
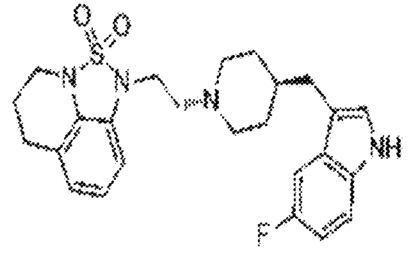
FIG. 5 illustrates 9 molecular scaffolds identified by combinatorial virtual screening methods to target 5-$HT_{1A}$ and SERT.
Figure 5:
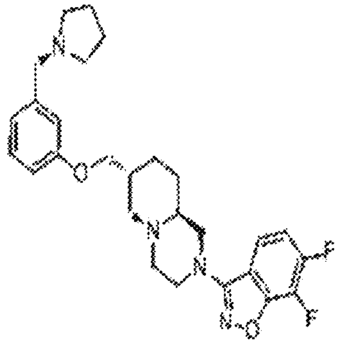
Figure 5:
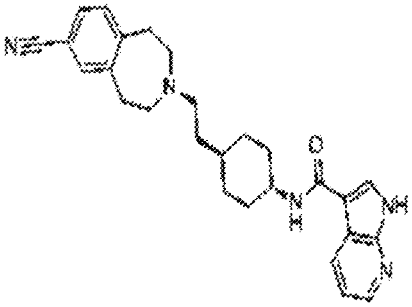
Figure 5:
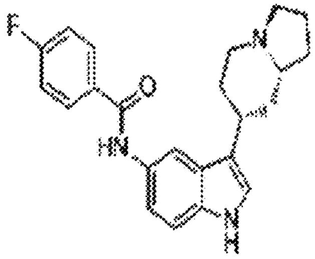
Figure 5:
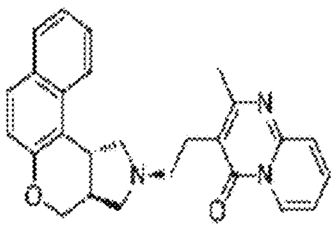
Figure 5:
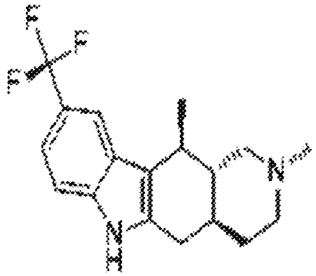
Figure 5:
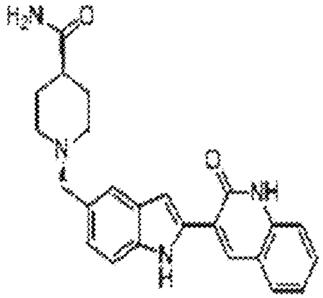
Figure 5:
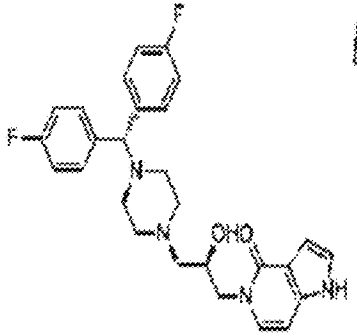
Figure 5:
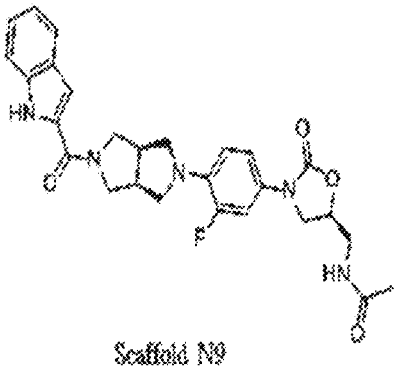

When investigating 5-HT1BR, a main effect of treatment (x2, (3)=15.45, p=0.001; FIG. 4B) revealed that Vilazodone significantly reduced ALO AIMs compared to vehicle (Z=−2.38, p=0.017), and NAS-181 alone (NAS; Z=−2.38, p=0.017). Importantly, NAS did not significantly alter AIMs or their reduction by Vilazodone.

DISCUSSION

Aberrant serotonergic neurotransmission is associated with LID, yet loss of L-DOPA efficacy and side effects have hindered clinical translation of 5-HT compounds. Independently, SERT or 5-HT1AR convey beneficial anti-dyskinetic effects, but prior studies have not simultaneously targeted both sites to optimize their application. Vilazodone, acting through both SERT and 5-HT1AR, dramatically reduces LID development and expression, while maintaining or with chronic administration even improving the pro-motor benefits of L-DOPA. Moreover, chronic Vilazodone attenuates aberrant striatal monoamine signaling, c-Fos mRNA, and PPD mRNA associated with LID.

Throughout chronic Vilazodone treatment, LID and motor performance were evaluated to characterize potential therapeutic efficacy. In L-DOPA-primed and L-DOPA-naïve rodents, Vilazodone treatment stably reduced AIMs. Within a week of treatment, Vilazodone 10 mg/kg also facilitated stepping improvements, the effective pre-clinical anti-depressant dose (Oosting et al., 2016). While other 5-HT compounds suppress experimental LID, loss of L-DOPA efficacy, 5-HT side effects, have hindered therapeutic application (Conti et al., 2014; Fidalgo et al., 2015; Iravani et al., 2006; Lindenbach et al., 2015). Compound selectivity, dose, and timing relative to L-DOPA treatment produce variable and limited clinical efficacy (Dell'Agnello et al., 2001; Mazzucchi et al., 2015). With respect to 5-HT strategies, timing is of importance. Similar to SSRIs like citalopram and paroxetine, Vilazodone treatment acutely suppressed L-DOPA-induced motor improvements (Conti et al., 2014; Fidalgo et al., 2015), but this was transient and side effects, like 5-HT syndrome, weren't observed at any time point (Lindenbach et al., 2015). Indeed, effective adjuvant strategies will require chronic administration, which will change 5-HT neurotransmission. For example, emerging improvements in stepping may have occurred through 5-HT1AR desensitization (Ashby Jr et al., 2013; El Mansari et al., 2015). Thus, it is possible that chronic Vilazodone stimulation of DRN 5-HT1ARs normalized DA efflux without compromising movement as previously seen (Iravani et al., 2006; Goetz et al., 2007; Bezard et al., 2013).

Striatal neurochemistry was assayed after chronic treatment to isolate Vilazodone's mechanism of action. Traditional SSRI and 5-HT1A agonist effects on LID have been attributed to both short-term alterations in DAergic neurotransmission and long-term neuroplasticity. Prior work has shown that in dyskinetic rat, chronic citalopram-L-DOPA co-administration increases striatal DA over L-DOPA treatment alone (Conti et al., 2014). The 5-HT1AR agonist buspirone reportedly normalizes extracellular DA following L-DOPA administration (Politis et al., 2014). In the current work, HPLC analysis revealed that, as expected, 6—OHDA MFB lesions significantly depleted striatal DA values, but only Vilazodone-L-DOPA co-treatment significantly increased striatal DA, compared to vehicle, similar to experiments with citalopram (Conti et al., 2014). Although these effects were observed in post-mortem tissue, Kannari et al. (2006) demonstrated that in vivo local SERT blockade led to increased extracellular striatal DA after L-DOPA treatment. This effect contributes to the observed maintenance of L-DOPA's motor facilitation with chronic Vilazodone administration. Of note, L-DOPA also resulted in significantly increased levels of DA and DOPAC in the DRN, reflecting the global compensatory role of 5-HTergic neurons in taking up L-DOPA and converting it to DA for release (Arai et al., 1996; Navailles et al., 2010; Eskow-Jaunarajs et al., 2012). Importantly, Vilazodone also had significant effects on 5-HT neurotransmission, significantly attenuating striatal 5-HIAA and reducing DRN 5-HT turnover. These results suggest reduced 5-HT reuptake and metabolism, a common feature of chronic SSRI administration in rodents, non-human primates, and humans (De *Bellis* et al., 1993; Honig et al., 2009; Kreiss and Lucki, 1995; Smith et al., 2000). In fact, Vilazodone-induced elevations in raphe 5-HT levels may elicit anti-dyskinetic actions of endogenous 5-HT at raphe 5-HT1AR autoreceptors (Eskow et al., 2009). The 5-HT1AR antagonist WAY100635 partially reversed the anti-LID efficacy of Vilazodone and other SSRIs, like citalopram (Conti et al., 2014). While a prior work suggests that co-stimulation of 5-HT1AR and 5-HT1B receptors can synergistically reduce LID (Muñoz et al., 2008; Svenningsson et al., 2015), Vilazodone, despite increasing endogenous 5-HT, doesn't seem to act through this mechanism. NAS-181, a selective 5-HT1B antagonist, failed to reverse Vilazodone's anti-dyskinetic effects.

c-Fos mRNA increased in the dorsal striatum following chronic L-DOPA treatment (Bishop et al., 2009; Lopez et al., 2001; Mura et al., 2002). Vilazodone attenuated this dyskinesiogenic c-Fos induction, a key feature of anti-dyskinetic compounds (Bishop et al., 2009; Cenci, 2002; Lindenbach et al., 2011). Since c-Fos does not provide striatal pathway specificity, the opioid pre-cursors PPD and PPE, associated with D1R direct and D2R indirect pathway activity, respectively, were also measured (Gerfen et al., 1990; Sgroi et al., 2016). LID is associated with D1R direct pathway overactivity and increased PPD mRNA expression is consistently observed in DA-lesioned, L-DOPA-treated *striata* (Aubert et al., 2005; Bishop et al., 2009; Gross et al., 2003; Lindenbach et al., 2011; Tamim et al., 2010). L-DOPA (6 mg/kg) increases striatal PPD, compared to sham animals, and, more importantly is normalized by Vilazodone co-treatment. The role of D2R-coupled indirect pathway activity in LID is less clear (Politis et al., 2017). Striatal DA loss is associated with increased striatal PPE mRNA expression in rodents and non-human primates and this is exacerbated in the off-state following L-DOPA priming (Ravenscroft et al., 2004; Tamim et al., 2010). DA-lesioned L-DOPA-treated rats displayed striatal PPE mRNA upregulation. Only Vilazodone (20 mg/kg) attenuated this increase, suggesting an indirect pathway-independent mechanism for reducing LID. While Vilazodone significantly altered markers of striatal activation, it did not affect striatal 5-HT1AR mRNA. However, Real-Time RT-PCR does not measure protein levels or cellular localization so Vilazodone may alter 5-HT1AR expression post-transcriptionally, or alter receptor trafficking and sensitivity.

SERT and 5-HT1AR are well-characterized anti-dyskinetic targets. Vilazodone's unique pharmacologic profile predicted robust anti-LID efficacy. Vilazodone-L-DOPA co-administration significantly suppressed LID development and expression over a 3-week period with minimal effects on L-DOPA-induced motor facilitation. Vilazodone reduces LID via multiple points of neural articulation. Neurochemically, Vilazodone appears to maintain striatal L-DOPA-derived DA while augmenting aberrant signaling via endogenous 5-HT1AR neurotransmission, providing pro-motor and anti-dyskinetic effects coincidently. Such actions modulate downstream dyskinesia-associated striatal gene expression.

Example 2

6—OHDA-induced dopaminergic lesions: Adult male Sprague-Dawley rats were randomly assigned to groups receiving either a 6—OHDA or sham lesion. All rats received desipramine (10 mg/kg i.p.) 30 min prior to surgery to prevent the lesioning of norepinephrine neurons by 6—OHDA. A single injection of 6-OHDA (8 μg of 6—OHDA free base in 4 μl of 0.1% ascorbic acid) was delivered into the right medial forebrain bundle (coordinates taken from bregma: −4.3 mm AP, 1.6 mm ML,-8.3 mm DV). The same experimental treatment was performed for the sham-operated rats using vehicle (4 μl of 0.1% ascorbic acid). A standard stepping test was used to evaluate the effectiveness of the 6—OHDA lesion. Rats exhibiting a significant lesion-induced decrease in adjusting steps (>75%) in the forelimb contralateral to the lesion were selected for further study. [Altwal 2019].

Unilateral 6—OHDA-lesioned rats modeling PD were treated with either vehicle and L-DOPA (5.0 mg/kg), vilazodone (10 mg/kg) and L-DOPA (5.0 mg/kg), or escitalopram (12.5 mg/kg) and L-DOPA (5.0 mg/kg). Rats were treated for 5 consecutive days/week (Mon-Fri), for 2 weeks. On the second day of each week, stepping tests were performed prior to drug administration, and 60 minutes post L-DOPA treatment.

Figure 7:
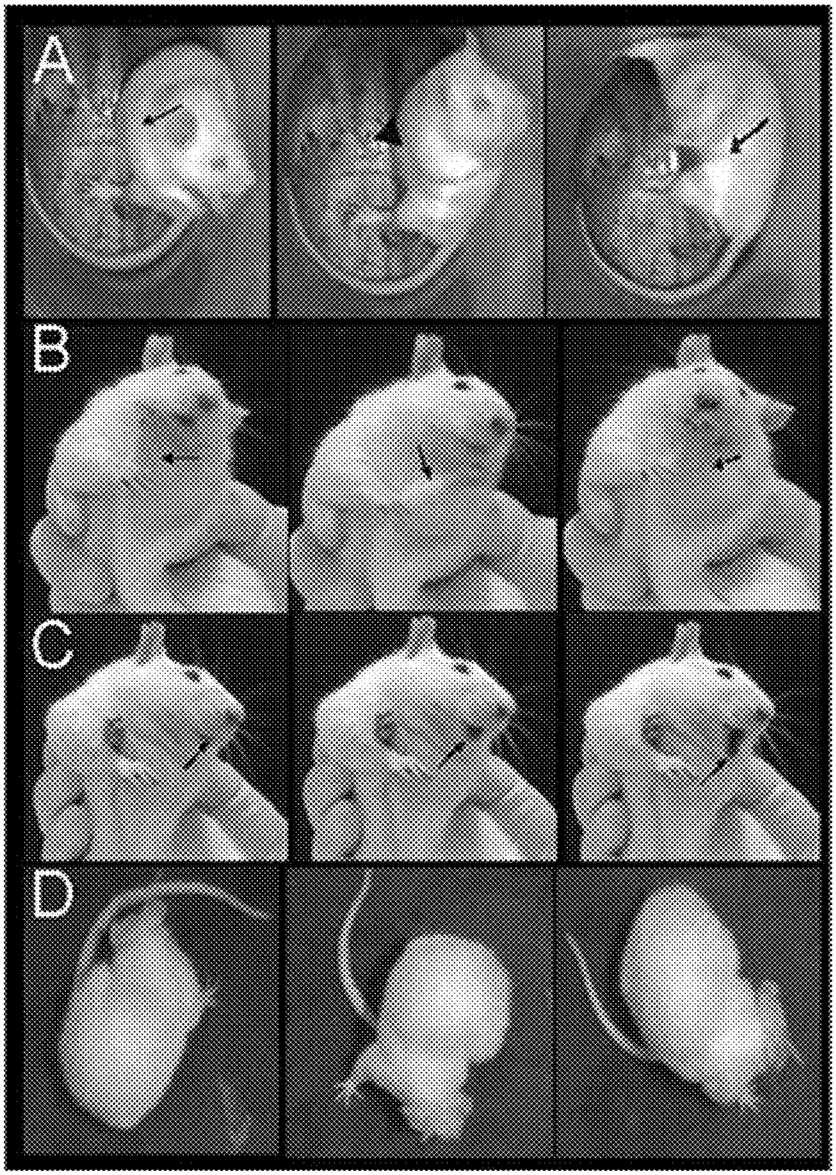
FIGS. 7A-7D (Prior Art) show abnormal involuntary movements following L-DOPA chronic treatment in parkinsonian rats.

All rats were evaluated three times per week for the presence of L-DOPA-induced dyskinesias (LIDs) (Wed-Fri) and once for the stepping test (Tue). LIDs were videotaped (2 min) at 30 min intervals (30-180 min) post-injection. Scores were given over 1 min epochs and classified as axial, limb, orolingual and locomotive. FIG. 7 shows abnormal involuntary movements following L-DOPA chronic treatment in parkinsonian rats.

The severity of each LID was scored using a standard scale. Each dyskinetic behavior was given an intensity and frequency score, which were then multiplied. The average sum of the products of each LID was determined in each animal. These data were then analyzed using a two-way RM ANOVA with a Tukey post-hoc test and outcomes exhibiting p-values of <0.05 were considered significant.

Escitalopram pretreatment significantly reduced LIDs severity following L-DOPA injection of 5 mg/kg. However, it affected L-DOPA therapeutic efficacy. Vilazodone pretreatment had the most significant effect on attenuating LIDs in 6—OHDA lesioned rats, and had no effects on forelimb akinesia or L-DOPA-induced prokinetic effects. Blocking the 5-HT1A partial agonism property of vilazodone using WAY100635 reverses the beneficial effects of vilazodone on LIDs. Vilazodone beneficial effects on LIDs is likely as a result of normalizing corticostriatal glutamatergic drive and GABAergic output of MSNs, as shown in electrophysiological studies.

Figures 8A, 8B, 8C:
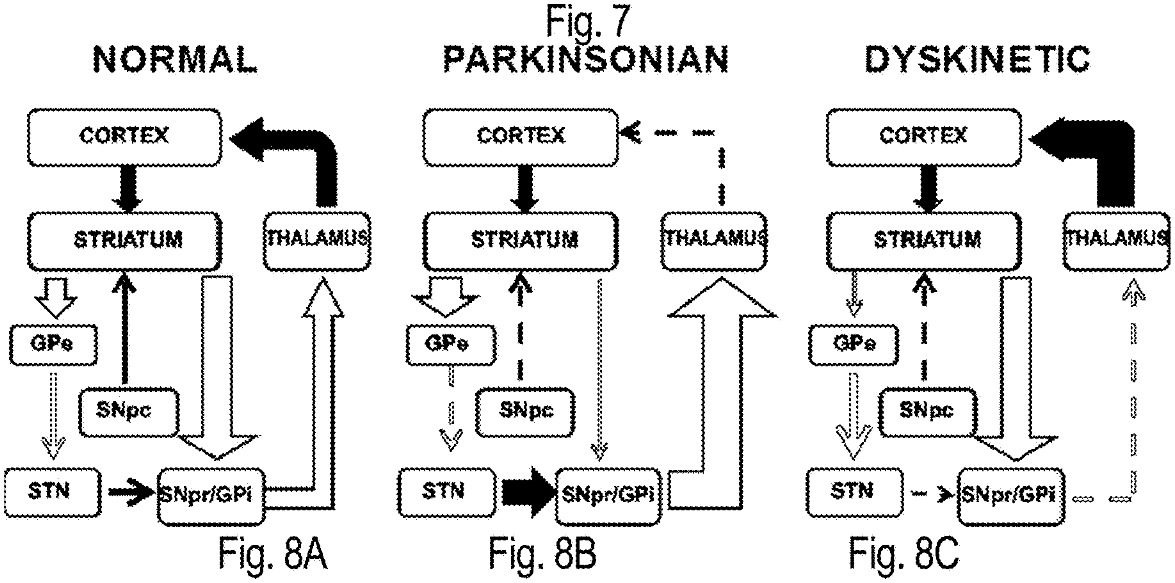
FIGS. 8A-8C shows the impact of vilazodone inhibition on striatal output and basal ganglia function in dyskinetic parkinsonian animals. Arrows=inhibitory input; dashed arrows=compromised function.
Figure 9A:
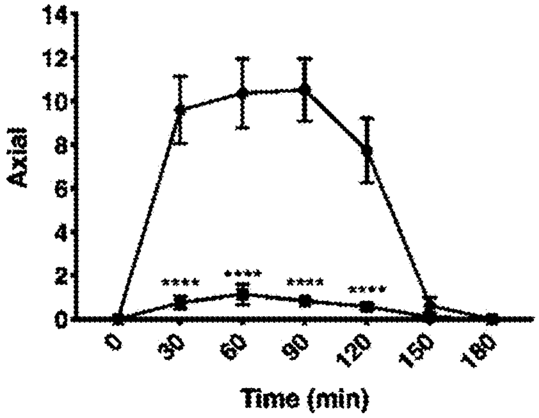
FIGS. 9A-9D and FIG. 10 show co-administration of escitalopram with L-DOPA attenuates LIDs, but affects its therapeutic efficacy.
Figure 9B:
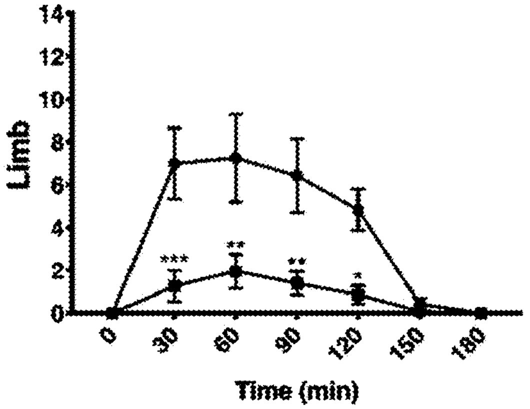
Figure 9C:
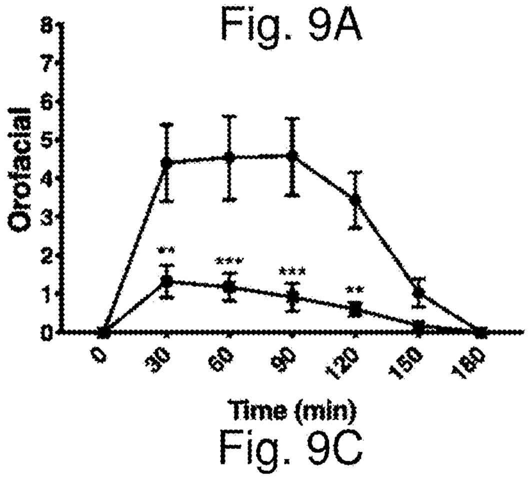
Figure 9D:
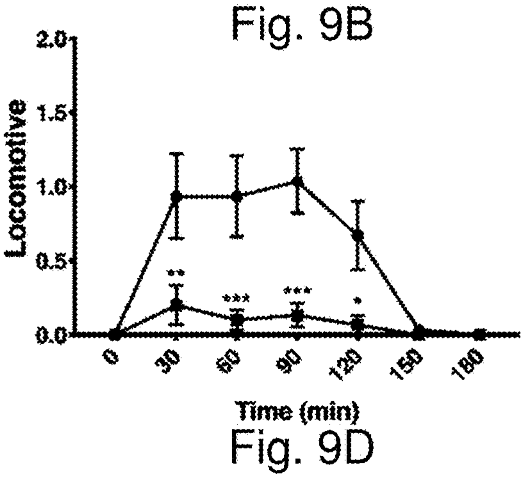
Figure 10:
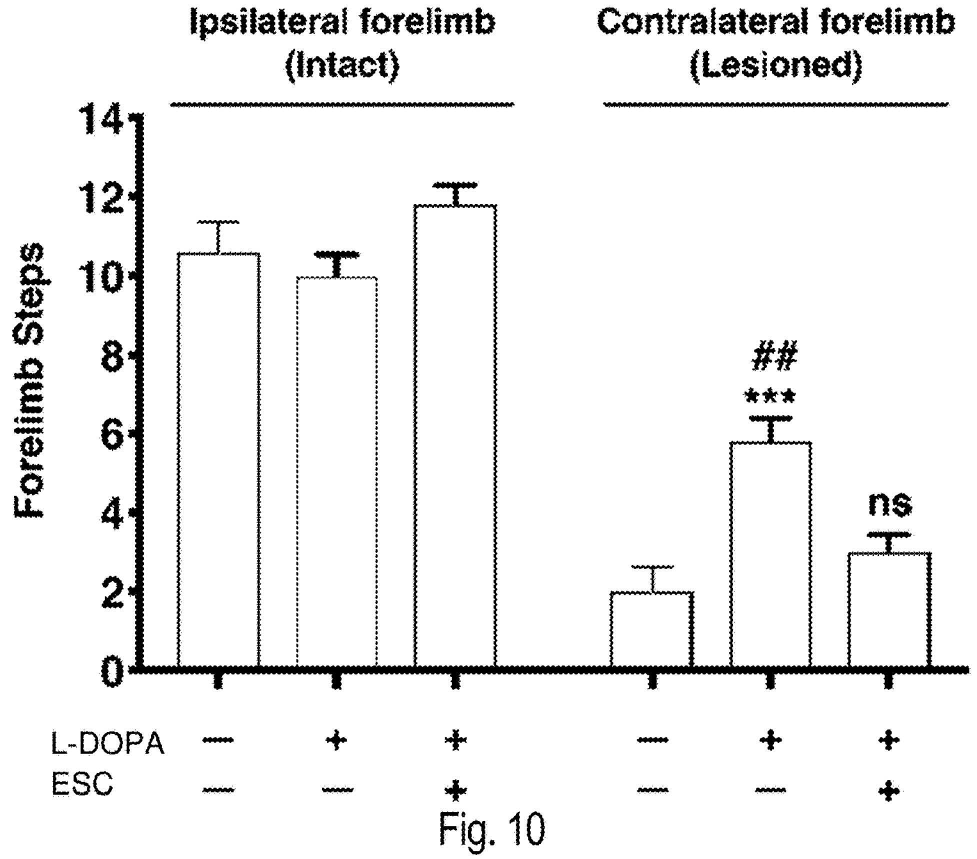
Figure 11A:
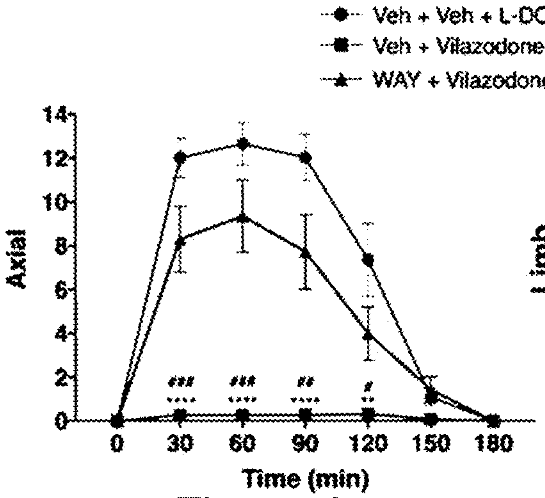
FIGS. 11A-11F shows co-administration of vilazodone with L-DOPA attenuates LIDs significantly, without reducing the prokinetic effects of L-DOPA. 5HT1A antagonist reverse these beneficial effects of vilazodone.
Figure 11B:
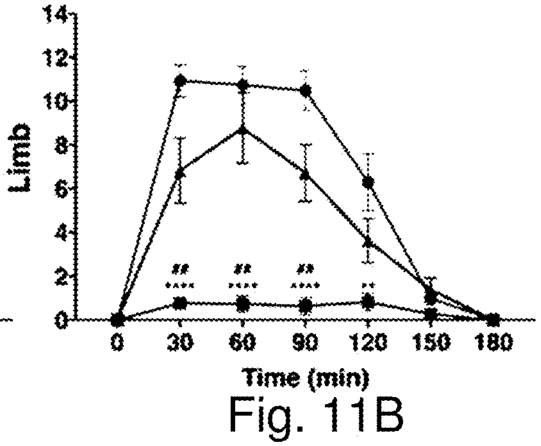
Figure 11C:
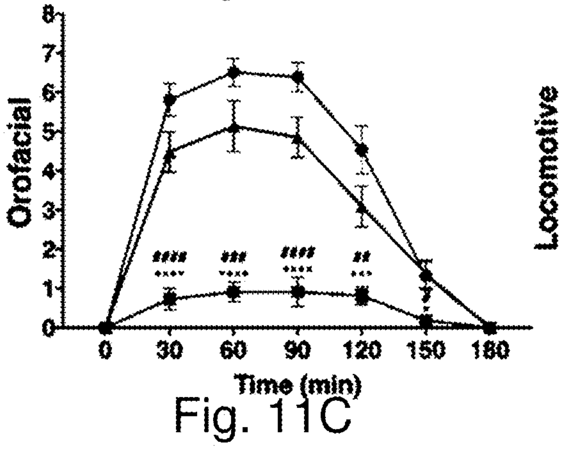
Figure 11D:
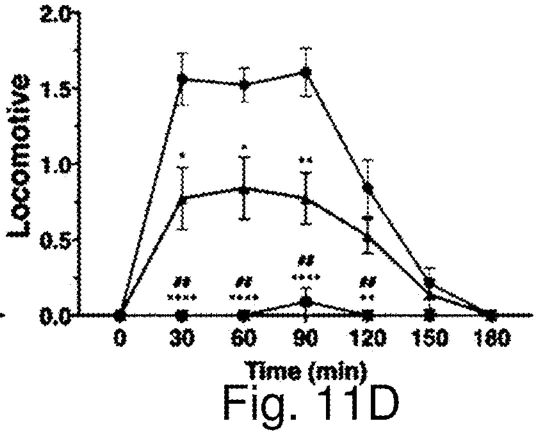
Figure 11E:
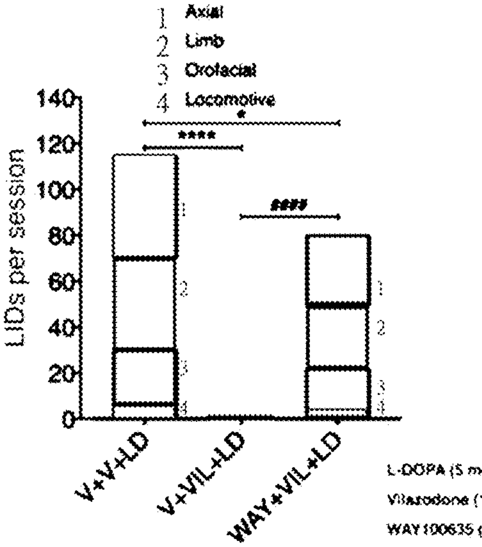
Figure 11F:
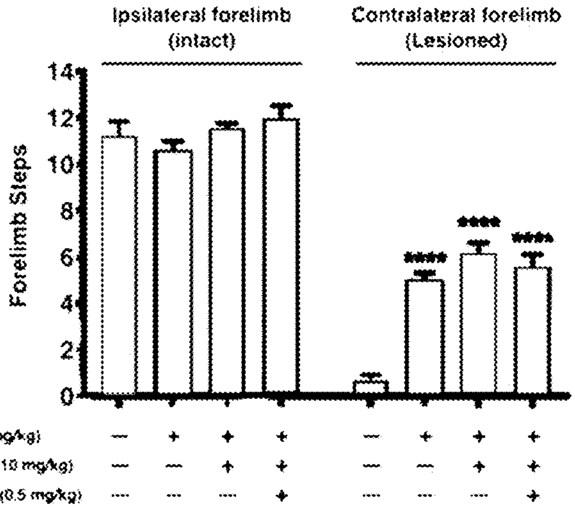
Figure 12A:
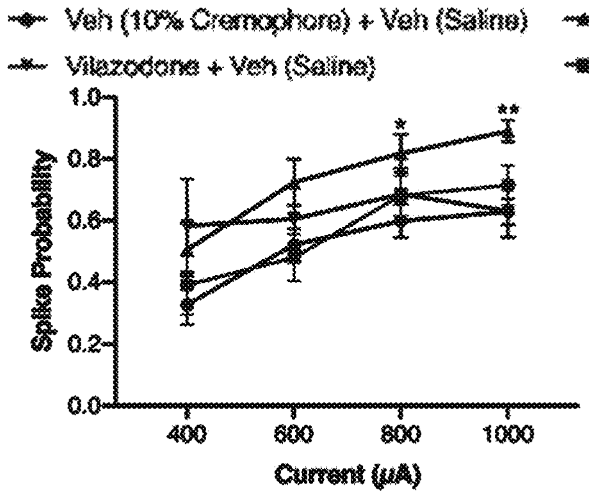
FIGS. 12A-12H shows vilazodone co-administration normalizes spike probability and onset latency in dyskinetic 6—OHDA-lesioned rats.
Figure 12B:
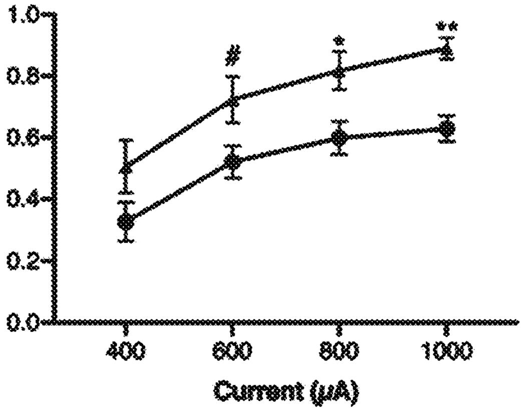
Figure 12C:
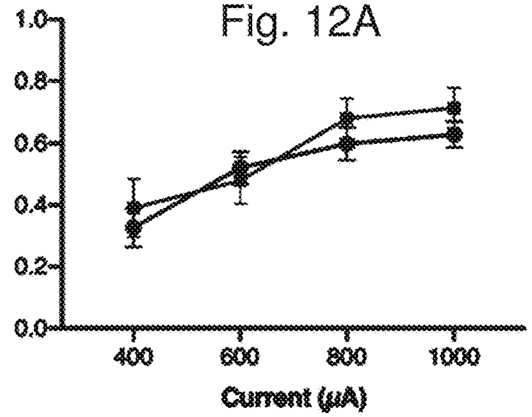
Figure 12D:
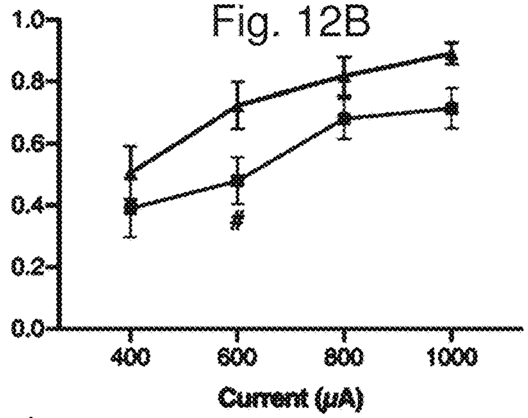
Figure 12E:
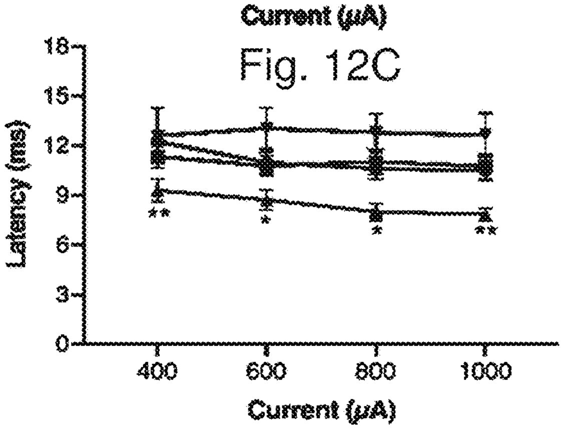
Figure 12F:
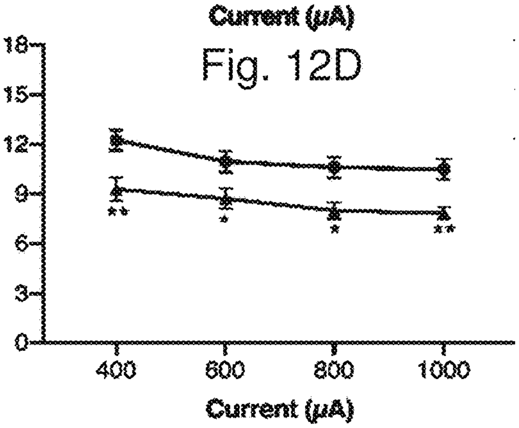
Figure 12G:
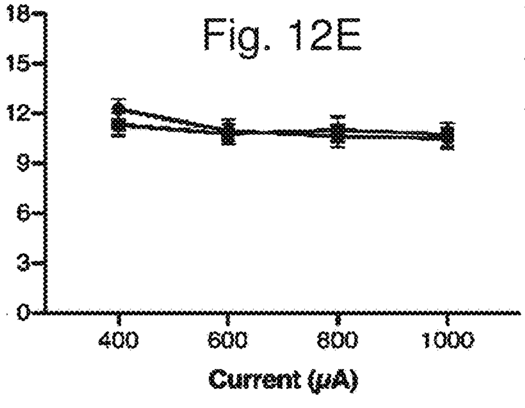
Figure 12H:
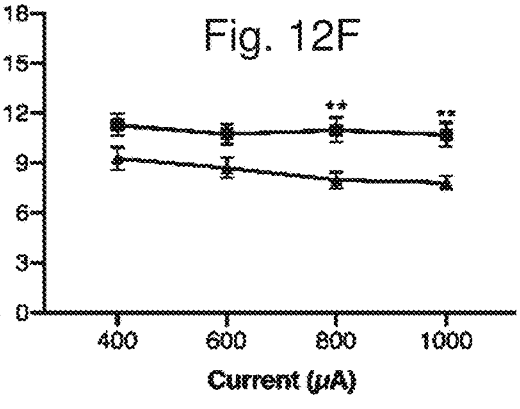

FIGS. 8A-8C show the impact of Vilazodone on striatal output and basal ganglia function in dyskinetic parkinsonian animals. FIG. 8A shows a model of the intact basal ganglia. FIG. 8B shows the effects of dopamine depletion, like that seen in Parkinson's disease. FIG. 8C shows a proposed effect of vilazodone inhibition on direct striatal output (se dashed circle) and thus basal ganglia-thalamocortical circuits in parkinsonian rats. Cortex, thalamus, STN afferent excitatory input; SNpriGPI, striatum, SNpc, SNpr/GPI, GPc afferent inhibitory. Arrows represent inhibitory input; dashed arrows represent compromised function.

FIGS. 9A-9D and FIG. 10 show co-administration of escitalopram with L-DOPA attenuates LIDs, but affects its therapeutic efficacy.

FIGS. 11A-11F show co-administration of vilazodone with L-DOPA attenuates LIDs significantly, without reducing the prokinetic effects of L-DOPA. 5HT1A antagonist reverse these beneficial effects of vilazodone.

Figure 13:
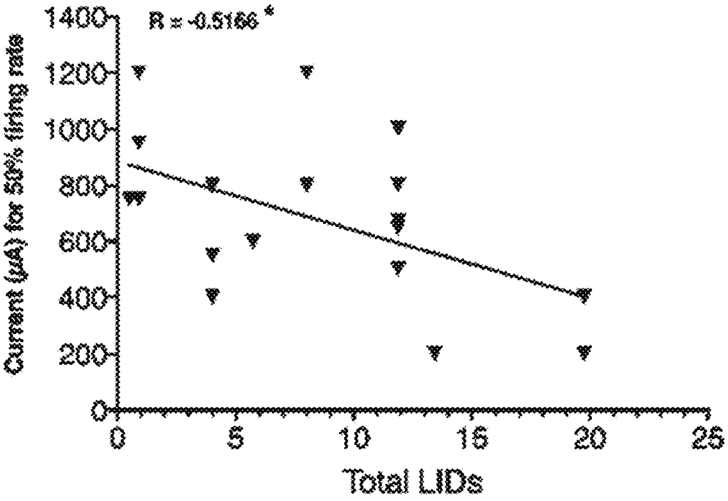
FIG. 13 shows that the current needed to stimulate a 50% firing rate in MSNs of dyskinetic 6-OHDA-lesioned rats is negatively correlated with total LIDs score, after vilazodone co-administration.

FIGS. 12A-12H shows vilazodone co-administration normalizes spike probability and onset latency in dyskinetic 6—OHDA-lesioned rats. FIG. 13 shows that the current needed to stimulate a 50% firing rate in MSNs of dyskinetic 6—OHDA-lesioned rats is negatively correlated with total LIDs score, after vilazodone co-administration.

Example 3

[Sellnow 2019] report that the hallmark motor symptoms in Parkinson's disease (PD) arise following substantial dopaminergic denervation within the striatum. Denervation results from the death of tyrosine hydroxylase (TH) expressing DA neurons of the substantia nigra pars *compacta* (SNc) as the disease progresses [Hoehn 1967, Kordower 2013]. The lack of proper DA signaling to the striatum creates an imbalance of the basal ganglia motor circuit, thus, causing bradykinesia, rigidity, tremor, and gait problems characteristic of PD [Goldman 2014]. Current treatment strategies, while not able to affect disease progression, are aimed at treating these primary motor symptoms. Since the late 1960s, L-3,4-dihydroxyphenylalanine (levodopa or L-DOPA) has been used as a catecholamine replacement therapy to alleviate motor symptoms [Cotzias 1967]. L-DOPA remains the gold-standard pharmacological treatment for PD.

While effective initially, the therapeutic window of L-DOPA narrows with the continuous loss of SNc neurons as the disease progresses, and higher doses are required to maintain the anti-akinetic effects of L-DOPA. Moreover, chronic treatment with L-DOPA leads to the development of L-DOPA-induced dyskinesias (LID), a series of motor symptoms distinct and independent from the PD motor deficits being treated (reviewed in [Bastide 2015]). These symptoms, comprised of painful and disrupting movements including hyperkinesia, dystonia, and chorea, occur in a majority of PD patients, developing in up to 50% of patients within 5 years of beginning treatment, and up to 90% of patients within 10 years [Ahlskog 2001] [Manson 2012].

Studies show that LID development is a multifaceted process. However, it is largely agreed upon that the intermittent oral dosing of L-DOPA results in large variations in extracellular DA. Ultimately, this pulsatile release of DA, together with the denervated state of the striatum, results in maladaptive molecular and structural changes in the DA-responsive neurons of the striatum, specifically medium spiny neurons (MSNs), leading to altered basal ganglia signaling (reviewed in [Cenci 2010]). Given the extreme nigrostriatal denervation at the time of diagnosis [Kordower 2013], the actual source of striatal DA following L-DOPA administration has been debated over the past half century. The leading hypothesis is that uptake of L-DOPA and its subsequent dysregulated metabolism to DA, and release by serotonergic 5-hydroxytryptamine (5-HT) neurons in the dorsal raphe nucleus (DRN) may be linked to dyskinesogenesis (reviewed in [De Deurwaerdère 2016]). These neurons express aromatic L-amino acid decarboxylase (AADC) and can therefore convert L-DOPA into DA. However, DRN neurons do not express the regulatory mechanisms to monitor and control DA synthesis and release into the synapse, allowing for the unregulated release of DA into a hypersensitized striatum [Maeda 1999]. Additionally, serotonergic innervation of the striatum increases substantially following DA denervation, allowing the majority of L-DOPA to be metabolized and released as DA by serotonergic terminals [Lundblad 2002] [Maeda 2005] [Roussakis 2016] [Rylander 2010] [Yamada 2007]. This overwhelming exposure of the DA-depleted striatal MSNs to exogenous DA is hypothesized to be a large contributor to LID. In fact, studies in rats show that specifically lesioning the DRN [Carta 2007] [Eskow 2009] or co-administering L-DOPA with 5-HT1 receptor agonists [Bezard 2013] [Ghiglieri 2016] [Meadows 2017] [Politis 2014], effectively reduces or eliminates LID.

Normal regulation of DA signaling is mediated presynaptically primarily through the DA active transporter (DAT) and the DA autoreceptor. DAT directly regulates the levels of DA in the synapse by transporting synaptic DA back into the terminal. The dopamine autoreceptor (D2Rs) is an isoform of the D2 DA receptor (D2RL) missing 29 amino acids from the third intracellular loop [Dal Toso 1989]. D2Rs detects synaptic DA levels and regulates DA signaling in three ways, 1) by downregulating DA production through TH regulation, 2) regulation of reuptake through DAT, and 3) by directly inhibiting DA release (reviewed in [Ford 2014]). Each of these modes of action are mediated through the inhibitory Gi alpha protein signaling pathways following D2Rs activation.

These canonical G-protein-coupled receptor (GPCR) signaling pathways similarly inhibit serotonergic signaling in DRN neurons through 5-HT1 autoreceptor activation [Harrington 1988] [Okada Previous studies using 5-HT1 agonists show promising reductions in LID. Unfortunately, these drugs can negate the anti-parkinsonian therapeutic benefits of L-DOPA animal models, and in some cases worsen PD symptoms in clinical trials [Cheshire 2012] [Iravani 2006] [Kannari 2002] [Olanow 2004].

While current evidence suggests a crucial role of serotonergic input and activity in LID, direct evidence of the abnormal dopaminergic neurotransmission and dysregulated DA release is lacking. Unequivocal evidence is provided for the role of serotonergic DA neurotransmission in dyskinesogenesis and examine a novel therapeutic approach of modulating this non-physiological adaptation in the parkinsonian brain. To do this, serotonergic neurons were provided with DAergic regulatory mechanisms by ectopically expressing the D2Rs autoreceptor in the DRN of parkinsonian 6—OHDA lesioned rats, and evaluated the effect of ectopic D2Rs activity on L-DOPA efficacy, LID formation, response to DA agonists, and striatal DA release.

Adeno-associated virus production: The D2Rs and GFP coding sequences were cloned into AAV genomes under the control of the chicken β-actin/cytomegalovirus (CBA/CMV) promoter for ubiquitous and robust expression. AAV 2/9 was produced via triple-transfection of HEK 293T cells with the genome and helper plasmids. Virus was recovered from cells using freeze-thaw cycles, purified using an iodixanol gradient (Optiprep Density Gradient, Sigma-Aldrich, St. Louis, MO), followed by buffer exchange and concentration using concentrator columns (Orbital Biosciences, Topsfield, MA) as described previously [Benskey 2016 (B)]. The viral titer was determined using digital droplet PCR (ddPCR) and normalized to $1\times10^{13}$ vector genomes (pg)/ml using Balanced Salt Solution (Sigma-Aldrich, St. Louis, MO).

Animals and surgeries: Studies were performed using adult male Fischer F344 rats (200-220g upon arrival; Charles River, Wilmington, MA).

All 6—OHDA and vector surgeries were performed under 2% isoflurane. After being anesthetized, animals were placed in a stereotaxic frame and were injected using a glass capillary needle fitted to a Hamilton syringe (Hamilton, Reno, NV) [Benskey 2016 (A)]. Three weeks following lesion surgery, animals were tested for spontaneous forepaw use (cylinder test) to estimate lesion efficacy. Vector treatment groups were normalized using forepaw deficits in order to ensure equal lesions between the treatment groups.

For lesion surgeries 5 mg/ml 6—OHDA hydrobromide (Sigma-Aldrich, St. Louis, MO) was prepared in 0.2 mg/ml ascorbic acid immediately prior to the injections. Animals received 2 μl injections of 6—OHDA into the medial forebrain bundle (MFB) (from bregma: Anterior Posterior (AP)-4.3 mm, Medial Lateral (ML)+1.6 mm, Dorsal Ventral (DV)-8.4 mm from skull) and the SNc (from bregma: AP-4.8 mm, ML+1.7 mm, DV-8.0 mm from skull), for a total of 10 ug 6—OHDA per site and 20 ug per animal. The glass needle was lowered to the site and the injection started after 30s. 6—OHDA was injected at a rate of 0.5 μl/minute. The needle was removed 2 minutes after the injection was finished and cleaned between each injection.

Vector delivery was performed 3 weeks following the 6—OHDA lesion via stereotaxic delivery [Benskey 2016 (A)]. A subset of animals (N=7) destined for electrophysiological measures did not receive a 6—OHDA lesion. Using the same procedure as described for the lesion surgeries, animals received a single midline 2 μl injection of virus (AAV2/9-DRs, $1\times10^{13}$ μg/ml; AAV2/9-GFP, $1\times10^{13}$ μg/ml) to the DRN (from bregma: AP-7.8, ML-3.1, DV-7.5 from skull). The stereotaxic arm was positioned in a 30° lateral angle in order to avoid the cerebral aqueduct.

Rats were tested for baseline forepaw adjusting steps. Thereafter, microdialysis cannulation surgery was performed under 2-3% isoflurane in oxygen with the tooth bar set to 5 mm below the interaural line. Five minutes before surgery and 24 h after surgery rats received an injection of Buprinex (0.03 mg/kg, i.p.). A unilateral dorsal striatal-directed cannula (CMA 12 Elite; Stockholm, Sweden) was implanted ipsilateral to lesion (from bregma AP: 1.2 mm; ML: −2.8 mm; DV: −3.7 mm). The cannula was fixed in place by four jeweler's screws, jet liquid, and dental acrylic (Lang Dental, Wheeling, IL). Two weeks following cannulation surgery, rats underwent behavioral testing.

Burr holes (~1 mm in diameter) were drilled in the skull overlying the DRN of non-lesioned rats. Prior to experimentation all animals were anesthetized with urethane (1.5g/kgi.p.) and placed in a stereotaxic apparatus. Bipolar stimulating/recording electrodes were implanted in the frontal cortex and DRN on the right side using a micromanipulator (coordinates from Bregma: AP: 3.2 mm; ML: 0.8 mm lateral; DV: 4.4 mm ventral (frontal cortex) or AP: 7.8 mm;

ML 3.1 mm; DV: 7.5 mm with the manipulator angled 30 degrees toward Bregma) as previously described [Chakroborty 2017].

Abnormal involuntary movement (AIM) ratings and drug treatments: Animals were allowed to recover for 3 weeks following vector injections, and to allow for peak expression of the viral transgene [Reimsnider 2007]. After this time, L-DOPA treatment and abnormal involuntary movement (AIM) scale ratings began (see time line in FIG. 14A). As described previously, the AIM rating scale can be used to evaluate the severity of LID and has been adapted for animal use [Lundblad 2002] [Steece-Collier 2003]. Briefly, AIMs are evaluated by scoring the level of dystonia of the limbs and body, hyperkinesia of the forelimbs, and orolingual movements. Each AIM is given two numerical scores-one indicating the intensity (0=absent, 1=mild, 2=moderate, or 3=severe) and frequency (0=absent, 1=intermittently present for >50% of the observation period, or 3=uninterruptable and present through the entire rating period) [Maries 2006]. Each AIM is given a severity score by multiplying the intensity and frequency, and the total AIM score is a sum of all the behaviors severities. An animal is considered non-dyskinetic with a score of ≤4, as non-dyskinetic parkinsonian rats can display low level AIMs from exhibiting normal chewing behavior and a mild parkinsonian dystonic posture [Zhang 2013].

Figure 14A:
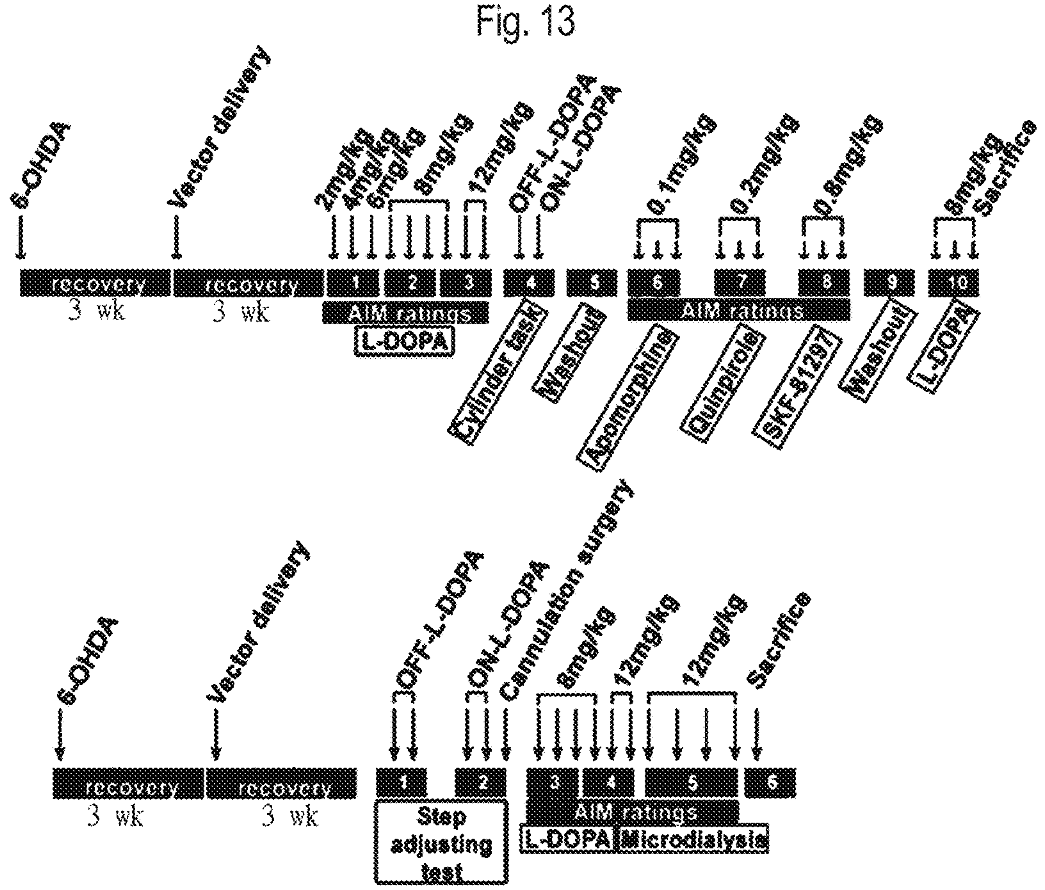
FIGS. 14A-14P show experimental design and model validation.

Animals received subcutaneous injections of L-DOPA/benserazide (Sigma-Aldrich, St. Louis, MO) three times per week and were rated using the AIM scale in 25-min intervals post-injection until all LID behavior had subsided. L-DOPA doses ranged between 2 mg/kg-12 mg/kg (FIG. 14A). Benserazide doses (12 mg/kg) remained constant for all L-DOPA injections. The same injection and rating paradigm was used for AIM evaluations with the non-selective DA agonist apomorphine (0.1 mg/kg, R&D Systems, Minneapolis, MN), the D2/D3 receptor agonist quinpirole (0.2 mg/kg, Sigma-Aldrich, St. Louis, MO) and the D1 receptor agonist SKF-81297 (0.8 mg/kg, Sigma-Aldrich, St. Louis, MO). DA agonist doses were selected based on doses known to induce AIMs in parkinsonian rats [Bhide 2015] [Lindenbach 2015]. Peak AIM scores of DA agonists were determined based off the highest average AIM scores of control animals during the rating period.

Parkinsonian motor evaluation: To assess whether D2Rs viral therapy affects the anti-parkinsonian properties of L-DOPA therapy, parkinsonian motor behavior on and off L-DOPA was evaluated using the cylinder task and the forepaw adjusting steps (FAS) test. Rats with significant lesions perform poorly on both these tests, with impairment to the forepaw contralateral to the lesion that is alleviated with L-DOPA treatment [Chang 1999] [Schallert 2006]. The cylinder task was conducted as previously reported [Manfredsson 2007]. Animals were placed in a clear Plexiglas cylinder on top of a light box for 5 to 7 minutes while being recorded. Each animal was rated by counting ~ 20 weight-bearing forepaw placements on the cylinder (contralateral to the lesion, ipsilateral to the lesion, both) to determine the percentage use of the forepaw contralateral to the lesion, which is derived by dividing the sum of contralateral touches and half of both forepaw touches by the total forepaw touches, and multiplying this number by 100. Trials were performed following the initial L-DOPA treatment (AIM evaluation) period, and tested either off L-DOPA or, on the following day, 50 min after receiving a 6 mg/kg L-DOPA injection (12 mg/kg benserazide).

The FAS test was performed per [Meadows 2017]. Briefly, rats were restrained by an experimenter so that only one forepaw was free to touch the counter. Rats were then dragged laterally along a 90 cm distance over 10 s while a trained rater blind to the experimental condition counted the number of steps. Data are represented as forehand percent intact, which are derived by taking the number of steps taken by the contralateral forehand and dividing it by the ipsilateral forehand, and then multiplying this number by 100. The test was performed over 2 days either off L-DOPA or 60 min following an 8 mg/kg or 12 mg/kg L-DOPA injection.

Tissue collection: Two hours following the final L-DOPA administration, animals from the AIM experimentation were sacrificed via sodium pentobarbital overdose and intracardially perfused with Tyrode's solution (137 mM sodium chloride, 1.8 mM calcium chloride dihydrate, 0.32 mM sodium phosphate monobasic dihydrate, 5.5 mM glucose, 11.9 mM sodium bicarbonate, 2.7 mM potassium chloride). Brains were rapidly removed and coronally hemisected, with the rostral portion of the left and right striatum dissected out and flash frozen in liquid nitrogen for biochemical analysis. The caudal portion of the brain was postfixed for 72 h in 4% paraformaldehyde (PFA) in phosphate-buffered saline and then cryoprotected by saturation in 30% sucrose. Brains were frozen and sectioned coronally at 40 μm thickness using a sliding microtome into free floating sections and stored in cryoprotectant (30% ethylene glycol, 0.8 mM sucrose in 0.5× tris-buffered saline) until further use.

Immunohistochemistry: A 1:6 series of free-floating tissue was stained immunohistochemically for TH (MAB318, MilliporeSigma, Burlington, MA), D2R (AB5084P, MilliporeSigma, Burlington, MA), GFP (AB290, Abcam, Cambridge, United Kingdom), IBA1 (019-19,741, Wako Life Sciences, Richmond, VA), or 5-HT (NT-102, Protos Biotech, New York, NY) using methods previously reported [Benskey 2018]. Sections were washed in 1x Tris-buffered saline (TBS) with 0.25% Triton x-100, incubated in 0.3% $H_2O_2$ for 30 min, and rinsed and blocked in 10% normal goat serum for 2 h. Tissue was incubated in primary antibody (TH 1:4000, D2R 1:1000, GFP 1:20,000, IBA1 1:4000, 5-HT 1:10,000) overnight at room temperature. After washing, tissue was incubated in secondary antibody (biotinylated horse anti-mouse IgG 1:500, BA-2001; Vector Laboratories, Burlingame, CA; biotinylated goat anti-rabbit IgG 1:500, AP132B, Millipore-Sigma, Burlington, MA) followed by the Vectastain ABC kit (Vector Laboratories, Burlingame, CA). Tissue staining was developed with 0.5 mg/ml 3,3' diaminobenzidine (DAB, Sigma-Aldrich, St. Louis, MO) and 0.03% $H_2O_2$. Sections were mounted on glass slides, dehydrated, and coverslipped with Cytoseal (ThermoFisher, Waltham, MA).

Tissue for immunofluorescence dual labeling of D2Rs or GFP with SERT (340-004, Synaptic Systems, Goettingen, Germany) were washed with 1x TBS with 0.25% Triton x-100, blocked in 10% normal goat serum for 2 h, and probed with primary antibody overnight (D2Rs 1:1000, GFP 1:20,000, SERT 1:300). Tissue was incubated with secondary antibody (A11008 1:500, A11076 1:500; ThermoFischer, Waltham, MA) in the dark for 2 hours, and washed in TBS before being mounted and coverslipped with Vectashield Hardset Antifade Mounting Medium (Vector Laboratories, Burlingame, CA). Images were taken on a Nikon Eclipse 90i microscope with a QICAM fast 1394 camera (fluorescence; QImaging, Surrey, British Columbia, Canada) or a Nikon D-1 camera (brightfield microscopy; Nikon, Tokyo, Japan). The figures were made using Photoshop 7.0 (Adobe, San Jose, CA) with the brightness, sharpness, and saturation adjusted only as needed to best represent the staining as it is viewed directly under the microscope.

In vivo microdialysis: As outlined above, a separate cohort of parkinsonian rats treated with GFP or D2Rs were utilized for in vivo microdialysis. The night before the procedure, striatal probes (CMA 12 Elite; membrane length=3 mm; 20,000 Da; Stockholm, Sweden) were inserted into the guide cannula so that they extended from bregma DV: −3.7 to −6.7 mm within the dorsal striatum. Rats underwent microdialysis at least 2 days following the last L-DOPA administration. During microdialysis, rats received intrastriatal infusion of filtered artificial cerebrospinal fluid (aCSF) (128 mM NaCl, 2.5 mM KCl, 1.3 mM $CaCl_2$, 2.1 mM $MgCl_2$, 0.9 mM $NaH_2PO_4$, 2.0 mM $Na_2HPO_4$, and 1.0 mM glucose, pH 7.4). Dialysate samples were collected every 20 min. Briefly, rats were habituated to microdialysis for 1 h. Fifty minutes into the procedure, rats received a subcutaneous injection of L-DOPA vehicle, which consisted of 0.9% NaCl, and 0.1% ascorbate. Rats then underwent baseline testing for 1 hour to determine baseline levels of monoamines prior to L-DOPA treatment. After that a new collection tube was used and 10 minutes later rats received an injection of L-DOPA (12 mg/kg+12 mg/kg Benserazide, s.c.). Samples were taken every 20 min for 3 h. Following the procedure, rats were removed from the microdialysis bowl and striatal probes were replaced with a dummy probe. At least 2 days after microdialysis, rats were sacrificed via rapid decapitation, the anterior striatum was taken for verification of cannula placement, the posterior striatum was taken for HPLC, and the hindbrain was placed in 4% PFA for 3 days before being placed in 30% sucrose in phosphate-buffered saline (PBS). Brains were shipped on ice in a 50 ml conical containing 30% sucrose in 0.1 M PBS to MSU.

High-performance liquid chromatography for monoamine tissue analysis: Striatal tissue and in vivo microdialysis samples were analyzed using HPLC. Reverse-phase HPLC was performed on striatal tissue samples as previously described [Kilpatrick 1986] [Meadows 2017]. Briefly, tissue samples were homogenized in ice-cold perchloric acid (0.1 M) with 1% ethanol and 0.02% ethylenediaminetetraacetic acid (EDTA). Homogenate was spun at 4° C. for 45 min at 14,000 g. Supernatant was removed and, using an ESA solvent delivery system (Model 542; Chelmsford, MA, USA) ESA autoinjector (Model 582), analyzed for levels of norepinephrine, 3,4-dihydroxyphenylacetic acid (DOPAC), DA, 5-hydroxyindoleacetic acid (5-HIAA), and 5-HT. Monoamines and metabolites were detected as a generated current as a function of time by EZCHROM ELITE software via a Scientific Software, Inc. (SS240×) Module. Data are displayed as peaks for monoamines and metabolites, which are compared to a standard curve made from monoamine and metabolite samples of known concentrations ranging from 1e-6 to 1e-9. Values were then normalized to tissue weight and lesion deficits are reported as percent depletion, which is equal to 100 (1-M Lesion/M Intact).

Dialysate samples were analyzed via reverse-phase HPLC on an Eicom HTEC-500 System (Amuza Inc., San Diego, CA). Briefly, 10 μL of each dialysate sample was analyzed for NE, DA, and 5-HT using an Eicompak CAX column maintained at 35° C. with a flow rate of 250 μL/min. Mobile phase (75 mM Ammonium acetate, 9.36 mM acetic acid, 1.33 mM EDTA, 0.94 mM Methanol, 50 mM sodium sulfate). Samples were compared to known concentrations of monoamines (100, 10, 1, 0.1, and 0.05 ng/uL dissolved in a potassium phosphate buffer (0.1 mM potassium phosphate monobasic, 0.1 mM ethylenediaminetetraacetic acid, 0.02 mM phosphoric acid), resulting in a final value of monoamine in ng/μL.

Total enumeration of TH+ and 5-HT+neurons: Lesion severity was determined using total enumeration of TH-positive neurons in three representative sections within the SNc identified by the presence and proximity to the medial terminal nucleus (MTN) of the accessory optic tract at levels equivalent to −5.04 mm, −5.28 mm and −5.52 mm relative to bregma according to a previously validated method [Gombash 2014]. Briefly, the intact and lesion SNc were quantified for all TH immunoreactive cells using a 20× objective and MicroBrightfield StereoInvestigator software (MicroBrightfield Bioscience, Williston, VT). The total number of TH cells on the intact and lesioned hemispheres were averaged, and lesion efficacy was derived by dividing the lesioned hemisphere average by the intact hemisphere average and multiplying that value by 100.

Total number of 5-HT positive neurons in the DRN were also quantified with total enumeration [Gombash 2014]. Three sections of the DRN were quantified for all 5-HT immunoreactive cells under a 20x objective using MicroBrightfield StereoInvestigator (MicroBrightfield Bioscience, Williston, VT). The total number of from all three sections per animal were summed to give a total number of 5-HT neurons.

Electrophysiology: Recording microelectrodes were manufactured from 2.0 mm OD borosilicate glass capillary tubing and filled with sodium chloride (2M) solution. Electrode impedance was 5-15MQ. The signal to noise ratio for all recordings was >4:1. The level of urethane anesthesia was periodically verified via the hind limb compression reflex and maintained using supplemental administration as previously described [Padovan-Neto 2015] [Sammut 2010]. Temperature was monitored using a rectal probe and maintained at 37C° using a heating pad (VI-20F, Fintronics Inc., Orange, CT). Electrical stimuli (duration=500 us, intensity=1000 μA) were generated using a Grass stimulator and delivered in single pulses (0.5 Hz) while searching for cells [Padovan-Neto 2015]. Once isolated, recordings consisted of basal (pre-drug), saline vehicle, and drug-treatment-(see below) induced changes in spike activity recorded in a series of 3 min duration epochs.

All compounds and physiological 0.9% saline were prepared daily and administered intravenously (i.v.) through the lateral tail vein to enable rapid examination of potential acute effects of vehicle or drug on DRN neuronal activity. The selective 5-HT1A agonist 8—OH-DPAT (5 ug/kg, i.v.), the selective 5-HT1A antagonist WAY100635 (100 ug/kg, i.v.), and the D2R agonist Quinpirole (500 ug/kg, i.v.) were dissolved in vehicle and administered systemically to either BFP or D2Rs rats. DRN 5-HT neuron activity was recorded prior to and immediately following drug administration as described above.

Statistical analysis: Statistical analysis was performed using Statview (version 5.0) or in SPSSversion 23 with a set to 0.05. All graphs were created in GraphPad Prism version 7.0 (GraphPad Software, La Jolla, CA) or Excel (Microsoft, Redmond, WA). Lesion status was evaluated using unpaired, one-tailed t-tests. AIMs were evaluated using a non-parametric Mann-Whitney U test, with $p \leq 0.05$ being considered statistically significant. Bonferroni post-hoc tests were employed when significant main effects were detected. Cylinder and FAS data for forehand and backhand stepping were submitted to a mixed model ANOVA with within-subjects factors of treatment (2: Baseline, L-DOPA) and between-subjects factors of vector (GFP, D2R). Overall percent intact values for FAS were determined by taking the overall number of right paw steps divided by the number of left paw steps and multiplying the quotient by 100. Similarly, overall percent intact values were analyzed via a repeated-measures ANOVA with within-subjects factor of treatment and between subjects factor of vector. Monoamine content (as determined by HPLC) was submitted to a mixed-model ANOVA with within-subjects factor of treatment (2: Vehicle, L-DOPA) and between-subjects factor of vector. Fisher's least significant difference (LSD) post-hocs and planned paired-samples t-tests were employed as appropriate to clarify significant effects. Additionally, independent-samples t-tests were employed to reveal effects of vector on the timing of DA, NE, and 5-HT efflux. HPLC values for striatal tissue were submitted to a mixed-model ANOVA with within-subjects factor of side and between-subjects factor of vector. Subsequently, since DA depletion did not vary as a function of vector, values for each monoamine for each side were collapsed across treatments and compared via paired-samples t-tests. For electrophysiology experiments, the difference between the spontaneous and evoked electrophysiological activity of identified DRN-5-HT neurons across groups was determined and served as the dependent variable for analyses. A two-way repeated measures ANOVA (GFP vs. gene therapy (ectopic expression of the DA D2 AR in 5-HT DR neurons) x2 (vehicle vs. drug treatment) with a set to 0.05 and all "n's" adequately powered for electrophysiological studies was conducted using Sigma Stat software (San Jose, CA), and the potential two-way interaction effect was examined to determine how treatment effects differ as a function of drug treatment or gene therapy [Padovan-Neto 2015].

Figure 14B:
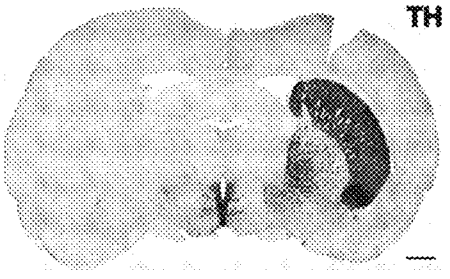
Figure 14C:
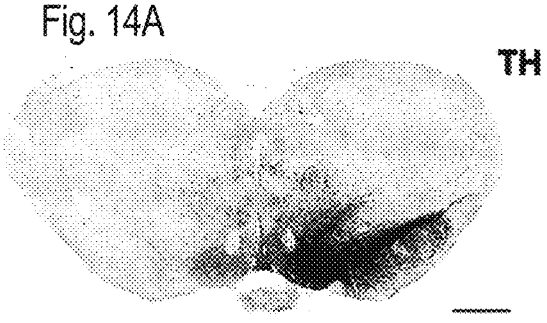
Figure 20A:
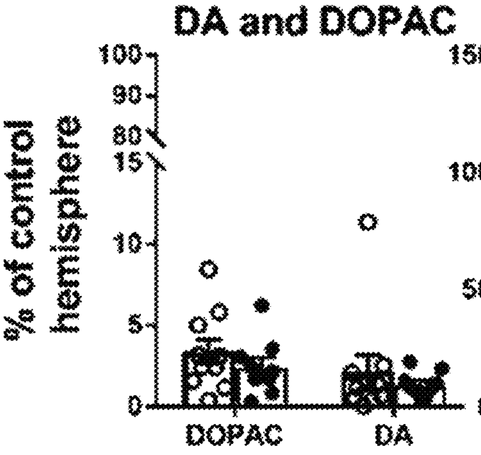
FIGS. 20A-20C show concentrations of Monoamines in Lesioned vs. Intact side of brain.
Figure 20B:
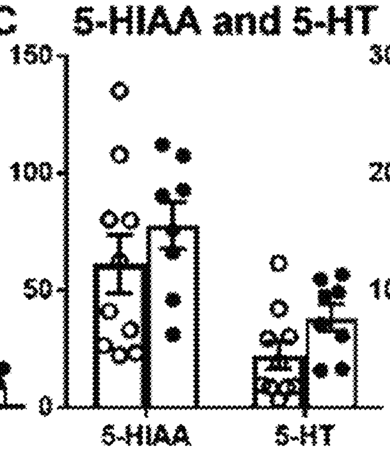
Figure 20C:
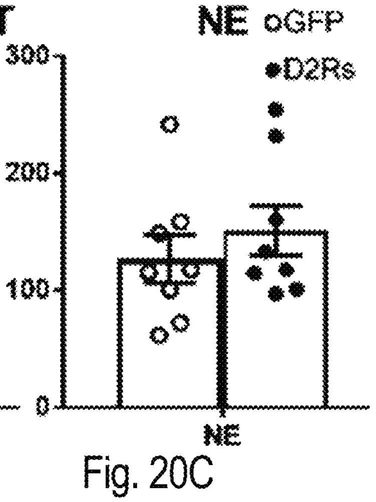

Validation of lesion and transgene expression: In order to assess if exogenous expression of D2Rs in the DRN could inhibit LID development or decrease LID severity, adult Fischer rats were rendered parkinsonian with 6—OHDA delivered to the SNc and MFB. Because LID is dependent on the severity of the lesion [Winkler 2002] sufficient nigrostriatal denervation was validated post mortem. Immunohistochemistry of the striatum (FIG. 14*b*) and the SNc (FIG. 14*c*) showed a near complete ablation of TH immunoreactivity with no difference in the number of SNc DA neurons between groups (FIG. 14 d; GFP=1.29%+0.29% remaining; D2Rs=1.45%+0.41% remaining; t (9)=0.31, p>0.05). Similarly, HPLC analysis of DA and DOPAC levels from striatal tissue from rats employed in the microdialysis experiment confirmed that all animals displayed an almost near complete reduction in striatal DA levels in the lesioned hemisphere as compared to the intact hemisphere (DOPAC=18.11+6.68% of intact hemisphere, DA=3.48+1.36% of intact hemisphere) (FIG. 20). There was no difference in striatal DA depletion between groups (DOPAC t (13)=0.73, p>0.05, DA t (13)=17.21, p>0.05).

After a three-week recovery period, rAAV 2/9 expressing either D2Rs or GFP was delivered by stereotaxic injection into the DRN. Following sacrifice, transduction was confirmed with immunohistochemistry (IHC) of D2Rs or GFP (FIGS. 13E-13J, FIG. 20). Significant transgene expression was observed in the soma (D2Rs FIG. 14F, 14G; GFP FIG. 141, 14J) of the DRN as well as in DRN efferent projections (D2Rs FIG. 14E; GFP FIG. 14H, FIG. 20). The two transgenes exhibited a slightly different subcellular expression pattern where more GFP expression was seen in projections as compared to D2Rs expression (FIG. 20). It is unclear if this is due to increased 5-HT innervation in dyskinetic (i.e., GFP treated) animals [Maeda 2003], or due to a different distribution pattern specific to the transgenes. The latter is to be expected as GFP is a soluble protein and typically fills the entire neuron. Transduction expression was observed throughout the brain, however, all transgene immunoreactivity anterior to the DR was localized to projections and not cell bodies (FIG. 15*c*, 15*d*, 15*g*, 15*h*). An evaluation of Iba1 immunoreactivity indicated that transduction of either vector did not result in inflammation, as the only increase in Iba1 was seen at the injection site itself (FIG. 15*e*, 15*i*) and this response did not differ between groups. Vector transduction and transgene expression of either construct did not adversely affect SERT expression in the DRN (FIGS. 14K-14P). Additionally, total enumeration of 5-HT positive neurons in the DRN showed no effect of vector expression on the number of cells (FIG. 15L). Four animals (rAAV-D2Rs: n=2, rAAV-GFP: n=2) that lacked sufficient vector expression in the DRN were removed from the analysis, leaving a total of n=15 rats included in the analysis (rAAV-D2Rs: n=7, rAAV-GFP: n=8).

Figure 15A:
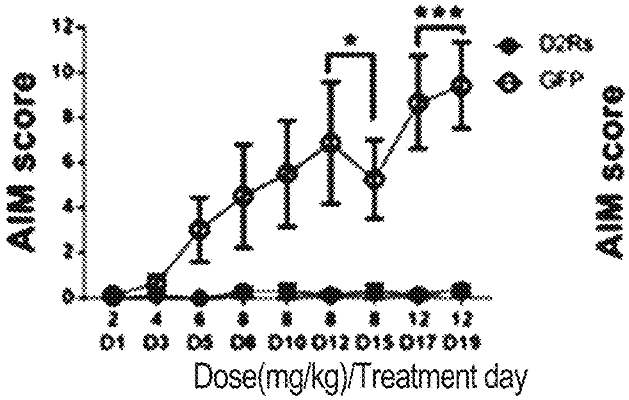
FIGS. 15A-15F DRN D2Rs expression blocks LID development.
Figure 15B:
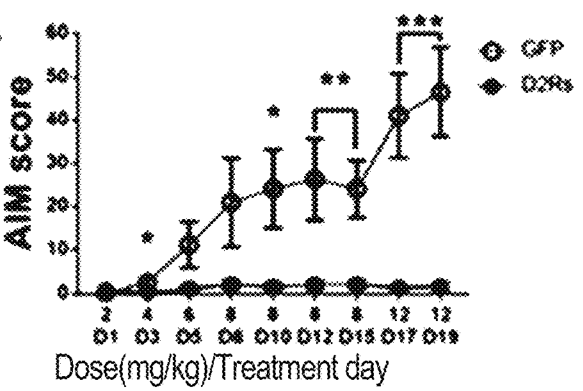
Figure 15C:
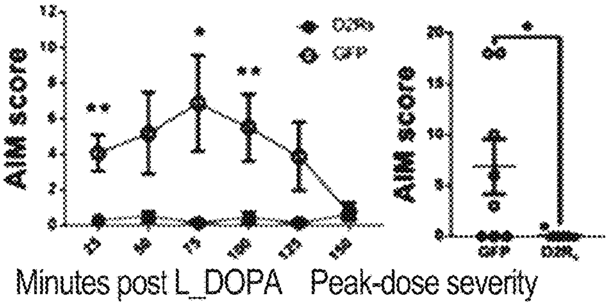
Figure 15D:
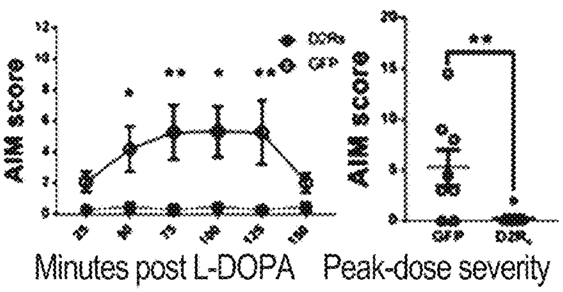
Figure 15E:
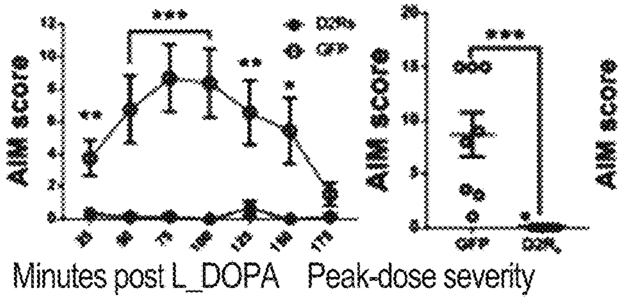
Figure 15F:
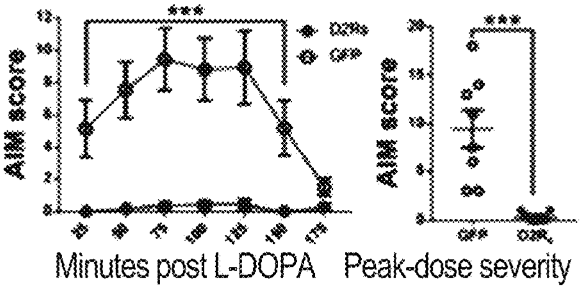

D2Rs delivery to the dorsal raphe eliminates LID: After a 4-week recovery period to allow for optimal transgene expression [Reimsnider 2007], animals were treated with L-DOPA and rated for AIMs (see FIG. 14A for experimental timeline). With L-DOPA, rAAV-D2Rs treated animals did not show significant LID at the typical peak-dose time point (75 min post L-DOPA delivery) LID (defined as an AIM score≥4) [Zhang 2013] at any dose level (2 mg/kg AIMs=0+0, 4 mg/kg AIMs=0.14+0.14, 6 mg/kg AIMs=0+0, 8 mg/kg day 8 AIMs=0.29+0.18, 8 mg/kg day 10 AIMs=0.29+0.29, 8 mg/kg day 12 AIMs=0.14+0.14, 8 mg/kg day 15 AIMs=0.29+0.29, 12 mg/kg day 17 AIMs=0.14+0.14, 12 mg/kg day 19 AIMs=0.36+0.18) (FIG. 14A, FIG. 22). rAAV-GFP controls began to show mild-to moderate peak-dose AIMS with a moderate L-DOPA dose (6 mg/kg peak dose AIMs=3+1.43), which increased to more significant levels of severity with higher doses of L-DOPA (8 mg/kg peak dose AIMs: day 8=4.5+2.29, day 10=5.5+2.36, day 12=6.88+2.72, day 15=5.25+1.76; 12 mg/kg peak dose AIMs: day 17=8.69+2.06, day 19=9.44+1.93) (FIG. 15*a*, FIG. 21). When compared to rAAV-D2Rs subjects, rAAV-GFP animals showed significantly higher total peak dose AIM scores per session starting with 8 mg/kg doses (day 12 rAAV-D2Rs (Md=0), rAAV-GFP (Md=4), U=12, p<0.05; day 15 rAAV-D2Rs (Md=0), rAAV-GFP (Md=4.5), U=12, p<0.05; Mann-Whitney U test) (FIG. 15*b*). This difference was maintained with the high dose of L-DOPA (12 mg/kg-day 17 rAAV-D2Rs (Md=0), rAAV-GFP (Md=8.5), U=0.5, p<0.001; day 19 rAAV-D2Rs (Md=0), rAAV-GFP (Md=9.25), U=0, p<0.001) (FIG. 15*c*-15*f*, FIG. 21). Taken together, these data show that D2Rs expression in the DRN completely blocks the development of LID in parkinsonian rats, even with administration of high L-DOPA doses.

Figure 16A:
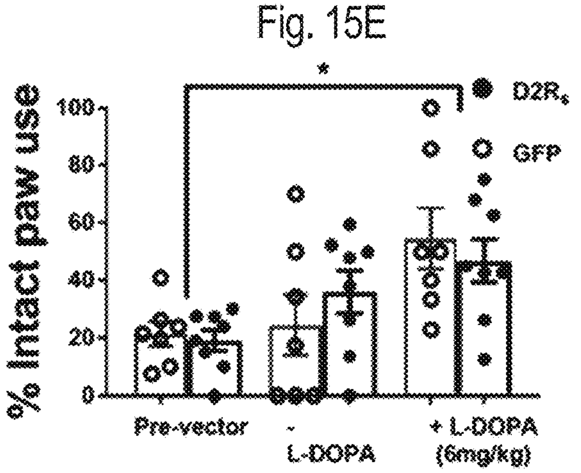
FIGS. 16A-16B shoe that rAAV-D2Rs does not impact L-DOPA efficacy.

D2Rs does not affect parkinsonian motor behavior: To assess if rAAV-D2Rs treatment alters the anti-akinetic properties of L-DOPA, motor behavior was examined using the cylinder task (FIG. 16*a*). There were no significant differences between the rAAV treatment groups without L-DOPA (F (1,13)=0.008, p>0.05). Pre-vector scores for both groups and post-vector scores for rAAV-GFP showed a marked decrease from normal contralateral forepaw use, indicating significant impairment. rAAV-D2Rs animals post-vector showed a trend towards more balanced forepaw use, but the differences were not significant. Both groups showed a significant increase from baseline increase towards balanced contralateral forepaw use while on L-DOPA (6 mg/k) (F (2,26)=7.11, p<0.01). No significant differences were seen in impairment or improvement between vector treatment groups (F (2,26)=0.72, p>0.05). A separate group of animals (microdialysis cohort) which were treated identical (lesion, vector delivery, L-DOPA paradigm) to the initial cohort of animals, underwent the adjusting steps test, both off and on (8-12 mg/kg) L-DOPA. Both vector treatment groups showed significantly impaired adjusting steps without L-DOPA (GFP baseline=3.57%+0.49% intact stepping; D2Rs baseline=6.33%+3.02% intact stepping; t (11)=0.98, p>0.05), however, this deficit was rescued with the administration of both doses of L-DOPA (FIG. 16*b*; F (2,22)=9, p<0.01). As with the cylinder task, no differences in impairment nor improvement while on L-DOPA were seen between groups (F (2,22)=0.24, p>0.05). Together, this suggests that ectopic D2Rs expression in the DRN does not interfere with the anti-parkinsonian motor benefits of L-DOPA.

Dopamine receptor agonists do not induce significant AIMs in L-DOPA-primed rAAV-D2Rs rats: Next, it dopamine agonists were examined for their ability to induce AIMs in the rAAV-D2Rs treated rats that had remained resistant to LID after the L-DOPA dosing paradigm. Animals received three repeated doses each of a non-selective DA agonist (apomorphine, 0.1 mg/kg), a D2/3-specific receptor agonist (quinpirole, 0.2 mg/kg), and a D1-specific receptor agonist (SKF-81297, 0.8 mg/kg) and were evaluated for AIM severity (see timeline in FIG. 14*a*). These DA agonists can induce AIMs in both L-DOPA-primed and unprimed parkinsonian animals [Boraud 2001] [Boyce 2001] [Chondrogiorgi 2014]. Directly activating the DA receptors with an agonist was hypothesized to bypass any protective effects of the rAAV-D2Rs treatment in normalizing aberrant DA release, as these agonists do not require processing and release by DAergic or serotonergic terminals, and therefore would not be affected by exogenous regulatory mechanisms. They also allowed us to compare DA receptor supersensitivity status between treatment groups. Interestingly, rAAV-D2Rs animals challenged with both apomorphine and quinpirole did not show significant peak AIMs (rAAV-D2Rs apomorphine third treatment 25 min AIMS=1.86+1.32; quinpirole third treatment 25 min AIMs=−1.57+0.66), while rAAV-GFP animals continued to express moderate-to-severe AIM behaviors (rAAV-GFP apomorphine third treatment 25 min AIMS=10.75+2.10; quinpirole third treatment 25 min AIMs=−11.81+2.45) (FIG. 17*a*-17*f*). rAAV-D2Rs animals exhibited significantly lower peak-dose AIMs with both apomorphine and quinpirole treatment compared to rAAV-GFP animals (apomorphine third treatment 25 min AIMs rAAV-D2Rs (Md=0), rAAV-GFP (Md=12.75), U=4.5, p<0.01; quinpirole third treatment 25 min AIMs rAAV-D2Rs (Md=1.5), rAAV-GFP (Md=13), U=3.5, p<0.01). Treatment with SKF-81297 did induce mild-to-moderate AIM scores in rAAV-D2Rs treated animals (third treatment 50 min AIMs=3.92+0.73), but these scores remained significantly less severe than their control counterparts (third treatment 50 min AIMs rAAV-D2Rs (Md=3.5), rAAV-GFP (Md=13), U=2, p<0.001) (FIG. 16*g*-16*i*).

Figure 18A:
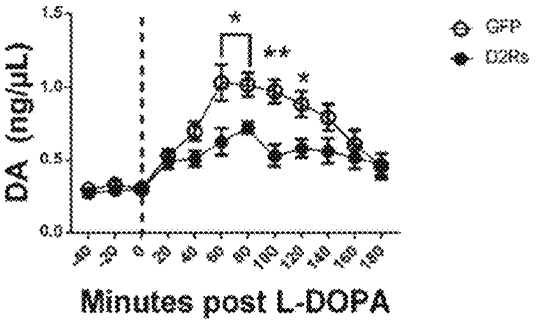
FIGS. 18A-18B show that DRN D2Rs reduced striatal efflux of DA.

D2Rs expression in the dorsal raphe reduces striatal dopamine efflux following L-DOPA delivery: In order to determine if ectopic D2Rs expression in the DRN was inhibiting LID by moderating DA release from serotonergic neurons, a second cohort of animals was generated in order to perform in vivo microdialysis (rAAV-D2Rs n=6, rAAV-GFP n=7). Animals were lesioned and received vector in an identical manner to the first cohort, and subsequently treated with L-DOPA to establish LID. In order to determine differences between vector groups in the absence of L-DOPA, striatal dialysate was analyzed via HPLC and data for monoamine content were examined using a 2 (vector)×2 (treatment) mixed-model ANOVA. Overall, DA values were dependent upon treatment, F (1,11)=124.35, p<0.05, and vector, F (1,11)=7.39, p<0.05. Planned pairwise comparisons revealed that L-DOPA treatment increased striatal DA efflux in both groups. However, rats treated with the D2Rs viral vector had lower levels of DA efflux than did rats treated with the GFP vector (p<0.05) (FIG. 18*a*). Finally, there was a vector by treatment interaction, F (1, 11)=6.66, p<0.05, such that rats with the D2Rs vector had lower levels of DA efflux than rats with the GFP vector, but only after L-DOPA treatment. Striatal NE efflux was also dependent upon treatment, F (1,11)=52.10, p<0.05. There was no effects of vector or treatment on striatal 5-HT efflux (FIG. 18*b*; F (11,121)=0.867, p>0.05). DA values for each time point were also submitted to paired-samples t-tests in order to examine the effect of vector on DA efflux at each time point during microdialysis. There were significant differences between vector groups 60 (t (5)=3.42, p<0.05), 80 (t (5)=2.77, p<0.05), 100 (t (5)=4.68, p<0.01), and 120 (t (5)=2.59, p<0.05) minutes after L-DOPA administration, showing that rats with the GFP vector had elevated striatal DA efflux as compared to the rats with the D2Rs vector. This is the first direct evidence showing that mishandled DA by DRN neurons can be regulated exogenously, and this regulation reduces DA release in the striatum, thus suppressing LID.

D2Rs expression inhibits 5-HT neuron activity: In order to demonstrate that the ectopically expressed D2Rs have the capacity to inhibit the activity of identified 5-HT neurons, electrophysiological recordings were performed on a separate cohort of (intact, non-L-DOPA-treated, non-dyskinetic) animals. Animals received a stereotaxic delivery of either vector as described above, and 4-12 weeks later in vivo single-unit extracellular recordings of DRN neurons were performed. Putative 5-HT neurons were identified based initially on their firing characteristics (e.g., long-duration action potentials, regular firing pattern interrupted with burst activity). Next, neurons were identified as serotonergic based on well characterized responses to systemic administration (i.v.) of 5HT1AR agonist (8—OH-DPAT) and reversal with antagonist (WAY-100635) which restored 5-HT neuron firing to that of baseline (FIG. 19*b*-19*d*) [Celada 2013] [Hajos FIG. 6*a* shows typical traces of 5-HT and non-5HT DR neurons. Importantly, electrophysiologically identified 5-HT neurons recorded in the dorsal raphe of rats transduced with AAV expressing BFP or D2Rs responded similarly to systemic administration of vehicle, 5-HT1AR agonist, and reversal of 5-HT1AR inhibition by 5-HT1AR antagonism. Moreover, 5-HT cells recorded in AAV-D2Rs injected rats administered the D2 agonist quinpirole (i.v.) exhibited clear inhibitory effects, whereas responses to quinpirole were variable and sometimes excitatory in BFP controls (FIG. 19*e*-19*f*). These data show that ectopic expression of D2Rs in confirmed 5-HT neurons can act as a functional autoreceptor and inhibit impulse activity in serotonergic neurons.

CONCLUSIONS rAAV was used to ectopically express the dopamine autoreceptor (D2Rs) in order to equip DRN 5-HT neurons with a DA-mediated autoregulatory mechanism. Dysregulated DA release from 5-HT neurons through a phenomenon known as "false neurotransmission" has been extensively implicated as a key contributor to LID development [Bibbiani 2001] [Carta 2007] [Eskow 2009] [Maeda 2003] [Maeda 1999] [Maeda 2005] [Muñoz 2009]. The data demonstrate that providing DA-dependent autoregulation in 5-HT neurons can prevent LID formation, thus, providing unambiguous evidence that 5-HT neurons play a central role in DA-dependent symptomology.

Studies supporting the serotonin hypothesis of LID suggest that DA synthesis and release from striatal 5-HT terminals is involved in AIM presentation. Specifically, studies ablating DRN neurons or dampening their activity with serotonin autoreceptor agonists have been shown to reduce or eliminate LID; the hypothesized reasoning being that reducing aberrant serotonergic neuronal activity following L-DOPA administration leads to a reduction in striatal DA release from ectopically sprouted DRN terminals [Carta

[Eskow 2007] [Iravani 2006]. Although the mechanism by which 5-HT neurons process L-DOPA and release DA is not fully established, it is well known that the synthesis and vesicular packaging mechanisms are present in serotonergic neurons [Arai 1995] [Gantz 2015] [Tanaka 1999].

When DRN are induced to ectopically express D2Rs autoreceptors, 1) hyper-DA release in the striatum following L-DOPA is significantly dampened, presumably by providing DA-dependent autoregulation in striatal 5-HT terminals and 2) that this approach can completely prevent LID formation without compromising motor benefit. These data provide unambiguous evidence that 5-HT neurons play a central role in the DA-dependent pathophysiology of LID.

Dopamine autoregulation in the dorsal raphe blocks 5-HT neuron activity and LID development: Expressing DA regulatory factors in 5-HT neurons decreases LID severity. 5-HT autoreceptors share a canonical signaling cascade with the D2-type DA autoreceptors-both are inhibitory G-protein coupled receptors (GPCRs) that reduce cellular cAMP to inhibit neuronal signaling [Harrington 1988] [Neve 2004]. Ectopically expressing the DA autoreceptor D2Rs in DRN neurons can serve a physiological autoregulatory function. D2Rs autoreceptor expression in the DRN of naïve mice results in a reduction of 5-HT-mediated currents [Gantz 2015]. Direct recordings of single 5-HT neurons in the DRN reveal that ectopic D2Rs expression can provide an inhibitory neuromodulatory effect in 5-HT neurons, characterized by a strong decrease in spontaneous firing following systemic DA D2R agonist administration. rAAV targeted to the DRN in hemiparkinsonian rats that subsequently received a LID-inducing dosing regimen of L-DOPA, revealed that DRN expression of D2Rs provided complete protection against the development of LID, an effect that also persisted at high doses of L-DOPA. There was no difference in the extent of nigrostriatal denervation between the groups, nor was there any demonstrable toxicity due to either treatment in the DRN. Thus, prevention of LID was explicitly due to expression of D2Rs in the DRN.

Dopamine efflux into the striatum is reduced with dorsal raphe D2Rs expression: Although there is a wealth of research supporting the abnormal serotonergic input in LID development [Arai 1995] [Nicholson 2002][Scholtissen 2006], direct evidence showing that the contribution is due to an increase in DA release from these neurons is limited. Using in vivo microdialysis, L-DOPA mediated DA efflux into the striatum was shown to be significantly modulated by negatively regulating DRN serotonin neurons with D2Rs expression. A total blockade of LID development was observed with a partial reduction in DA efflux in the striatum. This indicates that a complete block of DA signaling in the striatum is not required for LID inhibition, but rather, mitigation of the pulsatile DAergic tone that occurs with oral administration of L-DOPA is required. Additionally, achieving a total depletion of DA release in the striatum would likely result in a loss of L-DOPA efficacy, as the primary source of L-DOPA metabolism and DA release in severely DA denervated animals originates from DRN neurons. The data suggests that partial DA efflux reduction and proper DAergic regulation is sufficient to ameliorate LID in the animal model.

In contrast to DA efflux, there was no evidence of decreased 5-HT efflux in the striatum in rAAV-D2Rs animals, suggesting 5-HT release was not affected. This is surprising given the finding that autoreceptor stimulation effectively reduces 5-Ht neuron firing. One likely explanation for this observation is that the lack of impact on striatal 5-HT release was due to a lack of direct stimulation of 5-HT release concomitant with L-DOPA treatment, thus, the measurements reflected baseline 5-HT release. Nevertheless, the findings demonstrate that D2Rs can induce DAergic regulation in 5-HT neurons, by 'hijacking' endogenous signaling cascades and reducing neuronal activity following L-DOPA administration.

The in vivo electrophysiology and microdialysis data together suggest that the mechanism by which expression of D2Rs in DRN neurons provides complete protection against the development of LID is through a neuromodulatory feedback mechanism. This is further supported based on equal levels of nigral DA neuron loss between rAAV-D2R and rAAV-GFP groups, supporting that this antidyskinetic efficacy was explicitly due to expression of D2Rs in the DRN.

The data indicate that exogenously provided D2Rs can couple with Gai subunits in DRN neurons, and induce the appropriate signaling cascades to reduce neuronal activity in the presence of exogenous L-DOPA. In conjunction with the LID studies utilizing serotonin agonists, the data confirm that reducing the activity of the serotonin system can dramatically inhibit LID. However, the critical advantage of this target-specific gene therapy approach over pharmacological therapy [Cheshire 2012] [Iravani 2006] [Kannari

[Olanow 2004] is that there is no decrease in motor benefit of L-DOPA. Serotonergic neurons, when supplied exogenously with a single DA-regulatory factor, can modulate DA release and completely prevent the induction of LID in a 'prevention' scenario.

Ectopic D2Rs expression in the dorsal raphe blocks: L-DOPA priming in the striatum In order to better understand the global impact of striatal DA regulation via DRN D2Rs expression on an array of DA therapies in parkinsonian subjects, the hypothesis that the protective effects of this autoreceptor treatment would be negated in the presence of DA-receptor agonists which directly bind to DA receptors on striatal medium spiny neurons (MSNs) was tested. Since the DA regulation thru the D2Rs is a presynaptic mechanism, treatment with DA receptor agonists, which act at postsynaptic receptors that become supersensitive with striatal DA depletion and result in dyskinesias in animal models and patients [Boraud 2001] [Boyce 2001] [Chondrogiorgi 2014] [Gomez-Mancilla 1992], should induce AIMs in rAAV-D2Rs-treated animals resistant to LID. Treatment with D1—, D2-specific, or pan-DA agonists did not induce severe AIMs in rAAV-D2Rs animals, and only a mild-to-modest dyskinetic response was seen with the D1 agonist SKF-81297, the last of the three DA agonist drugs tested. This suggests that D2Rs therapy disallowed LID priming to occur in striatal MSNs. The autoreceptor allows for proper regulation of DA signaling from DRN neurons, removing the pulsatile stimulation induced by intermittent DA dosing which is important in LID development. Thus, the MSNs of rAAV-D2Rs treated animals first exposure to abnormal DA signaling would be at the initial agonist challenge, where priming could begin.

This increase in AIMs behavior with the D1 agonist may have been due to a mild degree of DA-agonist induced priming, a phenomenon that is to be expected as direct MSN DA receptor activation would not be mitigated by DRN D2Rs expression. This is supported by the experimentation by Carta and colleagues, where the co-administration of apomorphine with the 5-HT1A agonist after an induction period where L-DOPA was administered over 3 weeks, did not alleviate LID, suggesting that the induction phase irreversibly primed the neurons to LID [Carta 2007].

It is well established that LID development is associated with a "priming-period" consisting of discontinuous, non-physiological, striatal DA tone that results in morphological and molecular changes to the MSNs [Carta 2003] [Cenci 2010] [Morelli 1989] [Pinna 1997] [Simola 2009] [Steece-Collier 2009] [Zhang 2013]. The data therefore indicates that D2Rs-treated animals were blocked from the L-DOPA priming by counteracting the non-physiological surges of DA release, thereby preventing a host of pathological molecular mechanisms that may include normalizing post-synaptic striatal DA receptor supersensitivity. The fact that at the end of the treatment a mild-to-moderate increase in AIM presentation in rAAV-D2Rs animals with DA agonist treatment was observed as compared to L-DOPA, suggest that these animals were in the early stages of priming, a phenomenon that is to be expected as direct MSN DA receptor activation would not be mitigated by DRN D2Rs expression. While there was a break between L-DOPA and DA agonist treatment (FIG. 14A) this would not affect the primed state or future maintenance of LID, as this type of 'drug holiday' does not ameliorate LID when a patient or animal model is reintroduced to a DAergic therapy [Taylor 2005] [Weiner 1980].

Inhibition of dorsal raphe serotonergic neurons does not mitigate the anti-parkinsonian benefits of L-DOPA: As briefly discussed above, it was important to confirm that D2Rs expression in the DRN does not negatively affect the therapeutic efficacy of L-DOPA in the PD model, as this has been an issue with serotonin agonist-type therapies in clinical trials for LID [Cheshire 2012] [Kannari 2002] [Olanow 2004], and an imperative problem to mitigate for all future therapies. The current studies demonstrate that this gene therapy approach of providing DA autoregulatory properties to DRN neurons results in no changes in motor improvement between control and D2Rs animals. This was confirmed in two separate cohorts of rats and using two different motor tests. Both tests demonstrated that rats with the D2Rs in DRN neurons maintain a significant improvement in motor function with the administration of L-DOPA, reflecting recovery back to a pre-lesion state. This shows that D2Rs activity in serotonergic terminals of the striatum (or elsewhere) does not interfere with the pharmacological benefits of L-DOPA, and implicates D2Rs therapy as a potential potent treatment option for LID. It is important to note that while many preclinical studies using 5-HT agonists did not show an effect on L-DOPA-induced motor improvement, these results have not translated clinically. While multiple trials have used a variety of 5-HT agonists and seen reductions in AIM scores, many of these compounds contribute to worsening of parkinsonian symptoms and OFF L-DOPA periods, or have been abandoned due to lack of antidyskinetic efficacy (reviewed in [Cheshire 2012]). The discrepancy between the D2Rs approach and the use of agonists is unclear given that these two approaches conceivably evoke the same mechanism. Nevertheless, 5-HT1 compounds may produce their own side effects [Lindenbach 2015]. Second, their effects are dependent on an exogenously administered compound and hold a potential for suboptimal dosing (and timing of administration) as opposed to a gene therapy approach. Nevertheless, further studies are warranted to determine if D2Rs expression in the raphe is successful in other preclinical models of LID.

Pharmacological manipulations of 5-HT neurons in the treatment of LID, although successful pre-clinically, have not been fully translated. The transient nature of the anti-dyskinetic effect of currently available 5-HT approaches may be due to pharmacologic limitations of these drugs, including lack of specificity and potency for the specific receptor. Moreover, timing and comparative pharmacodynamics with L-DOPA delivery may be preventative [Mazzucchi 2015]. Because of this, a genetic approach in the form of continuous 5-HT inhibition should bypass such pharmacological limitations and provide meaningful and lasting protection against LID. Moreover, the finding that D2Rs gene therapy does not interfere with L-DOPA efficacy in the rat model provides promise for such an approach. Of course, the DR innervates a large part of the brain, providing many crucial functions, and the D2Rs therapy undertaken here does not distinguish between various projections. Thus, understanding any off-target effects from DA-mediated regulation of 5-HT neurons remains one important caveat that requires further research. The study was limited, and provided no genetic precision with the vector delivery as would be afforded in, for instance, a CRE animal. Although a majority of somatic transduction was observed in the area of the DR, it is also possible that other circuits were transduced with the vectors.

Changes in 5-HT innervation occur concomitant with nigrostriatal denervation and PD. Both 5-HT hyperinnervation [Bedard 2011] [Politis 2010] [Rylander 2010] as well as a decrease in 5-HT terminals [Guttman 2007] [Kim 2003] [Kish 2008] [Scatton 1983] has been documented in human disease. Although the cause of these divergent findings is unknown, it is highly likely that 5-HT neurons play an important role in PD symptomology and, as the findings would suggest, in LID. As nigrostriatal denervation in human PD is near complete at the time of diagnosis [Kordower 2013] it is conceivable to speculate that changes in 5-HT innervation and function- and the capacity of these neurons to release DA-is a crucial component to dyskinesogenesis. To that end, understanding both the mechanisms of how 5-HT neurons process and release DA, and the underlying etiology of presynaptic 5-HT changes are important components to understand LID etiology and PD non-motor symptoms, and represents a new therapeutic modality.

In conclusion, DA release from DRN 5-HT neurons can be regulated with ectopic expression of D2Rs, altering the activity and DA release properties of these neurons in a therapeutically meaningful way.

FIGS. 14A-14P show experimental design and model validation. 14A Experimental timeline showing LID-inducing L-DOPA paradigm, motor behavior evaluations, and DA agonist treatments. AIM score ratings were taken at each injection where indicated. 14B and 14C Representative TH immunoreactivity in the striatum (14B) and substantia nigra (14C) showing complete loss of TH-positive neurons and projections following 6—OHDA lesions (scale bar=1 mm). 14D Total enumeration of remaining TH neurons in the substantia nigra. e and f IHC for the D2 receptor (14E) or GFP (14F) in the DRN, showing successful targeting of the structure and robust expression of the transgene (scale bar=1 mm). Cell bodies were efficiently transduced in the DRN (14E and 14F, bottom insets, scale bar=50 μm) and could be seen filling projection fibers in the peduncles (14E and 14F, top insets, scale bar=50 μm). 14K-14P Dual labeling transgene expression and SERT in rAAV-D2Rs k-m and rAAV-GFP (14N-14P) animals. Transgene expression was visualized with D2Rs (14L) or GFP (140) staining, and serotonin fiber and cell integrity were confirmed by staining for SERT (14M and 14P). No adverse effects on SERT fibers were observed following vector transduction with either construct (14K and 14N) (14K-14P scale bar=100 μm)

FIGS. 15A-15F show that DRN D2Rs expression blocks LID development. FIG. 15A shows rAAV-D2Rs-injected animals did not develop LID over the course of 19 days of treatment with increasing doses of L-DOPA, where rAAV-GFP controls developed AIMs. FIG. 15B shows the total AIM score for each rating session was significantly different between groups starting on treatment day 8 with 8m/kgL-DOPA. D2Rs animals remained LID-. FIGS. 15C-15F show AIM scores from days 12, 15, 17, and 19 showing LID severity in 25 min intervals. GFP animals displayed a typical dyskinetic response to chronic L-DOPA treatment, with increasing AIM severity seen at higher doses. The peak-dose severity (AIM score at 75 min-post L-DOPA injection) was significantly higher in GFP animals than D2Rs animals in the last 4 days of the L-DOPA paradigm. (*=p≤0.05, =p≤0.01, *=p≤0.001).

Figure 16B:
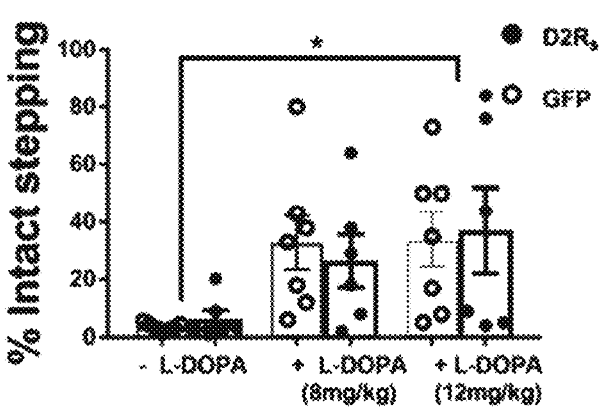

FIGS. 16A-16B show that rAAV-D2Rs does not impact L-DOPA efficacy. FIG. 16A shows a cylinder task performed 3 weeks post-lesion (pre-vector), off L-DOPA (post-vector, post-L-DOPA paradigm) and on L-DOPA (6 mg/kg, 50 min post injection). Both vector groups showed significant impairment following lesion and vector delivery, which was recovered with L-DOPA treatment. There were no significant differences between vector groups. FIG. 16B shows a second cohort received the same lesions and vector deliveries and motor function was evaluated using the adjusting steps tests. While all animals in both groups showed significant impairment on the test without L-DOPA, motor function was restored while on drug (8 mg/kg and 12 mg/kg). There were no differences between vector groups. *=p≤0.01.

Figure 17A:
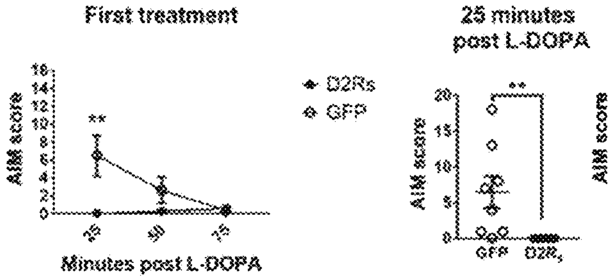
Figure 17B:
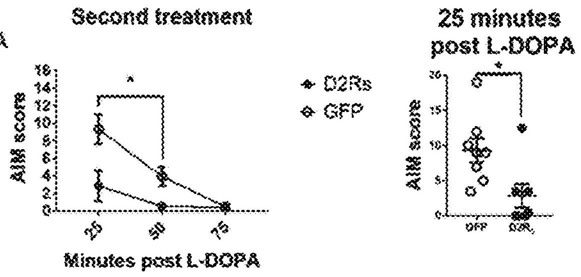
Figure 17C:
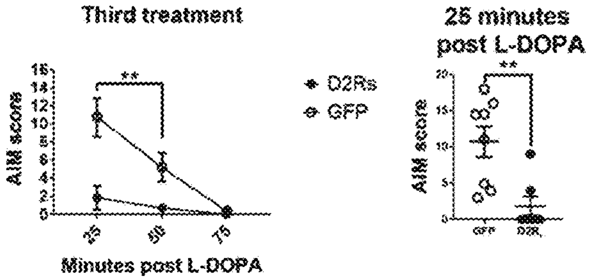
Figure 17D:
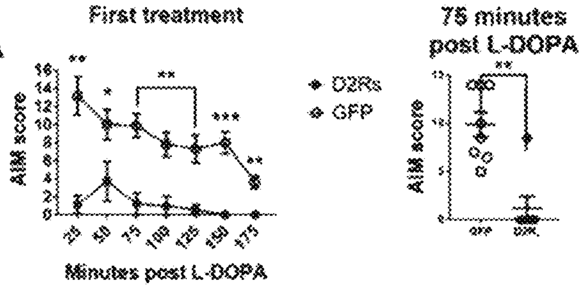
Figure 17E:
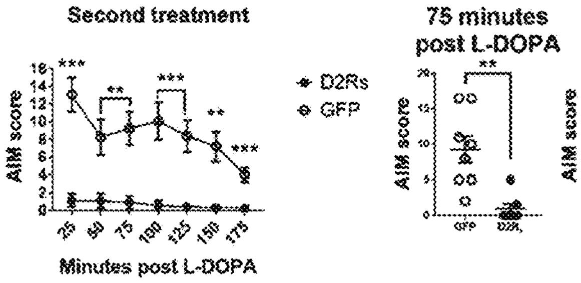
Figure 17F:
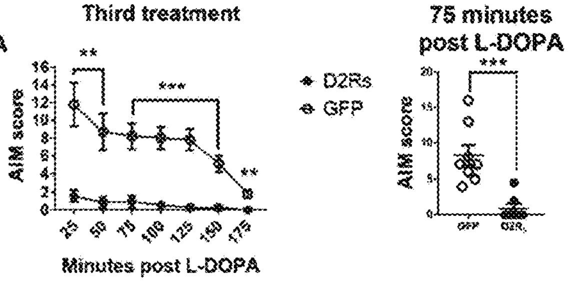
Figure 17G:
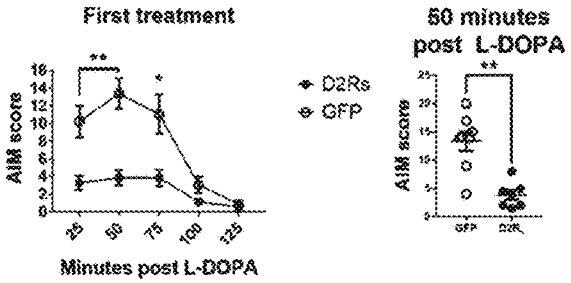
Figure 17H:
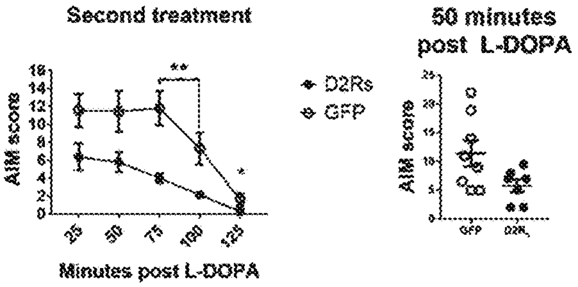
Figure 17I:
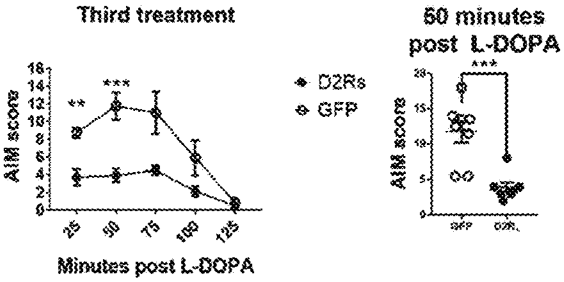

FIG. 17A-171 show that D2Rs-injected animals do not develop severe AIMs with DA agonist treatment. Animals were treated three times each with apomorphine (FIGS. 17A-17C) quinpirole (FIGS. 17D-17F) or SKF-81297 (FIGS. 17G-171). FIGS. 17A-17C show rAAV-D2Rs-injected animals remained AIM resistant with 0.1m/kg pan-DA agonist apomorphine treatment, while rAAV-GFP animals continued to exhibit dyskinetic behaviors. FIGS. 17D-17F show 0.2 mg/kg quinpirole (D2 agonist) did not elicit AIMs in rAAVD2Rs animals, where rAAV-GFP animals continued to exhibit moderate to severe AIMs. FIGS. 17G-171 show that rAAV-D2Rs began to show mild-to-moderate AIMs with 0.8 mg/kg of the D1 agonist SKF-81297 treatments, but remained significantly less severe than their rAAV-GFP counterparts. (*=p≤0.05, =p≤0.01, *=p≤0.001).

Figure 18B:
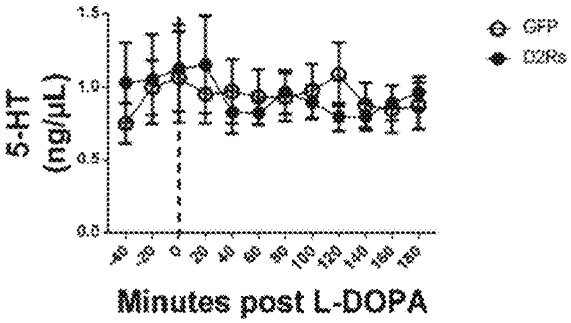

FIGS. 18A-18B show DRN D2Rs reduced striatal efflux of DA. FIGS. 18A and 18B In vivo microdialysis of rAAV-D2Rs and rAAV-GFP animals in twenty-minute intervals following L-DOPA injection (12 mg/kg+12 mg/kg Benserazide, s.c.). 17A rAAV-D2Rs animals showed significantly decreased DA efflux in the striatum 60-120 min following injection. FIG. 18B shows no changes in serotonin efflux in the striatum between vector groups was observed following L-DOPA injection. (*=p≤0.05, =p≤0.01, *=p≤0.001).

Figure 19A:
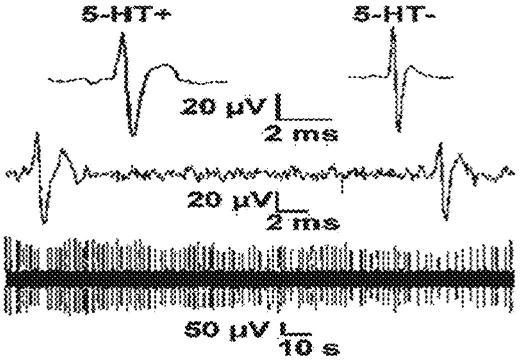
FIG. 19A-19F show ectopic DRN D2Rs expression reduces 5HT neuronal firing.
Figure 19B:
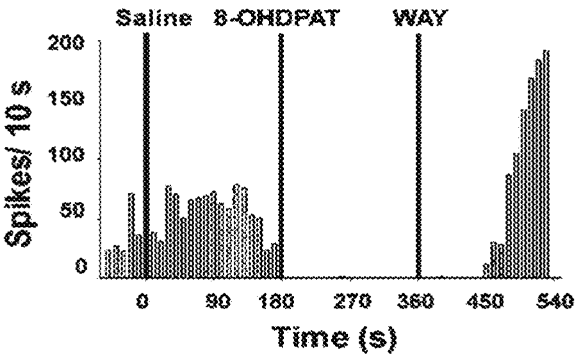
Figure 19C:
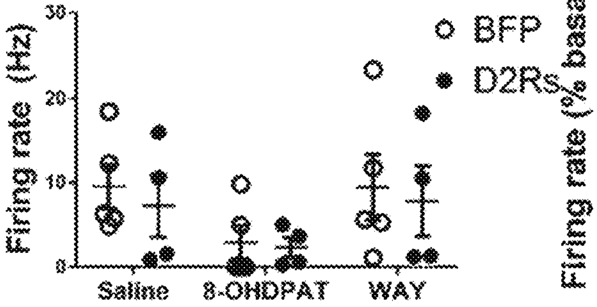
Figure 19D:
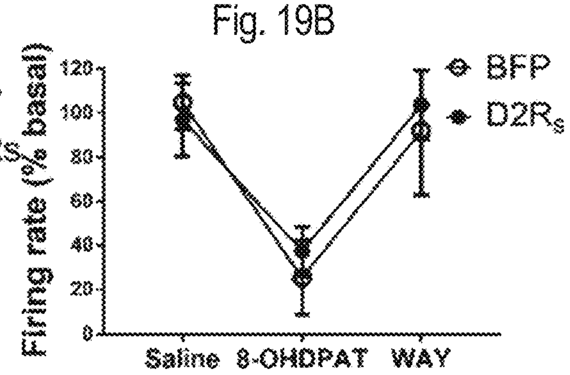
Figure 19E:
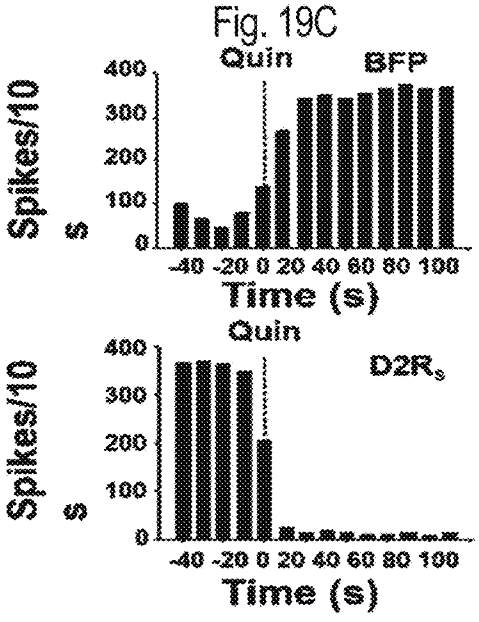
Figure 19F:
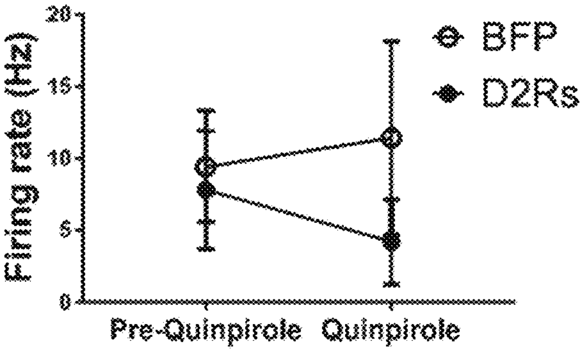

FIGS. 19A-19F show ectopic DRN D2Rs expression reduces 5HT neuronal firing. FIG. 19A, Top, shows traces show typical single-unit recordings of isolated DRN 5-HT neurons (5-HT+) (left) and non-serotonergic (5-HT-) neurons (right). FIG. 19A, Middle/Bottom, show 5-HT neurons often exhibit burst firing with short inter-spike intervals as well as regular spiking. FIG. 19B shows systemic administration of the selective 5-HT1A agonist 8—OH-DPAT (1 ug/kg, i.v.), but not saline (0.9%) vehicle, suppressed the spontaneous firing of a DRN neuron exhibiting spike characteristic of a 5-HT cell. A return to baseline firing was observed after the local application of WAY-100635 ((100 ug/kg, i.v.), vertical blue bars). FIGS. 19C-19D show the firing rate distributions of DRN neurons recorded in BFP and D2Rs expressing rats before and after the application of saline, 8—OH-DPAT and WAY-100635. Putative 5-HT neurons in both groups exhibited similar inhibitory responses to 5-HT1AR agonist and reversal of inhibition by 5-HT1AR antagonism. FIG. 19E shows the firing rate histograms showing the effects of the D2R agonist quinpirole (500 μg/kg, i.v.) on 5-HT neurons recorded in BFP (top) or AAV-D2Rs (bottom) injected rats. Control neurons that responded to Quin increased their firing activity to varying degrees, whereas the majority of 5-HT cells recorded in AAV-D2Rs injected rats were inhibited. FIG. 19F shows the cumulative electrophysiological data showing the mean+S.E.M. firing rates of 5-HT DRN cells transfected with BFP or D2Rs prior to, and after Quin administration.

FIG. 20 shows concentrations of monoamines in lesioned vs. intact side of brain. Concentration (picograms per microliter) of monoamines and metabolites for striatal tissue taken from animals used in microdialysis experiments. A drastic reduction in DA (>~98% of intact hemisphere) and DOPAC (>~89% of intact hemisphere) levels was observed in the lesioned striatum of either vector group, indicating successful lesions. There were no significant differences in any monoamine concentrations in GFP vs rAAV-D2R rats.

Figure 21A:
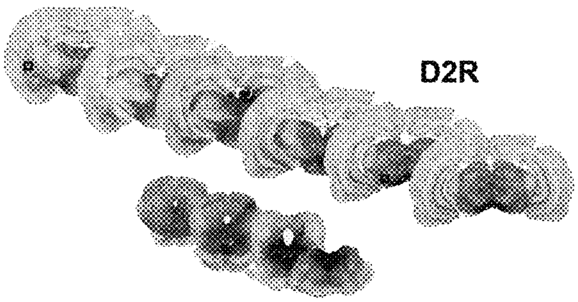
FIGS. 21A-21K show evaluation of transgene expression and effect on DRN neurons.
Figure 21B:
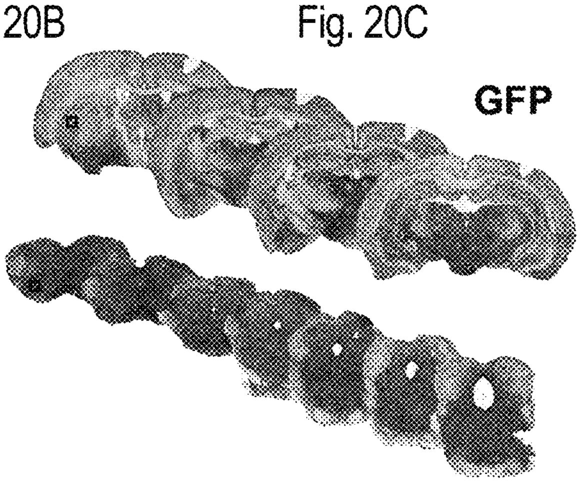
Figure 21C:
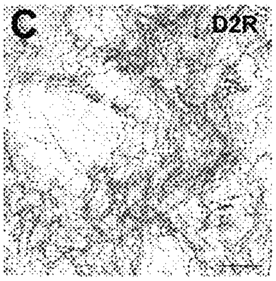
Figure 21D:
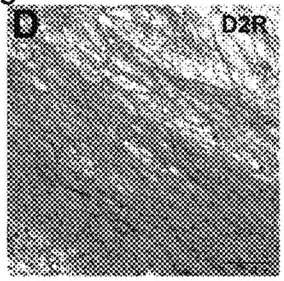
Figure 21G:
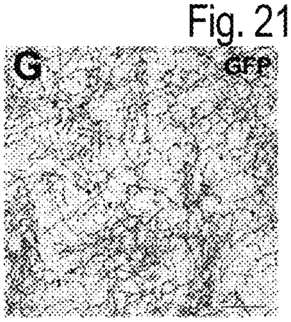
Figure 21H:
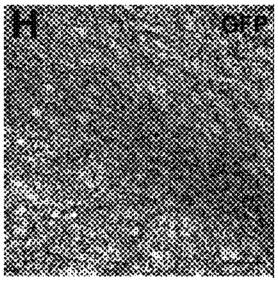
Figure 21E:
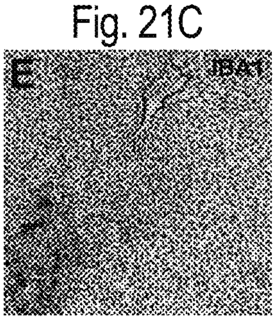
Figure 21F:
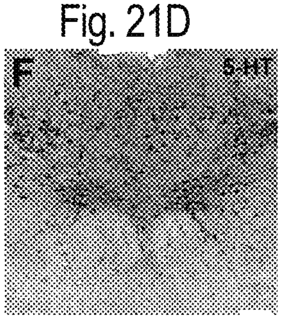
Figure 21I:
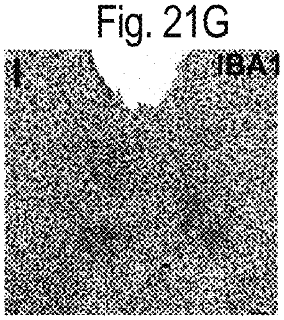
Figure 21J:
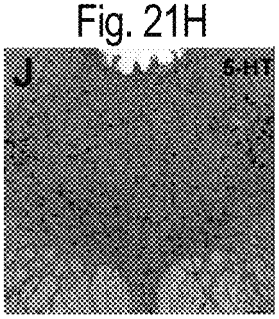
Figure 21K:
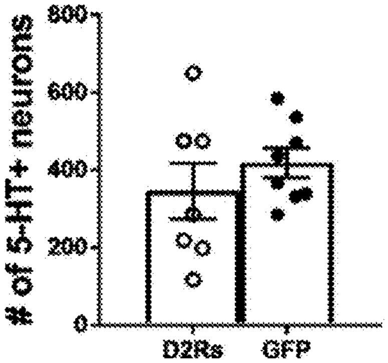
Figure 22A:
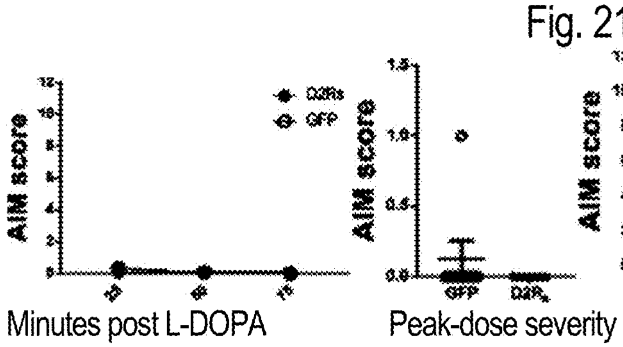
FIGS. 22A-22E show AIM scores in L-DOPA dosing paradigm.
Figure 22B:
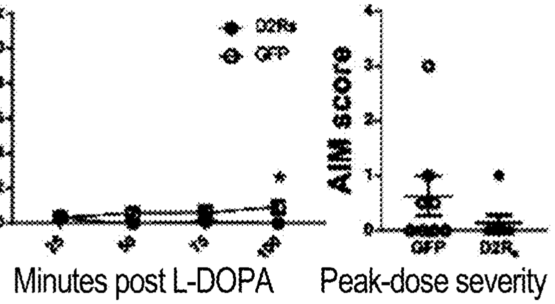
Figure 22C:
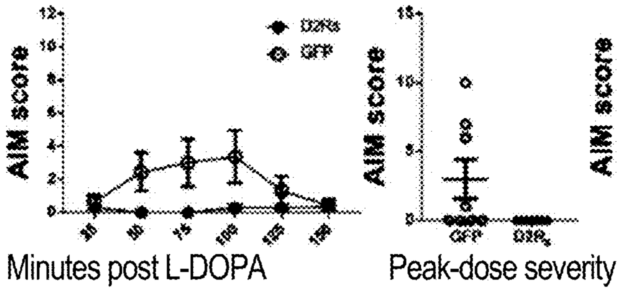
Figure 22D:
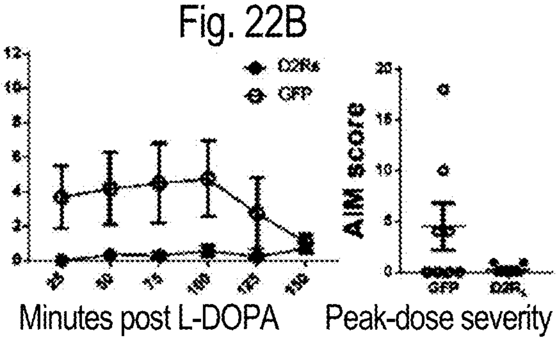
Figure 22E:
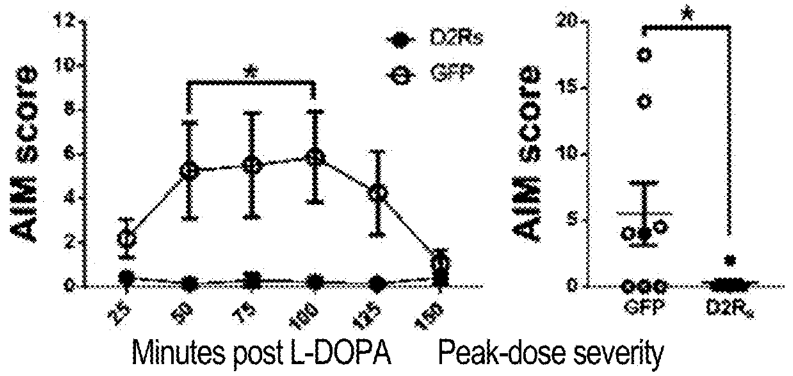

FIGS. 21A-21K shows evaluation of transgene expression and effect on DRN neurons. (FIGS. 21A and 21B) IHC for virally expressed transgenes D2Rs (FIG. 21A) or GFP (FIG. 21B) show substantial expression throughout brain. The widespread immunoreactivity indicates DRN innervation targets. Transgene was observed in striatal projection fibers from the DRN (FIGS. 21C, 21G). No cell bodies were transduced in regions outside of the raphe, including the SNc (FIGS. 21D, 21H). IBA1 immunoreactivity showed a slight microgliosis at the injection site in both vector groups (FIGS. 21E, 21I) but not elsewhere. 5-HT immunoreactivity was comparable between groups (FIGS. 21F, 21J) and the number of 5-HT+DRN neurons was the same in both groups (FIG. 21K). Scale bars: FIGS. 21A, 21B=1 mm; FIGS. 21C, 21D, 21G, 21H=50 μm; FIGS. 21E, 21F, 21I, 21J=100 μm. Boxes in FIGS. 21A and 21B outlines areas of magnification in FIGS. 21C, 21D and 21G, 21H respectively.

FIG. 22 shows AIM scores in L-DOPA dosing paradigm. AIM scores for days 1-10 in the L-DOPA dosing regimen, ranging from 2 mg/kg-8 mg/kg. Significantly more severe AIMs were observed in rAAuGFP animals starting on day 10 with 8 mg/kg. Peak-dose severity scores taken at 75 min post L-DOPA. (*=p≤0.05, =p≤0.01, *=p≤0.001).

As used herein, the term "combinations" shall be taken to mean one or more substances which can be administered together, one after the other or separately in one combined unit dosage form or in two separate unit dosage forms.

Administration of the dosage forms may be concomitantly, simultaneously, part-simultaneously, separately or sequentially. The dosage forms of the combination may not necessarily be of the same dosage form and may comprise one or more of: Enteral: Oral (capsule, tablet, solution), Rectal (suppository) Parenteral: Intravenous injection, subcutaneous injection, intramuscular injection, intraperitoneal injection, intramammary injection Respiratory: Inhalation, Intranasal, Intratracheal Topical: Mucous membrane application, skin application.

In addition, the release profiles of the medicaments may not be the same, for example one or more component of the combination may be of extended release form.

Compounds having mGluR modulating activity, in particular antagonistic activity, may be used to treat Parkinson's Disease and disorders associated with Parkinson's Disease. See, U.S. Pat. No. 8,703,809. In particular, mGluR modulators may be used to treat dyskinesia, a disorder associated with Parkinson's Disease and treatment thereof. In particular, it has been found that mGluR5 modulators, e.g., mGluR5 antagonists, may be used to treat Parkinson's Disease and associated disorders e.g., LID.

For the above-mentioned indications (the conditions and disorders) the appropriate dosage(s) will vary depending upon, for example, the compound(s) employed, the host, the mode of administration and the nature and severity of the condition being treated. For compounds disclose in the prior art literature, the recommendations and regulatory agency approved package inserts provide reasonable guidelines for predictable administration of the respective agents, though due care should be exercised for combinations of agents that may act additively, synergistically, or antagonistically at the same receptors, or in their functional results.

For use according to the invention, the various agents and compositions may be administered as single active agent or in combination with other active agents, in any usual manner, e.g., orally, for example in the form of tablets or capsules, or parenterally, for example in the form of injection solutions or suspensions. Moreover, these may be in association with at least one pharmaceutical carrier or diluent for use in the treatment of, e.g., Parkinson's Disease or LID. Such compositions may be manufactured in conventional manner.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules. The pharmaceutical compositions of the present invention are prepared in a manner known per se, for example by means of conventional dissolving, lyophilizing, mixing, granulating or confectioning processes. Such processes are exemplified in WO 2005/079802, WO 2003/047581, WO 2004/000316, WO 2005/044265, WO 2005/044266, WO 2005/044267, WO 2006/114262 and WO 2007/071358.

Pharmaceutical compositions and medicaments may be described as mixtures of two or more components "by volume," which is herein defined as the volume due to one component divided by the volume of all components of the composition. This ratio may be converted to or reported as a percentage of the total composition volume. Such a quantity may also be indicated by "v/v" or "percent v/v." Similarly, the phrases "by weight" and "by mass" describe the weight or mass due to one component divided by the weight or mass of all components of the composition. This ratio may be converted to or reported as a percentage of the total composition weight or mass. Such a quantity may also be indicated by "w/w", "mass percent," or percent w/w."

A further aspect of the present invention is a kit for the prevention of, delay of progression of, treatment of a disease or condition according to the present invention comprising (a) an amount of a SERT-active agent having 5-HT1A receptor agonistic properties, or a pharmaceutically acceptable salt thereof, in a first unit dosage form; (b) an amount of at least one active ingredient selected from L-DOPA, and/or a DOPA decarboxylase inhibitor, or a catechol-O-methyl transferase inhibitor, or a dopamine agonist or, in each case, where appropriate, a pharmaceutically acceptable salt thereof; and (c) a container for containing said first, second etc. unit forms.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points.

The parts of the kit of parts can then e.g., be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The present invention thus also relates to a kit of parts comprising (a) an amount of the agent or a pharmaceutically acceptable salt thereof in a first unit dosage form; (b) an amount of at least one active ingredient selected from L-DOPA, and/or a DOPA decarboxylase inhibitor, or a catechol-O-methyl transferase inhibitor, or a dopamine agonist or, in each case, where appropriate, a pharmaceutically acceptable salt thereof, in the form of two or three or more separate units of the components (a) to (b), especially for the prevention of, delay of progression of, treatment of a disease or condition according to the present invention.

The invention furthermore relates to a commercial package comprising the combination according to the present invention together with instructions for simultaneous, separate or sequential use.

In a preferred embodiment, the (commercial) product is a commercial package comprising as active ingredients the combination according to the present invention (in the form of two or three or more separate units of the components (a) or (b)), together with instructions for its simultaneous, separate or sequential use, or any combination thereof, in the delay of progression or treatment of the diseases as mentioned herein.

All the preferences mentioned herein apply to the combination, composition, use, method of treatment, "kit of parts" and commercial package of the invention.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubilizing or lyophilizing processes. Thus, pharmaceutical preparations for oral use can be obtained by combining the active compound(s) with solid excipients, if desired granulating a mixture which has been obtained, and, if required or necessary, processing the mixture or granulate into tablets or coated tablet cores after having added suitable auxiliary substances. The dosage of the active compound can depend on a variety of factors, such as mode of administration, homeothermic species, age and/or individual condition. Preferred dosages for the active ingredients of the pharmaceutical combination according to the present invention are therapeutically effective dosages, especially those which are commercially available. The dosage of the active compound can depend on a variety of factors, such as mode of administration, homeothermic species, age and/or individual condition.

The pharmaceutical composition according to the present invention as described hereinbefore may be used for simultaneous use or sequential use in any order, for separate use or as a fixed combination.

One skilled in the art will readily appreciate that the specific methods and results discussed are merely illustrative of the invention as described more fully in the claims which follow thereafter.

REFERENCES (Each of which is Expressly Incorporated Herein by Reference in its Entirety)

"Australian Public Assessment Report for vortioxetine hydrobromide" (PDF). p. 11. 2017 Aug. 1.
"Efficacy and Safety of Vortioxetine (Lu AA21004) for Treatment of Generalized Anxiety Disorder in Adults".
"Epidiolex (Cannabidiol) FDA Label" (PDF). fda.gov. 2018.
"Fact Sheet-Sativex". Health Canada. 2013.
"Lodosyn", Drugs, 2nd, 2012
"Lundbeck's "Serotonin Modulator and Stimulator" Lu AA21004: How Novel? How Good?-GLG News ". 2011 Jul. 24.
"Medicare D". Medicare. 2014.
"Parkinson's Disease Information Page". NINDS. 2016.
"Parkinson's Disease vs. Parkinsonism" (PDF). National Parkinson Foundation. 2017
"Parkinson's-"the shaking palsy". GlaxoSmithKline. 2009.
"Queen Square Brain Bank diagnostic criteria for Parkinson's disease". 2017.
"Relapse-prevention Study With Lu AA21004 (Vortioxetine) in Patients With Generalized Anxiety Disorder".
"Sativex-FASS Allmänhet". www.fass.se.
"Sativex (Cannabidiol/Tetrahydrocannabinol) Bayer Label" (PDF). bayer.ca. 2018.
"Sativex Oromucosal Spray-Summary of Product Characteristics (SPC)-(eMC)". Medicines.org.uk. 2016.
"Study Reveals Details Of Mussels' Tenacious Bonds". Science Daily. Aug. 16, 2006.
"Synthetic scheme for total synthesis of DOPA, L-(Monsanto)". UW Madison, Department of Chemistry. 2013.
"TGA eBS-Product and Consumer Medicine Information Licence". www.ebs.tga.gov.au. 2018.
"VIIBRYD (vilazodone hydrochloride) tablet VIBRYD (vilazodone hydrochloride) kit [Forest Laboratories, Inc.]". DailyMed. Forest Laboratories, Inc. December 2012.
"World's first Parkinson's vaccine is trialled". New Scientist. London. 7 Jun. 2012.
Xconomy, "Xconomy: Blend Therapeutics Taps Former Clinical Data Chief Fromkin As New CEO". xconomy.com. 13 Apr. 2015.
Aarsland D, Londos E, Ballard C (April 2009) [28 Jan. 2009]. "Parkinson's disease dementia and dementia with Lewy bodies: different aspects of one entity". International Psychogeriatrics. 21 (2): 216-9. doi: 10.1017/S1041610208008612. PMID 19173762.
Ahlskog JE (July 2011). "Does vigorous exercise have a neuroprotective effect in Parkinson disease?". Neurology. 77 (3): 288-94. doi: 10.1212/wnl.0b013e318225ab66. PMC 3136051. PMID 21768599.
Ahlskog JE, Muenter MD (2001) Frequency of levodopa-related dyskinesias and motor fluctuations as estimated from the cumulative literature. Mov Disord 16:448-458
Ahrens J, Demir R, Leuwer M, de la Roche J, Krampfl K, Foadi N, Karst M, Haeseler G: The nonpsychotropic cannabinoid cannabidiol modulates and directly activates alpha-1 and alpha-1-Beta glycine receptor function. Pharmacology. 2009; 83 (4): 217-22. doi: 10.1159/000201556. Epub 2009 Feb. 10. [PubMed: 19204413]
Aizpurua-Olaizola O, Soydaner U, Öztürk E, Schibano D, Simsir Y, Navarro P, Etxebarria N, Usobiaga A (February 2016). "Evolution of the Cannabinoid and Terpene Content during the Growth of *Cannabis sativa* Plants from Different Chemotypes". Journal of Natural Products. 79 (2): 324-31. doi: 10.1021/acs.jnatprod.5b00949. PMID 26836472.
Allen NM, Lin JP, Lynch T, King MD. Status dystonicus: a practice guide. Dev Med Child Neurol 2014; 56:105-112.
Altwal, Feras; Ritger, Alex; Voelkner, *Nivea* Falcao; Dhargalkar, Janhavi; Malik, Rabia; Olivera, Valentina; West, Anthony R.; "Using Multimodal Serotoninergic Drugs as Adjunct Treatments for Parkinson's Disease", Rosalind Franklin University 2019
Anttila, Sami AK, and Esa VJ Leinonen. "A review of the pharmacological and clinical profile of mirtazapine." CNS drug reviews 7, no. 3 (2001): 249-264.
Aquino CC, Fox SH (January 2015) . "Clinical spectrum of levodopa-induced complications". Movement Disorders. 30 (1): 80-9. doi: 10.1002/mds.26125. PMID 25488260.
Arai R, Karasawa N, Geffard M, Nagatsu I (1995) L-DOPA is converted to dopamine in serotonergic fibers of the striatum of the rat: a double-labeling immunofluorescence study. Neurosci Lett 195:195-198
Arai, R., Karasawa, N., & Nagatsu, I. (1996). Dopamine produced from L-DOPA is degraded by endogenous monoamine oxidase in neurons of the dorsal raph nucleus of the rat an immunohistochemical study. Brain Res, 722 (1-2): 181-184.
Ashby Jr, Charles R., John H. Kehne, Gerd D. Bartoszyk, Matthew J. Renda, Maria Athanasiou, Kerri A. Pierz, and Christoph A. Seyfried. "Electrophysiological evidence for rapid 5-HT1A autoreceptor inhibition by vilazodone, a 5-HT1A receptor partial agonist and 5-HT reuptake inhibitor." European journal of pharmacology 714, no. 1-3 (2013): 359-365.

Aubert, I., Guigoni, C., Håkansson, K., Li, Q., Dovero, S., Barthe, N., et al (2005). Increased D1 dopamine receptor signaling in levodopa-induced dyskinesia. Ann Neur, 57 (1): 17-26.

Australian Medicines Handbook 2013. The Australian Medicines Handbook Unit Trust; 2013.

B.G. Michael, Azabicyclic 5-HT1 receptor ligands, patent WO 9952907 A1, January 1999.

Bandolier, "L-dopa for RLS". 2007. www.bandolier.org.uk/booth/RLS/dopa.html Bang-Andersen B, Ruhland T, Jørgensen M, et al. (May 2011). "Discovery of 1-[2-(2,4-dimethylphenylsulfanyl)phenyl]piperazine (Lu AA21004): a novel multimodal compound for the treatment of major depressive disorder". Journal of Medicinal Chemistry. 54 (9): 3206-21. doi: 10.1021/jm101459g. PMID 21486038.

Bang-Andersen, Benny, Andre Faldt, Arne Mork, Heidi Lopez de Diego, Rene Holm, Tine Bryan Stensbol, and Nicholas Moore. "1-[2-(2,4-dimethylphenylsulfanyl)-phenyl]piperazine as a compound with combined serotonin reuptake, 5-HT3 and 5-HT1A activity for the treatment of cognitive impairment." U.S. Pat. No. 8,722,684, issued May 13, 2014.

Banich MT, Compton RJ (2011). "Motor control". Cognitive neuroscience. Belmont, CA: Wadsworth, Cengage learning. pp. 108-44. ISBN 978-O-8400-3298-0.

Barichella M, Cereda E, Pezzoli G (October 2009). "Major nutritional issues in the management of Parkinson's disease". Movement Disorders. 24 (13): 1881-92. doi: 10.1002/mds.22705. PMID 19691125.

Barnum, C.J., Eskow, K. L., Dupre, K., Blandino Jr., P., Deak, T., & Bishop, C. (2008). Exogenous corticosterone reduces L-DOPA-induced dyskinesia in the hemi-parkinsonian rat: Role for interleukin-1B. J Neurosci, 156 (1): 30-41.

Baron EP: Comprehensive Review of Medicinal Marijuana, Cannabinoids, and Therapeutic Implications in Medicine and Headache: What a Long Strange Trip It's Been. . . . Headache. 2015 June; 55 (6): 885-916. doi: 10.1111/head.12570. Epub 2015 May 25. [PubMed: 26015168]

Barranco Quintana JL, Allam MF, Del Castillo AS, Navajas RF (February 2009). "Parkinson's disease and tea: a quantitative review". Journal of the American College of Nutrition. 28 (1): 1-6. doi: 10.1080/07315724.2009.10719754. PMID 19571153.

Barreto, George E.; larkov, Alexander, Moran, Valentina Echeverria (January 2015). "Beneficial effects of nicotine, cotinine and its metabolites as potential agents for Parkinson's disease". Frontiers in Aging Neuroscience. 6:340. doi: 10.3389/fnagi.2014.00340. PMC 4288130. PMID 25620929.

Barth M, Serre V, Hubert L, et al. Kinetic analyses guide the therapeutic decision in a novel form of moderate aromatic acid decarboxylase deficiency. JIMD Rep 2012; 3:25-32.

Bastide MF, Meissner WG, Picconi B, Fasano S, Fernagut P—O, Feyder M, Francardo V, Alcacer C, Ding Y, Brambilla R et al (2015) Pathophysiology of L-dopa-induced motor and non-motor complications in Parkinson's disease. Prog Neurobiol 132:96-168. doi.org/10.1016/j.pneurobio.2015.07.002

Bedard C, Wallman MJ, Pourcher E, Gould PV, Parent A, Parent M (2011) Serotonin and dopamine striatal innervation in Parkinson's disease and Huntington's chorea. Parkinsonism Relat Disord 17:593-598. doi.org/10.1016/j.parkreldis.2011.05.012

Benskey MJ, Manfredsson FP (2016) Intraparenchymal Stereotaxic Delivery of rAAV and Special Considerations in Vector Handling. Methods Mol Biol 1382: 199-215. doi.org/10.1007/978-1-4939-3271-9_14 (A)

Benskey MJ, Sandoval IM, Manfredsson FP (2016) Continuous Collection of Adeno-Associated Virus from Producer Cell Medium Significantly Increases Total Viral Yield. Human gene therapy methods 27:32-45. doi.org/10. 1089/hgtb.2015.117 (B)

Benskey MJ, Sellnow RC, Sandoval IM, Sortwell CE, Lipton JW, Manfredsson FP (2018) Silencing Alpha Synuclein in Mature Nigral Neurons Results in Rapid Neuroinflammation and Subsequent Toxicity. Front Mol Neurosci 11:36. doi.org/10.3389/fnmol.2018.00036

Berg D, Postuma RB, Adler CH, Bloem BR, Chan P, Dubois B, Gasser T, Goetz CG, Halliday G, Joseph L, Lang AE, Liepelt-Scarfone I, Litvan I, Marek K, Obeso J, Oertel W, Olanow CW, Poewe W, Stern M, Deuschl G (October 2015). "MDS research criteria for prodromal Parkinson's disease". Movement Disorders. 30 (12): 1600-11. doi: 10.1002/mds.26431. PMID 26474317.

Berke, J. D., Paletzki R. F., Aronson, G. J., Hyman, S. E., & Gerfen, C. R. (1998). A complex program of striatal gene expression induced by dopaminergic stimulation. J. Neurosci., 18, 5301-5310.

Bezard E, Tronci E, Pioli EY, Li Q, Porras G, Bj.rklund A, Carta M. Study of the antidyskinetic effect of eltoprazine in animal models of levodopa-induced dyskinesia. Movement Disorders. 2013 Jul. 1;28 (8): 1088-96. doi.org/10.1002/mds. 25366

Bhide N, Lindenbach D, Barnum CJ, George JA, Surrena MA, Bishop C (2015) Effects of the beta-adrenergic receptor antagonist Propranolol on dyskinesia and L-DOPA-induced striatal DA efflux in the hemi-parkinsonian rat. J Neurochem 134:222-232. doi.org/10.1111/jnc.13125

Bibbiani F, Oh JD, Chase TN (2001) Serotonin 5-HT1A agonist improves motor complications in rodent and primate parkinsonian models. Neurology 57:1829-1834

Birkmayer W, Hornykiewicz O (1961). "The L-3,4-dioxyphenylalanine (DOPA)-effect in Parkinson-akinesia". Wien Klin Wochenschr. 73:787-8. PMID 13869404.

Bishop C, George JA, Buchta W, Goldenberg AA, Mohamed M, Dickinson SO, Eissa S, Eskow Jaunarajs KL. Serotonin transporter inhibition attenuates I-DOPA-induced dyskinesia without compromising I-DOPAefficacy in hemi-parkinsonian rats. European Journal of Neuroscience. 2012 Sep. 1;36 (6): 2839-48.

Bishop C., Krolewski D.M., Eskow K.L., Barnum C.J., Dupre K.B., Deak T., Walker P.D. (2009). Contribution of the striatum to the effects of 5-HT1A Receptor Stimulation in L-DOPA-treated Hemiparkinsonian Rats. Journal of Neuroscience, 87, 1645-1658.

Bisogno T, Hanus L, De Petrocellis L, Tchilibon S, Ponde DE, Brandi I, Moriello AS, Davis JB, Mechoulam R, Di Marzo V: Molecular targets for cannabidiol and its synthetic analogues: effect on vanilloid VR1 receptors and on the cellular uptake and enzymatic hydrolysis of anandamide. Br J Pharmacol. 2001 October;134 (4): 845-52. doi: 10.1038/sj.bjp.0704327. [PubMed: 11606325]

Blessing, E. M; Steenkamp, M. M; Manzanares, J; Marmar, C. R (2015). "Cannabidiol as a Potential Treatment for Anxiety Disorders". Neurotherapeutics. 12 (4): 825-36. doi: 10.1007/s13311-015-0387-1. PMC 4604171. PMID 26341731.

Blum D, Torch S, Lambeng N, Nissou M, Benabid AL, Sadoul R, *Verna* JM (October 2001). "Molecular pathways involved in the neurotoxicity of 6—OHDA, dopamine and MPTP: contribution to the apoptotic theory in Parkinson's disease". Progress in Neurobiology. 65 (2): 135-72. doi: 10.1016/S0301-0082 (01) 00003-X. PMID 11403877.

Bolognini, D; Rock, EM; Cluny, NL; Cascio, MG; Limebeer, CL; Duncan, M; Stott, CG; Javid, FA; Parker, LA; Pertwee, RG; "Cannabidiolic acid prevents vomiting in Suncus *murinus* and nausea-induced behaviour in rats by enhancing 5-HT1A receptor activation"

Boot, J. R., S. L. Boulet, B. P. Clark, M. J. Cases-Thomas, L. Delhaye, K. Diker, J. Fairhurst et al. "N-Alkyl-N-arylmethylpiperidin-4-amines: Novel dual inhibitors of serotonin and norepinephrine reuptake." Bioorganic & medicinal chemistry letters 16, no. 10 (2006): 2714-2718.

Boraud T, Bezard E, Bioulac B, Gross CE (2001) Dopamine agonist-induced dyskinesias are correlated to both firing pattern and frequency alterations of pallidal neurones in the MPTP-treated monkey. Brain 124:546-557. doi.org/10.1093/brain/124.3.546

Borgelt LM, Franson KL, Nussbaum AM, Wang GS (February 2013). "The pharmacologic and clinical effects of medical cannabis" (Submitted manuscript). Pharmacotherapy (Review). 33 (2): 195-209. doi: 10.1002/phar.1187. PMID 23386598.

Bornheim LM, Kim KY, Li J, Perotti BY, Benet LZ (August 1995). "Effect of cannabidiol pretreatment on the kinetics of tetrahydrocannabinol metabolites in mouse brain". Drug Metabolism and Disposition. 23 (8): 825-831. PMID 7493549.

Boy, Kenneth M., Michael Dee, Joseph Yevich, John Torrente, Qi Gao, Lawrence Iben, Arlene Stark, and Ronald J. Mattson. "Ligand conformation has a definitive effect on 5-HT 1A and serotonin reuptake affinity." Bioorganic & medicinal chemistry letters 14, no. 17 (2004): 4467-4470.

Boyce S, Rupniak NM, Steventon MJ, Iversen SD (2001) Differential effects of D1 and D2 agonists in MPTP-treated primates: functional implications for Parkinson's disease. 1990. Neurology 57: S27-S33

Brey RL (April 2006). "Muhammad Ali's Message: Keep Moving Forward". Neurology Now. 2 (2): 8. doi: 10.1097/01222928-200602020-00003. 2011.

Brierley, Daniel I., James Samuels, Marnie Duncan, Benjamin J. Whalley, and Claire M. Williams. "Neuromotor tolerability and behavioural characterisation of cannabidiolic acid, a phytocannabinoid with therapeutic potential for anticipatory nausea." Psychopharmacology 233, no. 2 (2016): 243-254.

Brilliant, Murray H.; Vaziri, Kamyar; Connor, Thomas B.; Schwartz, Stephen G.; Carroll, Joseph J.; McCarty, Catherine A.; Schrodi, Steven J.; Hebbring, Scott J.; Kishor, Krishna S.; Flynn, Harry W.; Moshfeghi, Andrew A.; Moshfeghi, Darius M.; Fini, M Elizabeth; Mckay, Brian S. (October 2015). "Mining Retrospective Data for Virtual Prospective Drug Repurposing: L-DOPA and Age-related Macular Degeneration". The American Journal of Medicine. 129:292-8. doi: 10.1016/j.amjmed.2015.10.015. PMC 4841631. PMID 26524704.

Broadley KJ (March 2010). "The vascular effects of trace amines and amphetamines". Pharmacol. Ther. 125 (3): 363-375. doi: 10.1016/j.pharmthera.2009.11.005. PMID 19948186.

Brockes E (11 Apr. 2009). "It's the gift that keeps on taking". The Guardian. 25 Oct. 2010.

Bronstein J M, et al. (February 2011). "Deep brain stimulation for Parkinson disease: an expert consensus and review of key issues". Archives of Neurology. 68 (2): 165. doi: 10.1001/archneurol.2010.260. PMC 4523130. PMID 20937936.

Brooks DJ (April 2010). "Imaging approaches to Parkinson disease". Journal of Nuclear Medicine. 51 (4): 596-609. doi: 10.2967/jnumed.108.059998. PMID 20351351.

Brown KJ, Laun AS, Song ZH: Cannabidiol, a novel inverse agonist for GPR12. Biochem Biophys Res Commun. 2017 Nov. 4;493 (1): 453-454. doi: 10.1016/j.bbrc.2017.09.001. Epub 2017 Sep. 6. [PubMed: 28888984]

Caballol N, Martí MJ, Tolosa E (September 2007). "Cognitive dysfunction and dementia in Parkinson disease". Movement Disorders. 22 Suppl 17 (Suppl 17): S358-66. doi: 10.1002/mds.21677. PMID 18175397.

Camargos S, Scholz S, Simon-Sanchez J, et al. DYT16, a novel young-onset dystonia-parkinsonism disorder: identification of a segregating mutation in the stress-response protein PRKRA. Lancet Neurol 2008; 7:207-215.

Campone M, Rademaker-Lakhai JM, Bennouna J, Howell SB, Nowotnik DP, Beijnen JH, Schellens JH: Phase I and pharmacokinetic trial of AP5346, a DACH-platinum-polymer conjugate, administered weekly for three out of every 4 weeks to advanced solid tumor patients. Cancer Chemother Pharmacol. 2007 September;60 (4): 523-33. Epub 2007 Feb. 17. [PubMed: 17308894]

Campos AC, Guimarães FS (August 2008). "Involvement of 5HT1A receptors in the anxiolytic-like effects of cannabidiol injected into the dorsolateral periaqueductal gray of rats". Psychopharmacology. 199 (2): 223-30. doi: 10.1007/s00213-008-1168-x. PMID 18446323.

Campos AC, Moreira FA, Gomes FV, Del Bel EA, Guimarães FS (December 2012). "Multiple mechanisms involved in the large-spectrum therapeutic potential of cannabidiol in psychiatric disorders". Philosophical Transactions of the Royal Society of London. Series B, Biological Sciences (Review). 367 (1607): 3364-78. doi: 10.1098/rstb.2011.0389. PMC 3481531. PMID 23108553.

Carlson, Neil, Pearson Education, Inc., ed. Psychology of Behavior (11 ed.). pp. 533-538 (2012).

Carrier EJ, Auchampach JA, Hillard CJ: Inhibition of an equilibrative nucleoside transporter by cannabidiol: a mechanism of cannabinoid immunosuppression. Proc Natl Acad Sci USA. 2006 May 16;103 (20): 7895-900. doi: 10.1073/pnas.0511232103. Epub 2006 May 3. [PubMed: 16672367]

Carroll, William M. (2016). International Neurology. John Wiley & Sons. p. 188. ISBN 9781118777367. 8 September 2017.

Carta M, Carlsson T, Munoz A, Kirik D, Bjorklund A. Involvement of the serotonin system in L-dopa-induced dyskinesias. Parkinsonism & related disorders. 2008 Jul. 31;14: S154-8.

Carta AR, Fenu S, Pala P, Tronci E, Morelli M (2003) Selective modifications in GAD67 mRNA levels in striatonigral and striatopallidal pathways correlate to dopamine agonist priming in 6-hydroxydopamine-lesioned rats. Eur J Neurosci 18:2563-2572

Carta M, Carlsson T, Kirik D, Bjorklund A (2007) Dopamine released from 5HT terminals is the cause of L-DOPA-induced dyskinesia in parkinsonian rats. Brain 130:1819-1833. doi.org/10.1093/brain/awm082

Carta M., Tronci E. (2014). Serotonin system implication in L-DOPA-induced dyskinesia: from animal models to clinical investigations. Frontiers in Neurology, 5, article 78.

Casey G (August 2013). "Parkinson's disease: a long and difficult journey". Nursing New Zealand. 19 (7): 20-4. PMID 24195263.

Castaigne P, Rondot P, Ribadeau-Dumas JL, Said G. Progressive extra-pyramidal disorder in 2 young brothers: remarkable effects of treatment with L-dopa [in French]. Rev Neurol 1971; 124:162-166.

Celada P, Puig MV, Artigas F (2013) Serotonin modulation of cortical neurons and networks. Front Integr Neurosci 7:25. doi.org/10.3389/fnint.2013.00025

Celada, Pau, Analía Bortolozzi, and Francesc Artigas. "Serotonin 5-HT 1A receptors as targets for agents to treat psychiatric disorders: rationale and current status of research." CNS drugs 27, no. 9 (2013): 703-716.

Cenci MA, Lundblad M. Post-versus presynaptic plasticity in L-DOPA-induced dyskinesia. Journal of neurochemistry. 2006 Oct. 1;99 (2): 381-92.

Cenci MA, Konradi C (2010) Maladaptive striatal plasticity in L-DOPA-induced dyskinesia. Prog Brain Res 183:209-233. doi.org/10.1016/S0079-6123 (10) 83011-0

Cenci, M.A. (2002). Transcription factors involved in the pathogenesis of L-DOPA-induced dyskinesia in a rat model of Parkinson's disease. Amino Acids, 23 (1-3): 105-109.

Cenci, M.A., Lee, S., & Bjorklund, A. (1998). L-dopa-induced dyskinesia in the rat is associated with striatal overexpression of prodynorphine and glutamic acid decarboxylase mRNA. European J. Neuroscience, 10, 2694-2706.

Ceravolo R, Frosini D, Rossi C, Bonuccelli U (December 2009). "Impulse control disorders in Parkinson's disease: definition, epidemiology, risk factors, neurobiology and management". Parkinsonism & Related Disorders. 15 Suppl 4 (Suppl 4): S111-5. doi: 10.1016/S1353-8020 (09) 70847-8. PMID 20123548.

Chahine LM, Stern MB, Chen-Plotkin A (January 2014). "Blood-based biomarkers for Parkinson's disease". Parkinsonism & Related Disorders. 20 Suppl 1: S99-103. doi: 10.1016/S1353-8020 (13) 70025-7. PMC 4070332. PMID 24262199.

Chakroborty S, Geisbush TR, Dale E, Pehrson AL, Sanchez C, West AR (2017) Impact of Vortioxetine on Synaptic Integration in Prefrontal-Subcortical Circuits: Comparisons with Escitalopram. Front Pharmacol 8:764. doi. org/10.3389/fphar.2017.00764

Chang FC, Josephs KA. Levodopa responsiveness in adult-onset lower limb dystonia is associated with the development of Parkinson's disease. Tremor other Hyperkinet Mov 2013; 3.

Chang J.W., Wachtel S.R., Young D., Kang U.J. (1999). Biochemical and anatomical characteristics of forepaw adjusting steps in rat models of parkinson's disease: studies on medial forebrain bundle and striatal lesions. Neuroscience, 88, 617-628.

Chang YT, Sharma R, Marsh J L, et al. Levodopa-responsive aromatic L-amino acid decarboxylase deficiency. Ann Neurol 2004; 55:435-438.

Charcot, Jean-Martin; Sigerson, George (1879). Lectures on the diseases of the nervous system (Second ed.). Philadelphia: Henry C. Lea. p. 113.

Charlesworth G, Mohire MD, Schneider SA, Stamelou M, Wood NW, Bhatia KP. Ataxia telangiectasia presenting as dopa-responsive cervical dystonia. Neurology 2013; 81:1148-1151.

Chen, Fang-ping, Yun-man LI, and Guo-qing Liu. "Research and Development of 5-HT_(1A) Receptor Agonists, a New Class of Antidepressants [J]." Progress In Pharmaceutical Sciences 4 (2003): 005.

Chen, Hong-Xia, Xiao-Dan Xu, Rui Xue, Li Yuan, Ri-Fang Yang, And Yun-Feng LI. "Antidepressant-like effects of YL-0919, a novel dual-acting antidepressant with 5-HT_(1A) receptor agonist and serotonin reuptake inhibitor [J]." Military Medical Sciences 9 (2011).

Chen, Hong-xia, Zeng-liang Jin, Li-ming Zhang, Rui Xue, Xiao-dan Xu, Nan Zhao, Zhi-kun Qiu et al. "Antidepressant-like activity of YL-0919: a novel combined selective serotonin reuptake inhibitor and 5-HT1A receptor agonist." PloS one 8, no. 12 (2013): e83271.

Chen NH, Reith ME. Monoamine interactions measured by microdialysis in the ventral tegmental area of rats treated systemically with (+)-8-Hydroxy-2-(Di-n-Propylamino)tetralin. J Neurochem. 1995;64 (4): 1585-1597.

Chen, X.Q., K. Dai and P.C. Fan, Preparation of fused indole derivatives as MCHR modulators for treatment of obesity, patent WO 2002089729 A2, November 2002.

Chen, Xiao-fei, Zeng-liang Jin, Ying Gong, Nan Zhao, Xiao-yun Wang, Yu-hua Ran, You-zhi Zhang, Li-ming Zhang, and Yun-Feng Li. "5-HT6 receptor agonist and memory-enhancing properties of hypidone hydrochloride (YL-0919), a novel 5-HT1A receptor partial agonist and SSRI." Neuropharmacology 138 (2018): 1-9.

Cheshire PA, Williams DR (2012) Serotonergic involvement in levodopa-induced dyskinesias in Parkinson's disease. Journal of clinical neuroscience: official journal of the Neurosurgical Society of Australasia 19:343-348. doi.org/10.1016/j.jocn.2011.09.008

Chondrogiorgi M, Tatsioni A, Reichmann H, Konitsiotis S (2014) Dopamine agonist monotherapy in Parkinson's disease and potential risk factors for dyskinesia: a meta-analysis of levodopa-controlled trials. Eur J Neurol 21:433-440. doi.org/10.1111/ene. 12318

Christensen, Michael Cronquist, Henrik Loft, Ioana *Florea*, and Roger S. Mcintyre. "Efficacy of vortioxetine in working patients with generalized anxiety disorder." CNS spectrums (2017): 1-9.

Cicchetti F, Drouin-Ouellet J, Gross RE (September 2009). "Environmental toxins and Parkinson's disease: what have we learned from pesticide-induced animal models?". Trends in Pharmacological Sciences. 30 (9): 475-83. doi: 10.1016/j.tips.2009.06.005. PMID 19729209.

Cloud LJ, Jinnah HA. Treatment strategies for dystonia. Expert Opin Pharmacother 2010; 11:5-15.

Coffey RJ (March 2009). "Deep brain stimulation devices: a brief technical history and review". Artificial Organs. 33 (3): 208-20. doi: 10.1111/j.1525-1594.2008.00620.x. PMID 18684199.

Commissioner, Office of the. "Safety Alerts for Human Medical Products-Brintellix (vortioxetine): Drug Safety Communication-Brand Name Change to Trintellix, to Avoid Confusion With Antiplatelet Drug Brilinta (ticagrelor)". www.fda.gov. 2016 May 2.

Connolly BS, Lang AE (23-30 Apr. 2014). "Pharmacological treatment of Parkinson disease: a review". JAMA. 311 (16): 1670-83. doi: 10.1001/jama.2014.3654. PMID 24756517.

Connolly, KR; Thase, ME (2016). "Vortioxetine: a New Treatment for Major Depressive Disorder". Expert Opinion on Pharmacotherapy. 17 (3): 421-31. doi: 10.1517/14656566.2016.1133588. PMID 26679430. The authors suggest that vortioxetine is currently a good second-line antidepressant option and shows promise, pending additional long-term data, to become a first-line antidepressant option.

Conti M.M., Ostock C.Y., Lindenbach D, Goldenberg AA, Kampton E, Dell'isola R et al. (2014). Effects of prolonged selective serotonin reuptake inhibition on the development and expression of I-DOPA-induced dyskinesia in hemi-parkinsonian rats. Neuropharmacology, 77, 1-8.

Conti, M.M., Meadows, S.M., Melikhov-Sosin, M., Lindenbach, D., Hallmark, J., Werner, D. F., et al (2016). Monoamine transporter contributions to L-DOPA effects in hemi-parkinsonian rats. Neuropharmacology, 110 (Pt A): 125-134.

Cooper G, Eichhorn G, Rodnitzky RL (2008). "Parkinson's disease". In Conn PM. Neuroscience in medicine. Totowa, NJ: Humana Press. pp. 508-12. ISBN 978-1-60327-454-8.

Costa J, Lunet N, Santos C, Santos J, Vaz-Carneiro A (2010). "Caffeine exposure and the risk of Parkinson's disease: a systematic review and meta-analysis of observational studies". Journal of Alzheimer's Disease. 20 Suppl 1 (Suppl 1): S221-38. doi: 10.3233/JAD-2010-091525. PMID 20182023.

Cotzias GC, Papavasiliou PS, Gellene R (1969). "L-DOPA in Parkinson's syndrome". The New England Journal of Medicine. 281 (5): 272-273. doi: 10.1056/NEJM196907312810518. PMID 5791298.

Cotzias GC, Van Woert MH, Schiffer LM (1967) Aromatic amino acids and modification of parkinsonism. N Engl J Med 276:374-379. doi.org/10. 1056/nejm196702162760703

Cruz MP (2012). "Vilazodone HCl (Viibryd): A Serotonin Partial Agonist and Reuptake Inhibitor For the Treatment of Major Depressive Disorder". P T. 37 (1): 28-31. PMC 3278186. PMID 22346333.

D.T. La Vielle and Muller Olivier Gillert, Preparation of pyrimidin-4-one derivatives, their pharmaceutical compositions and use as 2/5-HT2c double antagonists, patent EP 1256583, October 2002.

Dal Toso R, Sommer B, Ewert M, Herb A, Pritchett DB, Bach A, Shivers BD, Seeburg PH (1989) The dopamine D2 receptor. two molecular forms generated by alternative splicing. EMBO J 8:4025-4034

Davidson, Colin, and Jonathan A. Stamford. "Evidence that 5-hydroxytryptamine release in rat dorsal raphe nucleus is controlled by 5-HT1A, 5-HT1B and 5-HT1D autoreceptors." British journal of pharmacology 114, no. 6 (1995): 1107-1109.

Davie CA (2008). "A review of Parkinson's disease". British Medical Bulletin. 86 (1): 109-27. doi: 10.1093/bmb/ldn013. PMID 18398010.

Davis P (3 May 2007). "Michael J. Fox". The TIME 100. Time. 25 Apr. 2011.

Dawson, Lee A. "The discovery and development of vilazodone for the treatment of depression: a novel antidepressant or simply another SSRI?." Expert opinion on drug discovery 8, no. 12 (2013): 1529-1539.

De Bellis, M.D., Geracioti Jr, T.D., Altemus, M., & Kling, M.A. (1993). Cerebrospinal fluid monoamine metabolites in fluoxetine-treated patients with major depression and in healthy volunteers. Biol Psychiatry, 33 (8-9): 636-641.

De Deurwaerdère P, Di Giovanni G, Millan MJ (2016) Expanding the repertoire of L-DOPA's actions: A comprehensive review of its functional neurochemistry. Progress in Neurobiology: Doi. doi.org/10.1016/j.pneurobio.2016.07.002 de la Fuente-Fernández, R., Sossi, V., Huang, Z., Furtado, S., Lu, J. Q., Calne, D. B., . . . & Stoessl, A. J. (2004). Levodopa-induced changes in synaptic dopamine levels increase with progression of Parkinson's disease: implications for dyskinesias. Brain, 127 (12): 2747-2754.

de Lau LM, Breteler MM (June 2006). "Epidemiology of Parkinson's disease". The Lancet. Neurology. 5 (6): 525-35. doi: 10.1016/S1474-4422 (06) 70471-9. PMID 16713924.

de Paulis, Tomas. "Drug evaluation: Vilazodone--a combined SSRI and 5-HT1A partial agonist for the treatment of depression." IDrugs: the investigational drugs journal 10, no. 3 (2007): 193.

De Petrocellis L, Ligresti A, Moriello AS, Allara M, Bisogno T, Petrosino S, Stott CG, Di Marzo V: Effects of cannabinoids and cannabinoid-enriched *Cannabis* extracts on TRP channels and endocannabinoid metabolic enzymes. Br J Pharmacol. 2011 August;163 (7): 1479-94. doi: 10.1111/j.1476-5381.2010.01166.x. [PubMed: 21175579]

De Petrocellis L, Orlando P, Moriello AS, Aviello G, Stott C, Izzo AA, Di Marzo V: Cannabinoid actions at TRPV channels: effects on TRPV3 and TRPV4 and their potential relevance to gastrointestinal inflammation. Acta Physiol (Oxf). 2012 February;204 (2): 255-66. doi: 10.1111/j.1748-1716.2011.02338.x. Epub 2011 Aug. 12. [PubMed: 21726418]

Deardorff, William James, and George T. Grossberg. "A review of the clinical efficacy, safety and tolerability of the antidepressants vilazodone, levomilnacipran and vortioxetine." Expert opinion on pharmacotherapy 15, no. 17 (2014): 2525-2542.

Dell'Agnello, G., Ceravolo, R., Nuti, A., Bellini, G., Piccinni, A., D'Avino, C., et al. (2001). SSRIs do not worsen Parkinson's disease: evidence from an open-label, prospective study. Clin Neuropharmacol, 24 (4): 221-227.

Delnooz CC, van de Warrenburg BP. Current and future medical treatment in primary dystonia. Ther Adv Neurol Disord 2012; 5:221-240.

Deng, Ming, Jing-lai LI, Li-jun ZHOU, Yuan DU, and Zhen-qing ZHANG. "Tissue distribution of YL-0919, a novel dual-acting antidepressant with 5-HT_(1A) receptor agonist and serotonin reuptake inhibitor in mice." Military Medical Sciences 2 (2012): 10.

Dereli EE, Yaliman A (April 2010). "Comparison of the effects of a physiotherapist-supervised exercise programme and a self-supervised exercise programme on quality of life in patients with Parkinson's disease".

Clinical Rehabilitation. 24 (4): 352-62. doi: 10.1177/0269215509358933. PMID 20360152.

Dickson DV (2007). "Neuropathology of movement disorders". In Tolosa E, Jankovic JJ. Parkinson's disease and movement disorders. Hagerstown, MD: Lippincott Williams & Wilkins. pp. 271-83. ISBN 978-O-7817-7881-7.

Dimond PF (16 Aug. 2010). "No New Parkinson Disease Drug Expected Anytime Soon". GEN news highlights. GEN-Genetic Engineering & Biotechnology News. 31 Oct. 2010.

Dinnendahl, V; Fricke, U, eds. (1998). Arzneistoff-Profile (in German). 10 (13 ed.). Eschborn, Germany: Govi Pharmazeutischer Verlag. ISBN 978-3-7741-9846-3.

Dixon L, Duncan D, Johnson P, Kirkby L, O'Connell H, Taylor H, Deane KH (July 2007). Deane K, ed. "Occupational therapy for patients with Parkinson's disease". The Cochrane Database of Systematic Reviews (3): CD002813. doi: 10.1002/14651858.CD002813.pub2. PMID 17636709.

Done C, Sharp T. Biochemical evidence for the regulation of central noradrenergic activity by 5-HT 1A and 5-HT 2 receptors: microdialysis studies in the awake and anaesthetized rat. Neuropharmacology. 1994;33 (3): 411-421

Donovan, Stephen. "Parkinson's Disease Treatment". 16 Apr. 2014.

du Jardin, Kristian Gaarn, Jesper Bornø Jensen, Connie Sanchez, and Alan L. Pehrson. "Vortioxetine dose-dependently reverses 5-HT depletion-induced deficits in spatial working and object recognition memory: a potential role for 5-HT1A receptor agonism and 5-HT3 receptor antagonism." European Neuropsychopharmacology 24, no. 1 (2014): 160-171.

Dupre, K. B., Eskow, K. L., Negron, G., & Bishop, C. (2007). The differential effects of 5-HT1A receptor stimulation on dopamine receptor-mediated abnormal involuntary movements and rotations in the primed hemiparkinsonian. Brain Research, 1158, 135-143.

Ehringer H, Homykiewicz O (1960). "Distribution of noradrenaline and dopamine (3-hydroxytyramine) in the human brain and their behavior in diseases of the extrapyramidal system". Klin Wochenschr. 38:1236-9. PMID 13726012.

El Mansari, M., Crnic, A., Oosterhof, C., & Blier, P. (2015). Long-term administration of the antidepressant vilazodone modulates rat brain monoaminergic system. Neuropharm, 99:696-704.

Elbers RG, Verhoef J, van Wegen EE, Berendse HW, Kwakkel G (October 2015). "Interventions for fatigue in Parkinson's disease". The Cochrane Database of Systematic Reviews (10): CD010925. doi: 10.1002/14651858.CD010925.pub2. PMID 26447539.

Elsohly MA, Slade D: Chemical constituents of marijuana: the complex mixture of natural cannabinoids. Life Sci. 2005 Dec. 22;78 (5): 539-48. doi: 10.1016/j.Ifs.2005.09.011. Epub 2005 Sep. 30. [PubMed: 16199061]

Eskow KL, Gupta V, Alam S, Park JY, Bishop C (2007) The partial 5-HT1A agonist buspirone reduces the expression and development of I-DOPA-induced dyskinesia in rats and improves I-DOPA efficacy. Pharmacol Biochem Behav 87:306-314. doi.org/10.1016/j.pbb.2007.05.002

Eskow, K.L., Dupre, K.B., Barnum, C.J., Dickinson, S.O., Park, J.Y., & Bishop, C. (2009). The role of the dorsal raphe nucleus in the development, expression and treatment of LID in hemiparkinsonian rats. Synapse, 63 (7): 610-620. doi.org/10.1002/syn.20630

Fahn S (2008). "The history of dopamine and levodopa in the treatment of Parkinson's disease". Movement Disorders. 23 Suppl 3 (Suppl 3): S497-508. doi: 10.1002/mds.22028. PMID 18781671.

Fahn S. The medical treatment of Parkinson disease from James Parkinson to George Cotzias. Mov Disord 2015; 30:4-18.

Fala, Loretta. "Brintellix Tablets (Vortioxetine) Approved by the FDA for the Treatment of Major Depressive Disorder."

Feng LR, Maguire-Zeiss KA (March 2010). "Gene therapy in Parkinson's disease: rationale and current status". CNS Drugs. 24 (3): 177-92. doi: 10.2165/11533740-000000000-00000. PMC 2886503. PMID 20155994.

Fernández-Ruiz, J; Sagredo, O; Pazos, M. R; García, C; Pertwee, R; Mechoulam, R; Martínez-Orgado, J (2013). "Cannabidiol for neurodegenerative disorders: Important new clinical applications for this phytocannabinoid?". British Journal of Clinical Pharmacology. 75 (2): 323-33. doi: 10.1111/j.1365-2125.2012.04341.x. PMC 3579248. PMID 22625422.

Ferrell B, Connor SR, Cordes A, Dahlin CM, Fine PG, Hutton N, Leenay M, Lentz J, Person JL, Meier DE, Zuroski K (June 2007). "The national agenda for quality palliative care: the National Consensus Project and the National Quality Forum". Journal of Pain and Symptom Management 33 (6): 737-44. doi: 10.1016/j.jpainsymman.2007.02.024. PMID 17531914.

Ferri, Fred F. (2010). Femi's differential diagnosis: a practical guide to the differential diagnosis of symptoms, signs, and clinical disorders (2nd ed.). Philadelphia, PA: Elsevier/Mosby. p. Chapter P. ISBN 978-0323076999.

Fidalgo, C., Ko, W.K., Tronci, E., Li, Q., Stancampiano, R., Chuan, Q., et al (2015). Effect of serotonin transporter blockade on L-DOPA-induced dyskinesia in animal models of Parkinson's disease. Neuroscience, 289:389-396.

Filla, K.J.H., A. Sandra and Schaus John Mehnet, Substituted heteroaromatic 5-HT1F agonists, including (octahydroindolizinyl) indoles and analogs, useful as antimigraine agents, patent U.S. Pat. No. 5,874,427 A, February 1999.

Findley LJ (September 2007). "The economic impact of Parkinson's disease". Parkinsonism & Related Disorders. 13 Suppl (Suppl): S8-S12. doi: 10.1016/j.parkreldis.2007.06.003. PMID 17702630.

Fischer, B; Russell, C; Sabioni, P; Van Den Brink, W; Le Foll, B; Hall, W; Rehm, J; Room, R (2017). "Lower-Risk *Cannabis* Use Guidelines: A Comprehensive Update of Evidence and Recommendations". American Journal of Public Health. 107 (8): e1-e12. doi: 10.2105/AJPH.2017.303818. PMID 28644037.

Ford CP (2014) The role of D2-autoreceptors in regulating dopamine neuron activity and transmission. Neuroscience 282:13-22. doi.org/10.1016/j.neuroscience.2014.01.025

Foster H.D.; Hoffer A. (2004). "The Two Faces of L-DOPA: Benefits and Adverse Side Effects in the Treatment of Encephalitis Lethargica, Parkinson's Disease, Multiple Sclerosis and Amyotrophic Lateral Sclerosis". Med Hypotheses. 62 (2): 177-81. doi: 10.1016/S0306-9877 (03) 00318-9. PMID 14962622.

Fournier G, Beherec O, Bertucelli S (2003). "Intérêt du rapport A-9-THC/CBD dans le contrôle des cultures de chanvre industriel" [The advantage of the A-9-THC/CBD ratio in the control of industrial hemp crops]. Annales de Toxicologie Analytique (in French). 15 (4): 250-259. doi: 10.1051/ata/2003003.

Fox CM, Ramig LO, Ciucci MR, Sapir S, McFarland D H, Farley BG (November 2006). "The science and practice of LSVT/LOUD: neural plasticity-principled approach to treating individuals with Parkinson disease and other neurological disorders". Seminars in Speech and Language. 27 (4): 283-99. doi: 10.1055/s-2006-955118. PMID 17117354.

Frampton, James E. "Vilazodone." CNS drugs 25, no. 7 (2011): 615-627.

Frattarelli DA, Galinkin JL, Green T P, et al. Of-label use of drugs in children. Pediatrics 2014; 133:563-567.

Friedman JH (November 2010). "Parkinson's disease psychosis 2010: a review article". Parkinsonism & Related Disorders. 16 (9): 553-60. doi: 10.1016/j.parkreldis.2010.05.004. PMID 20538500.

Fu, Jie; Peng, Lilei; Li, Xiaogang (2016-04-19). "The efficacy and safety of multiple doses of vortioxetine for generalized anxiety disorder: a meta-analysis". Neuropsychiatric Disease and Treatment. 12:953-959. doi: 10.2147/NDT.S104050. ISSN 1176-6328. PMC 4844447. PMID 27143896.

Fung VS, Thompson PD (2007). "Rigidity and spasticity". In Tolosa E, Jankovic. Parkinson's disease and movement disorders. Hagerstown, MD: Lippincott Williams & Wilkins. pp. 504-13. ISBN 978-O-7817-7881-7.

Gagne JJ, Power MC (March 2010). "Anti-inflammatory drugs and risk of Parkinson disease: a meta-analysis". Neurology. 74 (12): 995-1002. doi: 10.1212/WNL.0b013e3181d5a4a3. PMC 2848103. PMID 20308684.

Galpern WR, Lang AE (March 2006) [17 Feb. 2006]. "Interface between tauopathies and synucleinopathies: a tale of two proteins". Annals of Neurology. 59 (3): 449-58. doi: 10.1002/ana.20819. PMID 16489609.

Gan-Or Z, Dion PA, Rouleau GA (2 Sep. 2015). "Genetic perspective on the role of the autophagy-lysosome pathway in Parkinson disease". Autophagy. 11 (9): 1443-57. doi: 10.1080/15548627.2015.1067364. PMC 4590678. PMID 26207393.

Gantz Stephanie C, Levitt Erica S, Llamosas N, Neve Kim A, Williams John T (2015) Depression of Serotonin Synaptic Transmission by the Dopamine Precursor LDOPA. Cell Rep 12:944-954. doi.org/10.1016/j.celrep.2015.07.005 Gaoni Y, Mechoulam R (1966). "Hashish-VII The isomerization of cannabidiol to tetrahydrocannabinols". Tetrahedron. 22 (4): 1481-1488. doi: 10.1016/S0040-4020 (01) 99446-3.

García Ruiz PJ (December 2004). "[Prehistory of Parkinson's disease]" [[Prehistory of Parkinson's disease]. Neurologia (in Spanish). 19 (10): 735-7. PMID 15568171.

García-Ruiz, P.J., del Val, J., Fernández, I.M., & Herranz, A. (2011). What factors influence motor complications in Parkinson's disease?: A 10-year prospective study. Clin Neuropharmacol, 35 (1): 1-5.

Garcia-Ptacek S, Kramberger MG (September 2016). "Parkinson Disease and Dementia". Journal of Geriatric Psychiatry and Neurology. 29 (5): 261-70. doi: 10.1177/0891988716654985. PMID 27502301.

Gerfen, C.R., Engber, T.M., Mahan, L.C., Susel, Z., Chase, T.N., Monsma Jr., F.J., et al (1990). D1 and D2 dopamine receptor-regulated gene expression of striatonigral and striatopallidal neurons. Science, 250 (4986): 1429-1432.

Ghiglieri V, Mineo D, Vannelli A, Cacace F, Mancini M, Pendolino V, Napolitano F, di Maio A, Mellone M, Stanic J et al (2016) Modulation of serotonergic transmission by eltoprazine in L-DOPA-induced dyskinesia: Behavioral, molecular, and synaptic mechanisms. Neurobiol Dis 86:140-153. doi.org/10.1016/j.nbd.2015.11.022

Ghoche R (December 2012). "The conceptual framework of palliative care applied to advanced Parkinson's disease". Parkinsonism & Related Disorders. 18 Suppl 3 (Suppl 3): S2-5. doi: 10.1016/j.parkreldis.2012.06.012. PMID 22771241.

Ghovanloo MR, Shuart NG, Mezeyova M, Dean RA, Ruben PC, Goodchild SJ (September 2018). "Inhibitory effects of cannabidiol on voltage-dependent sodium currents". Journal of Biological Chemistry. doi: 10.1074/jbc.RA118.004929.

Gibb WR, Lees AJ (June 1988). "The relevance of the Lewy body to the pathogenesis of idiopathic Parkinson's disease". Journal of Neurology, Neurosurgery, and Psychiatry. 51 (6): 745-52. doi: 10.1136/jnnp.51.6.745. PMC 1033142. PMID 2841426.

Gilbert, Adam M., Thomas Coleman, Jason Kodah, Richard E. Mewshaw, Rosemary Scerni, Lee E. Schechter, Deborah L. Smith, and Terrance H. Andree. "Novel aryloxy-8-azabicyclo[3.2.1]oct-3-enes with 5-HT transporter and 5-HT 1A affinity." Bioorganic & medicinal chemistry letters 14, no. 21 (2004): 5281-5284.

Glazer WM. A new antidepressant. Behav Healthc. 2011; 31 (6): 39-40.

Gobert A, Rivet J-M, Audinot V, et al. Simultaneous quantification of serotonin, dopamine and noradrenaline levels in single frontal cortex dialysates of freely-moving rats reveals a complex pattern of reciprocal auto-and heteroreceptor-mediated control of release. Neuroscience. 1998;84 (2): 413-429.

Goetz, C.G., Damier, P., Hicking, C., Laska, E., Müller, T., Olanow, C. W., et al (2007). Sarizotan as a treatment for dyskinesias in parkinson's disease: A double-blind, placebo-controlled trial. Movement Disorders, 22 (2): 179-186.

Goldenberg MM (October 2008). "Medical management of Parkinson's disease". P & T. 33 (10): 590-606. PMC 2730785. PMID 19750042.

Goldman JG, Postuma R (2014) Premotor and nonmotor features of Parkinson's disease. Curr Opin Neurol 27:434-441. doi.org/10.1097/wco.0000000000000112

Gombash SE, Manfredsson FP, Mandel RJ, Collier TJ, Fischer DL, Kemp CJ, Kuhn NM, Wohlgenant SL, Fleming SM, Sortwell CE (2014) Neuroprotective potential of pleiotrophin overexpression in the striatonigral pathway compared with overexpression in both the striatonigral and nigrostriatal pathways. Gene Ther 21:682-693. doi.org/10.1038/gt.2014.42

Gomez-Mancilla B, Bédard PJ (1992) Effect of chronic treatment with (+)-PHNO, a D2 agonist in MPTP-treated monkeys. Exp Neurol 117:185-188. doi.org/10.1016/0014-4886 (92) 90125-A Gomperts SN (April 2016). "Lewy Body Dementias: Dementia With Lewy Bodies and Parkinson Disease Dementia". Continuum (Minneap Minn) (Review). 22

(2 Dementia): 435-63. doi: 10.1212/CON.0000000000000309. PMC 5390937. PMID 27042903.

Gonca E, Darici F: The effect of cannabidiol on ischemia/reperfusion-induced ventricular arrhythmias: the role of adenosine A1 receptors. J Cardiovasc Pharmacol Ther. 2015 January;20 (1): 76-83. doi: 10.1177/1074248414532013. Epub 2014 May 22. [PubMed: 24853683]

Goodarzi, Zahra, and Zahinoor Ismail. "A practical approach to detection and treatment of depression in Parkinson disease and dementia." Neurology: Clinical Practice (2017): 10-1212.

Goodwin VA, Richards SH, Taylor RS, Taylor AH, Campbell JL (April 2008). "The effectiveness of exercise interventions for people with Parkinson's disease: a systematic review and meta-analysis". Movement Disorders. 23 (5): 631-40. doi: 10.1002/mds.21922. PMID 18181210.

Gross, C.E., Ravenscroft, P., Dovero, S., Jaber, M., Bioulac, B., & Bezard, E. (2003). Pattern of levodopa-induced striatal changes is different in normal and MPTP-lesioned mice. J Neurochem, 84 (6): 1246-1255.

Guridi J, Lozano AM (November 1997). "A brief history of pallidotomy". Neurosurgery. 41 (5): 1169-80, discussion 1180-3. doi: 10.1097/00006123-199711000-00029. PMID 9361073.

Guttman M, Boileau I, Warsh J, Saint-Cyr JA, Ginovart N, Mccluskey T, Houle S, Wilson A, Mundo E, Rusjan P et al (2007) Brain serotonin transporter binding in non-depressed patients with Parkinson's disease. Eur J Neurol 14:523-528. doi.org/10.1111/j.1468-1331.2007.01727.x Haavik, J; Toska, K. (June 1998). "Tyrosine Hydroxylase and Parkinson's". Mol. Neurobiol. 16 (3): 285-309. doi: 10.1007/BF02741387. PMID 9626667.

Haberzett, Robert, Heidrun Fink, and Bettina Bert. "Role of 5-HT1A-and 5-HT2A receptors for the murine model of the serotonin syndrome." Journal of pharmacological and toxicological methods 70, no. 2 (2014): 129-133.

Hadley, J.C.N., Michael Stewart MacDonald, Gregor James, Preparation of tetrahydrobenzazepine derivatives as modulators of dopamine D3 receptors (antipsychotic agents), patent WO 2000021951 A1, April 2000.

Hajos M, Allers KA, Jennings K, Sharp T, Charette G, Sik A, Kocsis B (2007) Neurochemical identification of stereotypic burst-firing neurons in the rat dorsal raphe nucleus using juxtacellular labelling methods. Eur J Neurosci 25:119-126. doi.org/10.1111/j.1460-9568.2006.05276.x Harrington MA, Oksenberg D, Peroutka SJ (1988) 5-Hydroxytryptamine 1A receptors are linked to a Gi-adenylate cyclase complex in rat hippocampus. Eur J Pharmacol 154:95-98 35. Hoehn MM, Yahr MD (1967) Parkinsonism: onset, progression and mortality. Neurology 17:427-442

Harvey BK, Wang Y, Hoffer BJ (2008). "Transgenic rodent models of Parkinson's disease". Acta Neurochirurgica. Supplement Acta Neurochirurgica Supplementum. 101:89-92. doi: 10.1007/978-3-211-78205-7_15. ISBN 978-3-211-78204-0. PMC 2613245. PMID 18642640.

Hasnain M, Vieweg WV, Baron MS, Beatty-Brooks M, Fernandez A, Pandurangi AK (July 2009). "Pharmacological management of psychosis in elderly patients with parkinsonism". The American Journal of Medicine. 122 (7): 614-22. doi: 10.1016/j.amjmed.2009.01.025. PMID 19559160.

Hatzenbuhler, Nicole T., Deborah A. Evrard, Boyd L. Harrison, Donna Huryn, Jennifer Inghrim, Christina Kraml, James F. Mattes et al. "Synthesis and biological evaluation of novel compounds within a class of 3-aminochroman derivatives with dual 5-HT1A receptor and serotonin transporter affinity." Journal of medicinal chemistry 49, no. 15 (2006): 4785-4789.

Hayakawa K, Mishima K, Hazekawa M, Sano K, Irie K, Orito K, Egawa T, Kitamura Y, Uchida N, Nishimura R, Egashira N, Iwasaki K, Fujiwara M (January 2008). "Cannabidiol potentiates pharmacological effects of Delta (9)-tetrahydrocannabinol via CB (1) receptor-dependent mechanism". Brain Research. 1188:157-64. doi: 10.1016/j.brainres.2007.09.090. PMID 18021759.

Hayakawa K, Mishima K, Nozako M, Ogata A, Hazekawa M, Liu AX, Fujioka M, Abe K, Hasebe N, Egashira N, Iwasaki K, Fujiwara M (March 2007). "Repeated treatment with cannabidiol but not 49-tetrahydrocannabinol has a neuroprotective effect without the development of tolerance". Neuropharmacology. 52 (4): 1079-87. doi: 10.1016/j.neuropharm.2006.11.005. PMID 17320118.

Heinrich, Timo, Henning Böttcher, Gerd D. Bartoszyk, Hartmut E. Greiner, Christoph A. Seyfried, and Christoph van Amsterdam. "Indolebutylamines as selective 5-HT1A agonists." Journal of medicinal chemistry 47, no. 19 (2004): 4677-4683.

Heinrich, Timo, Henning Böttcher, Kai Schiemann, Günter Hölzemann, Michael Schwarz, Gerd D. Bartoszyk, Christoph van Amsterdam, Hartmut E. Greiner, and Christoph A. Seyfried. "Dual 5-HT1A agonists and 5-HT re-uptake inhibitors by combination of indole-butyl-amine and chromenonyl-piperazine structural elements in a single molecular entity." Bioorganic & medicinal chemistry 12, no. 18 (2004): 4843-4852.

Heinrich, Timo, Henning Böttcher, Rolf Gericke, Gerd D. Bartoszyk, Soheila Anzali, Christoph A. Seyfried, Hartmut E. Greiner, and Christoph van Amsterdam. "Synthesis and structure-activity relationship in a class of indolebutylpiperazines as dual 5-HT1A receptor agonists and serotonin reuptake inhibitors." Journal of medicinal chemistry47, no. 19 (2004): 4684-4692.

Herold, Franciszek, Andrzej Chodkowski, Łukasz Izbicki, Jadwiga Turło, Maciej Dawidowski, Jerzy Kleps, Gabriel Nowak et al. "Novel 4-aryl-pyrido[1,2-c]pyrimidines with dual SSRI and 5-HT 1A activity. Part 3." European journal of medicinal chemistry 46, no. 1 (2011): 142-149.

Herold, Franciszek, Andrzej Chodkowski, Łukasz Izbicki, Marek Krol, Jerzy Kleps, Jadwiga Turło, Gabriel Nowak, Katarzyna Stachowicz, Małgorzata Dybała, and Agata Siwek. "Novel 4-aryl-pyrido[1,2-c]pyrimidines with dual SSRI and 5-HT 1A activity, part 1." European journal of medicinal chemistry 44, no. 4 (2009): 1710-1717.

Herold, Franciszek, Łukasz Izbicki, Andrzej Chodkowski, Maciej Dawidowski, Marek Król, Jerzy Kleps, Jadwiga Turlo et al. "Novel 4-aryl-pyrido[1,2-c]pyrimidines with dual SSRI and 5-HT 1A activity: Part 2." European journal of medicinal chemistry 44, no. 11 (2009): 4702-4715.

Herrera D.G., Robertson H.A., (1996). Activation of c-fos in the brain. Progress in Neurobiology, 50, 83-107. Herrero MT, Augood SJ, Hirsch EC, Javoy-Agid F, Luquin MR, Agid Y, Obeso JA, and Emson PC (1995) Effects of L-DOPA on preproenkephalin and preprotachykinin gene expression in the MPTP-treated monkey striatum. Neuroscience 68:1189-1198.

Hiroshima Y1, Miyamoto H; Nakamura, F; et al. (January 2014). "The protein Ocular albinism 1 is the orphan GPCR GPR143 and mediates depressor and bradycardic responses to DOPA in the nucleus tractus solitari". Br J Pharmacol. 171 (2): 403-14. doi: 10.1111/bph.12459. PMC 3904260.

Hirsch EC (December 2009). "Iron transport in Parkinson's disease". Parkinsonism & Related Disorders. 15 Suppl 3 (Suppl 3): S209-11. doi: 10.1016/S1353-8020(09) 70816-8. PMID 20082992.

Hoehn MM, Yahr MD (May 1967). "Parkinsonism: onset, progression and mortality". Neurology. 17 (5): 427-42. doi: 10.1212/wnl.17.5.427. PMID 6067254.

Honig, G., Jongsma, M.E., can der Hart, M.C., & Tecott, L.H. (2009). Chronic citalopram administration causes a sustained suppression of serotonin synthesis in the mouse forebrain. PLOS One, 4 (8): e6797.

Hornykiewicz O (2002). "L-DOPA: from a biologically inactive amino acid to a successful therapeutic agent". Amino Acids. 23 (1-3): 65-70. doi: 10.1007/s00726-001-0111-9. PMID 12373520.

Hornykiewicz O. A brief history of levodopa. J Neurol 2010; 257: S249-S252.

Hughes, Z. A., Starr, K. R., Langmead, C. J., Hill, M., Bartoszyk, G. D., Hagan, J. J., et al. (2005). Neurochemical evaluation of the novel 5-HT 1a receptor partial agonist/serotonin reuptake inhibitor, vilazodone. European Journal of Pharmacology, 510, 49-57.

Huot, P., Johnston, T.H., Fox, S.H., Newman-Tancredi, A., & Brotchie, J.M. (2015). The highly-selective 5-HT (1A) agonist F15599 reduces L-DOPA-induced dyskinesia without compromising anti-parkinsonian benefits in the MPTP-lesioned macaque. Neuropharmacology, 97:306-311.

Hurd YL, Yoon M, Manini AF, Hernandez S, Olmedo R, Ostman M, Jutras-Aswad D (October 2015). "Early Phase in the Development of Cannabidiol as a Treatment for Addiction: Opioid Relapse Takes Initial Center Stage". Neurotherapeutics. 12 (4): 807-15. doi: 10.1007/s13311-015-0373-7. PMC 4604178. PMID 26269227.

Hyland K, Clayton PT (December 1992). "Aromatic L-amino acid decarboxylase deficiency: diagnostic methodology" (PDF). Clinical Chemistry. 38 (12): 2405-10. PMID 1281049.

Iannotti FA, Hill CL, Leo A, Alhusaini A, Soubrane C, Mazzarella E, Russo E, Whalley BJ, Di Marzo V, Stephens GJ: Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability. ACS Chem Neurosci. 2014 Nov. 19;5 (11): 1131-41. doi: 10.1021/cn5000524. Epub 2014 Jul. 29. [PubMed: 25029033]

Ibeas Bih C, Chen T, Nunn AV, Bazelot M, Dallas M, Whalley BJ: Molecular Targets of Cannabidiol in Neurological Disorders. Neurotherapeutics. 2015 October; 12 (4): 699-730. doi: 10.1007/s13311-015-0377-3. [PubMed: 26264914]

Ichinose H, Ohye T, Takahashi E, et al. Hereditary progressive dystonia with marked diurnal fluctuation caused by mutations in the GTP cyclohydrolase I gene. Nat Genet 1994; 8:236-242.

Ifland K, Grotenhermen F (2017). "An Update on Safety and Side Effects of Cannabidiol: A Review of Clinical Data and Relevant Animal Studies". *Cannabis* Cannabinoid Res. 2 (1): 139-154. doi: 10.1089/can.2016.0034. PMC 5569602. PMID 28861514.

Illarioshkin SN, Periquet M, Rawal N, et al. Mutation analysis of the parkin gene in Russian families with autosomal recessive juvenile parkinsonism. Mov Disord 2003; 18:914-919.

Ingle, PK (May-June 2003). "L-DOPA bearing plants". Natural Product Radiance. 2 (3): 126-133. Iravani MM, Tayarani-Binazir K, Chu WB, Jackson MJ, Jenner P (2006) In 1Methyl-4-phenyl-1,2,3,6-tetrahydropyridine-Treated Primates, the Selective 5Hydroxytryptamine 1a Agonist (R)-(+)-8—OHDPAT Inhibits Levodopa-Induced Dyskinesia but Only with\ Increased Motor Disability. J Pharmacol Exp Ther 319:1225-1234. doi.org/10.1124/jpet 106.110429

Iravani, M.M., Tayarani-Binazir, K., Chu, W., Jackson, M.J., & Jenner, P. (2006). In 1-Methyl-4-phenyl-1,2,3,6-tetrahydropyridine-treated primates, the selective 5-hydroxytryptamine 1A agonist (R)-(+)-8—OHDPAT inhibits levodopa-induced dyskinesia but only with increased motor disability. J Pharmacol Exp Ther, 319 (3): 1225-1234.

Iseger TA, Bossong MG (March 2015). "A systematic review of the antipsychotic properties of cannabidiol in humans". Schizophrenia Research. 162 (1-3): 153-61. doi: 10.1016/j.schres.2015.01.033. PMID 25667194.

Ito, S; Kato, T; Shinpo, K; Fujita, K. "Oxidation of tyrosine residues in proteins by tyrosinase. Formation of protein-bonded 3,4-dihydroxyphenylalanine and 5-S-cysteinyl-3,4-dihydroxyphenylalanine". Biochem J. 222:407-11. PMC 1144193. PMID 6433900.

Jankovic J (April 2008). "Parkinson's disease: clinical features and diagnosis". Journal of Neurology, Neurosurgery, and Psychiatry. 79 (4): 368-76. doi: 10.1136/jnnp.2007.131045. PMID 18344392.

Jinnah HA, Factor SA. Diagnosis and treatment of dystonia. Neurol Clin 2015; 33:77-100.

Jones PG, Falvello L, Kennard O, Sheldrick GM, Mechoulam R (1977). "Cannabidiol". Acta Crystallogr. B. 33 (10): 3211-3214. doi: 10.1107/S0567740877010577.

Jones, H. Royden (2013). The Netter collection of medical illustrations. a compilation of paintings (2nd ed.). Philadelphia, PA: Saunders Elsevier. p. 161. ISBN 9781455733873. 8 Sep. 2017.

Jubault T, Brambati SM, Degroot C, Kullmann B, Strafella AP, Lafontaine AL, Chouinard S, Monchi O (December 2009). Gendelman HE, ed. "Regional brain stem atrophy in idiopathic Parkinson's disease detected by anatomical MRI". PLOS One. 4 (12): e8247. Bibcode: 2009PLoSO . . . 4.8247J. doi: 10.1371/journal-.pone.0008247. PMC 2784293. PMID 20011063.

Jürgen Martens, Kurt Günther, Maren Schickedanz: "Resolution of Optical Isomers by Thin-Layer Chromatography: Enantiomeric Purity of Methyldopa", Arch. Pharm. (Weinheim) 1986, 319, S. 572-574. (DOI: 10.1002/ardp.19863190618)

Jurkus, R; Day, H. L; Guimarães, F. S; Lee, J. L; Bertoglio, L. J; Stevenson, C. W (2016). "Cannabidiol Regulation of Learned Fear: Implications for Treating Anxiety-Related Disorders". Frontiers in Pharmacology. 7:454. doi: 10.3389/fphar.2016.00454. PMC 5121237. PMID 27932983.

Kalia LV, Lang AE (August 2015). "Parkinson's disease". Lancet 386 (9996): 896-912. doi: 10.1016/s0140-6736 (14) 61393-3. PMID 25904081.

Kannari K, Kurahashi K, Tomiyama M, Maeda T, Arai A, Baba M, Suda T, Matsunaga M (2002) Tandospirone citrate, a selective 5-HT1A agonist, alleviates L-DOPA-induced dyskinesia in patients with Parkinson's disease. No to shinkei=Brain and nerve 54:133-137

Kannari, K., Kurahashi, K., Tomiyama, M., Maeda, T., Arai, A., Baba, M., . . . & Matsunaga, M. (2002). Tandospirone citrate, a selective 5-HT1A agonist, alleviates L-DOPA-induced dyskinesia in patients with Parkinson's disease. No to shinkei=Brain and nerve, 54 (2): 133-137.

Kannari, K., Shen, H., Arai, A., Tomiyama, M., & Baba, M. (2006). Reuptake of L-DOPA-derived extracellular dopamine in the striatum with dopaminergic denervation via serotonin transporters. Neurosci Lett, 402 (1-2): 62-65.

Kathmann M, Flau K, Redmer A, Tränkle C, Schlicker E (February 2006). "Cannabidiol is an allosteric modulator at mu-and delta-opioid receptors". Naunyn-Schmiedeberg's Archives of Pharmacology. 372 (5): 354-61. doi: 10.1007/s00210-006-0033-x. PMID 16489449.

Kaur R, Ambwani SR, Singh S: Endocannabinoid System: A Multi-Facet Therapeutic Target Curr Clin Pharmacol. 2016; 11 (2): 110-7. [PubMed: 27086601]

Keeler, R. F., (30 Nov. 1983). Handbook of Natural Toxins. CRC Press. p. 477. ISBN 978-O-8247-1893-0.

Kehne JH, Bartoszyk GD, Greiner HE, editors. In vitro characterization of vilazodone as a dual-acting serotonin reuptake receptor and 5-HT1A receptor partial agonist. Poster presented at 65th Annual Meeting of the Society of Biological Psychiatry Meeting; 2010.

Kelliny M, Croarkin PE, Moore KM, Bobo WV. Profile of vortioxetine in the treatment of major depressive disorder: an overview of the primary and secondary literature. Ther Clin Risk Manag. 2015 Aug. 12; 11:1193-212. doi: 10.2147/TCRM.S55313PMID 26316764 Archived 2018 Apr. 29 at the Wayback Machine.

Khan, Arif. "Vilazodone, a novel dual-acting serotonergic antidepressant for managing major depression." Expert opinion on investigational drugs 18, no. 11 (2009): 1753-1764.

Kilpatrick IC, Jones MW, Phillipson OT (1986) A semi-automated analysis method for catecholamines, indoleamines, and some prominent metabolites in microdissected regions of the nervous system: an isocratic HPLC technique employing coulometric detection and minimal sample preparation. J Neurochem 46:1865-1876

Kim SE, Choi JY, Choe YS, Choi Y, Lee WY (2003) Serotonin transporters in the midbrain of Parkinson's disease patients: a study with 1231-beta-CIT SPECT. Journal of nuclear medicine: official publication, Society of Nuclear Medicine 44:870-876

Kim YE, Jeon BS (1 Jan. 2014). "Clinical implication of REM sleep behavior disorder in Parkinson's disease". Journal of Parkinson's Disease. 4 (2): 237-44. doi: 10.3233/jpd-130293. PMID 24613864.

Kish SJ, Tong J, Homykiewicz O, Rajput A, Chang LJ, Guttman M, Furukawa Y (2008) Preferential loss of serotonin markers in caudate versus putamen in Parkinson's disease. Brain 131:120-131. doi.org/10.1093/brain/awm239

Klein C, Karanges E, Spiro A, Wong A, Spencer J, Huynh T, Gunasekaran N, Karl T, Long LE, Huang XF, Liu K, Arnold JC, McGregor I S (November 2011). "Cannabidiol potentiates A9-tetrahydrocannabinol (THC) behavioural effects and alters THC pharmacokinetics during acute and chronic treatment in adolescent rats". Psychopharmacology. 218 (2): 443-457. doi: 10.1007/s00213-011-2342-0. PMID 21667074.

Klingelhoefer, L; Reichmann, H (2017). "The Gut and Nonmotor Symptoms in Parkinson's Disease". Int. Rev. Neurobiology. 134:787-809. doi: 10.1016/bs.irn.2017.05.027. ISBN 9780128126035. PMID 28805583.

Knowles, W. S. (March 1986). "Application of organometallic catalysis to the commercial production of L-DOPA". Journal of Chemical Education. 63 (3): 222. doi: 10.1021/ed063p222.

Knowles, William S. (1983). "Asymmetric hydrogenation". Accounts of Chemical Research. 16 (3): 106-112. doi: 10.1021/ar00087a006.

Kobayashi Y, Takeuchi A, Wang YG (June 2006). "Synthesis of cannabidiols via alkenylation of cyclohexenyl monoacetate". Organic Letters. 8 (13): 2699-702. doi: 10.1021/01060692h. PMID 16774235.

Koch G (2010). "ITMS effects on levodopa induced dyskinesias in Parkinson's disease patients: searching for effective cortical targets". Restorative Neurology and Neuroscience. 28 (4): 561-8. doi: 10.3233/RNN-2010-0556. PMID 20714078.

Koehler PJ, Keyser A (September 1997). "Tremor in Latin texts of Dutch physicians: 16th-18th centuries". Movement Disorders. 12 (5): 798-806. doi: 10.1002/mds.870120531. PMID 9380070.

Köhler S, Cierpinsky K, Kronenberg G, Adli M. The serotonergic system in the neurobiology of depression: Relevance for novel antidepressants. J Psychopharmacol. 2016 January;30 (1): 13-22. doi: 10.1177/0269881115609072 PMID 26464458

Kohnstamm P (1934). Über die Beteiligung der beiden Schichten der Substantia nigra am Prozeß der Encephalitis epidemica. J Psychol Neurol 46 (1): 22-37;

Kordower JH, Olanow CW, Dodiya HB, Chu Y, Beach TG, Adler CH, Halliday GM, Bartus RT (2013) Disease duration and the integrity of the nigrostriatal system in Parkinson's disease. Brain 136:2419-2431. doi.org/10.1093/brain/awt192

Koukouni V, Martino D, Arabia G, Quinn NP, Bhatia KP. The entity of young onset primary cervical dystonia. Mov Disord 2007; 22:843-847.

Koy A, Lin JP, Sanger TD, Marks WA, Mink JW, Timmermann L. Advances in management of movement disorders in children. Lancet Neurol 2016; 15:719-735.

Kreiss, D.S. & Lucki, I. (1995). Effects of acute and repeated administration of antidepressant drugs on extracellular levels of 5-hydrocytryptamine measured in vivo. J Pharmacol Exp Ther, 274 (2): 866-876.

Krekeler, Andreas, Dimitri Neumann, and Michael Sedlmayr. "Pharmaceutical Composition Of Vortioxetine Hydrobromide Comprising Vortioxetine Hydrobromide In A Polyethylene Oxide Matrix." U.S. patent application Ser. No. 15/386,566, filed Jun. 29, 2017.

Lacivita, Enza, Pantaleo Di Pilato, Paola De Giorgio, Nicola A. Colabufo, Francesco Berardi, Roberto Perrone, and Marcello Leopoldo. "The therapeutic potential of 5-HT 1A receptors: a patent review." Expert opinion on therapeutic patents 22, no. 8 (2012): 887-902.

Langston JW, Ballard P, Tetrud JW, Irwin I (February 1983). "Chronic Parkinsonism in humans due to a product of meperidine-analog synthesis". Science. 219 (4587): 979-80. Bibcode: 1983Sci . . . 219 . . . 979L. doi: 10.1126/science.6823561. PMID 6823561.

Lanska DJ (2010). "Chapter 33: the history of movement disorders". Handbook of Clinical Neurology. 95:501-46. doi: 10.1016/S0072-9752 (08) 02133-7. ISBN 9780444520098. PMID 19892136.

Laprairie RB, Bagher AM, Kelly ME, Denovan-Wright EM: Cannabidiol is a negative allosteric modulator of the cannabinoid CB1 receptor. Br J Pharmacol. 2015 October; 172 (20): 4790-805. doi: 10.1111/bph.13250. Epub 2015 Oct. 13. [PubMed: 26218440]

Larsen, M.B., Sonders, M.S., Mortensen, O.V., Larson, G.A., Zahniser, N.R., & *Amara*, S.G. (2011). Dopamine transport by the serotonin transporter: a mechanistically distinct mode of substrate translocation. J Neurosci, 31 (17): 6605-6615.

Laughren TP, Gobburu J, Temple RJ, Unger EF, Bhattaram A, Dinh PV, Fossom L, Hung HM, Klimek V, Lee JE, Levin RL, Lindberg CY, Mathis M, Rosloff BN, Wang SJ, Wang Y, Yang P, Yu B, Zhang H, Zhang L, Zineh I (September 2011). "Vilazodone: clinical basis for the US Food and Drug Administration's approval of a new antidepressant". The Journal of Clinical Psychiatry. 72 (9): 1166-73. doi: 10.4088/JCP.11r06984. PMID 21951984.

Laun AS, Shrader SH, Brown KJ, Song ZH (June 2018). "GPR3, GPR6, and GPR12 as novel molecular targets: their biological functions and interaction with cannabidiol". Acta Pharmacol. Sin. doi: 10.1038/s41401-018-0031-9. PMID 29941868.

Lauterbach, Edward C. "Repurposing psychiatric medicines to target activated microglia in anxious mild cognitive impairment and early Parkinson's disease." American J. neurodegenerative disease 5, no. 1 (2016): 29.

Lee MS, Ernst E (January 2009). "Qigong for movement disorders: A systematic review". Movement Disorders. 24 (2): 301-3. doi: 10.1002/mds.22275. PMID 18973253.

Lee MS, Lam P, Ernst E (December 2008). "Effectiveness of tai chi for Parkinson's disease: a critical review". Parkinsonism & Related Disorders. 14 (8): 589-94. doi: 10.1016/j.parkreldis.2008.02.003. PMID 18374620.

Lee MS, Shin BC, Kong JC, Ernst E (August 2008). "Effectiveness of acupuncture for Parkinson's disease: a systematic review". Movement Disorders. 23 (11): 1505-15. doi: 10.1002/mds.21993. PMID 18618661.

Lees AJ (September 2007). "Unresolved issues relating to the shaking palsy on the celebration of James Parkinson's 250th birthday". Movement Disorders. 22 Suppl 17 (Suppl 17): S327-34. doi: 10.1002/mds.21684. PMID 18175393.

Lees AJ, Hardy J, Revesz T (June 2009). "Parkinson's disease". Lancet 373 (9680): 2055-66. doi: 10.1016/S0140-6736 (09) 60492-X. PMID 19524782.

Lesage S, Brice A (April 2009). "Parkinson's disease: from monogenic forms to genetic susceptibility factors". Human Molecular Genetics. 18 (R1): R48-59. doi: 10.1093/hmg/ddp012. PMID 19297401.

LeWitt P A, Rezai AR, Leehey MA, Ojemann SG, Flaherty AW, Eskandar EN, Kostyk SK, Thomas K, Sarkar A, Siddiqui MS, Tatter SB, Schwalb JM, Poston KL, Henderson JM, Kurlan RM, Richard IH, Van Meter L, Sapan CV, During MJ, Kaplitt MG, Feigin A (April 2011). "AAV2-GAD gene therapy for advanced Parkinson's disease: a double-blind, sham-surgery controlled, randomised trial". The Lancet. Neurology. 10 (4): 309-19. doi: 10.1016/S1474-4422 (11) 70039-4. PMID 21419704.

Li, Ai Jun, Xiao Hua Zhang, Xue Qin Zhou, and Dong Zhi Liu. "New 3-(4-arylpiperazin-1-yl)-1-(benzo[b] thiophen-3-yl)-2-methylpropanol derivatives: Synthesis and evaluation for dual 5-HT1A/SSRI activities." Chinese Chemical Letters 19, no. 4 (2008): 412-414.

Lindemann L, Hoener MC (May 2005). "A renaissance in trace amines inspired by a novel GPCR family". Trends Pharmacol. Sci. 26 (5): 274-281. doi: 10.1016/j.tips.2005.03.007. PMID 15860375.

Lindenbach D, Conti MM, Ostock CY, Dupre KB, Bishop C (2015) Alterations in primary motor cortex neurotransmission and gene expression in hemiparkinsonian rats with drug-induced dyskinesia. Neuroscience 310:12-26. doi.org/10.1016/j.neuroscience.2015.09.018

Lindenbach D, Palumbo N, Ostock CY, Vilceus N, Conti MM, Bishop C (2015) Side effect profile of 5-HT treatments for Parkinson's disease and L-DOPA-induced dyskinesia in rats. Br J Pharmacol 172:119-130. doi.org/10. 1111/bph.12894

Lindenbach, D., Ostock, C.Y., Eskow Jaunarajs, K.L., Dupre, K.B., Bamum, C.J., Bhide, N., et al (2011). Behavioral and cellular modulation of L-DOPA-induced dyskinesia by B-adrenoreceptor blockade in the 6-hydroxydopamine-lesioned rat J Pharmacol Exp Ther, 337 (3): 755-765.

Ling H, Massey LA, Lees AJ, Brown P, Day BL (April 2012). "Hypokinesia without decrement distinguishes progressive supranuclear palsy from Parkinson's disease". Brain. 135 (Pt 4): 1141-53. doi: 10.1093/brain/aws038. PMC 3326257. PMID 22396397.

Longmore M, Wilkinson IB, Turmezei T, Cheung CK (4 Jan. 2007). Oxford Handbook of Clinical Medicine. Oxford University Press. p. 486. ISBN 978-O-19-856837-7.

Lopez, A., Muñoz, A., Guerra, M.J., & Labandeira-Garcia, J.L. (2001). Mechanisms of the effects of exogenous levodopa on the dopamine denervated striatum. Neuroscience, 103 (3): 639-651.

Lopez, VM; Decatur, CL; Stamer, WD; Lynch, RM; Mckay, BS (2008). "L-DOPA is an endogenous ligand for OA1". PLOS Biol. 6 (9): e236. doi: 10.1371/journal.pbio.0060236. PMC 2553842. PMID 18828673.

Lorenzl S, Nübling G, Perrar KM, Voltz R (2013). "Palliative treatment of chronic neurologic disorders". Handbook of Clinical Neurology. 118:133-9. doi: 10.1016/B978-O-444-53501-6.00010-X. ISBN 9780444535016. PMID 24182372.

Louis ED (November 1997). "The shaking palsy, the first forty-five years: a journey through the British literature". Movement Disorders. 12 (6): 1068-72. doi: 10.1002/mds.870120638. PMID 9399240.

Lovell, Peter J., Frank E. Blaney, Caroline J. Goodacre, Claire M. Scott, Paul W. Smith, Kathryn R. Starr, Kevin M. Thewlis, Antonio KK Vong, Simon E. Ward, and Jeannette M. Watson. "3, 4-Dihydro-2H-benzoxazinones as dual-acting 5-HT1A receptor antagonists and serotonin reuptake inhibitors." Bioorganic & medicinal chemistry letters 17, no. 4 (2007): 1033-1036.

Lubarr N, Bressman S. Treatment of generalized dystonia. Curr Treat Options Neurol 2011; 13:274-289.

Ludecke B, Dworniczak B, Bartholome K. A point mutation in the tyrosine hydroxylase gene associated with Segawa's syndrome. Hum Genet 1995; 95:123-125.

Lumsden DE, Kaminska M, Tomlin S, Lin JP. Medication use in childhood dystonia. Eur J Paediatr Neurol 2016; 20:625-629.

Lundblad M, Andersson M, Winkler C, Kirik D, Wierup N, Cenci M.A. (2002). Pharmacological validation of behavioural measures of akinesia and dyskinesia in a rat model of parkinson's disease. European Journal of Neursocience, 15, 120-132.

Ma C, Liu Y, Neumann S, Gao X (2017). "Nicotine from cigarette smoking and diet and Parkinson disease: a review". Translational Neurodegeneration. 6:18. doi: 10.1186/s40035-017-0090-8. PMC 5494127. PMID 28680589.

MacCallum CA, Russo EB: Practical considerations in medical *cannabis* administration and dosing. Eur J Intern Med. 2018 March; 49:12-19. doi: 10.1016/j.ejim.2018.01.004. Epub 2018 Jan. 4. [PubMed: 29307505]

Macur, Juliet (26 Mar. 2008). "For the Phinney Family, a Dream and a Challenge". The New York Times. 6 Nov. 2014.

Maeda T, Kannari K, Shen H, Arai A, Tomiyama M, Matsunaga M, Suda T (2003) Rapid induction of serotonergic hyperinnervation in the adult rat striatum with extensive dopaminergic denervation. Neurosci Lett 343:17-20 Maeda T, Kannari K, Suda T, Matsunaga M (1999) Loss of regulation by presynaptic dopamine D2 receptors of exogenous L-DOPA-derived dopamine release in the dopaminergic denervated striatum. Brain Res 817:185-191

Maeda T, Nagata K, Yoshida Y, Kannari K (2005) Serotonergic hyperinnervation into the dopaminergic denervated striatum compensates for dopamine conversion from exogenously administered I-DOPA. Brain Res 1046:230-233. doi.org/10.1016/j.brainres.2005.04.019

Mahlknecht P, Krismer F, Poewe W, Seppi K (April 2017). "Meta-analysis of dorsolateral nigral hyperintensity on magnetic resonance imaging as a marker for Parkinson's disease". Movement Disorders. 32 (4): 619-623. doi: 10.1002/mds.26932. PMID 28151553.

Malek N, Fletcher N, Newman E. Diagnosing dopamine-responsive dystonias. Pract Neurol 2015; 15:340-345.

Manfredsson FP, Burger C, Sullivan LF, Muzyczka N, Lewin AS, Mandel RJ (2007) rAAV-mediated nigral human parkin over-expression partially ameliorates motor deficits via enhanced dopamine neurotransmission in a rat model of Parkinson's disease. Exp Neurol 207:289-301. doi.org/10. 1016/j.expneurol.2007.06.019

Manson A, Stirpe P, Schrag A (2012) Levodopa-induced-dyskinesias clinical features, incidence, risk factors, management and impact on quality of life. J Parkinsons Dis 2:189-198. doi.org/10.3233/jpd-2012-120,103

Maria, Nord (2017). Levodopa pharmacokinetics-from stomach to brain A study on patients with Parkinson's disease. Linköping: Linköping University Electronic Press. p. 10. ISBN 9789176855577. OCLC 993068595.

Maries E, Kordower JH, Chu Y, Collier TJ, Sortwell CE, Olaru E, Shannon K, Steece-Collier K (2006) Focal not widespread grafts induce novel dyskinetic behavior in parkinsonian rats. Neurobiol Dis 21:165-180. doi.org/10. 1016/j.nbd.2005.07.002

Marino, Michael (11 Nov. 2003). "Allosteric modulation of group III metabotropic glutamate receptor 4: A potential approach to Parkinson's disease treatment". PNAS. 100 (23): 13668-13673. Bibcode: 2003PNAS. 10013668M. doi: 10.1073/pnas. 1835724100. PMC 263871. PMID 14593202.

Mark Hallett; Werner Poewe (13 Oct. 2008). Therapeutics of Parkinson's Disease and Other Movement Disorders. John Wiley & Sons. p. 417. ISBN 978-O-470-71400-3. 8 Sep. 2017.

Marks MD, Tian L, Wenger JP, Omburo SN, Soto-Fuentes W, He J, Gang DR, Weiblen GD, Dixon RA (2009). "Identification of candidate genes affecting 49-tetrahydrocannabinol biosynthesis in *Cannabis sativa*". Journal of Experimental Botany. 60 (13): 3715-26. doi: 10.1093/jxb/erp210. PMC 2736886. PMID 19581347.

Marsden CD. The problem of adult-onset idiopathic torsion dystonia and other isolated dyskinesias in adult life (including blepharospasm, oromandibular dystonia, dystonic writer's cramp, and torticollis, or axial dystonia). Adv Neurol 1976; 14:259-276.

Martinez, Javier, Silvia Pérez, Ana M. Oficialdegui, Begoña Heras, Lara Orús, Helena Villanueva, Juan A. Palop et al. "New 3-[4-(aryl) piperazin-1-yl]-1-(benzo [b] thiophen-3-yl) propane derivatives with dual action at 5-HT1A serotonin receptors and serotonin transporter as a new class of antidepressants." European journal of medicinal chemistry 36, no. 1 (2001): 55-61.

Martínez-Esparza, Javier, Ana-M. Oficialdegui, Silvia Pérez-Silanes, Begoña Heras, Lara Orús, Juan-A. Palop, Berta Lasheras et al. "New 1-aryl-3-(4-arylpiperazin-1-yl) propane derivatives, with dual action at 5-HT1A serotonin receptors and serotonin transporter, as a new class of antidepressants." Journal of medicinal chemistry 44, no. 3 (2001): 418-428.

Matthews W (April 2006). "Ali's Fighting Spirit". Neurology Now. 2 (2): 10-23. doi: 10.1097/01222928-200602020-00004. 2 Apr. 2011.

Matzen, Lisa, Christoph van Amsterdam, Wilfried Rautenberg, Hartmut E. Greiner, Jürgen Harting, Christoph A. Seyfried, and Henning Böttcher. "5-HT reuptake inhibitors with 5-HT1B/1D antagonistic activity: a new approach toward efficient antidepressants." Journal of medicinal chemistry 43, no. 6 (2000): 1149-1157.

Mayo Clinic Staff. "Parkinson's Disease." Diagnosis at Mayo Clinic. Mayo Foundation for Medical Education and Research, 2014. Web. 12 Mar. 2014.

Mazzucchi S, Frosini D, Ripoli A, Nicoletti V, Linsalata G, Bonuccelli U, Ceravolo R (2015) Serotonergic antidepressant drugs and L-dopa-induced dyskinesias in Parkinson's disease. Acta Neurol Scand 131:191-195. doi.org/10.1111/ane.12314

Mazzucchi, S., Frosini, D., Ripoli, A., Nicoletti, V., Linsalata, G., Bonuccelli, U., et al (2015). Serotonergic antidepressant drugs and L-dopa-induced dyskinesias in Parkinson's disease. Acta Neurol Scand, 131 (3): 191-195.

Mckeon A, Matsumoto JY, Bower JH, Ahlskog JE. The spectrum of disorders presenting as adult-onset focal lower extremity dystonia. Parkinsonism Relat Disord 2008; 14:613-619.

Meadows SM, Chambers NE, Conti MM, Bossert SC, Tasber C, Sheena E, Varney M, Newman-Tancredi A, Bishop C (2017) Characterizing the differential roles of striatal 5-HT1A auto- and hetero-receptors in the reduction of I-DOPA-induced dyskinesia. Exp Neurol 292: 168-178. doi.org/10.1016/j.expneurol.2017.03.013

Meadows, Samantha M., Melissa M. Conti, Libby Gross, Nicole E. Chambers, Yarden Avnor, Corinne Y. Ostock, Kathryn Lanza, and Christopher Bishop. "Diverse serotonin actions of vilazodone reduce I-3, 4-dihidroxyphenylalanine-induced dyskinesia in hemi-parkinsonian rats." Movement Disorders 33, no. 11 (2018): 1740-1749.

Mechoulam R, Ben-Zvi Z, Gaoni Y (August 1968). "Hashish-13. On the nature of the Beam test". Tetrahedron. 24 (16): 5615-24. doi: 10.1016/0040-4020 (68) 88159-1. PMID 5732891.

Mechoulam R, Parker LA, Gallily R (November 2002). "Cannabidiol: an overview of some pharmacological aspects". Journal of Clinical Pharmacology. 42 (11 Suppl): 11S-19S. doi: 10.1002/j.1552-4604.2002.tb05998.x. PMID 12412831.

Mechoulam R, Peters M, Murillo-Rodriguez E, Hanus LO (August 2007). "Cannabidiol-recent advances". Chemistry & Biodiversity (Review). 4 (8): 1678-92. doi: 10.1002/cbdv.200790147. PMID 17712814.

Mencacci NE, Isaias IU, Reich M M, et al. Parkinson's disease in GTP cyclohydrolase 1 mutation carriers. Brain 2014; 137:2480-2492.

Mercuri, N.B., & Bernardi, G. (2005) The 'magic' of L-DOPA: why is it the gold standard Parkinson's disease therapy?. Trends in Pharmacological Sciences, 26 (7): 341-344.

Merims D, Giladi N (2008). "Dopamine dysregulation syndrome, addiction and behavioral changes in Parkinson's disease". Parkinsonism Relat Disord. 14 (4): 273-280. doi: 10.1016/j.parkreldis.2007.09.007. PMID 17988927.

Mewshaw, Richard E., Dahui Zhou, Ping Zhou, Xiaojie Shi, Geoffrey Homby, Taylor Spangler, Rosemary Scerni, Deborah Smith, Lee E. Schechter, and Terrance H. Andree. "Studies toward the discovery of the next generation of antidepressants. 3. Dual 5-HT1A and serotonin transporter affinity within a class of N-aryloxyethylindolylalkylamines." Journal of medicinal chemistry 47, no. 15 (2004): 3823-3842.

Mhyre, R T., JT. Boyd, R W. Hamil, K A. Maguire-Zeiss (2012). Sub-Cellular Biochemistry. Springer, Dordrecht. pp. 389-455. ISBN 978-94-007-5415-7.

Miguelez C, Benazzouz A, Ugedo L, De Deurwaerdère P. Impairment of Serotonergic Transmission by the Antiparkinsonian Drug L-DOPA: Mechanisms and Clinical Implications. Frontiers in cellular neuroscience. 2017 Sep. 12; 11:274.

Mink JW. Dopa-responsive dystonia in children. Curr Treat Options Neurol 2003; 5:279-282.

Mishima K, Hayakawa K, Abe K, Ikeda T, Egashira N, Iwasaki K, Fujiwara M (May 2005). "Cannabidiol prevents cerebral infarction via a serotonergic 5-hydroxytryptamine 1A receptor-dependent mechanism". Stroke. 36 (5): 1077-82. doi: 10.1161/01.STR.0000163083.59201.34. PMID 15845890.

Moens K, Higginson IJ, Harding R (October 2014). "Are there differences in the prevalence of palliative care-related problems in people living with advanced cancer and eight non-cancer conditions? A systematic review". Journal of Pain and Symptom Management. 48 (4): 660-77. doi: 10.1016/j.jpainsymman.2013.11.009. PMID 24801658.

Moore, N.; B. Bang-Andersen; L. Brennum; K. Fredriksen; S. Hogg; A. Mork; T. Stensbol; H. Zhong; C. Sanchez; D. Smith (August 2008). "Lu AA21004: a novel potential treatment for mood disorders". European Neuropsychopharmacology. 18 (Supplement 4): S321. doi: 10.1016/S0924-977X (08) 70440-1. 2018 Jan. 21.

Morales P, Reggio PH, Jagerovic N: An Overview on Medicinal Chemistry of Synthetic and Natural Derivatives of Cannabidiol. Front Pharmacol. 2017 Jun. 28; 8:422. doi: 10.3389/fphar.2017.00422. eCollection 2017. [PubMed: 28701957]

Morelli M, Fenu S, Garau L, Di Chiara G (1989) Time and dose dependence of the 'priming' of the expression of dopamine receptor supersensitivity. Eur J Pharmacol 162:329-335

Morillo, Connie Sanchez. "Compositions comprising vortioxetine and donepezil." U.S. Pat. No. 9,211,288, issued Dec. 15, 2015.

Mosley, Anthony D. (2010). The encyclopedia of Parkinson's disease (2nd ed.). New York: Facts on File. p. 89. ISBN 9781438127491. 8 Sep. 2017.

Muñoz A, Carlsson T, Tronci E, Kirik D, Björklund A, Carta M (2009) Serotonin neuron-dependent and-independent reduction of dyskinesia by 5-HT1A and 5-HT1B receptor agonists in the rat Parkinson model. Exp Neurol 219:298-307. doi.org/10.1016/j.expneurol.2009.05.033

Muñoz, A., Li, Q., Gardoni, F., Marcello, E., Qin, C., Carlsson, T., et al (2008). Combined 5-HT1A and 5-HT1B receptor agonists for the treatment of L-DOPA-induced dyskinesia. Brain, 131 (Pt 12): 3380-3394.

Munts AG, Koehler PJ. How psychogenic is dystonia? Views from past to present. Brain 2010; 133:1552-1564.

Mura, A., Mintz, M., & Feldon, J. (2002). Behavioral and anatomical effects of long-term L-dihydoxyphenylalanine (L-DOPA) administration in rats with unilateral lesions of the nigrostriatal system. Exp Neurol, 177 (1): 252-264.

Mussel Adhesive Protein Mimetics Archived 2006 May 29 at the Wayback Machine.

Mutschler, Emst; Schäfer-Korting, Monika (2001). Arzneimittelwirkungen (in German) (8 ed.). Stuttgart: Wissenschaftliche Verlagsgesellschaft pp. 313-316. ISBN 3-8047-1763-2.

Nadulski T, Pragst F, Weinberg G, Roser P, Schnelle M, Fronk EM, Stadelmann AM (December 2005). "Randomized, double-blind, placebo-controlled study about the effects of cannabidiol (CBD) on the pharmacokinetics of 49-tetrahydrocannabinol (THC) after oral application of THC verses standardized *cannabis* extract". Ther Drug Monit 27 (6): 799-810. PMID 16306858.

Nandagopal R, Moorthy SG. Dramatic levodopa responsiveness of dystonia in a sporadic case of spinocerebellar ataxia type 3. Postgrad Med J 2004; 80:363-365.

Navailles, S., Bioulac, B., Gross, C., & De Deurwaerdère, P. (2010). Serotonergic neurons mediate ectopic release of dopamine induced by L-DOPA in a rat model of Parkinson's disease. Neurobiol Dis, 38 (1): 136-143.

Neve KA, Seamans JK, Trantham-Davidson H (2004) Dopamine receptor signaling. J Recept Signal Transduct Res 24:165-205

Ng J, Papandreou A, Heales SJ, Kurian MA. Monoamine neurotransmitter disorders-clinical advances and future perspectives. Nat Rev Neurol 2015; 11:567-584.

Nicholson SL, Brotchie JM (2002) 5-hydroxytryptamine (5-HT, serotonin) and Parkinson's disease-opportunities for novel therapeutics to reduce the problems of levodopa therapy. Eur J Neurol 9 (Suppl 3): 1-6 NIH DailyMed. "Sinemet". 21 Aug. 2014.

NINDS. "NINDS Parkinson's Disease Information Page." Parkinson's Disease Information Page: National Institute of Neurological Disorders and Stroke (NINDS). National Institute of Neurological Disorders and Stroke, 12 Mar. 2014. Web. 12 Mar. 2014.

Nomura Y, Ikeuchi T, Tsuji S, Segawa M. Two phenotypes and anticipation observed in Japanese cases with early onset torsion dystonia (DYT1): pathophysiological consideration. Brain Dev 2000; 22 (suppl 1): S92-S101.

Noyce AJ, Bestwick JP, Silveira-Moriyama L, Hawkes CH, Giovannoni G, Lees AJ, Schrag A (December 2012). "Meta-analysis of early nonmotor features and risk factors for Parkinson disease". Annals of Neurology. 72 (6): 893-901. doi: 10.1002/ana.23687. PMC 3556649. PMID 23071076.

Nuytemans K, Theuns J, Cruts M, Van Broeckhoven C (July 2010) [18 May 2010]. "Genetic etiology of Parkinson disease associated with mutations in the SNCA, PARK2, PINK1, PARK7, and LRRK2 genes: a mutation update". Human Mutation. 31 (7): 763-80. doi: 10.1002/humu.21277. PMC 3056147. PMID 20506312.

Nygaard TG, Marsden CD, Duvoisin RC. Dopa-responsive dystonia. Adv Neurol 1988; 50:377-384.

Nygaard TG. Dopa-responsive dystonia: delineation of the clinical syndrome and clues to pathogenesis. Adv Neurol 1993; 60:577-585.

Obeso JA, Rodríguez-Oroz MC, Benitez-Temino B, Blesa FJ, Guridi J, Marin C, Rodriguez M (2008). "Functional organization of the basal ganglia: therapeutic implications for Parkinson's disease". Movement Disorders. 23 Suppl 3 (Suppl 3): S548-59. doi: 10.1002/mds.22062. PMID 18781672.

Obeso JA, Rodriguez-Oroz MC, Goetz CG, Marin C, Kordower JH, Rodriguez M, Hirsch EC, Farrer M, Schapira AH, Halliday G (June 2010). "Missing pieces in the Parkinson's disease puzzle". Nature Medicine. 16 (6): 653-61. doi: 10.1038/nm.2165. PMID 20495568.

Oertel WH (13 Mar. 2017). "Recent advances in treating Parkinson's disease". F1000Research. 6:260. doi: 10.12688/f1000research.10100.1. PMC 5357034. PMID 28357055.

Oficialdegui, A. M., J. Martinez, S. Perez, B. Heras, M. Irurzun, J. A. Palop, R. Tordera, B. Lasheras, J. Del Rio, and A. Monge. "Design, synthesis and biological evaluation of new 3-[(4-aryl) piperazin-1-yl]-1-arylpropane derivatives as potential antidepressants with a dual mode of action: serotonin reuptake inhibition and 5-HT1A receptor antagonism." Il Farmaco 55, no. 5 (2000): 345-353.

Okada F, Tokumitsu Y, Nomura Y (1989) Pertussis toxin attenuates 5hydroxytryptamine 1A receptor-mediated inhibition of forskolin-stimulated adenylate cyclase activity in rat hippocampal membranes. J Neurochem 52:1566-1569 Olanow CW, Damier P, Goetz CG, Mueller T, Nutt J, Rascol O, Serbanescu A, Deckers F, Russ H (2004) Multicenter, open-label, trial of sarizotan in Parkinson disease patients with levodopa-induced dyskinesias (the SPLENDID Study). Clin Neuropharmacol 27:58-62

Olanow, C. Warren., Stocchi, Fabrizio., Lang, Anthony E., "The non-motor and non-dopaminergic features of PD". Parkinson's Disease: Non-Motor and Non-Dopaminergic Features. Wiley-Blackwell. 2011. ISBN 978-1405191852. OCLC 743205140.

Olsson, M., Nikkhah, G., Bentlage, C. & Björklund, A. Forelimb akinesia in the rat Parkinson model: diferential effects of dopamine agonists and nigral transplants as assessed by a new stepping test. J Neurosci 15, 3863-75 (1995).

Oosting et al., R.S., Chan, J.S., Olivier, B., Banerjee, P., Choi, Y.K., & Tarazi, F. (2016). Differential effects of vilazodone versus citalopram and paroxetine on sexual behaviors and serotonin transporter and receptors in male rats. Psychopharm, 233 (6): 1025-1034.

Orús, Lara, Silvia Pérez-Silanes, Ana-M. Oficialdegui, Javier Martínez-Esparza, Juan-C. Del Castillo, Marisa Mourelle, Thierry Langer et al. "Synthesis and molecular modeling of new 1-aryl-3-[4-arylpiperazin-1-yl]-1-propane derivatives with high afinity at the serotonin transporter and at 5-HT1A receptors." Journal of medicinal chemistry 45, no. 19 (2002): 4128-4139.

O'Sullivan SB, Schmitz TJ (2007). "Parkinson's Disease". Physical Rehabilitation (5th ed.). Philadelphia: F.A. Davis. pp. 856-57.

Owen, R.T. (2011). Vilazodone: a new treatment option for major depressive disorder. Drugs Today (Barc), 47 (7), 531-537.

Padovan-Neto FE, Sammut S, Chakroborty S, Dec AM, Threlfell S, Campbell PW, Mudrakola V, Harms JF, Schmidt CJ, West AR (2015) Facilitation of corticostriatal transmission following pharmacological inhibition of striatal phosphodiesterase 10A: role of nitric oxide-soluble guanylyl cyclase-cGMP signaling pathways. J Neurosci 35:5781-5791. doi.org/10.1523/jneurosci.1238-14.2015

Page ME, Cryan JF, Sullivan A, et al. (September 2002). "Behavioral and neurochemical effects of 5-(4-[4-(5-Cyano-3-indolyl)-butyl)-butyl]-1-piperazinyl)-benzofuran-2-carboxamide (EMD 68843): a combined selective inhibitor of serotonin reuptake and 5-hydroxytryptamine (1A) receptor partial agonist". The Journal of Pharmacology and Experimental Therapeutics. 302 (3): 1220-7. doi: 10.1124/jpet.102.034280. PMID 12183683.

Page ME, Detke MJ, Dalvi A, et al. Serotonergic mediation of the effects of fluoxetine, but not desipramine, in the rat forced swimming test. Psychopharmacology. 1999;147 (2): 162-167.

Pankaj Oudhia. "Kapikachu or Cowhage". Nov 3,2013.

Parker KL, Lamichhane D, Caetano MS, Narayanan NS (October 2013). "Executive dysfunction in Parkinson's disease and timing deficits". Frontiers in Integrative Neuroscience. 7:75. doi: 10.3389/fnint.2013.00075. PMC 3813949. PMID 24198770.

Parkinson's UK. "Anticholinergics". 30 Apr. 2014.

Paxinos, G., & Watson, W. (1998). The Rat Brain in Stereotaxic Coordinates, 4th ed. Academic Press: San Diego, CA.

Pedrosa DJ, Timmermann L (2013). "Review: management of Parkinson's disease". Neuropsychiatric Disease and Treatment. 9:321-40. doi: 10.2147/NDT.S32302. PMC 3592512. PMID 23487540.

Pehrson, A., Y. Li, N. Haddjeri, M. Gulinello, and C. Sanchez. "P. 1. g. 014 Vortioxetine, a novel multimodal antidepressant, modulates GABA and glutamate neurotransmission via serotonergic mechanisms." European Neuropsychopharmacology 23 (2013): S196-S197.

Pehrson, Alan L., and Connie Sanchez. "Serotonergic modulation of glutamate neurotransmission as a strategy for treating depression and cognitive dysfunction." CNS spectrums 19, no. 2 (2014): 121-133.

Perez, M., P. J. Pauwels, I. Pallard-Sigogneau, C. Fourrier, P. Chopin, C. Palmier, V. Colovray, and S. Halazy. "Design and synthesis of new potent, silent 5-HT1A antagonists by covalent coupling of aminopropanol derivatives with selective serotonin reuptake inhibitors." Bioorganic & medicinal chemistry letters 8, no. 23 (1998): 3423-3428.

Perrone, Roberto, Francesco Berardi, Nicola A. Colabufo, Enza Lacivita, Carmela Larizza, Marcello Leopoldo, and Vincenzo Tortorella. "Design and synthesis of long-chain arylpiperazines with mixed affinity for serotonin transporter (SERT) and 5-HT1A receptor." Journal of pharmacy and pharmacology 57, no. 10 (2005): 1319-1327.

Perry D, Birthi P, Salles S, McDowell S. Neuroleptic malignant syndrome associated with the use of carbidopa/-levodopa for dystonia in persons with cerebral palsy. PM R 2012; 4:383-384.

Pertwee RG: The diverse CB1 and CB2 receptor pharmacology of three plant cannabinoids: 49-tetrahydrocannabinol, cannabidiol and 49-tetrahydrocannabivarin. Br J Pharmacol. 2008 January; 153 (2): 199-215. doi: 10.1038/sj.bjp.0707442. Epub 2007 Sep. 10. [PubMed: 17828291]

Pertwee, Roger G; Rock, Erin M; Guenther, Kelsey; Limebeer, Cheryl L; Stevenson, Lesley A; Haj, Christeene; Smoum, Reem; Parker, Linda A; Mechoulam, Raphael; "Cannabidiolic acid methyl ester, a stable synthetic analogue of cannabidiolic acid, can produce 5-HT1A receptor-mediated suppression of nausea and anxiety in rats"

Perucca E (December 2017). "Cannabinoids in the Treatment of Epilepsy: Hard Evidence at Last?". J Epilepsy Res. 7 (2): 61-76. doi: 10.14581/jer.17012. PMC 5767492. PMID 29344464.

Petrzilka T, Haefliger W, Sikemeier C, Ohloff G, Eschenmoser A (March 1967). "[Synthesis and optical rotation of the (−)-cannabidiols]". Helvetica Chimica Acta. 50 (2): 719-23. doi: 10.1002/hlca.19670500235. PMID 5587099.

Pierz, Kemi A., and Michael E. Thase. "A review of vilazodone, serotonin, and major depressive disorder." The primary care companion for CNS disorders 16, no. 1 (2014).

Pinna A, Morelli M, Drukarch B, Stoof JC (1997) Priming of 6-hydroxydopamine-lesioned rats with L-DOPA or quinpirole results in an increase in dopamine D1 receptor-dependent cyclic AMP production in striatal tissue. Eur J Pharmacol 331:23-26

Pisanti S, Malfitano AM, Ciaglia E, Lamberti A, Ranieri R, Cuomo G, Abate M, Faggiana G, Proto MC, Fiore D, Laezza C, Bifulco M (July 2017). "Cannabidiol: State of the art and new challenges for therapeutic applications". Pharmacol. Ther. 175:133-150. doi: 10.1016/j.pharmthera.2017.02.041. PMID 28232276.

Platz T, Rothwell JC (2010). "Brain stimulation and brain repair-rTMS: from animal experiment to clinical trials-what do we know?". Restorative Neurology and Neuroscience. 28 (4): 387-98. doi: 10.3233/RNN-2010-0570. PMID 20714064.

Poewe W (December 2006). "The natural history of Parkinson's disease". Journal of Neurology. 253 Suppl 7 (Suppl 7): VII2-6. doi: 10.1007/s00415-006-7002-7. PMID 17131223.

Poewe W, Wenning G (November 2002). "The differential diagnosis of Parkinson's disease". European Journal of Neurology. 9 Suppl 3 (Suppl 3): 23-30. doi: 10.1046/j.1468-1331.9.s3.3.x. PMID 12464118.

Politis M, Wu K, Loane C, Brooks DJ, Kiferle L, Turkheimer FE, Bain P, Molloy S, Piccini P (2014) Serotonergic mechanisms responsible for levodopa-induced dyskinesias in Parkinson's disease patients. J Clin Invest 124:1340-1349. doi.org/10.1172/jci71640

Politis M, Wu K, Loane C, Kiferle L, Molloy S, Brooks DJ, Piccini P (2010) Staging of serotonergic dysfunction in Parkinson's disease: an in vivo 11CDASB PET study. Neurobiol Dis 40:216-221. doi.org/10.1016/j.nbd. 2010.05.028

Politis, M., Wu, K., Loane, C., Brooks, D.J., Kiferle, L., Turkheimer, F. E., et al (2014). Serotonergic mechanisms responsible for levodopa-induced dyskinesias in Parkinson's disease patients. J Clin Invest, 124 (3): 1340-1349.

Postuma RB, Berg D, Stern M, Poewe W, Olanow CW, Oertel W, Obeso J, Marek K, Litvan I, Lang AE, Halliday G, Goetz CG, Gasser T, Dubois B, Chan P, Bloem BR, Adler CH, Deuschl G (October 2015). "MDS clinical diagnostic criteria for Parkinson's disease". Movement Disorders. 30 (12): 1591-601. doi: 10.1002/mds.26424. PMID 26474316.

Pozin I, Bdolah-Abram T, Ben-Pazi H. Levodopa does not improve function in individuals with dystonic cerebral palsy. J Child Neurol 2014; 29:534-537.

Prud'Homme, M; Cata, R; Jutras-Aswad, D (2015). "Cannabidiol as an Intervention for Addictive Behaviors: A Systematic Review of the Evidence". Substance Abuse: Research and Treatment. 9:33-8. doi: 10.4137/SART.S25081. PMC 4444130. PMID 26056464.

Putterman, D.B., Munhall, A.C., Kozell, L.B., Belknap, J.K., & Johnson, S.W. (2007). Evaluation of levodopa dose and magnitude of dopamine depletion as risk factors for levodopa-induced dyskinesia in a rat model of Parkinson's disease. J Pharmacol Exp Ther, 323: 277-284.

Qin, Juan-Juan, Hong-Xia Chen, Nan Zhao, Li Yuan, You-Zhi Zhang, Ri-Fang Yang, Li-Ming Zhang, and Yun-Feng Li. "The role of activation of the 5-HT 1A receptor and adenylate cyclase in the antidepressant-like effect of YL-0919, a dual 5-HT1A agonist and selective serotonin reuptake inhibitor." Neuroscience letters 582 (2014): 104-108.

Raguthu L, Varanese S, Flancbaum L, Tayler E, Di Rocco A (October 2009). "Fava beans and Parkinson's disease: useful 'natural supplement' or useless risk?". European Journal of Neurology. 16 (10): e171. doi: 10.1111/j.1468-1331.2009.02766.x. PMID 19678834.

Rajesh Pahwa; Kelly E. Lyons (25 Mar. 2003). Handbook of Parkinson's Disease (Third ed.). CRC Press. p. 76. ISBN 978-O-203-91216-4. 8 Sep. 2017.

Rampello, L., Chiechio, S., Raffaele, R., Vecchio, I., & Nicoletti, F. (2002). The SSRI, citalopram, improves bradykinesia in patients with Parkinson's disease treated with L-DOPA. Clin Neuropharmacol, 25 (1): 21-24.

Ran, Yu-hua, Xiao-xu Hu, Yu-lu Wang, Nan Zhao, Li-ming Zhang, Hua-xia Liu, and Yun-feng Li. "YL-0919, a dual 5-HT 1A partial agonist and SSRI, produces antidepressant- and anxiolytic-like effects in rats subjected to chronic unpredictable stress." Acta Pharmacologica *Sinica* 39, no. 1 (2018): 12.

Ran, Yuhua, Zengliang Jin, Xiaofei Chen, Nan Zhao, Xinxin Fang, Liming Zhang, Youzhi Zhang, and Yunfeng Li. "Hypidone hydrochloride (YL-0919) produces a fast-onset reversal of the behavioural and synaptic deficits caused by chronic stress exposure." Frontiers in Cellular Neuroscience 12 (2018): 395.

Rasmussen, DD; Ishizuka, B; Quigley, ME; Yen, SS (1983). "Effects of tyrosine and tryptophan ingestion on plasma catecholamine and 3,4-dihydroxyphenylacetic acid concentrations". J. Clin. Endocrinol. Metab. 57 (4): 760-3. doi: 10.1210/jcem-57-4-760. PMID 6885965.

Ravenscroft, P., Chalon, S., Brotchie, J.M., & Crossman, A.R. (2004). Ropinirole versus L-DOPA effects on striatal opiod peptide precursors in a rodent model of Parkinson's disease: implications for dyskinesia. Exp Neurol, 185 (1): 36-46.

Redmond DE (October 2002). "Cellular replacement therapy for Parkinson's disease-where we are today?". The Neuroscientist. 8 (5): 457-88. doi: 10.1177/107385802237703. PMID 12374430.

Reimsnider S, Manfredsson FP, Muzyczka N, Mandel RJ (2007) Time course of transgene expression after intrastriatal pseudotyped rAAV2/1, rAAV2/2, rAAV2/5, and rAAV2/8 transduction in the rat. Mol Ther 15:1504-1511. doi.org/10.1038/sj.mt. 6300227

Resstel LB, Tavares RF, Lisboa SF, Joca SR, Corrêa FM, Guimarães FS (January 2009). "5-HT1A receptors are involved in the cannabidiol-induced attenuation of behavioural and cardiovascular responses to acute restraint stress in rats". British Journal of Pharmacology. 156 (1): 181-8. doi: 10.1111/j.1476-5381.2008.00046.x. PMC 2697769. PMID 19133999.

Riga, Maurizio S., Connie Sanchez, Pau Celada, and Francesc Artigas. "Involvement of 5-HT3 receptors in the action of vortioxetine in rat brain: focus on glutamatergic and GABAergic neurotransmission." Neuropharmacology 108 (2016): 73-81.

Rizzo G, Copetti M, Arcuti S, Martino D, Fontana A, Logroscino G (February 2016). "Accuracy of clinical diagnosis of Parkinson disease: A systematic review and meta-analysis". Neurology. 86 (6): 566-76. doi: 10.1212/WVNL.0000000000002350. PMID 26764028.

Roberts, Claire, Jim J. Hagan, Gerd D. Bartoszyk, and James NC Kew. "Effect of vilazodone on 5-HT efflux and re-uptake in the guinea-pig dorsal raphe nucleus." European journal of pharmacology 517, no. 1-2 (2005): 59-63.

Rocco, Vincent P., Patrick G. Spinazze, Todd J. Kohn, Nicholas A. Honigschmidt, David L. Nelson, D. Bradley Wainscott, Laura J. Ahmad et al. "Advances toward new antidepressants beyond SSRIs: 1-aryloxy-3-piperidinylpropan-2-ols with dual 5-HT 1A receptor antagonism/SSRI activities. Part 4." Bioorganic & medicinal chemistry letters 14, no. 10 (2004): 2653-2656.

Rock, E M; Parker, L A; "Effect of low doses of cannabidiolic acid and ondansetron on LiCI-induced conditioned gaping (a model of nausea-induced behaviour) in rats"

Rock, Erin M., Cheryl L. Limebeer, Gavin N. Petrie, Lauren A. Williams, Raphael Mechoulam, and Linda A. Parker. "Effect of prior foot shock stress and A 9-tetrahydrocannabinol, cannabidiolic acid, and cannabidiol on anxiety-like responding in the light-dark emergence test in rats." Psychopharmacology 234, no. 14 (2017): 2207-2217.

Romero, Luz, Pau Celada, Raúl Martin-Ruiz, Llorenç Díaz-Mataix, Marisabel Mourelle, Joaquim Delgadillo, Ildefonso Hervás, and Francesc Artigas. "Modulation of serotonergic function in rat brain by VN2222, a serotonin reuptake inhibitor and 5-HT 1A receptor agonist" Neuropsychopharmacology 28, no. 3 (2003): 445.

Roussakis, A.A., Politis, M., Towey, D., & Piccini, P. (2016). Serotonin-to-dopamine transporter ratios in Parkinson disease: Relevance for dyskinesias. Neurology, 86 (12): 1152-1158. doi.org/10.1212/wnl.0000000000002494

Ruggiero RN, Rossignoli MT, De Ross JB, Hallak JEC, Leite JP, Bueno-Junior LS: Cannabinoids and Vanilloids in Schizophrenia: Neurophysiological Evidence and Directions for Basic Research. Front Pharmacol. 2017 Jun. 21; 8:399. doi: 10.3389/fphar.2017.00399. eCollection 2017. [PubMed: 28680405]

Russo EB, Burnett A, Hall B, Parker KK (August 2005). "Agonistic properties of cannabidiol at 5-HT1a receptors". Neurochemical Research. 30 (8): 1037-43. doi: 10.1007/s11064-005-6978-1. PMID 16258853.

Ryberg E, Larsson N, Sjogren S, Hjorth S, Hermansson NO, Leonova J, Elebring T, Nilsson K, Drmota T, Greasley PJ (December 2007). "The orphan receptor GPR55 is a novel cannabinoid receptor". British Journal of Pharmacology. 152 (7): 1092-101. doi: 10.1038/sj.bjp.0707460. PMC 2095107. PMID 17876302.

Rylander D, Parent M, O'Sullivan SS, Dovero S, Lees AJ, Bezard E, Descarries L, Cenci MA (2010) Maladaptive plasticity of serotonin axon terminals in levodopa-induced dyskinesia. Ann Neurol 68:619-628. doi.org/10. 1002/ana.22097

Rylander, D., Parent, M., O'Sullvan, S.S., Dovero, S., Lees, A.J., Bexard, E., et al (2010). Maladaptive plasticity of serotonin axon terminals in levodopa-induced dyskinesia. Ann Neurol, 68 (5): 619-628.

Sahlia, Zeyad T., Pradeep Banerjee, and Frank I. Tarazi, "The Preclinical and Clinical Effects of Vilazodone for the Treatment of Major Depressive Disorder", Expert Opinion On Drug Discovery, 2016, Vol. 11, No. 5, 515-523, dx.doi.org/10.1517/17460441.2016.1160051

Samii A, Nutt JG, Ransom BR (May 2004). "Parkinson's disease". Lancet 363 (9423): 1783-93. doi: 10.1016/S0140-6736 (04) 16305-8. PMID 15172778.

Sammut S, Threlfell S, West AR (2010) Nitric oxide-soluble guanylyl cyclase signaling regulates corticostriatal transmission and short-term synaptic plasticity of striatal projection neurons recorded in vivo. Neuropharmacology 58:624-631. doi.org/10.1016/j.neuropharm.2009.11.011

Sanchez, C; Asin, KE; Artigas, F (1 Jan. 2015). "Vortioxetine, a Novel Antidepressant with Multimodal Activity: Review of Preclinical and Clinical Data". Pharmacology & Therapeutics. 145:43-57. doi: 10.1016/j.pharmthera.2014.07.001. ISSN 1879-016X. PMID 25016186.

Scatton B, Javoy-Agid F, Rouquier L, Dubois B, Agid Y (1983) Reduction of cortical dopamine, noradrenaline, serotonin and their metabolites in Parkinson's disease. Brain Res 275:321-328

Schallert T (2006) Behavioral tests for preclinical intervention assessment. NeuroRX 3:497-504. doi.org/10.1016/j.nurx.2006.08.001

Schneider SA, Edwards MJ, Grill S E, et al. Adult-onset primary lower limb dystonia. Mov Disord 2006; 21:767-771.

Schoefter, Philippe, and Daniel Hoyer. "Centrally acting hypotensive agents with affinity for 5-HT1A binding sites inhibit forskolin-stimulated adenylate cyclase activity in calf hippocampus." British journal of pharmacology 95, no. 3 (1988): 975-985.

Scholtissen B, Verhey FR, Steinbusch HW, Leentjens AF (2006) Serotonergic mechanisms in Parkinson's disease: opposing results from preclinical and clinical data. J Neural Transm (Vienna) 113:59-73. doi.org/10.1007/s00702-005-0368-3.

Schrag A (2007). "Epidemiology of movement disorders". In Tolosa E, Jankovic JJ. Parkinson's disease and movement disorders. Hagerstown, Maryland: Lippincott Williams & Wilkins. pp. 50-66. ISBN 978-O-7817-7881-7.

Schulz-Schaeffer WJ (August 2010). "The synaptic pathology of alpha-synuclein aggregation in dementia with Lewy bodies, Parkinson's disease and Parkinson's disease dementia". Acta Neuropathologica. 120 (2): 131-43. doi: 10.1007/s00401-010-0711-0. PMC 2892607. PMID 20563819.

Schwartz, Thomas L., Umar A. Siddiqui, and Stephen M. Stahl. "Vilazodone: a brief pharmacological and clinical review of the novel serotonin partial agonist and reuptake inhibitor." Therapeutic advances in psychopharmacology 1, no. 3 (2011): 81-87.

Schwarz ST, Afzal M, Morgan PS, Bajaj N, Gowland PA, Auer DP (2014). "The 'swallow tail' appearance of the healthy nigrosome-a new accurate test of Parkinson's disease: a case-control and retrospective cross-sectional MRI study at 3T". PLOS One. 9 (4): e93814. Bibcode: 2014PLoSO . . . 993814S. doi: 10.1371/journal.pone.0093814. PMC 3977922. PMID 24710392.

Scuderi C, Filippis DD, luvone T, Blasio A, Steardo A, Esposito G (May 2009). "Cannabidiol in medicine: a review of its therapeutic potential in CNS disorders". Phytotherapy Research (Review). 23 (5): 597-602. doi: 10.1002/ptr.2625. PMID 18844286.

Scuderi C, Steardo L, Esposito G: Cannabidiol promotes amyloid precursor protein ubiquitination and reduction of beta amyloid expression in SHSY5YAPP+ cells through PPARgamma involvement. Phytother Res. 2014 July;28 (7): 1007-13. doi: 10.1002/ptr.5095. Epub 2013 Nov. 28. [PubMed: 24288245]

Segawa M, Hosaka A, Miyagawa F, Nomura Y, Imai H (1976). "Hereditary progressive dystonia with marked diurnal fluctuation". Advances in Neurology. 14:215-33. PMID 945938.

Segawa M, Ohmi K, Itoh S, Aoyama M, Hayahawa H. Childhood basal ganglia disease with remarkable response to L-DOPA, "hereditary basal ganglia disease with marked diumal fluctuation." Shinryo 1971; 24:667-672.

Sellnow, Rhyomi C., Jordan H. Newman, Nicole Chambers, Anthony R. West, Kathy Steece-Collier, Ivette M. Sandoval, Matthew J. Benskey, Christopher Bishop, and Fredric P. Manfredsson. "Regulation of dopamine neurotransmission from serotonergic neurons by ectopic expression of the dopamine D2 autoreceptor blocks levodopa-induced dyskinesia." Acta neuropathologica communications 7, no. 1 (2019): 8.

Sharma P, Murthy P, Bharath MM: Chemistry, metabolism, and toxicology of *cannabis*: clinical implications. Iran J Psychiatry. 2012 Fall;7 (4): 149-56. [PubMed: 23408483]

Shergill SS, Walker Z, Le Katona C (October 1998). "A preliminary investigation of laterality in Parkinson's disease and susceptibility to psychosis". Journal of Neurology, Neurosurgery, and Psychiatry. 65 (4): 610-1. doi: 10.1136/jnnp.65.4.610. PMC 2170290. PMID 9771806.

Shulman JM, De Jager PL, Feany MB (February 2011) [25 Oct. 2010]. "Parkinson's disease: genetics and pathogenesis". Annual Review of Pathology. 6:193-222. doi: 10.1146/annurev-pathol-011110-130242. PMID 21034221.

Silva, T. B; Balbino, C. Q; Weiber, A. F (2015). "The relationship between cannabidiol and psychosis: A review". Annals of Clinical Psychiatry: Oficial Journal of the American Academy of Clinical Psychiatrists. 27 (2): 134-41. PMID 25954940.

Simola N, Di Chiara G, Daniels WM, Schallert T, Morelli M (2009) Priming of rotational behavior by a dopamine receptor agonist in Hemiparkinsonian rats: movement-dependent induction. Neuroscience 158:1625-31. doi.org/10.1016/j.neuroscience.2008.11.009.

Singh M, Schwartz TL. Clinical utility of vilazodone for the treatment of adults with major depressive disorder and theoretical implications for future clinical use. Neuropsychiatr Dis Treat. 2012; 8:123.

Smith, T.D., Kuczenski, R., George-Friedman, K., Malley, J.D., & Foote, S.L. (2000). In vivo microdialysis assessment of extracellular serotonin and dopamine levels in awake monkeys during sustained fluoxetine administration. Synapse, 38 (4): 460-470.

Stahl, Stephen M. Stahl's Essential Psychopharmacology: Neuroscientific Basis and Practical Applications (4th ed.). Cambridge University Press. ISBN 978-1107686465.

Steece-Collier K, Collier TJ, Danielson PD, Kurlan R, Yurek DM, Sladek JR (2003) Embryonic mesencephalic grafts increase levodopa-induced forelimb hyperkinesia in parkinsonian rats. Movement disorders: official journal of the Movement Disorder Society 18:1442-1454. doi.org/10.1002/mds.10588

Steece-Collier K, Soderstrom KE, Collier TJ, Sortwell CE, Maries-Lad E (2009) Effect of levodopa priming on dopamine neuron transplant efficacy and induction of abnormal involuntary movements in parkinsonian rats. J Comp Neurol 515:15-30. doi.org/10.1002/cne.22037

Stockings E, Zagic D, Campbell G, Weier M, Hall WD, Nielsen S, Herkes GK, Farrell M, Degenhardt L (July 2018). "Evidence for *cannabis* and cannabinoids for epilepsy: a systematic review of controlled and observational evidence". J. Neurol. Neurosurg. Psychiatry. 89 (7): 741-753. doi: 10.1136/jnnp-2017-317168. PMID 29511052.

Suchowersky O, Gronseth G, Perlmutter J, Reich S, Zesiewicz T, Weiner WJ (April 2006). "Practice Parameter. neuroprotective strategies and alternative therapies for Parkinson disease (an evidence-based review): report of the Quality Standards Subcommittee of the American Academy of Neurology". Neurology. 66 (7): 976-82. doi: 10.1212/01.wnl.0000206363.57955.1b. PMID 16606908.

Suzuki M, Matsuda T, Asano S, et al. Increase of noradrenaline release in the hypothalamus of freely moving rat by postsynaptic 5-hydroxytryptamine 1A receptor activation. Br J Pharmacol. 1995;115 (4): 703-711

Sveinbjonsdottir S (October 2016). "The clinical symptoms of Parkinson's disease". Journal of Neurochemistry. 139 Suppl 1:318-324. Bibcode: 2006JNeur. 26.9606G. doi: 10.1111/jnc. 13691. PMID 27401947.

Svenningsson, P., Rosenblad, C., Af Edholm Arvidsson, K., Wictorin, K., Keywood, C., Shankar, B., et al (2015). Eltoprazine counteracts L-DOPA-induced dyskinesias in Parkinson's disease: a dose-finding study. Brain, 138 (Pt 4): 963-973.

Takeuchi, Kumiko, Todd J. Kohn, Nicholas A. Honigschmidt, Vincent P. Rocco, Patrick G. Spinazze, Daniel J. Koch, David L. Nelson et al. "Advances toward new antidepressants beyond SSRIs: 1-aryloxy-3-piperidinylpropan-2-ols with dual 5-HT1A receptor antagonism/SSRI activities. Part 1." Bioorganic & medicinal chemistry letters 13, no. 11 (2003): 1903-1905.

Takeuchi, Kumiko, Todd J. Kohn, Nicholas A. Honigschmidt, Vincent P. Rocco, Patrick G. Spinazze, Daniel J. Koch, Steven T. Atkinson et al. "Advances toward new antidepressants beyond SSRIs: 1-aryloxy-3-piperidinylpropan-2-ols with dual 5-HT1A receptor antagonism/SSRI activities. Part 2." Bioorganic & medicinal chemistry letters 13, no. 14 (2003): 2393-2397.

Takeuchi, Kumiko, Todd J. Kohn, Nicholas A. Honigschmidt, Vincent P. Rocco, Patrick G. Spinazze, Steven T.

Atkinson, Larry W. Hertel et al. "Advances toward new antidepressants beyond SSRIs: 1-aryloxy-3-piperidinylpropan-2-ols with dual 5-HT1A receptor antagonism/SSRI activities. Part 3." Bioorganic & medicinal chemistry letters 13, no. 22 (2003): 3939-3942.

Takeuchi, Kumiko, Todd J. Kohn, Nicholas A. Honigschmidt, Vincent P. Rocco, Patrick G. Spinazze, Susan K. Hemrick-Luecke, Linda K. Thompson et al. "Advances toward new antidepressants beyond SSRIs: 1-Aryloxy-3-piperidinylpropan-2-ols with dual 5-HT 1A receptor antagonism/SSRI activities. Part 5." Bioorganic & medicinal chemistry letters 16, no. 9 (2006): 2347-2351.

Tamim, M.K., Samadi, P., Morissette, M., Grégoire, L., Ouattara, B., Lévesque, D., et al (2010). Effect of non-dopaminergic drug treatment on levodopa induced dyskinesieas in MPTP monkeys: Common implications of striatal neuropeptides. Neuropharmacology, 58 (1): 286-296.

Tanaka H, Kannari K, Maeda T, Tomiyama M, Suda T, Matsunaga M (1999) Role of serotonergic neurons in L-DOPA-derived extracellular dopamine in the striatum of 6—OHDA-lesioned rats. Neuroreport 10:631-634

Tanya Simuni and Howard Hurtig. "Levadopa: A Pharmacologic Miracle Four Decades Later", in Parkinson's Disease: Diagnosis and Clinical Management (Google eBook). Eds. Stewart A Factor and William J Weiner. Demos Medical Publishing, 2008

Tassin J, Durr A, Bonnet A M, et al. Levodopa-responsive dystonia: GTP cyclohydrolase I or parkin mutations? Brain 2000; 123:1112-1121.

Tauber P (17 Jul. 1988). "Ali: Still Magic". The New York Times.

Taura F, Sirikantaramas S, Shoyama Y, Yoshikai K, Shoyama Y, Morimoto S (June 2007). "Cannabidiolic-acid synthase, the chemotype-determining enzyme in the fiber-type *Cannabis sativa*". FEBS Letters. 581 (16): 2929-34. doi: 10.1016/j.febslet.2007.05.043. PMID 17544411.

Taylor A., et al, "Prophylactic Effects of Atypical Anti-Depressant Vilazodone on L-DOPA-Induced Dyskinesia and Striatal Gene Expression" 2016 133.06/N2

Taylor D, Paton C, Kapur S, Taylor D. The Maudsley prescribing guidelines in psychiatry. 11th ed. Chichester, West Sussex: John Wiley & Sons; 2012.

Taylor JL, Bishop C, Walker PD (2005) Dopamine D1 and D2 receptor contributions toL-DOPA-induced dyskinesia in the dopamine-depleted rat. Pharmacol Biochem Behav 81:887-893. doi.org/10.1016/j.pbb.2005.06.013

Tel BC, Zeng BY, Cannizzaro C, Pearce RK, Rose S, and Jenner P (2002) Alterations in striatal neuropeptide mRNA produced by repeated administration of L-DOPA, ropinirole or bromocriptine correlate with dyskinesia induction in MPTP-treated common marmosets. Neuroscience 115:1047-1058.

Tetrud, JW; JW Langston (4 Aug. 1989). "The effect of deprenyl (selegiline) on the natural history of Parkinson's disease". Science. 245 (4917): 519-522. Bibcode: 1989Sci . . . 245 . . . 519T. doi: 10.1126/science.2502843. PMID 2502843.

The National Collaborating Centre for Chronic Conditions, ed. (2006) (NCCCC 2006). London: Royal College of Physicians. 24 Sep. 2010. ISBN 978-1-86016-283-1. "Diagnosing Parkinson's Disease". Parkinson's Disease. pp. 29-47. "Symptomatic pharmacological therapy in Parkinson's disease". "Palliative care in Parkinson's disease". pp. 147-51. "Non-motor features of Parkinson's disease". pp. 113-33. "Surgery for Parkinson's disease". pp. 101-11. "Other key interventions". pp. 135-46.

Tolosa E, Katzenschlager R (2007). "Pharmacological management of Parkinson's disease". In Tolosa E, Jankovic JJ. Parkinson's disease and movement disorders. Hagerstwon, MD: Lippincott Williams & Wilkins. pp. 110-45. ISBN 978-O-7817-7881-7.

Tordera, Rosa M., Antonio Monge, Joaquin Del Rio, and Berta Lasheras. "Antidepressant-like activity of VN2222, a serotonin reuptake inhibitor with high affinity at 5-HT1A receptors." European journal of pharmacology 442, no. 1-2 (2002): 63-71.

Tremlett, H; Bauer, KC; Appel-Cresswell, S; Finlay, BB; Waubant, E (March 2017). "The gut microbiome in human neurological disease: A review". Annals of Neurology. 81 (3): 369-382. doi: 10.1002/ana.24901. PMID 28220542. Trender-Gerhard I, Sweeney MG, Schwingenschuh P, et al.Autosomal-dominant GTPCH1-deficient DRD: clinical characteristics and long-term outcome of 34 patients. J Neurol Neurosurg Psychiatry 2009; 80:839-845.

Ujváry I, Hanuš L (2014). "Human Metabolites of Cannabidiol: A Review on Their Formation, Biological Activity, and Relevance in Therapy". *Cannabis* and Cannabinoid Research. 1 (1): 90-101. doi: 10.1089/can.2015.0012. PMC 5576600. PMID 28861484.

UMMC University of Maryland Medical Center. "Tyrosine". 30 Apr. 2014.

Van Ameringen, Michael, Beth Patterson, and Elizabeth Lee. "Serotonin reuptake and receptor blockers." Future Medicine Ltd, 2012.

Vesper J, Klostermann F, Funk T, Stockhammer F, Brock M. Deep brain stimulation of the globus pallidus internus (GPI) for torsion dystonia: a report of two cases. Acta Neurochir Suppl 2002; 79:83-88.

Visser JE, Schretlen DJ, Bloem BR, Jinnah HA. Levodopa is not a useful treatment for Lesch-Nyhan disease. Mov Disord 2011; 26:746-749.

Waite, J. Herbert; Andersen, Niels Holten; et al. (2005). "Mussel Adhesion: Finding the Tricks Worth Mimicking". J Adhesion. 81 (3-4): 1-21. doi: 10.1080/00218460590944602.

Wang X, Li J, Dong G, Yue J (February 2014). "The endogenous substrates of brain CYP2D". Eur. J. Pharmacol. 724:211-218. doi: 10.1016/j.ejphar.2013.12.025. PMID 24374199.

Wang Y-P, Chen Y-T, Tsai C-F, Li S-Y, Luo J-C, Wang S-J, et al. Short-Term Use of Serotonin Reuptake Inhibitors and Risk of Upper Gastrointestinal Bleeding. Am J Psychiatry [Internet]. 2013 Sep. 13 [cited 2013 Oct. 6]; Available from: ajp.psychiatryonline.org/article.aspx?articleid=1738031

Wang, Panpan, Fengyuan Yang, Hong Yang, Xiaofei Xu, Duo Liu, Weiwei Xue, and Feng Zhu. "Identification of dual active agents targeting 5-HT1A and SERT by combinatorial virtual screening methods." Bio-medical materials and engineering 26, no. s1 (2015): S2233-S2239.

Wang, Sheng-Min, Changsu Han, Soo-Jung Lee, Ashwin A. Patkar, Prakash S. Masand, and Chi-Un Pae. "Vilazodone for the treatment of major depressive disorder: focusing on its clinical studies and mechanism of action." Psychiatry investigation 12, no. 2 (2015): 155-163.

Wang, SM; Han, C; Lee, SJ; Patkar, AA; Masand, PS; Pae, CU (August 2013). "A review of current evidence for vilazodone in major depressive disorder". International Journal of Psychiatry in Clinical Practice. 17 (3): 160-9. doi: 10.3109/13651501.2013.794245. PMID 23578403.

Wang, Xin, Dong Zhi Liu, and Ai Jun Li. "1-(N-(2-(2-Methoxyphenylthio) benzyl)-N-methylamino-3-aryloxypropan-2-ols: Synthesis and evaluation for dual 5-HT1A/SSRI activities." Chinese Chemical Letters 19, no. 1 (2008): 40-42.

Wang, Xin, Dong Zhi Liu, and Ai Jun Li. "1-[2-(2-Methoxyphenylthio) benzyl]-4-arylpiperazines derivatives: Synthesis and evaluation for dual 5-HT1A/SSRI activities." Chinese Chemical Letters 19, no. 1 (2008): 37-39.

Watson, Jeannette M., and Lee A. Dawson. "Characterization of the Potent 5-HT1A/B Receptor Antagonist and Serotonin Reuptake Inhibitor SB-649915: Preclinical Evidence for Hastened Onset of Antidepressant/Anxiolytic Efficacy." CNS drug reviews 13, no. 2 (2007): 206-223.

Weiner WJ, Koller WC, Perlik S, Nausieda PA, Klawans HL (1980) Drug holiday and management of Parkinson disease. Neurology 30:1257-1261

Wijemanne S, Jankovic J. Dopa-responsive dystonia: clinical and genetic heterogeneity. Nat Rev Neurol 2015; 11:414-424.

Wilcox SK (January 2010). "Extending palliative care to patients with Parkinson's disease". British Journal of Hospital Medicine. 71 (1): 26-30. doi: 10.12968/hmed.2010.71.1.45969. PMID 20081638.

Wilder-Smith E, Tan EK, Law HY, Zhao Y, Ng I, Wong MC. Spinocerebellar ataxia type 3 presenting as an LDOPA responsive dystonia phenotype in a Chinese family. J Neurol Sci 2003; 213:25-28.

Willemsen MA, Verbeek MM, Kamsteeg E J, et al. Tyrosine hydroxylase deficiency: a treatable disorder of brain catecholamine biosynthesis. Brain 2010; 133: 1810-1822.

Winkler, C., Kirik, D., Bjorklund, A., Cenci, M.A. L-DOPA-induced dyskinesia in the intrastriatal 6-hydroxydopamine model of Parkinson's disease: relation to motor and cellular parameters of nigrostriatal function. Neurobiol Dis 10:165-86 (2002).

Wu, Xue Dan, Dong Zhi Liu, Ai Jun Li, and Xue Qin Zhou. "Arylpiperazine derivatives of diphenylsulfide: Synthesis and evaluation for dual 5-HT1A/SSRI activities." Chinese Chemical Letters 19, no. 3 (2008): 291-294.

Wu, Xue Dan, Dong Zhi Liu, Ai Jun Li, and Xue Qin Zhou. "N-(2-(2-Methoxyphenylthio) benzyl)-2-aryloxyethylamines: Synthesis and evaluation for dual 5-HT1A/SSRI activities." Chinese Chemical Letters 19, no. 3 (2008): 295-298.

Xiong W, Cui T, Cheng K, Yang F, Chen SR, Willenbring D, Guan Y, Pan HL, Ren K, Xu Y, Zhang L: Cannabinoids suppress inflammatory and neuropathic pain by targeting alpha3 glycine receptors. J Exp Med. 2012 Jun. 4;209 (6): 1121-34. doi: 10.1084/jem.20120242. Epub 2012 May 14. [PubMed: 22585736]

Yamada H, Aimi Y, Nagatsu I, Taki K, Kudo M, Arai R (2007) Immunohistochemical detection of I-DOPA-derived dopamine within serotonergic fibers in the striatum and the substantia nigra pars *reticulata* in Parkinsonian model rats. Neurosci Res 59:1-7. doi.org/10.1016/j. neures.2007.05.002

Yamaori S, Okushima Y, Masuda K, Kushihara M, Katsu T, Narimatsu S, Yamamoto I, Watanabe K: Structural requirements for potent direct inhibition of human cytochrome P450 1A1 by cannabidiol: role of pentylresorcinol moiety. Biol Pharm Bull. 2013; 36 (7): 1197-203. [PubMed: 23811569]

Yang KH, Galadari S, Isaev D, Petroianu G, Shippenberg TS, Oz M: The nonpsychoactive cannabinoid cannabidiol inhibits 5-hydroxytryptamine3A receptor-mediated currents in *Xenopus laevis* oocytes. J Pharmacol Exp Ther. 2010 May;333 (2): 547-54. doi: 10.1124/jpet 109.162594. Epub 2010 Feb. 16. [PubMed: 20160007]

Yao, S.C.; Hart, A.D.; Terzella, M.J. (May 2013). "An evidence-based osteopathic approach to Parkinson disease". Osteopathic Family Physician. 5 (3): 96-101. doi: 10.1016/j.osfp.2013.01.003.

Yilmaz U, Yuksel D, Atac FB, Yilmaz D, Verdi H, Senbil N. Atypical phenotypes of DYT1 dystonia in three children. Brain Dev 2013; 35:356-359.

Young, S. T., Porrino, L. J., & ladorola, M. J. (1991). Cocaine induces striatal c-Fos immunoreactive proteins via dopaminergic D1 receptors. Proceedings of the National Academy of Sciences. 88, 1291-1295.

Zanelati TV, Biojone C, Moreira FA, Guimarães FS, Joca SR (January 2010). "Antidepressant-like effects of cannabidiol in mice: possible involvement of 5-HT 1A receptors". British Journal of Pharmacology. 159 (1): 122-8. doi: 10.1111/j.1476-5381.2009.00521.x. PMC 2823358. PMID 20002102.

Zeng, B.Y., Iravani, M.M., Jackson, M.J., Rose, S., Parent, A., & Jenner, P. (2010). Morphological changes in sertoninergic neuritis in the striatum and globus pallidus in levodopa primed MPTP treated common marmosets with dyskinesia. Neurobiol Dis, 40 (3): 599-607.

Zhang J, Tan LC (2016). "Revisiting the Medical Management of Parkinson's Disease: Levodopa versus Dopamine Agonist". Current Neuropharmacology. 14 (4): 356-63. doi: 10.2174/1570159X14666151208114634. PMC 4876591. PMID 26644151.

Zhang QJ Li LB Niu XL Liu Jet al. (2011). The pyramidal neurons in the medial prefrontal cortex show decreased response to 5-hydroxytryptamine-3 receptor stimulation in a rodent model of Parkinson's disease. Brain Research 1384, 69-79. doi.org/10.1016/j.brainres.2011.01.086

Zhang Y, Meredith GE, Mendoza-Elias N, Rademacher DJ, Tseng KY, SteeceCollier K (2013) Aberrant restoration of spines and their synapses in LDOPA-induced dyskinesia: involvement of corticostriatal but not thalamostriatal synapses. J Neurosci Off J Soc Neurosci 33:11655-11,667. doi.org/10.1523/JNEUROSCI.0288-13.2013

Zhang, Li-Ming, Xiao-Yun Wang, Nan Zhao, Yu-Lu Wang, Xiao-Xu Hu, Yu-Hua Ran, Yan-Qin Liu, You-Zhi Zhang, Ri-Fang Yang, and Yun-Feng Li. "Neurochemical and behavioural effects of hypidone hydrochloride (YL-0919): a novel combined selective 5-HT reuptake inhibitor and partial 5-HT1A agonist." British journal of pharmacology 174, no. 9 (2017): 769-780

Zhornitsky S, Potvin S: Cannabidiol in humans—the quest for therapeutic targets. Pharmaceuticals (Basel). 2012 May 21;5 (5): 529-52. doi: 10.3390/ph5050529. [PubMed: 24281562]

Zhou, Dahui, Boyd L. Harrison, Uresh Shah, Terrance H. Andree, Geoffrey A. Hornby, Rosemary Scerni, Lee E. Schechter, Deborah L. Smith, Kelly M. Sullivan, and Richard E. Mewshaw. "Studies toward the discovery of the next generation of antidepressants. Part 5:3, 4-Dihydro-2H-benzo[1, 4]oxazine derivatives with dual 5-HT 1A receptor and serotonin transporter affinity." Bioorganic & medicinal chemistry letters 16, no. 5 (2006): 1338-1341.

Zhou, Dahui, Gary P. Stack, Jennifer Lo, Amedeo A. Failli, Deborah A. Evrard, Boyd L. Harrison, Nicole T. Hatzenbuhler et al. "Synthesis, potency, and in vivo evaluation of 2-piperazin-1-ylquinoline analogues as dual serotonin reuptake inhibitors and serotonin 5-HT1A receptor antagonists." Journal of medicinal chemistry 52, no. 15 (2009): 4955-4959.

Zhou, Dahui, Nicole T. Hatzenbuhler, Jonathan L. Gross, Boyd L. Harrison, Deborah A. Evrard, Michael Chlenov, Jeannette Golembieski et al. "Novel pyridyl-fused 3-amino chroman derivatives with dual action at serotonin transporter and 5-HT 1A receptor." Bioorganic & medicinal chemistry letters 17, no. 11 (2007): 3117-3121.

Zhou, Dahui, Ping Zhou, Deborah A. Evrard, Kristin Meagher, Michael Webb, Boyd L. Harrison, Donna M. Huryn et al. "Studies toward the discovery of the next generation of antidepressants. Part 6: Dual 5-HT 1A receptor and serotonin transporter affinity within a class of arylpiperazinyl-cyclohexyl indole derivatives." Bioorganic & medicinal chemistry 16, no. 14 (2008): 6707-6723.

Zlebnik, N. E; Cheer, J. F (2016). "Beyond the CB1 Receptor: Is Cannabidiol the Answer for Disorders of Motivation?". Annual Review of Neuroscience. 39:1-17. doi: 10.1146/annurev-neuro-070815-014038. PMC 5818147. PMID 27023732.

Zou S, Kumar U: Cannabinoid Receptors and the Endocannabinoid System: Signaling and Function in the Central Nervous System. Int J Mol Sci. 2018 Mar. 13;19 (3). pii: ijms19030833. doi: 10.3390/ijms19030833. [PubMed: 29533978]

CBD: See U.S. Patent and Published application Nos. 20180289665; 20180284145; 20180271924; 20180221396; 20180193399; 20180179564; 20180116998; 20180092392; 20180078504; 20180064055; 20180021247; 20170362195; 20170360745; 20170339907; 20170298399; 20170283837; 20170233778; 20170202170; 20170143664; 20170112801; 20170042791; 20160340629; 20160324091; 20160264917; 20160106705; 20160074357; 20160053220; 20150366154; 20150359188; 20150342922; 20140298511; 20140287068; 20110038958; 20060153941; 20040034102; 20040005354; 10,092,525; 9,956,186; 9,956,185; 9,956,184;9,956,183; 9,949,937; 9,949,936; 9,879,292; 9,730,911; 9,675,579; 9,642,317; 9,587,212; 9,585,867; 9,512,391; 9,474,726; 9,394,510; 9,370,164; 9,125,859; 9,095,554; 9,017,737; and 8,470,874.

Vortioxetine: U.S. Patent and Pub. App. Nos: 10005759; 10011588; 10034645; 10064833; 10071092; 10098861; 10100018; 5258387; 7138407; 7144884; 7148238; 7678363; 7678808; 7858611; 7985756; 7998971; 8138174; 8153127; 8299095; 8476279; 8507526; 8598348; 8664225; 8722684; 8883788; 8940746; 8969355; 8980888; 8980889; 9090575; 9090586; 9095588; 9101626; 9125908; 9125909; 9125910; 9133144; 9150588; 9156829; 9211288; 9227946; 9265772; 9278096; 9315459; 9353073; 9399039; 9440970; 9453015; 9458157; 9464060; 9475748; 9486453; 9493409; 9493432; 9499504; 9532983; 9550743; 9562024; 9687484; 9731026; 9732053; 9737531; 9744166; 9763896; 9775845; 9777000; 9790220; 9820984; 9822086; 9861630; 9896423; 9913839; 9920021; 9926286; 9943528; 9949983; 9956194; 9962379; 9963435; 9974755; 20040106655; 20050014740; 20050043379; 20050107444; 20050135999; 20060019938; 20060217394; 20070032435; 20070049576; 20070078083; 20070112017; 20070208029; 20070244143; 20070249544; 20070270449; 20080004448; 20080064671; 20080089835; 20080103105; 20080103165; 20080103186; 20080108574; 20080139569; 20080167291; 20080167363; 20080171750; 20080188457; 20080214559; 20080319024; 20090069281; 20090124652; 20090137794; 20090176983; 20090203705; 20090239946; 20090325949; 20100009983; 20100021539; 20100041891; 20100069463; 20100120842; 20100184806; 20100216734; 20100216805; 20100297240; 20110009421; 20110034565; 20110046090; 20110092464; 20110130384; 20110269717; 20110319386; 20130137675; 20130137700; 20130150344; 20130184291; 20130303524; 20140018348; 20140170157; 20140248355; 20140248356; 20140256943; 20140315921; 20140371453; 20140377363; 20140378447; 20140378448; 20150005318; 20150011864; 20150030602; 20150132327; 20150133448; 20150166536; 20150284362; 20150297585;

20150374684; 20160009670; 20160083359; 20160137620; 20160200698; 20160200732; 20160214949; 20160214950; 20160256398; 20160310488; 20160347751; 20160368884; 20170037006; 20170182034; 20170189394; 20170196855; 20170197927; 20170204074; 20170252358; 20170291897; 20170312275; 20170312363; 20170333424; 20170343554; 20170348263; 20170360777; 20180000815; 20180016330; 20180021334; 20180028492; 20180030008; 20180030064; 20180030114; 20180036267; 20180057470; 20180065971; 20180071306; 20180072690; 20180079742; 20180111891; 20180116911; 20180117291; 20180125794; 20180136230; 20180140568; 20180153881; 20180161321; 20180169081; 20180185375; 20180186797; 20180193334; 20180193340; 20180200207; 20180214455; 20180221396; 20180228695; 20180230116; 20180237386; 20180250300; 20180251435; 20180263976; 20180273499; 20180280381; 20180280382; 20180282309; 20180296554; 20180303772; and 20180303858.

YL-0919 See U.S. Patent and Published application Ser. Nos. 10/004,749; 10005759; 10010526; 10010615; 10011590; 10022355; 10028949; 10028962; 10030026; 10034859; 10039753; 10045941; 10052339; 10058584; 10064833; 10071095; 10072010; 10077267; 10077269; 10077272; 10093655; 10093981; 10098861; 10100044; 5214156; 5616610; 6376494; 6518272; 6656953; 6667322; 6673908; 6703383; 6713479; 6872716; 6936614; 7030122; 7037910; 7049330; 7098232; 7132551; 7189755; 7217823; 7220859; 7276603; 7276608; 7294637; 7314882; 7317012; 7326706; 7326707; 7345031; 7345178; 7354923; 7361766; 7365095; 7365211; 7368458; 7368477; 7368539; 7371769; 7378418; 7396857; 7402687; 7425558; 7452892; 7456184; 7494979; 7495111; 7507732; 7511141; 7517892; 7517900; 7517991; 7538123; 7572808; 7582767; 7601753; 7629342; 7632837; 7678363; 7678808; 7709484; 7709647; 7718802; 7727990; 7727991; 7728023; 7732451; 7754866; 7772188; 7790905; 7799916; 7812035; 7816357; 7816362; 7816375; 7834020; 7846953; 7855195; 7855289; 7858611; 7858639; 7879802; 7884096; 7884113; 7888362; 7905852; 7927613; 7964601; 7968548; 7968551; 7973043; 7981894; 7985752; 7985756; 7998971; 7998974; 8030306; 8030312; 8034782; 8044198; 8071600; 8088928; 8093401; 8101619; 8114844; 8119669; 8119808; 8138174; 8138188; 8150629; 8153127; 8158152; 8163908; 8168639; 8178536; 8193195; 8207295; 8227453; 8236804; 8263781; 8268854; 8304431; 8313774; 8318744; 8318813; 8332158; 8344009; 8349840; 8354447; 8357775; 8367645; 8367676; 8367800; 8399681; 8426423; 8426604; 8445690; 8486621; 8497348; 8530413; 8552055; 8552199; 8569246; 8575172; 8580796; 8580832; 8592403; 8598119; 8598162; 8604041; 8618109; 8623874; 8637030; 8642600; 8642760; 8648038; 8664225; 8664354; 8673921; 8680105; 8680120; 8686150; 8691813; 8691849; 8697673; 8697689; 8703772; 8703773; 8716224; 8716480; 8722680; 8722684; 8722894; 8735578; 8748491; 8748621; 8754238; 8759350; 8759364; 8772299; 8779090; 8785486; 8791138; 8796247; 8796256; 8802851; 8815870; 8815903; 8822456; 8822494; 8835635; 8841290; 8841323; 8846712; 8859494; 8859534; 8865706; 8883808; 8883831; 8901075; 8901130; 8901303; 8906939; 8916564; 8921375; 8921563; 8927552; 8927553; 8927566; 8933221; 8937060; 8946205; 8962616; 8969355; 8969514; 8993591; 8993761; 9006248; 9012448; 9012457; 9016221; 9023848; 9034852; 9045498; 9045499; 9045799; 9057726; 9062094; 9066903; 9067891; 9067934; 9085577; 9089567; 9089612; 9095588; 9101626; 9107923; 9114138; 9120788; 9125908; 9125909; 9125910; 9128101; 9132122; 9133181; 9133190; 9139561; 9145400; 9156796; 9156845; 9168258; 9169218; 9180191; 9186359; 9192612; 9192669; 9193726; 9198917; 9204835; 9206167; 9221816; 9226904; 9226930; 9227946; 9233981; 9238632; 9238677; 9259409; 9260455; 9265772; 9265774; 9266834; 9266926; 9271967; 9278094; 9315456; 9315520; 9326984; 9333203; 9345703; 9359302; 9364433; 9382208; 9382233; 9387182; 9387207; 9398761; 9399630; 9403846; 9428506; 9428523; 9468627; 9469876; 9480686; 9486494; 9493443; 9505744; 9505805; 9511149; 9527831; 9527843; 9533056; 9533949; 9540352; 9540375; 9550795; 9562024; 9567341; 9593125; 9597403; 9598401; 9598421; 9603937; 9603938; 9603939; 9605007; 9611264; 9616053; 9616061; 9617275; 9624204; 9642855; 9668995; 9670199; 9676782; 9682032; 9682946; 9682948; 9688698; 9694009; 9695171; 9700566; 9708300; 9708315; 9708322; 9708367; 9714232; 9724302; 9724345; 9730892; 9731026; 9737482; 9737483; 9737533; 9737548; 9744173; 9744191; 9745296; 9745300; 9745317; 9751847; 9751877; 9751895; 9757336; 9758516; 9758529; 9763896; 9765073; 9771379; 9775845; 9789155; 9790237; 9796695; 9808424; 9814752; 9815832; 9820984; 9822097; 9839637; 9840481; 9850232; 9856238; 9856263; 9861630; 9868744; 9884844; 9889198; 9890150; 9913839; 9914752; 9920095; 9926285; 9926529; 9938576; 9943528; 9949983; 9956187; 9956194; 9956201; 9957283; 9963435; 9968610; 9969721; 9974755; 9975868; 20010034023; 20010049368; 20020065265; 20020123499; 20020156075; 20020177607; 20030022814; 20030050309; 20030073681; 20030100570; 20030100579; 20030139449; 20030236283; 20040038983; 20040067960; 20040077706; 20040117125; 20040142974; 20040147581; 20040152134; 20040157264; 20040167201; 20040171056; 20040192730; 20040224957; 20040235832; 20040266808; 20050009870; 20050014786; 20050054659; 20050054688; 20050059673; 20050080078; 20050080087; 20050085463; 20050101614; 20050119248; 20050119249; 20050119253; 20050130988; 20050143381; 20050171110; 20050176728; 20050192278; 20050203130; 20050234093; 20050245539; 20050250767; 20050256103; 20050288355; 20060019968; 20060019969; 20060025420; 20060039866; 20060039867; 20060039903; 20060063776; 20060079556; 20060094658; 20060148835; 20060154938; 20060154955; 20060154956; 20060154958; 20060155126; 20060160850; 20060183757; 20060194831; 20060199807; 20060211685; 20060217394; 20060223857; 20060229265; 20060241134; 20060241172; 20060241176; 20060247254; 20060247276;

20060258680; 20060258714; 20060258715; 20060258732; 20060258739; 20060263299; 20060276416; 20060287322; 20060287323; 20060287324; 20060287330; 20060287331; 20060287332; 20060287333; 20060287335; 20060287341; 20060287342; 20060293361; 20070004772; 20070015138; 20070031853; 20070037809; 20070037810; 20070037827; 20070037865; 20070042014; 20070043050; 20070049576; 20070066601; 20070078083; 20070078162; 20070093450; 20070106479; 20070112017; 20070116729; 20070117177; 20070117844; 20070142399; 20070148246; 20070149466; 20070149585; 20070155670; 20070208029; 20070213370; 20070219179; 20070225279; 20070225331; 20070244143; 20070248590; 20070270449; 20070275957; 20080064671; 20080070925; 20080103105; 20080103155; 20080103165; 20080108574; 20080139546; 20080167290; 20080167291; 20080167363; 20080171750; 20080182891; 20080188457; 20080194625; 20080200459; 20080200541; 20080214559; 20080221179; 20080234289; 20080269321; 20080280955; 20080286265; 20080293943; 20090005722; 20090036459; 20090042874; 20090042905; 20090048175; 20090054319; 20090062207; 20090068290; 20090069224; 20090069301; 20090099170; 20090099251; 20090111855; 20090143376; 20090163476; 20090192083; 20090197859; 20090203731; 20090233942; 20090253634; 20090258901; 20090264404; 20090275563; 20090286760; 20090298831; 20090305960; 20090305993; 20090306026; 20090306121; 20090325949; 20090326014; 20100004259; 20100004262; 20100009983; 20100029656; 20100035871; 20100036139; 20100048612; 20100048713; 20100069306; 20100069399; 20100069463; 20100093635; 20100099753; 20100119622; 20100120694; 20100120842; 20100130479; 20100136614; 20100152118; 20100160411; 20100166889; 20100168084; 20100168119; 20100179322; 20100184806; 20100184852; 20100197717; 20100204202; 20100216734; 20100216805; 20100226943; 20100267691; 20100297240; 20100298382; 20100304391; 20100305500; 20110009422; 20110009496; 20110021419; 20110021564; 20110034565; 20110039825; 20110046090; 20110059982; 20110070319; 20110071080; 20110092464; 20110104315; 20110105519; 20110118264; 20110130387; 20110136814; 20110136865; 20110150864; 20110152286; 20110160120; 20110160543; 20110172251; 20110200586; 20110200587; 20110201617; 20110207776; 20110237625; 20110250264; 20110262442; 20110269717; 20110294780; 20110319343; 20110319386; 20120004165; 20120004166; 20120004167; 20120004187; 20120010242; 20120015936; 20120022039; 20120022254; 20120028920; 20120040397; 20120040892; 20120045430; 20120077813; 20120077818; 20120087986; 20120088902; 20120107396; 20120108510; 20120108571; 20120122931; 20120129890; 20120156259; 20120183600; 20120197013; 20120220526; 20120232862; 20120252758; 20120258172; 20120258984; 20120258994; 20120264703; 20120264722; 20120270215; 20120277249; 20120283411; 20120289460; 20120302544; 20130004574; 20130028842; 20130045979; 20130053301; 20130053373; 20130065894; 20130085128; 20130096071; 20130116199; 20130150340; 20130158044; 20130172248; 20130177633; 20130177634; 20130177635; 20130177636; 20130177637; 20130177638; 20130178383; 20130183372; 20130183373; 20130183375; 20130184286; 20130190343; 20130195965; 20130197032; 20130203766; 20130210849; 20130217673; 20130224151; 20130225818; 20130230577; 20130231369; 20130252965; 20130267533; 20130274204; 20130287772; 20130289019; 20130289047; 20130296308; 20130296367; 20130303497; 20130303524; 20130306759; 20130309330; 20130310328; 20130310385; 20130317065; 20130324554; 20130331378; 20140005183; 20140005270; 20140005395; 20140006042; 20140018335; 20140018400; 20140024605; 20140031334; 20140039029; 20140044786; 20140045790; 20140050783; 20140051701; 20140057925; 20140088104; 20140088111; 20140094450; 20140100249; 20140107087; 20140120185; 20140128374; 20140135274; 20140141986; 20140154313; 20140162888; 20140163015; 20140163039; 20140163227; 20140170157; 20140171436; 20140179713; 20140187470; 20140187524; 20140194479; 20140206740; 20140221385; 20140221388; 20140221395; 20140228356; 20140228421; 20140235562; 20140235612; 20140235631; 20140243254; 20140248355; 20140248356; 20140256943; 20140275542; 20140287001; 20140287002; 20140296257; 20140303179; 20140303185; 20140315921; 20140323402; 20140323474; 20140323498; 20140329738; 20140336176; 20140336199; 20140343089; 20140349977; 20140350064; 20140350255; 20140364426; 20140371227; 20140371453; 20140377363; 20140378472; 20150005313; 20150005318; 20150011864; 20150018275; 20150018370; 20150030602; 20150030701; 20150031709; 20150047060; 20150057235; 20150065577; 20150072990; 20150073148; 20150079172; 20150080422; 20150087541; 20150087637; 20150087835; 20150098931; 20150099270; 20150105399; 20150126525; 20150126526; 20150133432; 20150133438; 20150150846; 20150152348; 20150157575; 20150175573; 20150175583; 20150175645; 20150191481; 20150196561; 20150202199; 20150202317; 20150211067; 20150218639; 20150224110; 20150225792; 20150231144; 20150239871; 20150239908; 20150239934; 20150250203; 20150252000; 20150258197; 20150265637; 20150273013; 20150274692; 20150274721; 20150283202; 20150284362; 20150284386; 20150291621; 20150291625; 20150301055; 20150307486; 20150307494; 20150307522; 20150320739; 20150320742; 20150322030; 20150322065; 20150335649; 20150336928; 20150342946; 20150344474; 20150344490; 20150361081; 20150361099; 20150366874; 20150367366;

20150376207; 20160002264; 20160005320; 20160008360; 20160015684; 20160015720; 20160016887; 20160023826; 20160024008; 20160024058; 20160024088; 20160030333; 20160030425; 20160031885; 20160038559; 20160039810; 20160039828; 20160051548; 20160058762; 20160075713; 20160082123; 20160083359; 20160083370; 20160095844; 20160113942; 20160143848; 20160151382; 20160152637; 20160158176; 20160185770; 20160199347; 20160200698; 20160200711; 20160200732; 20160200766; 20160210401; 20160213625; 20160213683; 20160214940; 20160214950; 20160220798; 20160222007; 20160224755; 20160228430; 20160229847; 20160235807; 20160239966; 20160239968; 20160243188; 20160244429; 20160257685; 20160263138; 20160263224; 20160263229; 20160264597; 20160267809; 20160271141; 20160272624; 20160305963; 20160310484; 20160310489; 20160340390; 20160345827; 20160346249; 20160346278; 20160354315; 20160361260; 20160361298; 20160367623; 20160374957; 20160375016; 20170000786; 20170000843; 20170001987; 20170002000; 20170008911; 20170020885; 20170020892; 20170027887; 20170029468; 20170037048; 20170037049; 20170037053; 20170042911; 20170044174; 20170049709; 20170056347; 20170057947; 20170057960; 20170065536; 20170065560; 20170071522; 20170073343; 20170088547; 20170088556; 20170088558; 20170096428; 20170100395; 20170101409; 20170101412; 20170145022; 20170151252; 20170165225; 20170165270; 20170166566; 20170172971; 20170183350; 20170189393; 20170189398; 20170196855; 20170196908; 20170204064; 20170204099; 20170204131; 20170209449; 20170209531; 20170217939; 20170231983; 20170252358; 20170258788; 20170267655; 20170273989; 20170275260; 20170281531; 20170283417; 20170290778; 20170304312; 20170305876; 20170305905; 20170305931; 20170319607; 20170326127; 20170326139; 20170348263; 20170349630; 20170360777; 20170362230; 20170368060; 20170369506; 20170372030; 20180000815; 20180002305; 20180002331; 20180021259; 20180022712; 20180028492; 20180030007; 20180030055; 20180030064; 20180030114; 20180030538; 20180030539; 20180036267; 20180037571; 20180042898; 20180042922; 20180042923; 20180042985; 20180056022; 20180057470; 20180057506; 20180057884; 20180064649; 20180068056; 20180071285; 20180071298; 20180071299; 20180071306; 20180072674; 20180072750; 20180073079; 20180079742; 20180092847; 20180093974; 20180099982; 20180111891; 20180116911; 20180117291; 20180118727; 20180125794; 20180126014; 20180126100; 20180140568; 20180153881; 20180155282; 20180161321; 20180169081; 20180170868; 20180170935; 20180177760; 20180179188; 20180185375; 20180186762; 20180186797; 20180193330; 20180193340; 20180200253; 20180214444; 20180214455; 20180215710; 20180215737; 20180228695; 20180250300; 20180251435; 20180251449; 20180251450; 20180251451; 20180251455; 20180256542; 20180256601; 20180256756; 20180271869; 20180273586; 20180280342; 20180296556; and 20180296565.

What is claimed is:

1. A method of treating a L-DOPA-induced dyskinesia in a human patient, comprising daily administration of a pharmaceutically-acceptable dosage form containing vilazodone, in an amount of 2.5 to 5 mg per pharmaceutically-acceptable dosage form, concurrent with L-DOPA and for a sufficient duration, to treat the dyskinesia of the human patient and cause a downregulation of presynaptic 5-HT1A autoreceptors.

2. The method according to claim 1, wherein the patient is diagnosed with Parkinson's disease, the method further comprising concurrently administering L-DOPA and the pharmaceutically-acceptable dosage form to the patient diagnosed with Parkinson's disease, and the pharmaceutically-acceptable dosage form is administered according to a protocol effective to reduce L-DOPA induced dyskinesia (LID).

3. The method according to claim 2, wherein the pharmaceutically-acceptable dosage form comprises an effective amount of the L-DOPA to treat a movement disorder in the patient.

4. The method according to claim 2, further comprising administering at least one of carbidopa and benserazide to the human patient.

5. The method according to claim 1, further comprising administering at least one of entacapone, opicapone, tolcapone, selegiline, rasagiline, isocarboxazid, phenelzine, tranylcypromine, linezolid, methylene blue, apomorphine, bromocriptine, pramipexole, ropinirole, rotigotine, benzhexol, orphenadrine, benzatropine, diphenyhydramine, dimenhydrinate, and scopolamine to the human patient.

6. The method according to claim 1, wherein the vilazodone is present in an amount of 2.5 mg per pharmaceutically-acceptable dosage form.

7. The method according to claim 1, further comprising administering at least one of cannabidiol (CBD), and cannabidiolic acid (CBDA) to the human patient.

8. A method of treating an L-DOPA-induced dyskinesia in a human patient, comprising daily administration of a pharmaceutically-acceptable dosage form, comprising vilazodone in an amount of between 2.5 and 10 mg per pharmaceutically-acceptable dosage form of the daily administration concurrent with treatment with L-DOPA, to cause a downregulation of presynaptic 5-HT1A autoreceptors.

9. The method according to claim 8, wherein the pharmaceutically-acceptable dosage form is administered in a combined dosage form with L-DOPA.

10. The method according to claim 8, wherein is administered in a combined dosage form with at least one of carbidopa and benserazide.

11. The method according to claim 8, wherein the pharmaceutically-acceptable dosage form further comprises at least one of entacapone, opicapone, tolcapone, selegiline, rasagiline, isocarboxazid, phenelzine, tranylcypromine, linezolid, methylene blue, apomorphine, bromocriptine, pramipexole, ropinirole, rotigotine, benzhexol, orphenadrine, benzatropine, diphenyhydramine, dimenhydrinate, and scopolamine.

12. The method according claim 8, wherein the pharmaceutically-acceptable dosage form further comprises at least 100 mg L-DOPA, and at least 10 mg of at least one of carbidopa and benserazide.

13. The method according to claim 8, wherein the pharmaceutically-acceptable dosage form is an infusible dosage form.

14. The method according to claim 8, wherein the vilazodone is present in an amount of 2.5 mg per pharmaceutically-acceptable dosage form.

15. The method according to claim 8, wherein the pharmaceutically-acceptable dosage form is concurrently administered with at least one of cannabidiol (CBD), and cannabidiolic acid (CBDA).

16. A method of treating a human who receives L-DOPA and suffers from L-DOPA-induced dyskinesia, comprising daily administration of 2.5 mg to 10 mg of a pharmaceutically acceptable dosage form of vilazodone to the human while also being treated with L-DOPA, to treat the L-DOPA induced dyskinesia and cause a downregulation of presynaptic 5-HT1A autoreceptors.

17. The method according to claim 16, comprising daily administration of 2.5 mg of the pharmaceutically acceptable dosage form of vilazodone to the human.

18. The method according to claim 16, wherein the pharmaceutically acceptable dosage form further comprises L-DOPA.

19. The method according to claim 16, wherein the pharmaceutically acceptable dosage form further comprises a DOPA decarboxylase inhibitor.

20. The method according to claim 16, wherein the pharmaceutically acceptable dosage form further comprises a cannabinoid.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: GADPH forward primer

<400> SEQUENCE: 1
gtgccagcct cgtctcatag 20

<210> SEQ ID NO 2
<211> LENGTH: 20
<212> TYPE: DNA
<213> ORGANISM: Artificial Sequence
<220> FEATURE:
<223> OTHER INFORMATION: GADPH reverse primer

<400> SEQUENCE: 2
agagaaggca gccctggtaa 20

<210> SEQ ID NO 3
<211> LENGTH: 20
<212> TYPE: DNA
<213> ORGANISM: Artificial Sequence
<220> FEATURE:
<223> OTHER INFORMATION: c-Fos forward primer

<400> SEQUENCE: 3
ccaagcggag acagatcaac 20

<210> SEQ ID NO 4
<211> LENGTH: 20
<212> TYPE: DNA
<213> ORGANISM: Artificial Sequence
<220> FEATURE:
<223> OTHER INFORMATION: c-Fos reverse primer

<400> SEQUENCE: 4
aagtccaggg aggtcacaga 20

<210> SEQ ID NO 5
<211> LENGTH: 20
<212> TYPE: DNA
<213> ORGANISM: Artificial Sequence
<220> FEATURE:
<223> OTHER INFORMATION: PPD forward primer

<400> SEQUENCE: 5
gggttcgctg gattcaaata 20

<210> SEQ ID NO 6
<211> LENGTH: 20
<212> TYPE: DNA
<213> ORGANISM: Artificial Sequence
<220> FEATURE:
<223> OTHER INFORMATION: PPD reverse primer

<400> SEQUENCE: 6
tgtgtggaga gggacactca 20

<210> SEQ ID NO 7
<211> LENGTH: 20
<212> TYPE: DNA
<213> ORGANISM: Artificial Sequence
<220> FEATURE:
<223> OTHER INFORMATION: PPE forward primer

<400> SEQUENCE: 7
aaaatctggg agacctgcaa 20

<210> SEQ ID NO 8
<211> LENGTH: 20
<212> TYPE: DNA
<213> ORGANISM: Artificial Sequence
<220> FEATURE:
<223> OTHER INFORMATION: PPE reverse primer

<400> SEQUENCE: 8
catgaaaccg ccatacctct 20

<210> SEQ ID NO 9
<211> LENGTH: 20
<212> TYPE: DNA
<213> ORGANISM: Artificial Sequence
<220> FEATURE:
<223> OTHER INFORMATION: 5-HT1AR forward primer

<400> SEQUENCE: 9
gatctcgctc acttggctca 20

<210> SEQ ID NO 10

-continued

```
<211> LENGTH: 20
<212> TYPE: DNA
<213> ORGANISM: Artificial Sequence
<220> FEATURE:
<223> OTHER INFORMATION: 5-HT1AR reverse primer

<400> SEQUENCE: 10

aaagcgccga aagtggagta                                                  20
```